United States Patent
Chakravarty et al.

(10) Patent No.: US 9,211,287 B2
(45) Date of Patent: Dec. 15, 2015

(54) PYRIDO[4,3-B]INDOLE AND PYRIDO[3,4-B]INDOLE DERIVATIVES AND METHODS OF USE

(71) Applicant: Medivation Technologies, Inc., San Francisco, CA (US)

(72) Inventors: Sarvajit Chakravarty, Mountain View, CA (US); Barry Patrick Hart, Palo Alto, CA (US); Rajendra Parasmal Jain, Pune (IN)

(73) Assignee: Medivation Technologies, Inc., San Francisco, CA (US)

(*) Notice: Subject to any disclaimer, the term of this patent is extended or adjusted under 35 U.S.C. 154(b) by 0 days.

(21) Appl. No.: 14/666,101

(22) Filed: Mar. 23, 2015

(65) Prior Publication Data
US 2015/0258075 A1  Sep. 17, 2015

Related U.S. Application Data

(62) Division of application No. 14/000,179, filed as application No. PCT/US2012/025753 on Dec. 17, 2012, now Pat. No. 9,035,056.

(60) Provisional application No. 61/444,606, filed on Feb. 18, 2011, provisional application No. 61/568,064, filed on Dec. 7, 2011, provisional application No. 61/444,663, filed on Feb. 18, 2011, provisional application No. 61/568,061, filed on Dec. 7, 2011, provisional application No. 61/444,669, filed on Feb. 18, 2011, provisional application No. 61/568,068, filed on Dec. 7, 2011, provisional application No. 61/444,667, filed on Feb. 18, 2011.

(51) Int. Cl.
*A61K 31/437* (2006.01)
*A61K 31/4709* (2006.01)

(52) U.S. Cl.
CPC ............ *A61K 31/437* (2013.01); *A61K 31/4709* (2013.01)

(58) Field of Classification Search
None
See application file for complete search history.

(56) References Cited

U.S. PATENT DOCUMENTS

| | | | |
|---|---|---|---|
| 6,187,785 B1 | 2/2001 | Zefirov et al. |
| 7,071,206 B2 | 7/2006 | Zefirov et al. |
| 8,338,408 B2 | 12/2012 | Hung et al. |
| 8,338,447 B2 | 12/2012 | Hung et al. |
| 8,362,277 B2 | 1/2013 | McKnight et al. |
| 8,541,437 B2 | 9/2013 | Ivashchenko et al. |
| 8,546,381 B2 | 10/2013 | Hung et al. |
| 8,569,287 B2 | 10/2013 | Hung et al. |
| 8,604,074 B2 | 12/2013 | McKnight et al. |
| 8,735,440 B2 | 5/2014 | McKnight et al. |
| 8,741,919 B2 | 6/2014 | Jain et al. |
| 8,791,132 B2 | 7/2014 | Protter et al. |
| 8,815,843 B2 | 8/2014 | Protter et al. |
| 8,859,561 B2 | 10/2014 | Jain et al. |
| 8,877,797 B2 | 11/2014 | McKnight et al. |
| 8,906,925 B2 | 12/2014 | Hung et al. |
| 8,907,097 B2 | 12/2014 | Hung et al. |
| 8,927,571 B2 | 1/2015 | Jain et al. |
| 8,999,977 B2 | 4/2015 | Hung et al. |
| 8,999,978 B2 | 4/2015 | Hung et al. |
| 9,006,234 B2 | 4/2015 | Jain et al. |
| 9,006,263 B2 | 4/2015 | Protter et al. |
| 9,034,865 B2 | 5/2015 | Chakravarty et al. |
| 9,034,869 B2 | 5/2015 | Hung et al. |
| 9,034,880 B2 | 5/2015 | Hung et al. |
| 9,035,056 B2 | 5/2015 | Chakravarty et al. |
| 9,040,519 B2 | 5/2015 | Chakravarty et al. |
| 9,045,482 B2 | 6/2015 | Jain et al. |
| 9,051,314 B2 | 6/2015 | Hung et al. |
| 9,079,904 B2 | 7/2015 | Jain et al. |
| 9,085,580 B2 | 7/2015 | Jain et al. |
| 2001/0020028 A1 | 9/2001 | Zefirov et al. |
| 2002/0115682 A1 | 8/2002 | Zefirov et al. |
| 2004/0044022 A1 | 3/2004 | Zefirov, Jr. et al. |

(Continued)

FOREIGN PATENT DOCUMENTS

EP  2 236 511 A2  10/2010
WO  WO-2005/005951 A2  6/2005

(Continued)

OTHER PUBLICATIONS

Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics.* 287(2):508-514.

(Continued)

*Primary Examiner* — Timothy R Rozof
(74) *Attorney, Agent, or Firm* — Morrison & Foerster LLP

(57) ABSTRACT

This disclosure is directed to pyrido[4,3-b]indole and pyrido[3,4-b]indole derivatives. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder. The compounds may bind to and antagonize receptor α2B, α1B or α2A. The compounds may find use in therapy, e.g., to (i) reduce blood pressure and/or (ii) promote renal blood flow and/or (iii) decrease or inhibit sodium reabsorption, or to regulate blood glucose level, increase insulin secretion and treat diseases or conditions that are, or are expected to be, responsive to an increase in insulin production. The compounds may also be used to treat diseases or conditions that are expected to be responsive to a decrease in blood pressure. Use of the compounds to treat cardiovascular, renal disorders or type 2 diabetes is particularly described.

18 Claims, No Drawings

(56) References Cited

U.S. PATENT DOCUMENTS

| | | |
|---|---|---|
| 2006/0140866 A1 | 6/2006 | Zefirov et al. |
| 2007/0117834 A1 | 5/2007 | Hung |
| 2007/0117835 A1 | 5/2007 | Hung |
| 2007/0179174 A1 | 8/2007 | Bachurin et al. |
| 2007/0225316 A1 | 9/2007 | Bachurin et al. |
| 2008/0234310 A1 | 9/2008 | Bachurin et al. |
| 2009/0239854 A1 | 9/2009 | Hung et al. |
| 2010/0022580 A1 | 1/2010 | Hung et al. |
| 2010/0029706 A1 | 2/2010 | Miller et al. |
| 2010/0087471 A1 | 4/2010 | Schrimpf et al. |
| 2010/0099700 A1 | 4/2010 | Hung |
| 2010/0152108 A1 | 6/2010 | Hung et al. |
| 2010/0152225 A1 | 6/2010 | Hung |
| 2010/0178277 A1 | 7/2010 | Hung et al. |
| 2010/0249105 A1 | 9/2010 | Schrimpf et al. |
| 2010/0286188 A1 | 11/2010 | Bachurin et al. |
| 2011/0046368 A1 | 2/2011 | Ivashchenko et al. |
| 2011/0112132 A1 | 5/2011 | Bachurin et al. |
| 2011/0237582 A1 | 9/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |
| 2015/0182509 A1 | 7/2015 | Hung et al. |

FOREIGN PATENT DOCUMENTS

| | | |
|---|---|---|
| WO | WO-2005/005951 A3 | 6/2005 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/081115 A1 | 7/2010 |
| WO | WO-2010/127177 A1 | 11/2010 |
| WO | WO-2011/008312 A2 | 1/2011 |
| WO | WO-2011/008312 A3 | 1/2011 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012/006419 A3 | 1/2012 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112965 A1 | 8/2012 |
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |
| WO | WO-2014/105958 A2 | 7/2014 |
| WO | WO-2014/105958 A3 | 7/2014 |

OTHER PUBLICATIONS

Bartolini, L. et al. (1996). "Aniracetam Restores Object Recognition Impaired by Age, Scopolamine, and Nucleus Basalis Lesions," *Pharmacology Biochemistry Behavior* 53(2):277-283.

Berge, S.M. et al. (Jan. 1977). "Pharmaceutical Salts," *J Pharm Sci* 66(1):1-19.

Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.

(56) References Cited

OTHER PUBLICATIONS

Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.

Brown, C.M. et al. (1990). "$\alpha_2$-Adrenoceptor Subtypes and Imidazoline-Like Binding Sites in the Rat Brain," *Br. J. Pharmacol.* 99:803-809.

Burke, S.L. et al. (2011). "Effects of Chronic Sympatho-Inhibition on Renal Excretory Function in Renovascular Hypertension," *J Hypertension* 29(5):945-952.

Carter, et al. (2009). "A Practical Guide to Rodent Islet Isolation and Assesment." *Biol. Proced. Online* 11(1):3-31.

Chen, et al. (2011). "Sitagliptin Lowers Glucagon and Improves Glucose Tolerance in Prediabetic Obese SHROB Rats," *Exp. Biol. Med.* 236:309-414.

Cheng, Y. et al. (Sep. 15, 1973). "Relationship Between the Inhibition Constant ($K_1$) and the Concentration of Inhibitor Which Causes 50 Per Cent Inhibition ($I_{50}$) of an Enzymatic Reaction," *Biochem Pharmacol* 22(18):3099-3108.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Duprez, D.A. (2008). "Systolic Hypertension in the Elderly: Addressing an Unmet Need," *Am J Med* 121:179-184.

Ennaceur, A. et al. (1988). "A New One-Trial Test for Neurobiological Studies of Memory in Rats. 1: Behavioral Data," *Behav. Brain. Res.* 31:47-59.

Franklin, S.S. et al. (2011). "The Significance of Low DBP in US Adults with Isolated Systolic Hypertension," *J Hypertension* 29(6):1101-1108.

García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.

Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTP$\gamma$S Binding Assays," *Naunyn-Schmiedeberg's Archives of Pharmacology* 361:498-504.

Grandy, D.K. et al. (Dec. 1989). "Cloning of the cDNA and Gene for a Human D$_2$ Dopamine Receptor," *Proc. Natl. Acad. Sci. USA* 86:9762-9766.

Grossman, C.J. et al. (1993). "Development of a Radioligand Binding Assay for 5-HT$_4$ Receptors in Guinea-Pig and Rat Brain," *Br. J. Pharmacol.* 109:618-624.

Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.

Hoyer, D. et al. (1985). "Characterization of the 5-HT$_{1B}$ Recognition Site in Rat Brain: Binding Studies with (-)[$^{125}$I]Iodocyanopindolol," *European Journal of Pharmacology* 118:1-12.

International Search Report mailed on Aug. 3, 2012, for PCT Application No. PCT/US2012/25753, filed on Feb. 17, 2012, 4 pages.

Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.

Jerman, J.C. et al. (2001). "Pharmacological Characterisation of Human 5-HT$_2$ Receptor Subtypes," *European Journal of Pharmacology* 414:23-30.

Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.

Kohen, R. et al. (1996). "Cloning, Characterization, and Chromosomal Localization of a Human 5-HT$_6$ Serotonin Receptor," *J. Neurochem.* 66(1):47-56.

Krueger, K.M. et al. (Jul. 2005, e-published Apr. 8, 2005). "G Protein-Dependent Pharmacology of Histamine H$_3$ Receptor Ligands: Evidence for Heterogeneous Active State Receptor Conformations," *J Pharmacol Exp Ther* 314(1):271-281.

Kuhn, et al. (1987). "Exaggerated Peripheral Responses to Catecholamines Contributes to Stress-Induced Hyperglycemia in the Ob/Ob Mouse," *Pharmacol. Biochem. Behav.* 26:491-495.

Lohr, J. B. et al. (Aug. 28, 1995). "Motor Asymmetry, a Neurobiologic Abnormality in the Major Psychoses," *Psychiatry Research* 57(3):279-282.

Mancia, G. et al. (2007). 2007 Guidelines for the management of arterial hypertension: The Task Force for the Management of Arterial Hypertension of the European Society of Hypertension (ESH) and of the European Society of Cardiology (ESC) , Eur. Heart J., 28(12):1462-1536.

Martin, G.R. (1994). "Receptors for 5-Hydroxytryptamine: Current Perspectives on Classification and Nomenclature," *Neuropharmacology* 33(3/4):261-273.

May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.

Meister, B. et al. (1994). Patterns of Messenger RNA Expression for Adrenergic Receptor Subtypes in the Rat Kidney, *J Pharmacol Exp Therapeutics* 268(3):1606-1611.

Michel, A.D. et al. (1989). "Identification of a Single $\alpha_1$-Adrenoceptor Corresponding to the $\alpha_{1A}$-Subtype in Rat Submaxillary Gland," *Br J Pharmacol* 98:883-889.

Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.

Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.

Monsma, F.J. Jr. et al. (1993). "Cloning and Expression of a Novel Serotonin Receptor with High Affinity for Tricyclic Psychotropic Drugs," *Molecular Pharmacology* 43:320-327.

Non-Final Office Action mailed on Feb. 18, 2015, for U.S. Appl. No. 13/679,883, filed Nov. 16, 2012, 10 pages.

Non-Final Office Action mailed on Feb. 24, 2015, for U.S. Appl. No. 14/000,171, filed Nov. 27, 2013, 19 pages.

Non-Final Office Action mailed on Jul. 2, 2015, for U.S. Appl. No. 14/000,184, filed Nov. 27, 2013, 13 pages.

Non-Final Office Action mailed on Jul. 24, 2015, for U.S. Appl. No. 14/000,197, filed Nov. 22, 2013, 6 pages.

Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.

Perrin, R.J. et al. (2003). Epitope Mapping and Specificity of the Anti-$\alpha$-Synuclein Monoclonal Antibody Syn-1 in Mouse Brain and Cultured Cell Lines *Neurosci Lett* 349:133-135.

Pfaffl, (2001). "A New Mathematical Model for Relative Quantification in Real-Time RT-PCR," *Nucleic Acids Res* 29(9):e45, 6 pages.

Piercey, M.F. et al. (1988). "Dramatic Limbic and Cortical Effects Mediated by High Affinity PCP Receptors," *Life Sciences* 43(4):379-385.

Rahim, F. (2010). "An in Silico Development of Selective Inhibitor for Histamine Receptors," *Biotechnology* 9(2):157-163.

Rees, S. et al. (Oct. 11, 1994). "Cloning and Characterisation of the Human 5-HT$_{5A}$ Serotonin Receptor," *FEBS Letters* 355:242-246.

Regard, J.B. et al. (Oct. 31, 2008). "Anatomical Profiling of G Protein-Coupled Receptor Expression," *Cell* 135:561-571.

Rosengren et al. (Jan. 8, 2010). "Overexpression of Alpha2A-Adrenergic Receptors Contributes to Type 2 Diabetes," *Science* 327:217-20.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

(56) References Cited

OTHER PUBLICATIONS

Ruat, M. et al. (Mar. 1990). "Reversible and Irreversible Labeling and Autoradiographic Localization of the Cerebral Histamine $H_2$ Receptor Using [$^{125}$I]Iodinated Probes," *Proc. Natl. Acad. Sci. USA* 87(5):1658-1662.

Saperstein, et al., (May 1990). "Effects of an $\alpha_2$-Adrenoceptor Antagonist on Glucose Tolerance in the Genetically Obese Mouse (C57BL/6J ob/ob)," *Metabolism* 39:445-451.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Talmud, et al. (2011). "Variants of *ADRA2A* are Associated with Fasting Glucose, Blood Pressure, Body Mass Index and Type 2 Diabetes Risk: Meta-Analysis of Four Prospective Studies," *Diabetologia* 54:1710-1719.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vekrellis, K. et al. (2009). "Inducible Over-Expressing of Wild Type $\alpha$-Synuclein in Human Neuronal Cells Leads to Caspase-Dependent Non-Apoptotic Death," *J Neurochem* 109:1348-1362.

Velliquette R.A. et al. (2003). "The Role of $l_1$-Imidazoline and $\alpha(2)$-Adrenergic Receptors in the Modulation of Glucose Metabolism in the Spontaneously Hypertensive Obese Rat Model of Metabolic Syndrome X," *J. Pharmacol. Exp. Ther.* 306(2):646-657.

Wade, et al., (2001). "Inverse Agonist Activity at the $\alpha_{2A}$-Adrenergic Receptor," *Mol. Pharmacol.* 59(3):532-542.

Written Opinion mailed on Aug. 3, 2012, for PCT Application No. PCT/US2012/25753, filed on Feb. 17, 2012, 8 pages.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Yanai, K. et al. (1994). "Binding Characteristics of a Histamine $H_3$-Receptor Antagonist, [$^3$H]S-Methylthioperamide: Comparison with [$^3$H](R)$\alpha$-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

U.S. Appl. No. 14/000,171, filed Aug. 16, 2013, by Protter et al.
U.S. Appl. No. 14/000,184, filed Aug. 16, 2013, by Protter et al.
U.S. Appl. No. 14/485,238, filed Sep. 12, 2014, by Jain et al.
U.S. Appl. No. 14/531,915, filed Nov. 3, 2014, by Hung et al.
U.S. Appl. No. 14/423,027, filed Feb. 20, 2015, by Protter et al.
U.S. Appl. No. 14/631,615, filed Feb. 25, 2015, by Hung et al.
U.S. Appl. No. 14/641,232, filed Mar. 6, 2015, by Protter et al.
U.S. Appl. No. 14/666,101, filed Mar. 23, 2015, by Chakravarty et al.
U.S. Appl. No. 14/701,244, filed Apr. 30, 2015, by Chakravarty et al.
U.S. Appl. No. 14/738,465, filed Jun. 12, 2015, by Jain et al.
U.S. Appl. No. 14/758,194, filed Jun. 26, 2015, by Chakravarty et al.

PYRIDO[4,3-B]INDOLE AND PYRIDO[3,4-B]INDOLE DERIVATIVES AND METHODS OF USE

CROSS-REFERENCE TO RELATED APPLICATIONS

This application is a division of U.S. Non-provisional patent application Ser. No. 14/000,179, filed Nov. 26, 2013, now U.S. Pat. No. 9,035,056, issued on May 19, 2015, which is a national phase application under 35 U.S.C. §371 of International Application No. PCT/US2012/025753, filed Feb. 17, 2012, which claims priority to U.S. Provisional Patent Application No. 61/444,606 filed Feb. 18, 2011, U.S. Provisional Patent Application No. 61/568,064 filed Dec. 7, 2011, U.S. Provisional Patent Application No. 61/444,663 filed Feb. 18, 2011, U.S. Provisional Patent Application No. 61/568,061 filed Dec. 7, 2011, U.S. Provisional Patent Application No. 61/444,669 filed Feb. 18, 2011, U.S. Provisional Patent Application No. 61/568,068 filed Dec. 7, 2011, and U.S. Provisional Patent Application No. 61/444,667 filed Feb. 18, 2011, the disclosures of each of which are incorporated herein by reference in their entireties.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia (such as cognitive impairment associated with schizophrenia (CIAS), positive symptoms, disorganized symptoms, and negative symptoms of schizophrenia), anxiety, multiple sclerosis, stroke, traumatic brain injury, spinal cord injury, diabetic neuropathy, fibromyalgia, bipolar disorders, psychosis, depression, attention-deficit disorder (ADD), attention-deficit hyperactivity disorder (ADHD) and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the \agonist-antagonist binding site, are strongly conserved across mammalian species. Histamine receptors are found in most peripheral tissue and within the central nervous system. Compounds capable of modulating a histamine receptor may find use in therapy, e.g., histamine antagonists may find use as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. Hydrogenated pyrido[4,3-b]indoles and uses thereof have been disclosed in PCT Patent Application Nos. PCT/US2008/081390, PCT/US2009/032065 and PCT/US2009/038142. Hydrogenated pyrido[3,4-b]indoles and uses thereof have been described in PCT/US2009/038138. Azepino[4,5-b]indoles and uses thereof have been described in PCT/US2009/062872. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g., by in vitro and/or in vivo assays, may find use in additional diseases and conditions.

Hypertension is a serious condition that can damage vital organs, such as the heart and kidneys, and other parts of the body, such as the central nervous system. Individuals who have hypertension may have, or be at risk of developing, dangerous diseases such as coronary heart disease and kidney failure. Hypertension, which is the leading modifiable risk factor for cardiovascular disease mortality, causes more than 7 million deaths every year worldwide.

Hypertension is the most common chronic medical condition in developed countries as well as the most common indication for physician visits and prescription medication use. Hypertension affects more than 50 million individuals in the United States and over one billion individuals worldwide, and overall prevalence may continue to increase with the advancing age of the population.

Unfortunately, despite the importance of blood pressure control and the availability of multiple classes of antihypertensive agents, the treatment of hypertension remains suboptimal. Data from the most recent National Health and Nutrition Examination Survey demonstrate that only 34% of patients with hypertension have blood pressures at their therapeutic goal. Additionally, it was shown that the majority of patients with hypertension will require two or more antihypertensive agents to achieve their goal blood pressure. Even with optimal compliance with multiple antihypertensive agents of different classes, a significant fraction of patients will not be able to achieve their goal blood pressure. The overall prevalence of resistant hypertension, defined as elevated blood pressure in spite of the use of three or more antihypertensive agents, is unknown, but small studies suggest that it ranges from 5%-16% in primary care settings to greater than 50% in nephrology clinics. Given data suggesting that increasing age and obesity are important risk factors for the development of resistant hypertension, it is expected that the overall prevalence of this condition is likely to increase due to demographic changes in the population.

Systolic blood pressure tends to increase with age and systolic hypertension is an important health issue, prominent in the elderly (Duprez, *Am. J. Med.* 121:179-184 (2008)). It has been suggested that this occurs as large vessels such as the aorta lose their elasticity with age and is less able to buffer the pulsative nature of cardiac output. There exists a need for a treatment for patients in such clinical setting, for example, patients with systolic hypertension accompanied with low diastolic pressure (Franklin et al. *J. Hypertension* 29:1101-1108 (2011)).

Metabolic syndrome is a cluster of disorders including obesity, hypertension, hypertrigleridemia, hypercholesterolemia and elevated blood sugar. Individuals with this spectrum of disorders are at increased risk of diabetes, heart disease and stroke. Agents capable of treating more than one of these disorders are desirable.

Hypertensive emergencies are defined as severe elevations in blood pressure associated with resultant organ damage (i.e., pulmonary edema, renal impairment, visual impairment, intracranial hemorrhage, or encephalopathy). The treatment of hypertensive emergencies involves aggressive and controlled blood pressure lowering in a highly monitored intensive care setting using intravenous blood pressure lowering agents. Therapeutic agents and method of treatment is needed to gradually lower blood pressure and minimize damage of end organs such as the brain, kidney, heart, and eye.

The frequency of chronic kidney disease also continues to increase worldwide as does the prevalence of end-stage renal disease. Although chronic kidney disease is often caused by hypertension, other factors such as a decrease in renal blood flow and increase in sodium retention or reabsorption can lead to renal diseases. Increased age and diabetes can also contribute to renal disease. Especially the elderly, which are a growing segment of the world population, are at increased risk for renal disease. The presence of chronic kidney disease is also associated with a large increase in cardiovascular morbidity and mortality. Consequently, the identification and reduction of chronic kidney disease has become a vital public health priority.

Thus, there remains a need for new and useful agents that are capable of (i) reducing an individual's blood pressure and/or (ii) promoting renal blood flow and/or (iii) inhibiting or decreasing sodium reabsorption.

Type 2 diabetes is a serious and prevalent disease. This form of diabetes may involve insulin resistance and impaired insulin release. Approximately 25.8 million people in the United States alone suffer from diabetes, whereby type 2 diabetes accounts for about 90-95% of all diagnosed diabetes cases. From 1980 to 2008 the number of Americans with diabetes has more than tripled. Diabetes is also increasingly prevalent elsewhere, such as in certain Asian countries whose populations have experienced a dramatic increase in the disease. For example, in India and China, where rapid lifestyle and economic changes have led to a more sedentary lifestyle and poorer diet among the overall population, diabetes is becoming a major health concern. In addition, more than a third of adults at least 20 years old have pre-diabetes, which is a significant risk factor for developing type 2 diabetes. Other diseases and indications, such as glucose intolerance and metabolic syndrome may also be associated with impaired insulin release.

There remains a need for new and improved therapies that enhance insulin secretion and/or promote insulin release into the blood stream in individuals who have a reduced or impaired ability to secrete insulin and/or release insulin into the blood stream.

BRIEF SUMMARY OF THE INVENTION

Hydrogenated pyrido[4,3-b]indoles and pyrido[3,4-b]indoles and azepino[4,5-b]indoles are described. Compositions and kits comprising the compounds are also provided, as are methods of using and making the compounds. The compounds provided herein may find use as new histamine receptor modulators, as well as modulators of other neurotransmitters. Compounds provided may also find use in treating neurodegenerative diseases. Compounds provided may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

Compounds provided herein may also find use in treating a disease or condition that is, or is believed to be responsive to any one or more of: (i) a decrease in blood pressure; (ii) an increase in renal blood flow and (iii) a decrease or inhibition of sodium reabsorption. In one aspect, compounds provided herein are selective adrenergic receptor $\alpha_{2B}$ antagonists that may find use in treating a disease or condition that is, or is believed to be responsive to any one or more of: (i) a decrease in blood pressure; (ii) an increase in renal blood flow and (iii) a decrease or inhibition of sodium reabsorption. Compounds provided may also find use in treating diseases and/or conditions such as hypertension, congestive heart failure or a renal disease or condition.

In another aspect, compounds that promote mitochondrial health and cellular viability are also described. The compounds provided herein are selective adrenergic receptor $\alpha_{2B}$ antagonists that may find use in treating a disease or condition that is associated with dysfunction of mitochondria in a renal or cardiac cell. Compounds provided may also find use in treating diseases and/or conditions selected from the group consisting of acute renal failure, chronic renal failure, coronary ischemia, acute congestive heart failure, chronic congestive heart failure, coronary artery disease, sleep apnea, respiratory distress, hypertension, and peripheral vascular disease.

Compounds provided herein may find use in therapy, e.g., to regulate blood glucose level, increase insulin secretion and treat diseases or conditions that are, or are expected to be, responsive to an increase in insulin production. In one aspect, compounds provided herein are $\alpha_{2A}$ antagonists that may find use in therapy, e.g., to increase insulin secretion and treat diseases or conditions that are, or are expected to be, responsive to an increase in insulin production. Use of the compounds to treat type 2 diabetes is particularly described.

In one aspect, compounds of the formula (IA) are provided:

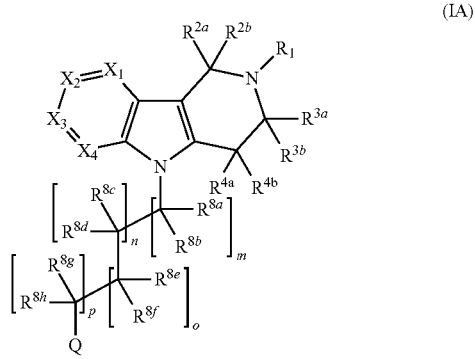

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)— aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —$CR^9$=$CR^{10a}R^{10b}$ or of the structure:

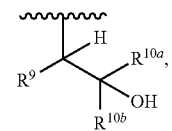

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In another aspect of the invention, compounds of the formula (IB) are provided:

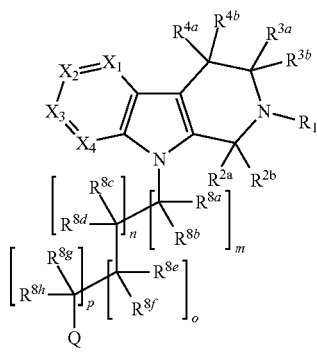

(IB)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkyleneealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkyleneealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a\text{-}h)}$ to form a substituted or unsubstituted methylene moiety or a moiety of the formula —$OCH_2CH_2O$—, or is taken together with a geminal $R^{8(a\text{-}h)}$ and the carbon to which they are attached to form a carbonyl moiety or a cycloalkyl moiety, or is taken together with a vicinal $R^{8(a\text{-}h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a\text{-}h)}$ to form a bond provided when an $R^{8(a\text{-}h)}$ is taken together with a vicinal $R^{8(a\text{-}h)}$ to form a bond, the geminal $R^{8(a\text{-}h)}$ is other than hydroxyl and thiol; and Q is a group of the formula —$CR^9$=$CR^{10a}R^{10b}$ or of the structure:

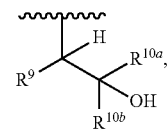

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In another aspect, the invention provides a method of treating a cognitive disorder, psychotic disorder, neurotransmitter-mediated disorder or a neuronal disorder in an individual comprising administering to an individual in need thereof an effective amount of a compound of formulae (IA), (IA1), (IA2), (IA3), (A1), (A2), (A3), (A4), (A5), (IB), (B1), (B2), (B3), (B4), (B5), (B6), (B7), (B8), (B9), (B10), (B11), (J-1), (J-2), (J-3), (J-4), (J-5), (J-1a), (J-2a), (J-3a), (J-4a), (J-5a), (K-1), (K-2), (K-3), (K-4), (K-5), (K-1a), (K-2a), (K-3a), (K-4a) or (K-5a).

In another aspect of the invention, compounds of the formulae (J-1) to (J-5) are provided:

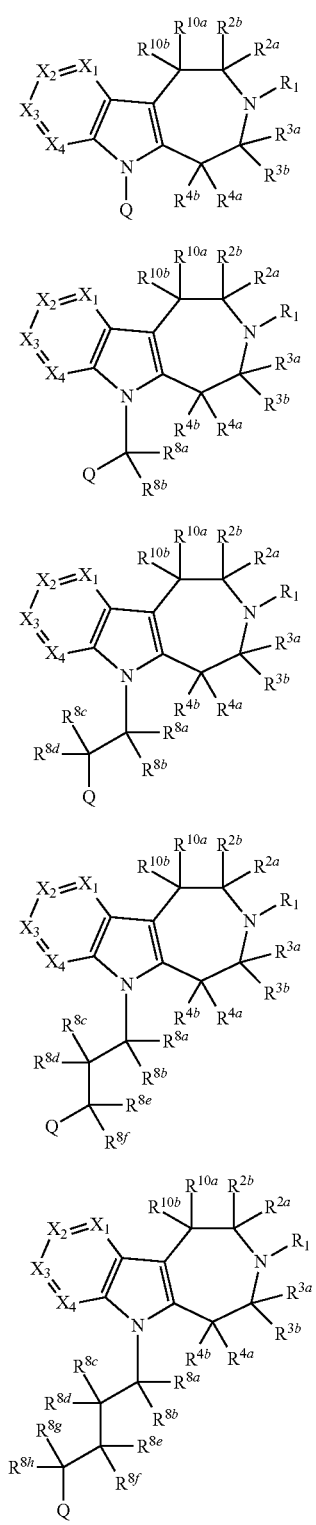

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $X^1$, $X^2$, $X^3$ and $X^4$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —CR$^9$═CR$^{10a}$R$^{10b}$ or of the structure:

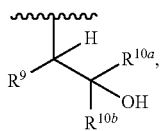

wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety.

In another aspect of the invention, compounds of formulae (K-1) to (K-5) are provided:

(K-1)
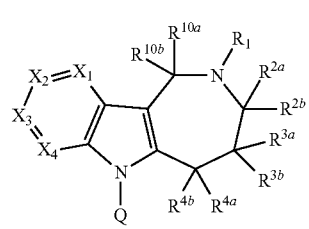

(K-2)
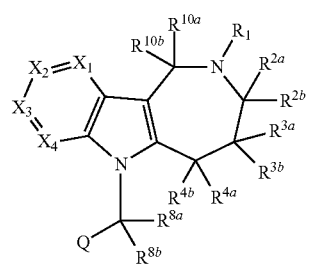

(K-3)
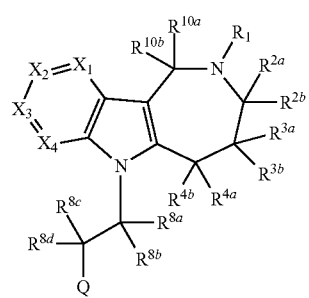

(K-4)
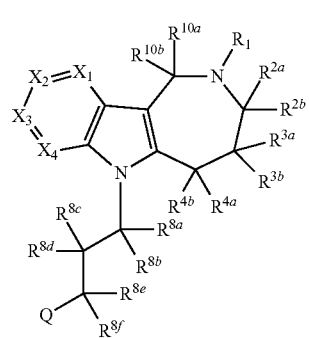

(K-5)
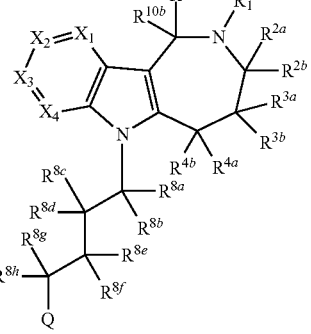

or a salt or solvate thereof, wherein:

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$, R$^{2b}$ R$^{3a}$, R$^{3b}$, R$^{4a}$, R$^{4b}$, R$^{10a}$ and R$^{10b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R$^2$, R$^3$, R$^4$ or R$^{10}$ to form a carbonyl moiety or a cycloalkyl moiety;

each X$^1$, X$^2$, X$^3$ and X$^4$ is independently N, CH or CR$^6$;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$, R$^{8f}$, R$^{8g}$ and R$^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal R$^{8(a-h)}$ to form a substituted or unsubstituted methylene moiety or a moiety of the formula —OCH$_2$CH$_2$O—, or is taken together with a geminal R$^{8(a-h)}$ and the carbon to which they are attached to form a carbonyl moiety or a cycloalkyl moiety, or is taken together with a vicinal R$^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal R$^{8(a-h)}$ to form a bond provided when an R$^{8(a-h)}$ is taken together with a vicinal R$^{8(a-h)}$ to form a bond, the geminal R$^{8(a-h)}$ is other than hydroxyl and thiol; and Q is a group of the formula —CR$^9$=CR$^{10a}$R$^{10b}$ or of the structure:

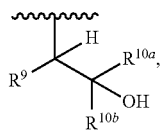

wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety.

In yet another aspect, compounds of formula (IA), (IB), (IA1-IA3), (A1) to (A5), (B1) to (B10), (J-1) to (J-5), (J-1a) to (J-5a), (K-1) to (K-5) and (K-1a) to (K-5a) are provided herein, wherein the Q group is of the structure:

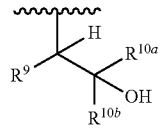

wherein R$^9$, R$^{10a}$ and R$^{10b}$ are as defined above.

In one aspect, a method is provided of lowering blood pressure in an individual in need thereof comprising administering to the individual a compound described herein.

In one variation, the individual has high blood pressure. In another variation, the method reduces the systolic blood pressure of the individual. In another variation, the method reduces the diastolic blood pressure. In another method, the method reduces mean arterial blood pressure. In another variation, the method does not substantially increase heart rate. In another variation, the method provides any one or more of the following beneficial effects on the individual: (1) reduction in arterial blood pressure; (2) reduction in pulse pressure; (3) tachycardia-preserved baroreceptor activity; and (4) bradycardia-reduced cardiac work load and added reduction on blood pressure reduction by further reducing cardiac output. In another variation, the method performs one or more of (i)-(v): (i) reduces elevated blood pressure, (ii) reduces tachycardia, (iii) reduces edema, (iv) reduces elevated blood urea nitrogen to creatinine (BUN/Cr) ratio, and (v) improves creatinine levels. In another variation, the individual has one or more risk factors for developing high blood pressure.

In another aspect, a method is provided of (i) increasing renal blood flow, and/or (ii) decreasing or inhibiting sodium reabsorption in an individual in need thereof comprising administering to the individual a compound described herein.

In one variation, the method results in increase in renal blood flow. In another variation, the method results in decrease or inhibition in sodium resorption. In another variation, the method results in increase in urine sodium content and/or increase in urine volume. In another variation, the individual has or is in risk of developing chronic congestive heart failure, acute decompensated congestive heart failure or renal failure.

In another aspect, a method is provided of treating a disease or condition that is responsive to any one or more of: (i) a decrease in blood pressure; (ii) an increase in renal blood flow; and (iii) a decrease or inhibition of sodium reabsorption, comprising administering to an individual in need thereof a compound described herein.

In one variation, the disease or condition is hypertension. In another variation, the disease or condition is treatment-resistant hypertension. In another variation, the disease or condition hypertensive emergency. In another variation, the disease or condition is a cardiac or renal disease or condition. In another variation, the compound is an adrenergic receptor α$_{2B}$ antagonist. In another variation, the compound is also an adrenergic receptor α$_{1B}$ antagonist. In another variation, the compound is also an adrenergic receptor α$_{1D}$ antagonist.

In another aspect, a method is provided of regulating blood glucose levels in an individual in need thereof comprising administering to the individual an effective amount of a compound described herein.

In one variation, the method reduces blood glucose level in the individual. In another variation, the method reduces blood glucose level in the individual for a period of more than 0.5 hour following administration. In another variation, the method stabilizes of blood glucose level in the individual.

In another aspect, a method is provided of (i) increasing insulin secretion, and/or (ii) promoting insulin release into the blood stream, in an individual in need thereof comprising administering to the individual an effective amount of a compound described herein.

In one variation, the method increases insulin secretion. In another variation, the method promotes insulin release into the blood stream. In another variation, the individual has a disease or condition that involves impaired insulin secretion. In another variation, the individual has one or more risk factors for developing a disease or condition that involves impaired insulin secretion. In another variation, the administration results in decrease of blood pressure in the individual.

In another aspect, a method is provided of treating a disease or condition that is responsive to an increase in insulin secretion, comprising administering to an individual in need thereof an effective amount of a compound described herein.

In another aspect, a method is provided of delaying the onset of a disease or condition that is responsive to an increase in insulin secretion, comprising administering to an individual in need thereof an effective amount of a compound described herein.

In one variation, the disease or condition is type 2 diabetes. In another variation, the individual is not responsive to standard treatment of type 2 diabetes. In another variation, the disease or condition is glucose intolerance. In another variation, the disease or condition is metabolic syndrome. In another variation, the method further comprising administering to the individual in need thereof one or more anti-diabetic agents. In another variation, at least one of the anti-diabetic agents is an insulin sensitizer. In another variation, the compound binds to and is an antagonist of the adrenergic receptor α$_{2A}$ and, wherein the compound either (a) also binds to and is an antagonist of the adrenergic receptor α$_{2B}$ or (b) the compound is not an antagonist of the adrenergic receptor α$_{2B}$ and the compound is administered in conjunction with a second agent that reduces blood pressure in the individual. In another variation, the compound binds to and is an antagonist of the adrenergic receptor $\alpha_{2B}$. In another variation, the compound binds to and is an antagonist of the adrenergic receptor $\alpha_{1B}$. In another variation, the compound is not an antagonist of the adrenergic receptor $\alpha_{2B}$ and the compound is administered in conjunction with a diuretic, an angiotensin-converting enzyme (ACE) inhibitor, an angiotensin-2 receptor antagonist, a beta blocker, a calcium channel blocker, or any combination thereof.

In another aspect, a kit is provided comprising (i) a compound described herein, or a pharmaceutically acceptable salt thereof, and (ii) instructions for use according to the methods described herein.

The invention also includes all salts of compounds referred to herein, such as pharmaceutically acceptable salts. The invention also includes N-oxides of the tertiary amines where one or more tertiary amine moieties are present in the compounds described. The invention also includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Unless olefin geometry is explicitly indicated, substituted olefinic bonds may be present as cis or trans or (Z) or (E) isomeric forms, or as mixtures thereof. In addition, where a specific stereochemical form is depicted, it is understood that other stereochemical forms are also embraced by the invention. For example, where only a Z form of a compound is specifically listed, it is understood that the E form of the compound is also embraced. All forms of the compounds are also embraced by the invention, such as crystalline or non-crystalline forms of the compounds. Compositions comprising a compound of the invention are also intended, such as a composition of substantially pure compound, which in some embodiments is a specific stereochemical form, including a specific geometric isomer. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, schizophrenia, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least two of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least three of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, each of the following receptors is modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least one of the following receptors is modulated: $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$ and $H_3$. In another variation, at least one of the following receptors is modulated: $\alpha_{1D}$, $\alpha_{2A}$, $\alpha_{2B}$, 5-$HT_{2A}$, 5-$HT_{2C}$, 5-$HT_6$, 5-$HT_7$, $D_2$, $H_1$, $H_2$ and $H_3$. In another variation, at least two or three or four or five or six or seven or eight or nine or ten or eleven of the following receptors are modulated: $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$ and $H_3$. In another variation, at least two or three or four or five or six or seven or eight or nine or ten or eleven of the following receptors are modulated: $\alpha_{1D}$, $\alpha_{2A}$, $\alpha_{2B}$, 5-$HT_{2A}$, 5-$HT_{2C}$, 5-$HT_6$, 5-$HT_7$, $D_2$, $H_1$, $H_2$ and $H_3$. In a particular variation, at least dopamine receptor $D_2$ is modulated. In still another variation, at least dopamine receptor $D_{2L}$ is modulated. In another particular variation, at least dopamine receptor $D_2$ and serotonin receptor 5-$HT_{2A}$ are modulated. In another particular variation, at least dopamine receptor $D_{2L}$ and serotonin receptor 5-$HT_{2A}$ are modulated. In a further particular variation, at least adrenergic receptors $\alpha_{1D}$, $\alpha_{2A}$, $\alpha_{2B}$ and serotonin receptor 5-$HT_6$ are modulated. In another particular variation, at least adrenergic receptors $\alpha_{1D}$, $\alpha_{2A}$, $\alpha_{2B}$, serotonin receptor 5-$HT_6$ and one or more of serotonin receptor 5-$HT_7$, 5-$HT_{2A}$, 5-$HT_{2C}$ and histamine receptor $H_1$ and $H_2$ are modulated. In a further particular variation, histamine receptor $H_1$ is modulated. In another variation, compounds of the invention exhibit any receptor modulation activity detailed herein and further stimulate neurite outgrowth and/or neurogenesis and/or enhance neurotrophic effects. In one variation, compounds detailed herein inhibit binding of a ligand to histamine receptor $H_1$ and/or $H_2$ by less than about 80% as determined by a suitable assay known in the art such as the assays described herein. In another variation, binding of a ligand to histamine receptor $H_1$ and/or $H_2$ is inhibited by less than about any of 75%, 70%, 65%, 60%, 55%, or 50% as determined by a suitable assay known in the art such as the assays described herein. In a further variation, compounds detailed herein:
(a) inhibit binding of a ligand to histamine receptor $H_1$ and/or $H_2$ by less than about 80% (which can in different variations be less than about any of 75%, 70%, 65%, 60%, 55%, or 50%) as determined by a suitable assay known in the art such as the assays described herein and (b) inhibit binding of a ligand to dopamine receptor $D_{2L}$ by greater than about any of 80%, 85%, 90%, 95%, 100% or between about 85% and about 95% or between about 90% and about 100%, as determined in a suitable assay known in the art such as the assays described herein. In a further variation, compounds detailed herein: (a) inhibit binding of a ligand to histamine receptor $H_1$ and/or $H_2$ by less than about 80% (which can in different variations be less than about any of 75%, 70%, 65%, 60%, 55%, or 50%) as determined by a suitable assay known in the art such as the assays described herein and (b) inhibit binding of a ligand to a dopamine receptor $D_2$ by greater than about any of 80%, 85%, 90%, 95%, 100% or between about 85% and about 95% or between about 90% and about 100%, as determined in a suitable assay known in the art such as the assays described herein.

DETAILED DESCRIPTION OF THE INVENTION

Definitions

Unless clearly indicated otherwise, the terms "a," "an," and the like, refer to one or more.

It is also understood and clearly conveyed by this disclosure that reference to "the compound" or "a compound" includes and refers to any compounds (e.g., selective adrenergic receptor $\alpha_{2B}$ antagonists) or pharmaceutically acceptable salt or other form thereof as described herein.

Reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human. The invention may find use in both human medicine and in the veterinary context.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

As used herein, "treatment" or "treating" is an approach for obtaining a beneficial or desired result, including clinical results.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient, or compound which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein includes an inert or inactive substance that may be used in the production of a drug or pharmaceutical, such as a tablet containing a compound detailed herein, or a pharmaceutically acceptable salt thereof, as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

An inverse agonist is a compound that binds to a receptor and inhibits the activity of the receptor in the absence of an agonist. An inverse agonist requires that the receptor have some constitutive basal activity in the absence of an agonist. While an agonist increases activity of the receptor over basal level an inverse agonist reduces receptor activity below basal level.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O-" and alkynyloxy refers to the group "alkynyl-O-". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —C(O)NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring.

"Aminoacyl" refers to the group —NR$_a$C(O)R$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, R$_a$ is H or alkyl.

"Aminosulfonyl" refers to the groups —NRSO$_2$-alkyl, —NRSO$_2$ substituted alkyl, —NRSO$_2$-alkenyl, —NRSO$_2$-substituted alkenyl, —NRSO$_2$-alkynyl, —NRSO$_2$-substituted alkynyl, —NRSO$_2$-cycloalkyl, —NRSO$_2$-substituted cycloalkyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-aralkyl, —SO$_2$-substituted aralkyl, —SO$_2$-heteroaryl, —SO$_2$-substituted heteroaryl, —SO$_2$-heterocyclic, and —SO$_2$-substituted heterocyclic.

"Aminocarbonylalkoxy" refers to the group —NR$_a$C(O)OR$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —C(O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.

"Cyano" refers to the group —CN.

"Oxo" refers to the moiety =O.

"Nitro" refers to the group —NO$_2$.

"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O— substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

Receptor Binding Profile

In some embodiments, compounds that bind to and are antagonists of the adrenergic receptor $\alpha_{2B}$, but which are not antagonists of the adrenergic receptor $\alpha_{2A}$, and pharmaceutically acceptable salts thereof, are provided. The compounds may find use in therapy for decreasing blood pressure in an individual and in treating diseases or conditions which are responsive to (i) a decrease in blood pressure and/or (ii) an increase in renal blood flow and/or (iii) a decrease or inhibition of sodium reabsorption or sodium retention. Thus, an individual who has a disease or condition that is responsive to (i) a decrease in blood pressure and/or (ii) an increase in renal blood flow and/or (iii) a decrease or inhibition of sodium reabsorption or sodium retention will experience one or more beneficial or desirable results upon administration of a compound provided herein, or pharmaceutically acceptable salt thereof. In one aspect, the beneficial or desirable result is a reduction in the individual's mean arterial blood pressure for a period of time following administration of the compound or pharmaceutically acceptable salt thereof. In another aspect, the beneficial or desirable result is a reduction in the individual's systolic blood pressure for a period of time following administration of the compound or pharmaceutically acceptable salt thereof. In a further aspect, the beneficial or desirable result is an increase in renal blood flow (e.g., by altering the vascular tone of renal efferent and afferent arterioles) for a period of time following administration of the compound or pharmaceutically acceptable salt thereof. In another aspect, the beneficial or desirable result is a decrease or inhibition in sodium reabsorption (e.g., thereby exerting a natriuretic and diuretic effect) for a period of time following administration of the compound or pharmaceutically acceptable salt thereof. In another aspect, the beneficial or desirable result is an increase in urine sodium and/or urine volume for a period of time following administration of the compound or pharmaceutically acceptable salt thereof. In one variation, the compounds may find use in therapy in treating diseases or conditions which are responsive to (i) a decrease in blood pressure and (ii) an increase in renal blood flow. In one variation, the compounds my find use in therapy in treating diseases or conditions which are responsive to (i) a decrease in blood pressure and (ii) a decrease or inhibition of sodium reabsorption. In one variation, the compounds may find use in treating diseases or conditions which are responsive to (i) an increase in renal blood flow and (ii) a decrease or inhibition of sodium reabsorption. In one variation, the compounds may find use in therapy in treating diseases or conditions which are responsive to (i) a decrease in blood pressure and (ii) an increase in renal blood flow and (iii) a decrease or inhibition of sodium reabsorption.

Compounds that bind to and are antagonists of the adrenergic receptor $\alpha_{2B}$ should reduce an individual's blood pressure. However, compounds that antagonize the adrenergic receptor $\alpha_{2A}$ in some instances may actually increase an individual's blood pressure. Thus, compounds that antagonize the adrenergic receptor $\alpha_{2B}$ but do not antagonize the adrenergic receptor $\alpha_{2A}$ (compounds referred to herein as "selective adrenergic receptor $\alpha_{2B}$ antagonists") are desirable agents in therapy. Selective adrenergic receptor $\alpha_{2B}$ antagonists find further use in therapy of cardiovascular and renal indications. The selective adrenergic receptor $\alpha_{2B}$ antagonists provided herein (i) bind to and are antagonists of the adrenergic receptor $\alpha_{2B}$, and (ii) are not antagonists of the adrenergic receptor $\alpha_{2A}$.

The selective adrenergic receptor $\alpha_{2B}$ antagonists may in some variations also bind to and be agonists of the adrenergic receptor $\alpha_{2A}$. The selective adrenergic receptor $\alpha_{2B}$ antagonists may also be used in conjunction with other agents that are agonists of the adrenergic receptor $\alpha_{2A}$.

The selective adrenergic receptor $\alpha_{2B}$ antagonists may in some variations also bind to and be antagonists of the adrenergic receptor $\alpha_{1B}$. The selective adrenergic receptor $\alpha_{2B}$ antagonists may also be used in conjunction with other agents that are antagonists of the adrenergic receptor $\alpha_{1B}$.

The selective adrenergic receptor $\alpha_{2B}$ antagonists may in some variations also bind to and be antagonists of the adrenergic receptor $\alpha_{1D}$. The selective adrenergic receptor $\alpha_{2B}$ antagonists may also be used in conjunction with other agents that are antagonists of the adrenergic receptor $\alpha_{1D}$.

The selective adrenergic receptor $\alpha_{2B}$ antagonists may in some variations both (i) bind to and be agonists of the adrenergic receptor $\alpha_{2A}$ and (ii) bind to and be antagonists of the adrenergic receptor $\alpha_{1B}$ and/or $\alpha_{1D}$.

In one variation, a selective adrenergic receptor $\alpha_{2B}$ antagonist exhibits (i) equal to or greater than about 60% inhibition of $\alpha_{2B}$ ligand binding at 0.03 µM and antagonist activity to adrenergic receptor $\alpha_{2B}$ and (ii) equal to or less than about 30% inhibition of $\alpha_{2A}$ ligand binding at 0.1 µM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 µM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 µM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 µM and antagonist activity to adrenergic receptor $\alpha_{2B}$ and (ii) equal to or less than about 30% inhibition of $\alpha_{2A}$ ligand binding at 0.1 µM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 µM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 µM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, and (ii) equal to or less than about 25% inhibition of $\alpha_{2A}$ ligand binding at 0.1 µM and absence of antagonist activity to adrenergic receptor $\alpha_{2A}$.

In one variation, a selective adrenergic receptor $\alpha_{2B}$ antagonist exhibits (i) equal to or greater than about 60% inhibition of $\alpha_{2B}$ ligand binding at 0.03 µM and antagonist activity to adrenergic receptor $\alpha_{2B}$ and (ii) equal to or less than about 30% inhibition of $\alpha_{2A}$ ligand binding at 0.03 µM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 µM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 µM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 µM and antagonist activity to adrenergic receptor $\alpha_{2B}$ and (ii) equal to or less than about 30% inhibition of $\alpha_{2A}$ ligand binding at 0.03 µM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 µM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 µM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, and (ii) equal to or less than about 25% inhibition of $\alpha_{2A}$ ligand binding at 0.03 µM and absence of antagonist activity to adrenergic receptor $\alpha_{2A}$.

In another variation, a selective adrenergic receptor $\alpha_{2B}$ antagonist has a Ki ratio of $\alpha_{2A}$ to $\alpha_{2B}$ that is greater than about any one of 5 or 15 or 50. Ki is the binding affinity from the Cheng-Prusoff equation: $Ki=IC_{50}/(1+[S]/Kd)$, wherein [S] is the concentration of the radioligand and Kd is dissociation constant (affinity) of the radioligand for the protein (Cheng, Y., Prusoff, W. H., *Biochem. Pharmacol.* 22:3099-3108, 1973). It is understood that the Ki ratio of $\alpha_{2A}$ to $\alpha_{2B}$ may be combined with any binding and/or other activity profile details described herein for selective adrenergic receptor $\alpha_{2B}$ antagonists the same as if each were specifically and individually listed. For example, in one variation, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, and (ii) equal to or less than about 25% inhibition of $\alpha_{2A}$ ligand binding at 0.1 µM and absence of antagonist activity to adrenergic receptor $\alpha_{2A}$; and a Ki ratio of $\alpha_{2A}$ to $\alpha_{2B}$ that is greater than about any one of 5 or 15 or 50.

The selective adrenergic receptor $\alpha_{2B}$ antagonists may in some variations also bind to and be antagonists of the adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ ligand binding at 0.03 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.03 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ ligand binding at 0.1 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ ligand binding at 0.1 µM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.1 µM and antagonist activity to adrenergic receptor $\alpha_{1B}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, (ii) equal to or less than about 25% inhibition of $\alpha_{2A}$ ligand binding at 0.1 µM and absence of antagonist activity to adrenergic receptor $\alpha_{2A}$, and (iii) equal to or greater than about 65% inhibition of $\alpha_{1B}$ ligand binding at 0.03 µM and antagonist activity to adrenergic receptor $\alpha_{1B}$. The selective adrenergic receptor $\alpha_{2B}$ antagonists may also be used in conjunction with other agents that antagonize the adrenergic receptor $\alpha_{1B}$. Administration in conjunction with another compound includes administration in the same or different composition, either sequentially, simultaneously, or continuously.

The selective adrenergic receptor $\alpha_{2B}$ antagonists may in some variations also bind to and be antagonists of the adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1D}$ ligand binding at 0.03 µM and antagonist activity to adrenergic receptor $\alpha_{1D}$. In another variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, (iii) equal to or greater than about 60% inhibition of $\alpha_{1B}$ ligand binding at 0.03 µM and antagonist activity to adrenergic receptor $\alpha_{1B}$ and (iv) equal to or greater than about 60% inhibition of $\alpha_{1D}$ ligand binding at 0.03 µM and antagonist activity to adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1D}$ and/or $\alpha_{1B}$ ligand binding at 0.03 µM and antagonist activity to adrenergic receptor $\alpha_{1D}$ and/or $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 µM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 μM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{B1}$ and/or $\alpha_{1D}$ ligand binding at 0.1 μM and antagonist activity to adrenergic receptor $\alpha_{1B}$ and/or $\alpha_{1D}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ and/or $\alpha_{1D}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, (ii) equal to or less than about 25% inhibition of $\alpha_{2A}$ ligand binding at 0.1 μM and absence of antagonist activity to adrenergic receptor $\alpha_{2A}$, and (iii) equal to or greater than about 65% inhibition of $\alpha_{1D}$ ligand binding at 0.03 μM and antagonist activity to adrenergic receptor $\alpha_{1D}$. The selective adrenergic receptor $\alpha_{2B}$ antagonists may also be used in conjunction with other agents that antagonize the adrenergic receptor $\alpha_{1D}$. Administration in conjunction with another compound includes administration in the same or different composition, either sequentially, simultaneously, or continuously.

In some instances, compounds provided herein bind to and are antagonists of adrenergic receptor $\alpha_{2B}$ and may also be antagonists for the adrenergic receptor $\alpha_{2A}$. In such instances, it is preferable that the compound is more potent at inhibiting the adrenergic receptor $\alpha_{2B}$ compared to the adrenergic receptor $\alpha_{2A}$. In one variation, the compound inhibit both the adrenergic receptor $\alpha_{2B}$ and the adrenergic receptor $\alpha_{2A}$, and wherein the compound has limited of no brain bioavailability and so cannot easily activate adrenergic $\alpha_{2A}$ receptors in the brain. In one variation, the compound inhibit both the adrenergic receptor $\alpha_{2B}$ and the adrenergic receptor $\alpha_{2A}$, and wherein the compound has brain bioavailability. In some other instances, compounds provided herein bind to and are antagonists of the adrenergic receptor $\alpha_{2B}$ and may be inverse agonists for the adrenergic receptor $\alpha_{2A}$. In some embodiments, the compound (1) binds to and is an antagonist of adrenergic receptor $\alpha_{2B}$, and (2) binds to and is an antagonist and/or inverse agonist of the adrenergic receptor $\alpha_{2A}$. In some embodiments, the compound (1) binds to and is an antagonist of adrenergic receptor $\alpha_{2B}$, (2) binds to and is an antagonist and/or inverse agonist of the adrenergic receptor $\alpha_{2A}$, and (3) binds to and is antagonist of the adrenergic receptor $\alpha_{1B}$ and/or the adrenergic receptor $\alpha_{1D}$. It is understood and clearly conveyed herein that an adrenergic receptor $\alpha_{2B}$ antagonist can exhibit any of the adrenergic receptor $\alpha_{2B}$ binding profiles (in terms of % inhibition at a given concentration and/or in terms of Ki) described herein in combination with any of the adrenergic receptor $\alpha_{1B}$ and/or $\alpha_{1D}$ binding profiles, as if each and every combination were listed separately.

The binding properties to adrenergic receptors of compounds disclosed herein may be assessed by methods known in the art, such as competitive binding assays. In one variation, compounds are assessed by the binding assays detailed herein. In one variation, inhibition of binding of a ligand to a receptor is measured by the assays described herein. In another variation, inhibition of binding of a ligand is measured in an assay known in the art.

In some embodiments, compounds provided herein bind to and are antagonists of the adrenergic receptor $\alpha_{2A}$. In one variation, compounds provided herein bind to and are antagonists of the adrenergic receptor $\alpha_{2A}$ and either (a) also bind to and are antagonists of the adrenergic receptor $\alpha_{2B}$ or (b) are not antagonists of the adrenergic receptor $\alpha_{2B}$ but are administered in the methods detailed herein in conjunction with a second agent that reduces, or is expected to reduce, blood pressure in an individual. By exhibiting the dual properties of binding to and being an antagonist of both the adrenergic receptor $\alpha_{2A}$ and the adrenergic receptor $\alpha_{2B}$, compounds provided herein may exert the beneficial effect of increasing insulin secretion and/or promoting insulin release in an individual while reducing or eliminating the side effect of an increase in blood pressure that may be associated with antagonizing the adrenergic receptor $\alpha_{2A}$. Alternatively, compounds provided herein that bind to and are antagonists of the adrenergic receptor $\alpha_{2A}$, but which do not bind to and are not antagonists of the adrenergic receptor $\alpha_{2B}$, may be used in therapy in conjunction with a second agent that reduces, or is expected to reduce, blood pressure in an individual, thereby allowing the adrenergic receptor $\alpha_{2A}$ antagonist to exert its therapeutic effects while reducing or eliminating the side effect of an increase in blood pressure that may be associated with antagonizing the adrenergic receptor $\alpha_{2A}$. Thus, it is understood that a second compound that reduces, or is expected to reduce, blood pressure in an individual includes a second compound that reduces or prevents an increase in an individual's blood pressure associated with antagonizing the adrenergic receptor $\alpha_{2A}$. It is further understood that any of the compounds provided herein may be administered in conjunction with a second agent that reduces, or is expected to reduce, blood pressure in an individual. For example, such a combination therapy may be utilized in an individual who has high blood pressure or has a propensity toward high blood pressure that is not associated with being administered a compound that antagonizes the adrenergic receptor $\alpha_{2A}$. Compounds that exhibit the dual properties of binding to and being an antagonist of both the adrenergic receptor $\alpha_{2A}$ and the adrenergic receptor $\alpha_{2B}$ may also be administered in conjunction with a second agent that reduces, or is expected to reduce, blood pressure in an individual.

Compounds that antagonize the adrenergic receptor $\alpha_{2A}$ and the adrenergic receptor $\alpha_{2B}$ may lower blood glucose and reduce blood pressure and be of therapeutic utility in individuals with high glucose and high blood pressure, for example individuals who have metabolic syndrome. Compounds that antagonize the adrenergic receptor $\alpha_{2A}$ and the adrenergic receptor $\alpha_{2B}$ may also block the adrenergic receptor $\alpha_{1B}$ and have utility in individuals with high blood glucose and high blood pressure.

The compounds provided herein may in some embodiments also bind to and be antagonists of the adrenergic receptor $\alpha_{1B}$, which activity may also help reduce or eliminate an increase in blood pressure in an individual in response to a compound that is an adrenergic receptor $\alpha_{2A}$ antagonist.

Thus, in one variation, compounds that bind to and are antagonists of the adrenergic receptor $\alpha_{2A}$ are provided, wherein the compounds also bind to and are antagonists of the adrenergic receptors $\alpha_{2B}$ and a m. In another variation, compounds that bind to and are antagonists of the adrenergic receptor $\alpha_{2A}$ are provided, wherein the compounds also bind to and are antagonists of the adrenergic receptor $\alpha_{1B}$ but which are not antagonists of the adrenergic receptor $\alpha_{2B}$. Such compounds, when are administered in the methods detailed herein, may be administered in conjunction with a second agent that reduces, or is expected to reduce, blood pressure in an individual.

The compounds provided herein may in some embodiments also bind to and be antagonists of the adrenergic receptor $\alpha_{1D}$, which activity may also help reduce or eliminate an increase in blood pressure in an individual in response to a compound that is an adrenergic receptor $\alpha_{2A}$ antagonist. Thus, in one variation, compounds that bind to and are antagonists of the adrenergic receptor $\alpha_{2A}$ are provided, wherein the compounds also bind to and are antagonists of the adrenergic receptors $\alpha_{2B}$, $\alpha_{1B}$ and $\alpha_{1D}$. In another variation, compounds that bind to and are antagonists of the adrenergic receptor $\alpha_{2A}$ are provided, wherein the compounds also bind to and are antagonists of the adrenergic receptor $\alpha_{1B}$ and $\alpha_{1D}$ but which are not antagonists of the adrenergic receptor $\alpha_{2B}$. In another variation, compounds that bind to and are antagonists of the adrenergic receptor $\alpha_{2A}$ are provided, wherein the compounds also bind to and are antagonists of the adrenergic receptor $\alpha_{2B}$ and $\alpha_{1D}$ but which are not antagonists of the adrenergic receptor $\alpha_{1B}$. In another variation, compounds that bind to and are antagonists of the adrenergic receptor $\alpha_{2A}$ are provided, wherein the compounds also bind to and are antagonists of the adrenergic receptors $\alpha_{1D}$, but which are not antagonists of the adrenergic receptor $\alpha_{2B}$ or $\alpha_{1B}$. Such compounds, when administered in the methods detailed herein, may be administered in conjunction with a second agent that reduces, or is expected to reduce, blood pressure in an individual.

The second agent that reduces, or is expected to reduce, blood pressure in an individual may be a diuretic, an angiotensin-converting enzyme (ACE) inhibitor, an angiotensin-2 receptor antagonist, a beta blocker, a calcium channel blocker, or any combination thereof. In one variation, the second agent that reduces, or is expected to reduce, blood pressure in an individual is a compound that binds to and is an antagonist of the adrenergic receptor $\alpha_{2B}$ but which is not an antagonist of the adrenergic receptor $\alpha_{2A}$. In one variation, the second agent is a single compound. However, it is understood that the second agent in one embodiment may be two or more compounds, such as a second agent that comprises a first compound that is a diuretic and a second compound that is an ACE-inhibitor.

In one variation, a compound provided herein exhibits equal to or greater than about 50% inhibition of $\alpha_{2A}$ ligand binding at 0.1 µM and antagonist activity to adrenergic receptor $\alpha_{2A}$. In one variation, a compound provided herein exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2A}$ ligand binding at 0.1 µM and antagonist activity to adrenergic receptor $\alpha_{2A}$. In one variation, a compound provided herein exhibits equal to or greater than about 50% inhibition of $\alpha_{2A}$ ligand binding at 0.03 µM and antagonist activity to adrenergic receptor $\alpha_{2A}$. In one variation, a compound provided herein exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2A}$ ligand binding at 0.03 µM and antagonist activity to adrenergic receptor $\alpha_{2A}$.

In another variation, a compound as provided herein (i) binds to and is an antagonist of adrenergic receptor $\alpha_{2A}$ and (ii) exhibits greater than or equal to about 50% inhibition of $\alpha_{2B}$ ligand binding at 0.1 µM and antagonist activity to adrenergic receptor $\alpha_{2B}$. In one such variation, a compound as provided herein exhibits (i) greater than or equal to about 50% inhibition of $\alpha_{2A}$ ligand binding at 0.1 µM and antagonist activity to adrenergic receptor $\alpha_{2A}$ and (ii) greater than or equal to about 50% inhibition of $\alpha_{2B}$ ligand binding at 0.1 µM and antagonist activity to adrenergic receptor $\alpha_{2B}$. When the compound exhibits greater than or equal to about 50% inhibition of $\alpha_{2B}$ ligand binding at 0.1 µM and antagonist activity to adrenergic receptor $\alpha_{2B}$, in some embodiments, it exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2B}$ ligand binding at 0.1 µM and antagonist activity to adrenergic receptor $\alpha_{2B}$ In another variation, a compound as provided herein exhibits (i) greater than or equal to about 50% inhibition of $\alpha_{2A}$ ligand binding at 0.03 µM and antagonist activity to adrenergic receptor $\alpha_{2A}$ and (ii) greater than or equal to about 50% inhibition of $\alpha_{2B}$ ligand binding at 0.03 µM and antagonist activity to adrenergic receptor $\alpha_{2B}$. In another variation, a compound as provided herein exhibits (i) greater than or equal to about 50% inhibition of $\alpha_{2A}$ ligand binding at 0.03 µM and antagonist activity to adrenergic receptor $\alpha_{2A}$ and (ii) greater than or equal to about 50% inhibition of $\alpha_{2B}$ ligand binding at 0.1 µM and antagonist activity to adrenergic receptor $\alpha_{2B}$. In another variation, a compound as provided herein exhibits (i) greater than or equal to about 50% inhibition of $\alpha_{2A}$ ligand binding at 0.1 µM and antagonist activity to adrenergic receptor $\alpha_{2A}$ and (ii) greater than or equal to about 50% inhibition of $\alpha_{2B}$ ligand binding at 0.03 µM and antagonist activity to adrenergic receptor $\alpha_{2B}$. When the compound exhibits greater than or equal to about 50% inhibition of $\alpha_{2B}$ ligand binding at 0.03 µM and antagonist activity to adrenergic receptor $\alpha_{2B}$, in some embodiments, it exhibits greater than or equal to about any one of 50%, 55%, 60%, 65%, 70%, 75%, 80%, 85%, 90% or 95% or between about 50% and about 90% or between about 60% and about 90% or between about 70% and about 90% or between about 80% and about 100% inhibition of $\alpha_{2B}$ ligand binding at 0.03 µM and antagonist activity to adrenergic receptor $\alpha_{2B}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, as if each and every combination were listed separately.

The adrenergic receptor $\alpha_{2A}$ antagonists may also be used in conjunction with other agents that antagonize the adrenergic receptor $\alpha_{2B}$. Administration in conjunction with another compound includes administration in the same or different composition, either sequentially, simultaneously, or continuously.

In one variation, compounds provided herein that bind to and are antagonists of the adrenergic receptor $\alpha_{2A}$ will also bind to and antagonize the adrenergic receptor $\alpha_{1B}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, will also bind to and antagonize the adrenergic receptor $\alpha_{1B}$. In some embodiments, compounds provided herein may exhibit greater than or equal to about 50% inhibition of $\alpha_{1B}$ ligand binding at 0.1 µM and antagonist activity to adrenergic receptor $\alpha_{1B}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.1 µM and antagonist activity to adrenergic receptor $\alpha_{1B}$. In some embodiments, compounds provided herein may exhibit greater than or equal to about 50% inhibition of $\alpha_{1B}$ ligand binding at 0.03 µM and antagonist activity to adrenergic receptor $\alpha_{1B}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.03 µM and antagonist activity to adrenergic receptor $\alpha_{1B}$. For example, in one variation, a compound provided herein exhibits equal to or greater than about 50% inhibition of $\alpha_{2A}$ ligand binding at 0.1 µM and antagonist activity to adrenergic receptor $\alpha_{2A}$ and greater than or equal to about 50% inhibition of $\alpha_{1B}$ ligand binding at 0.1 µM and antagonist activity to adrenergic receptor ale. In another variation, a compound provided herein exhibits equal to or greater than about 50% inhibition of $\alpha_{2A}$ ligand binding at 0.1 µM and antagonist activity to adrenergic receptor $\alpha_{2A}$, greater than or equal to about 50% inhibition of $\alpha_{2B}$ ligand binding at 0.1 µM and antagonist activity to adrenergic receptor $\alpha_{2B}$ and greater than or equal to about 50% inhibition of al ligand binding at 0.1 µM and antagonist activity to adrenergic receptor $\alpha_{1B}$. In one variation, a compound provided herein exhibits equal to or greater than about 50% inhibition of $\alpha_{2A}$ ligand binding at 0.1 µM and antagonist activity to adrenergic receptor $\alpha_{2A}$, greater than or equal to about 50% inhibition of $\alpha_{2B}$ ligand binding at 0.1 µM and antagonist activity to adrenergic receptor $\alpha_{2B}$ and greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1B}$ ligand binding at 0.1 µM and antagonist activity to adrenergic receptor $\alpha_{1B}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, and/or any of the adrenergic receptor $\alpha_{1B}$ binding profiles described herein as if each and every combination were listed separately.

The adrenergic receptor $\alpha_{2A}$ antagonists may also be used in conjunction with other agents that antagonize the adrenergic receptor am. Administration in conjunction with another compound includes administration in the same or different composition, either sequentially, simultaneously, or continuously.

In one variation, compounds provided herein that bind to and are antagonists of the adrenergic receptor $\alpha_{2A}$ will also bind to and antagonize the adrenergic receptor $\alpha_{1D}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, will also bind to and antagonize the adrenergic receptor $\alpha_{1D}$. In another variation, compounds provided herein that bind to and are antagonists of the adrenergic receptor $\alpha_{2A}$ and either (a) also bind to and are antagonists of the adrenergic receptor $\alpha_{2B}$ or (b) are administered in the methods detailed herein in conjunction with a second agent that reduces, or is expected to reduce, blood pressure in an individual, and bind to and are antagonists of the adrenergic receptor $\alpha_{1B}$ will also bind to and antagonize the adrenergic receptor $\alpha_{1D}$. In some embodiments, compounds provided herein may exhibit greater than or equal to about 50% inhibition of $\alpha_{1D}$ ligand binding at 0.1 µM and antagonist activity to adrenergic receptor $\alpha_{1D}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.1 µM and antagonist activity to adrenergic receptor $\alpha_{1D}$. In some embodiments, compounds provided herein may exhibit greater than or equal to about 50% inhibition of $\alpha_{1D}$ ligand binding at 0.03 µM and antagonist activity to adrenergic receptor $\alpha_{1D}$. In some embodiments, compounds provided herein may exhibit greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.03 µM and antagonist activity to adrenergic receptor $\alpha_{1D}$. For example, in one variation, a compound provided herein exhibits equal to or greater than about 50% inhibition of $\alpha_{2A}$ ligand binding at 0.1 µM and antagonist activity to adrenergic receptor $\alpha_{2A}$ and greater than or equal to about 50% inhibition of $\alpha_{1D}$ ligand binding at 0.1 µM and antagonist activity to adrenergic receptor $\alpha_{1D}$. In another variation, a compound provided herein exhibits equal to or greater than about 50% inhibition of $\alpha_{2A}$ ligand binding at 0.1 µM and antagonist activity to adrenergic receptor $\alpha_{2A}$, greater than or equal to about 50% inhibition of $\alpha_{2B}$ ligand binding at 0.1 µM and antagonist activity to adrenergic receptor $\alpha_{2B}$ and greater than or equal to about 50% inhibition of $\alpha_{1D}$ ligand binding at 0.1 µM and antagonist activity to adrenergic receptor $\alpha_{1D}$. In another variation, a compound provided herein exhibits equal to or greater than about 50% inhibition of $\alpha_{2A}$ ligand binding at 0.1 µM and antagonist activity to adrenergic receptor $\alpha_{2A}$, greater than or equal to about 50% inhibition of $\alpha_{2B}$ ligand binding at 0.1 µM and antagonist activity to adrenergic receptor $\alpha_{2B}$, greater than or equal to about 50% inhibition of $\alpha_{1B}$ ligand binding at 0.1 µM and antagonist activity to adrenergic receptor $\alpha_{1B}$, and greater than or equal to about 50% inhibition of $\alpha_{1D}$ ligand binding at 0.1 µM and antagonist activity to adrenergic receptor $\alpha_{1D}$. In one variation, a compound provided herein exhibits equal to or greater than about 50% inhibition of $\alpha_{2A}$ ligand binding at 0.1 µM and antagonist activity to adrenergic receptor $\alpha_{2A}$, greater than or equal to about 50% inhibition of $\alpha_{2B}$ ligand binding at 0.1 µM and antagonist activity to adrenergic receptor $\alpha_{2B}$, greater than or equal to about 50% inhibition of $\alpha_{1B}$ ligand binding at 0.1 µM and antagonist activity to adrenergic receptor $\alpha_{1B}$ and greater than or equal to about any one of 50%, 55%, 60%, 65%, 70%, 75%, 80%, 85%, 90%, or 95%, or between about 50% and about 90%, between about 60% and about 90%, between about 70% and about 90%, or between about 80% and about 100% inhibition of $\alpha_{1D}$ ligand binding at 0.1 µM and antagonist activity to adrenergic receptor $\alpha_{1D}$. It is understood and clearly conveyed herein that an adrenergic receptor $\alpha_{2A}$ antagonist can exhibit any of the adrenergic receptor $\alpha_{2A}$ binding profiles described herein in combination with any of the adrenergic receptor $\alpha_{2B}$ binding profiles described herein, and/or any of the adrenergic receptor $\alpha_{1B}$ binding profiles described herein and/or any of the adrenergic receptor $\alpha_{1D}$ binding profiles described herein as if each and every combination were listed separately.

The adrenergic receptor $\alpha_{2A}$ antagonists may also be used in conjunction with other agents that antagonize the adrenergic receptor $\alpha_{1D}$. Administration in conjunction with another compound includes administration in the same or different composition, either sequentially, simultaneously, or continuously.

The binding properties to adrenergic receptors of compounds disclosed herein may be assessed by methods known in the art, such as competitive binding assays. In one variation, compounds are assessed by the binding assays detailed herein. In one variation, inhibition of binding of a ligand to a receptor is measured by the assays described herein. In another variation, inhibition of binding of a ligand is measured in an assay known in the art.

Functional Assay Profile

Antagonist activity to the adrenergic receptor $\alpha_{2B}$ receptor may be assessed by methods known in the art, such as standard $\alpha_{2B}$ receptor cell membrane-based or intact cell-based activity assays. For example, the GTPγS binding or Aequorin-based assays may be used. In one variation, the selective adrenergic receptor $\alpha_{2B}$ antagonists exhibit an $IC_{50}$ value equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline corresponding to its $EC_{80}$ concentration as obtained by assay protocols described herein. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 480 nM oxymetazoline. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of guanfacine between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 500 nM guanfacine, which in a particular variation is 504 nM guanfacine.

The absence of antagonist activity to the adrenergic receptor $\alpha_{2A}$ may be assessed by methods known in the art, such as standard $\alpha_{2A}$ receptor intact cell-based activity assays. For example, the Aequorin-based assay may be used. It is understood and clearly conveyed that absence of antagonist activity to the adrenergic receptor $\alpha_{2A}$ intends activity that is sufficiently reduced, but not necessarily eliminated or undetectable, at the adrenergic receptor $\alpha_{2A}$. In one variation, a compound will exhibit an undetectable amount of antagonist activity to the adrenergic receptor $\alpha_{2A}$. In another variation, a compound will lack antagonist activity to the adrenergic receptor $\alpha_{2A}$ if it exhibits an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In one variation, the adrenergic receptor $\alpha_{2A}$ exhibits an $IC_{50}$ value in an $\alpha_{2A}$ antagonist assay that is greater than about 200 nM at a given concentration of agonist (e.g., concentration corresponding to $EC_{80}$ of UK14304). In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 corresponding to its $EC_{80}$ concentration as obtained by assay protocols described herein. In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 between about 0.4 nM and about 40 nM. In one variation, a selective adrenergic receptor $\alpha_{2B}$ antagonists exhibits an $IC_{50}$ value in an $\alpha_{2A}$ antagonist assay greater than about any one of 50 nM, 100 nM or 200 nM at a concentration of about 5 nM UK14304, which in a particular variation is 4.57 nM UK14304. Alternatively, a compound that does not bind the $\alpha_{2A}$ receptor will be neither an agonist nor antagonist of the $\alpha_{2A}$ receptor.

In some variations, regardless of $IC_{50}$ values obtained from $\alpha_{2B}$ and $\alpha_{2A}$ assays, a compound may nonetheless be a selective adrenergic receptor $\alpha_{2B}$ antagonist if it exhibits a Ki ratio of $\alpha_{2A}$ to $\alpha_{2B}$ that is higher than about any one of 5, 10, or 15. For example, where a compound exhibits an $IC_{50}$ value between about 50-100 nM in an $\alpha_{2B}$ antagonist assay at a given concentration of agonist (e.g., concentration corresponding to $EC_{80}$ of oxymetazoline) and an $IC_{50}$ value between about 50 and 100 nM in an $\alpha_{2A}$ antagonist assay at a given concentration of agonist (e.g., concentration corresponding to $EC_{80}$ of UK14304), the compound is considered, in one variation, a selective adrenergic receptor $\alpha_{2B}$ antagonist if it exhibits a Ki ratio of $\alpha_{2A}$ to $\alpha_{2B}$ higher than about any one of 5, 10, or 15.

Antagonist activity to adrenergic receptor $\alpha_{1B}$ may be assessed by methods known in the art, such as standard $\alpha_{1B}$ receptor intact cell-based activity assays, including the Aequorin-based assay. In one variation, a selective adrenergic receptor $\alpha_{2B}$ antagonist will also antagonize the adrenergic receptor $\alpha_{1B}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1B}$ antagonist assay. In one variation, a selective adrenergic receptor $\alpha_{2B}$ antagonist will also antagonize the adrenergic receptor $\alpha_{1B}$ and exhibit an $IC_{50}$ value equal or less about 10 nM at a given concentration of agonist (e.g., concentration corresponding to $EC_{80}$ of cirazoline) in an adrenergic receptor $\alpha_{1B}$ antagonist assay. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of about 25 nM cirazoline, which in a particular variation is 23.56 nM cirazoline.

Antagonist activity to adrenergic receptor $\alpha_{1D}$ may be assessed by methods known in the art, such as standard $\alpha_{1D}$ receptor intact cell-based activity assays, including the Aequorin-based assay. In one variation, a selective adrenergic receptor $\alpha_{2B}$ antagonist will also antagonize the adrenergic receptor $\alpha_{1D}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1D}$ antagonist assay. In one variation, a selective adrenergic receptor $\alpha_{2B}$ antagonist will also antagonize the adrenergic receptor $\alpha_{1D}$ and exhibit an $IC_{50}$ value equal or less about 10 nM at a given concentration of agonist (e.g., concentration corresponding to $EC_{80}$ of cirazoline) in an adrenergic receptor $\alpha_{1D}$ antagonist assay. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of about 25 nM cirazoline, which in a particular variation is 23.56 nM cirazoline.

In one variation, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In some variations, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{1B}$ ligand binding at 0.03 μM and an $IC_{50}$ value in an ale antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{2A}$ ligand binding at 0.03 μM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 μM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), (iii) equal to or greater than about 60% inhibition of $\alpha_{1B}$ ligand binding at 0.03 μM and an $IC_{50}$ value in an $\alpha_{1B}$ antagonist assay equal or less than about any one of 100 nM or 30 nM or 10 nM at a given concentration of agonist (e.g., concentration corresponding to $EC_{80}$ of cirazoline); and (iv) equal to or greater than about 60% inhibition of $\alpha_{1D}$ ligand binding at 0.03 μM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline).

In another variation, the selective adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) binding to and agonist activity to adrenergic receptor $\alpha_{2A}$.

In another variation, the adrenergic receptor $\alpha_{2B}$ antagonists exhibit (i) equal to or greater than about 60% inhibition of $\alpha_{2B}$ ligand binding at 0.03 μM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) greater than or equal to about 50% inhibition of $\alpha_{2A}$ ligand binding at 0.1 μM and $IC_{50}$ value in an adrenergic receptor $\alpha_{2A}$ antagonist assay equal to or less than about any one of 100 nM, 30 nM or 10 nM at a concentration of UK14304 (for Aequorin assay) corresponding to its $EC_{80}$ concentration obtained by assay protocols described herein.

It is understood and clearly conveyed herein that compounds provided herein, including selective adrenergic receptor $\alpha_{2B}$ antagonists provided herein can exhibit any of the binding profiles and any of the antagonist or agonist activity profiles detailed herein, the same as if each and every combination were individually listed. For example, in one variation, the selective adrenergic receptor $\alpha_{2B}$ antagonists exhibit (i) greater than about 65% inhibition of $\alpha_{2B}$ ligand binding at 0.03 μM and an $IC_{50}$ value in an $\alpha_{2B}$ antagonist assay equal to or less than about 10 nM at a concentration of oxymetazoline corresponding to its $EC_{80}$ concentration as obtained by assay protocols described herein, and (ii) less than about 25% inhibition of $\alpha_{2A}$ ligand binding at 0.1 µM and an $IC_{50}$ value in an $\alpha_{2A}$ antagonist assay that is greater than 200 nM at a concentration of UK14304 corresponding to its $EC_{80}$ concentration as obtained by assay protocols described herein, and (iii) equal to or greater than about 60% inhibition of $\alpha_{1B}$ ligand binding at 0.03 µM and an $IC_{50}$ value in an $\alpha_{1B}$ antagonist assay equal or less than 10 nM at a concentration of cirazoline corresponding to its $EC_{80}$ concentration as obtained by assay protocols described herein. In one aspect, such a compound will also exhibit a Ki ratio of $\alpha_{2A}$ to $\alpha_{2B}$ that is greater than about any one of 5 or 15 or 50.

Antagonist activity to the adrenergic receptor $\alpha_{2A}$, $\alpha_{2B}$, $\alpha_{1B}$ and $\alpha_{1D}$ may be assessed by methods known in the art, such as standard $\alpha_{2A}$, $\alpha_{2B}$, $\alpha_{1B}$ and $\alpha_{1D}$ receptor cell membrane-based or intact cell-based activity assays. For example, the Aequorin-based assay may be used to assess antagonist activity to the adrenergic receptor $\alpha_{2A}$, $\alpha_{2B}$, $\alpha_{1B}$ or $\alpha_{1D}$ and the cell membrane-based GTPγS binding assay may be used to assess antagonist activity to the adrenergic receptor $\alpha_{2B}$.

In one variation, adrenergic receptor $\alpha_{2A}$ antagonists as provided herein exhibit an $IC_{80}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay.

In another variation, a compound provided herein binds to and is an antagonist of the adrenergic receptor $\alpha_{2A}$, wherein the compound is also an antagonist of the adrenergic receptor $\alpha_{2B}$ and exhibits an $IC_{50}$ value that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an adrenergic receptor $\alpha_{2B}$ antagonist assay. In some embodiments, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay), and (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay). In another variation, a compound provided herein binds to and is an antagonist of the adrenergic receptor $\alpha_{2A}$, wherein the compound is also an antagonist of the adrenergic receptor $\alpha_{1B}$ and exhibits an $IC_{50}$ value that is equal to or less than about any one of 100 nM, 30 nM or 10 nM at a given concentration of agonist (e.g. concentration corresponding to $EC_{80}$ of cirazoline (for Aequorin assay) in an adrenergic receptor $\alpha_{1B}$ antagonist assay. In some embodiments, adrenergic receptor $\alpha_{2A}$ antagonists as provided herein exhibit: (i) an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay, and (ii) an $IC_{50}$ value equal to or less than about any one of 100 nM or 30 nM or 10 nM at a given concentration of agonist (e.g. concentration corresponding to $EC_{80}$ of cirazoline) in an adrenergic receptor $\alpha_{1B}$ antagonist assay. In yet another variation, a compound provided herein binds to and is an antagonist of the adrenergic receptor $\alpha_{2A}$, wherein the compound is also an antagonist of the adrenergic receptor $\alpha_{1D}$ and exhibits an $IC_{50}$ value that is equal to or less than about any one of 100 nM, 30 nM or 10 nM at a given concentration of agonist (e.g. concentration corresponding to $EC_{80}$ of cirazoline (for Aequorin assay) in an adrenergic receptor $\alpha_{1D}$ antagonist assay. In some embodiments, adrenergic receptor $\alpha_{2A}$ antagonists as provided herein exhibit: (i) an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay, and (ii) an $IC_{50}$ value equal or less than about any one of 100 nM or 30 nM or 10 nM at a given concentration of agonist (e.g. concentration corresponding to $EC_{80}$ of cirazoline) in an adrenergic receptor $\alpha_{1D}$ antagonist assay.

In yet another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay. In another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay. In another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay; and (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay.

In yet another embodiment, adrenergic receptor $\alpha_{2A}$ antagonists as provided herein exhibit: (i) an $IC_{50}$ value in an $\alpha_{2A}$ antagonist assay equal to or less than about any one of 100 nM, 30 nM or 10 nM at a given concentration of agonist (e.g. concentration corresponding to $EC_{80}$ of UK14304 (for Aequorin assay); (ii) an $IC_{50}$ value in an $\alpha_{2B}$ antagonist assay that is equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay); (iii) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay; and (iv) an $IC_{50}$ value equal or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay.

In one variation, adrenergic receptor $\alpha_{2A}$ antagonists as provided herein exhibit an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay. In one variation, adrenergic receptor $\alpha_{2A}$ antagonists as provided herein exhibit an $IC_{50}$ value equal to or less than about 10 nM at a given concentration of agonist (e.g. concentration corresponding to $EC_{80}$ of UK14304 (for Aequorin assay) in an adrenergic receptor $\alpha_{2A}$ antagonist assay. In one variation, adrenergic receptor $\alpha_{2A}$ antagonists as provided herein exhibit an $IC_{50}$ value in an adrenergic receptor $\alpha_{2A}$ antagonist assay equal to or less than about any one of 100 nM, 30 nM or 10 nM at a concentration of UK14304 (for Aequorin assay) corresponding to its $EC_{80}$ concentration obtained by assay protocols described herein. In one variation, adrenergic receptor $\alpha_{2A}$ antagonists as provided herein exhibit an $IC_{50}$ value equal to or less than about any one of 100 nM, 30 nM or 10 nM at a concentration of UK14304 between about 0.4 and about 40 nM in an adrenergic receptor $\alpha_{2A}$ (Aequorin) antagonist assay. In one variation, adrenergic receptor $\alpha_{2A}$ antagonists as provided herein exhibit an $IC_{50}$ value equal to or less than about any one of 100 nM, 30 nM or 10 nM at a concentration of about 4.57 nM UK14304 in an adrenergic receptor $\alpha_{2A}$ (Aequorin) antagonist assay.

In one variation adrenergic receptor $\alpha_{2A}$ antagonists as provided herein exhibit an $IC_{50}$ value equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay. In some embodiments, adrenergic receptor $\alpha_{2A}$ antagonists as provided herein exhibit an $IC_{50}$ value equal to or less than about 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay. In some embodiments, a compound described herein exhibits an $IC_{50}$ value in an $\alpha_{2B}$ antagonist assay equal to or less than about any one of 100 nM, 30 nM or 10 nM at a concentration of oxymetazoline corresponding to its $EC_{80}$ concentration as obtained by assay protocols described herein. In some embodiments, a compound described herein exhibits an $IC_{50}$ value in an $\alpha_{2B}$ antagonist (Aequorin) assay equal to or less than about any one of 100 nM, 30 nM or 10 nM at a concentration of oxymetazoline between about 50 nM to about 5000 nM. In some embodiments, a compound described herein exhibits an $IC_{50}$ value in an $\alpha_{2B}$ antagonist (Aequorin) assay equal to or less than about any one of 100 nM, 30 nM or 10 nM at a concentration of about 480 nM oxymetazoline. In some embodiments, a compound described herein exhibits an $IC_{50}$ value in an $\alpha_{2B}$ antagonist (GTPγS) assay equal to or less than about any one of 100 nM, 30 nM or 10 nM at a concentration of guanfacine between about 50 nM to about 5000 nM. In some embodiments, a compound described herein exhibits an $IC_{50}$ value in an $\alpha_{2B}$ antagonist assay equal to or less than about any one of 100 nM, 30 nM or 10 nM at a concentration of about 500 nM guanfacine, which is a particular variation, is 504 nM guanfacine.

In one variation, a compound described herein exhibits an $IC_{50}$ value in an $\alpha_{1B}$ antagonist assay equal to or less than about any one of 100 nM, 30 nM or 10 nM at a given concentration of agonist (e.g. concentration corresponding to $EC_{80}$ of cirazoline) in an adrenergic receptor $\alpha_{1B}$ antagonist assay. In some embodiments, a compound described herein exhibits an $IC_{50}$ value in an $\alpha_{1B}$ antagonist assay equal to or less than about 10 nM at a given concentration of agonist (e.g. concentration corresponding to $EC_{80}$ of cirazoline) in an adrenergic receptor $\alpha_{1B}$ antagonist assay. In some embodiments, a compound described herein exhibits an $IC_{50}$ value in an $\alpha_{1B}$ antagonist assay equal to or less than about any one of 100 nM, 30 nM or 10 nM at a concentration of cirazoline corresponding to its $EC_{80}$ concentration as obtained by assay protocols described herein. In some embodiments, a compound described herein exhibits an $IC_{50}$ value in an $\alpha_{1B}$ antagonist (Aequorin) assay equal to or less than about any one of 100 nM, 30 nM or 10 nM at a concentration of cirazoline between about 2.3 nM and about 230 nM. In some embodiments, a compound described herein exhibits an $IC_{50}$ value in an $\alpha_{1B}$ antagonist (Aequorin) assay equal to or less than about any one of 100 nM, 30 nM or 10 nM at a concentration of about 25 nM cirazoline, which in a particular variation is 23.56 nM cirazoline.

In one variation, a compound described herein exhibits an $IC_{50}$ value in an $\alpha_{1D}$ antagonist assay equal to or less than about any one of 100 nM, 30 nM or 10 nM at a given concentration of agonist (e.g. concentration corresponding to $EC_{80}$ of cirazoline) in an adrenergic receptor $\alpha_{1D}$ antagonist assay. In some embodiments, a compound described herein exhibits an $IC_{50}$ value in an $\alpha_{1D}$ antagonist assay equal to or less than about 10 nM at a given concentration of agonist (e.g. concentration corresponding to $EC_{80}$ of cirazoline) in an adrenergic receptor $\alpha_{1D}$ antagonist assay. In some embodiments, a compound described herein exhibits an $IC_{50}$ value in an $\alpha_{1D}$ antagonist assay equal to or less than about any one of 100 nM, 30 nM or 10 nM at a concentration of cirazoline corresponding to its $EC_{80}$ concentration as obtained by assay protocols described herein. In some embodiments, a compound described herein exhibits an $IC_{50}$ value in an $\alpha_{1D}$ antagonist assay equal to or less than about any one of 100 nM, 30 nM or 10 nM at a concentration of cirazoline between about 2.3 nM and about 230 nM. In some embodiments, a compound described herein exhibits an $IC_{50}$ value in an $\alpha_{1D}$ antagonist assay equal to or less than about any one of 100 nM, 30 nM or 10 nM at a concentration of about 25 nM cirazoline, which in a particular variation is 23.56 nM cirazoline.

In some embodiments, compounds provided herein exhibit inverse agonist activity for the adrenergic receptor $\alpha_{2A}$. In some embodiments, the compound binds to and is an inverse agonist of the adrenergic receptor $\alpha_{2A}$ and binds to and is antagonist of one or more of the adrenergic receptors $\alpha_{2B}$, $\alpha_{1B}$ and $\alpha_{1D}$. In one variation, the compound binds to and is an inverse agonist of the adrenergic receptor $\alpha_{2A}$ and binds to and is antagonist of any one of the adrenergic receptors $\alpha_{2B}$, $\alpha_{1B}$ and $\alpha_{1D}$. In another variation, the compound binds to and is an inverse agonist of the adrenergic receptor $\alpha_{2A}$ and binds to and is antagonist of any two of the adrenergic receptors $\alpha_{2B}$, $\alpha_{1B}$ and $\alpha_{1D}$. In yet another variation, the compound binds to and is an inverse agonist of the adrenergic receptor $\alpha_{2A}$ and binds to and is antagonist of adrenergic receptors $\alpha_{2B}$, $\alpha_{1B}$ and $\alpha_{1D}$. Inverse agonist activity to the adrenergic receptor $\alpha_{2A}$ may be assessed by methods known in the art, such as those described in Wade, S. M. et al., Mol. Pharmacol. 59:532-542 (2001).

It is understood and clearly conveyed herein that any of the binding profiles detailed herein can be combined with any of the antagonist profiles detailed herein, as if each and every combination were listed separately. For example, in one variation, a compound provided herein exhibits (i) greater than or equal to about any one of 50%, 55%, 60%, 65%, 70%, 80%, 85%, 90%, 95%, or between about 50% and 90%, between about 60% and about 90%, between about 70% and about 90%, or about 80% and about 100% inhibition of $\alpha_{2A}$ ligand binding at 0.1 µM to adrenergic receptor $\alpha_{2A}$ and an $IC_{50}$ value equal to or less than about any one of 100 nM, 30 nM or 10 nM at a given concentration of agonist (e.g. concentration corresponding to $EC_{80}$ of UK14304 (for Aequorin assay) in an adrenergic receptor $\alpha_{2A}$ antagonist assay; and (ii) greater than or equal to about any one of 50%, 55%, 60%, 65%, 70%, 80%, 85%, 90%, 95%, or between about 50% and 90%, between about 60% and about 90%, between about 70% and about 90%, or about 80% and about 100% inhibition of $\alpha_{2B}$ ligand binding at 0.1 µM to adrenergic receptor $\alpha_{2B}$ and $IC_{50}$ value equal to or less than about any one of 100 nM, 30 nM or 10 nM at a given concentration of agonist (e.g. concentration corresponding to $EC_{80}$ of oxymetazoline (for Aequorin assay) or guanfacine (for GTPγS assay) in an $\alpha_{2B}$ antagonist assay.

Medical Use

Without being bound by theory, it is believed that the compounds provided herein are capable of (i) reducing blood pressure and/or (ii) promoting renal blood flow and/or (iii) decreasing or inhibiting sodium reabsorption. In some embodiments, the compounds are adrenergic receptor $\alpha_{2B}$ antagonists (e.g., selective adrenergic receptor $\alpha_{2B}$ antagonists). In some embodiments, it is believed that the selective adrenergic receptor $\alpha_{2B}$ antagonists provided herein are capable of (i) reducing blood pressure and/or (ii) promoting renal blood flow and/or (iii) decreasing or inhibiting sodium reabsorption without concomitantly antagonizing the $\alpha_{2A}$ receptor, which would reduce or potentially eliminate the beneficial blood pressure lowering and renal effects modulated by antagonizing $\alpha_{2B}$. Furthermore, the selective adrenergic receptor $\alpha_{2B}$ antagonists provided herein may be capable of decreasing blood pressure sensitivity to salt, decreasing sodium retention, decreasing vasoconstriction in small arteries and veins, increasing insulin secretion, increasing basal metabolic rate, decreasing platelet aggregation and/or enhancing mitochondrial function. However, in certain cases where the compound has strong antagonist activities against adrenergic receptor $\alpha_{2B}$ and/or adrenergic receptor $\alpha_{1B}$, some antagonist activity against adrenergic receptor $\alpha_{2A}$ may be tolerated and even beneficial.

Compounds provided herein may be capable of mediating control of the renal function. Adrenergic $\alpha_{2B}$ receptors are located within the kidney. Regard et al. (Cell 2008; 135:561) have demonstrated that the gene for the adrenergic $\alpha_{2B}$ receptor is most abundantly expressed in the kidney. Meister et al. (J. Pharmacol. Exp. Therapeutics 1994; 268:1605) have shown by in situ hybridization that expression predominates in the medulla outer stripe with extensions into the cortical S3 segment of the proximal tubules. Adrenergic $\alpha_{2B}$ receptor antagonists provided herein may be capable of disrupting sodium reabsorption resulting in natriuresis and diuresis. Methods to determine effects of adrenergic $\alpha_{2B}$ antagonists on renal function in a rabbit model of hypertension have been described by Burke et al. (J Hypertens 29:945-952).

In addition to reducing blood pressure, compounds disclosed herein, including adrenergic $\alpha_{2B}$ antagonists, are capable of a reduction in blood volume that might result from diueresis and/or the movement of fluid from the vascular space to the extravascular space. Reduction of blood volume results in increase in hematocrit levels which can be measured by methods known in the art, for example by estimation of erythrocyte volume fraction. Characterization of the effect of $\alpha_{2B}$ antagonists on renal function are determined by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

The compounds detailed herein are expected to find use in therapy, particularly in cardiac and renal diseases and conditions, in addition to hypertension and other conditions in which a (i) reduction in blood pressure and/or (ii) increase in renal blood flow and/or (iii) decrease in sodium reabsorption would be beneficial. In the methods provided herein, an effective amount of a compound detailed herein is administered to an individual. Methods of using compounds as described herein to (i) reduce blood pressure and/or (ii) promote renal blood flow and/or (iii) decrease or inhibit sodium reabsorption in an individual in need thereof are provided. The compounds may also find use in treating a disease or condition that is, or is expected to be, responsive to (i) a reduction in an individual's blood pressure and/or (ii) an increase in renal blood flow and/or (iii) a decrease or inhibition of sodium reabsorption. The individual may be a human who has been diagnosed with or is suspected of having high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who exhibits one or more symptoms associated with high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who is genetically or otherwise predisposed to developing high blood pressure or a disease or condition that is, or is expected to be, responsive to (i) a reduction in an individual's blood pressure and/or (ii) an increase in renal blood flow and/or (iii) a decrease or inhibition of sodium reabsorption. In one variation, the compounds may find use in treating metabolic syndrome. In some embodiments, the compounds are adrenergic receptor $\alpha_{2B}$ antagonists. In one variation, the adrenergic receptor $\alpha_{2B}$ antagonists are selective adrenergic receptor $\alpha_{2B}$ antagonists. In one variation, a compound that is an adrenergic receptor $\alpha_{2B}$ antagonist also showing adrenergic receptor $\alpha_{2A}$ antagonist and/or inverse agonist activity may find use reducing blood pressure in an individual with hypertension who is also suffering from obesity, type-2 diabetes and/or metabolic syndrome. Thus, provided is a method for lowering blood pressure in hypertensive patients with a disease or condition that is responsive to treatment using an antagonist or inverse agonist of adrenergic receptor $\alpha_{2A}$, such as obesity and/or type-2 diabetes and/or metabolic syndrome.

Compounds detailed herein may be used in a method of treating a disease or condition that is responsive to (i) a reduction in an individual's blood pressure and/or (ii) an increase in renal blood flow and/or (iii) a decrease or inhibition of sodium reabsorption. For example, the compounds may find use in treating hypertension, including treatment-resistant hypertension. In some embodiments, the compounds may be used in a method of treating hypertension in an individual not suffering from obesity or type-2 diabetes. In some embodiments, the compounds are adrenergic receptor $\alpha_{2B}$ antagonists. In some embodiments, the compounds are selective adrenergic receptor $\alpha_{2B}$ antagonists.

In one aspect, the disease or indication is a cardiac or renal disease or indication for which (i) a reduction in an individual's blood pressure and/or (ii) an increase in renal blood flow and/or (iii) a decrease or inhibition of sodium reabsorption would be, or would be expected to be, beneficial. Such cardiac indications include, but are not limited to, heart failure, such as compensated heart failure, decompensated heart failure, acute decompensated congestive heart failure and chronic congestive heart failure, coronary heart disease, cardiac arrhythmias, myocardial ischemia, and hypertrophy. Such renal indications include, but are not limited to, renal failure such as chronic renal failure, acute renal failure and endstage renal failure, renal ischemia and chronic kidney disease. Other indications for which (i) a reduction in an individual's blood pressure and/or (ii) an increase in renal blood flow and/or (iii) a decrease or inhibition of sodium reabsorption would be, or would be expected to be, beneficial include but are not limited to sleep apnea and ischemic attacks.

Compounds detailed herein may also ameliorate symptoms of a disease or condition that have a cardiac or renal component in which (i) a reduction in an individual's blood pressure and/or (ii) an increase in renal blood flow and/or (iii) a decrease or inhibition of sodium reabsorption would be, or would be expected to be, beneficial. For example, the compounds may reduce elevated blood pressure, improve shortness of breath, reduce tachycardia, reduce edema, reduce elevated blood urea nitrogen to creatinine (BUN/Cr) ratio, improve creatinine levels, improve the ability to lie flat, reduce the incidence or severity of high blood pressure, reduce the risk and/or number of acute cardiac events (e.g., acute decompensation or myocardial infarction) an individual experiences over a period of time (e.g., one year, 2 years, 5 years, etc.), reduce the incidence of acute heart failure an individual experiences over a period of time (e.g., one year, 2 years, 5 years, etc.), reduce the severity and/or incidence of pulmonary congestion and/or reduce the risk of stroke, reduce shortness of breath and/or tachycardia in individuals after myocardial infarction, improve left ventricular ejection fraction (LVEF) post infarct and/or lower weight and blood pressure in obese individuals (e.g., men and women) with prehypertension. In some embodiments, the compounds are adrenergic receptor $\alpha_{2B}$ antagonists. In some embodiments, the compounds are selective adrenergic receptor $\alpha_{2B}$ antagonists.

Compounds detailed herein (such as the adrenergic receptor $\alpha_{2B}$ antagonists detailed herein) may find use in the treatment of hypertensive emergencies. Provided is a method of treating hypertensive emergencies, comprising administering intravenously an effective amount of an adrenergic receptor $\alpha_{2B}$ antagonist to an individual in need thereof. In some embodiments, the method comprises administering intravenously an effective amount of an adrenergic receptor $\alpha_{2B}$ antagonist to an individual in need thereof in a highly monitored intensive care setting, wherein the administration results in aggressive and controlled blood pressure lowering in the individual. In some embodiments, intravenous administration of an adrenergic receptor $\alpha_{2B}$ antagonist in an individual results in gradually lowering of blood pressure in the individual and minimizing damage of end organs such as the brain, kidney, heart, and eye. Particularly useful in the treatment of hypertensive emergencies or crisis are parenteral formulations of an adrenergic receptor $\alpha_{2B}$ antagonist detailed herein. In one variation, the compound is an adrenergic receptor $\alpha_{2B}$ antagonist. In some variations, the compound is a selective adrenergic receptor $\alpha_{2B}$ antagonist. In one variation, the adrenergic receptor $\alpha_{2B}$ antagonist also exhibits adrenergic receptor $\alpha_{2A}$ antagonist and/or inverse agonist activity.

In one variation, a method of decreasing the severity and/or incidence of shortness of breath, tachycardia, edema, and/or the inability to lie flat is provided, comprising administering an effective amount of a compound detailed herein to an individual who has or is suspected of having heart failure (e.g., compensated heart failure and decompensated heart failure). In another variation, a method of decreasing the severity and/or incidence of elevated BUN/Cr, and/or edema is provided comprising administering an effective amount of a compound detailed herein to an individual who has or is suspected of having renal failure (e.g., acute or chronic renal failure). In another variation, a method of reducing blood pressure in an individual is provided comprising administering an effective amount of a compound detailed herein to an individual who has or is suspected of having hypertension (e.g., treatment-resistant hypertension). In another variation, a method of decreasing the severity and/or incidence of shortness of breath, tachycardia, and/or improving LVEF post infarct in an individual is provided comprising administering an effective amount of a compound detailed herein to an individual who has experienced myocardial infarction (e.g., an individual who has recently experienced myocardial infarction such as within 30 minutes, 1, 3, 6, 12, or 24 hours of treatment). In some of the variations, the adrenergic receptor $\alpha_{2B}$ antagonist is a selective adrenergic receptor $\alpha_{2B}$ antagonist. In some of the variations, the adrenergic receptor $\alpha_{2B}$ antagonist also exhibits antagonist activity for the adrenergic receptor $\alpha_{2A}$. In some embodiments, the compounds are adrenergic receptor $\alpha_{2B}$ antagonists. In some embodiments, the compounds are selective adrenergic receptor $\alpha_{2B}$ antagonists.

In one variation, provided is method for lowering the blood pressure in an individual in need thereof comprising administering to the individual a compound described herein, or a pharmaceutically acceptable salt thereof. Administration of an adrenergic receptor $\alpha_{2B}$ antagonist detailed herein lowers the blood pressure in the individual from a level considered above the desired level for such individual. The blood pressure lowering therapy such as administration of compounds detailed herein is intended to help hypertensive individuals reach their blood pressure goals defined by their individual cardiovascular risk factors. For example, for otherwise healthy individuals without diabetes or known cardiovascular disease, goal blood pressure is less than about 140/90 mmHg; for patients with known cardiovascular disease (e.g., prior myocardial infarction, peripheral vascular disease) goal blood pressure is less than about 130-135/85 mmHg; for patients with diabetes, goal blood pressure is less than about 130/80 mmHg.

In one variation, compounds provided herein may have any one or more of the following beneficial effects on an individual: (1) reduce arterial blood pressure (e.g., in an individual with hypertension, certain forms of heart failure and/or renal failure); (2) reduce pulse pressure (e.g., in an individual with hypertension, certain forms of heart failure and/or renal failure); (3) tachycardia-preserved baroreceptor activity (e.g., in an individual whose systolic blood pressure is expected to or does fall in response to an $\alpha_{2B}$ antagonist), which may suggest a lack of orthostatic hypotension; and (4) bradycardia-reduced cardiac work load and added reduction on blood pressure reduction by further reducing cardiac output (e.g., in an individual who has been administered a therapy that is an $\alpha_{2B}$ and $\alpha_{1B}$ mixed antagonist).

In another variation, compounds provided herein may exert their therapeutic effect with no or reduced side-effects, such as when compared to other therapies used in the treatment of the same or similar indication. In one aspect, compounds provided herein exhibit no or reduced side effects upon administration to an individual, wherein the side effects may be any one or more of: (i) reduced libido, (ii) orthostatic hypotension, (iii) muscle weakness, (iv) fatigue, (v) erectile dysfunction, (vi) constipation, (vii) depression, (viii) dizziness, (ix) dry mouth, (x) impaired thinking, (xi) weight gain, (xii) persistent cough, (xiii) chest pain, (xiv) headache, (xv) fluid retention, (xvi) racing pulse, and (xvii) emesis.

In one aspect, compounds are provided that do not bind appreciably any one or more of the histamine, dopamine and serotonin receptors. In any of the methods detailed herein, in one variation the individual does not have a cognitive disorder, psychotic disorder, neurotransmitter-mediated disorder and/or neuronal disorder. As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI). As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression. As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

Individuals who have high blood pressure, or a disease or condition that is, or is expected to be, responsive to (i) a reduction in an individual's blood pressure and/or (ii) an increase in renal blood flow and/or (iii) a decrease or inhibition of sodium reabsorption may benefit from the compounds detailed herein, including the adrenergic receptor $\alpha_{2B}$ antagonists (e.g., the selective adrenergic receptor $\alpha_{2B}$ antagonist) detailed herein.

An individual who does not have high blood pressure or a disease or condition that is, or is expected to be, responsive to (i) a reduction in an individual's blood pressure and/or (ii) an increase in renal blood flow and/or (iii) a decrease or inhibition of sodium reabsorption may nevertheless benefit from the compounds detailed herein if the individual has one or more risk factors for high blood pressure, or a disease or condition that is, or is expected to be, responsive to (i) a reduction in an individual's blood pressure and/or (ii) an increase in renal blood flow and/or (iii) a decrease or inhibition of sodium reabsorption. Risk factors for developing high blood pressure may include gender, race, ethnicity, age, family history, weight and/or lifestyle. For example, African-Americans, men (particularly if over age 45), woman over age 55, anyone over age 60, pre-hypertension individuals (individuals with a blood pressure of 120-130/80-89 mmHg), individuals who are overweight or obese, individuals with sleep apnea (such as obstructive sleep apnea), individuals who smoke, individuals who have a high salt diet, individuals who have a low potassium diet, individuals with chronic heavy alcohol use, individuals with a sedentary lifestyle, individuals with moderate to high stress, individuals with compromised renal function or renal failure and individuals with close relatives who have high blood pressure are each at an increased risk of developing high blood pressure themselves, or diseases or conditions associated with high blood pressure. Individuals with more than one such risk factor are particularly susceptible to developing high blood pressure. Risk factors for developing kidney disease may include diabetes, high blood pressure (hypertension), cardiovascular diseases, smoking, obesity, high cholesterol, a family history of kidney disease, and/or age 65 or older. Members of certain ethnic groups are also at higher risk for kidney disease including people of Aboriginal, Asian, south Asian, Pacific Island, African/Caribbean, American Indian and Hispanic origin.

Without being bound by theory, it is believed that compounds that bind to and are antagonists of the adrenergic receptor $\alpha_{2A}$ affect an increase in insulin secretion and/or promote insulin release into the blood stream in an individual, which aids in glucose uptake. However, such compounds may also increase an individual's blood pressure. When the adrenergic receptor $\alpha_{2A}$ antagonists as provided herein also bind to and are antagonists of the adrenergic receptor $\alpha_{2B}$ and/or the adrenergic receptor $\alpha_{1B}$, and/or the adrenergic receptor $\alpha_{1D}$, it is believed that the increases in an individual's blood pressure due to antagonizing the adrenergic receptor $\alpha_{2A}$ may be reduced or eliminated. If an adrenergic receptor $\alpha_{2A}$ antagonist as provided herein is not also an antagonist of the adrenergic receptor $\alpha_{2B}$ and/or the adrenergic receptor $\alpha_{1B}$ and/or the adrenergic receptor $\alpha_{1D}$, then the increase in an individual's blood pressure as a result of the adrenergic receptor $\alpha_{2A}$ antagonist may be reduced or eliminated by administering the compound in conjunction with a second agent that reduces, or is expected to reduce, blood pressure in an individual.

Compounds provided herein, such as the adrenergic receptor $\alpha_{2A}$ antagonists provided herein, are expected to find use in therapy, particularly in indications in which an increase in an individual's insulin secretion and/or an increase in insulin release into the blood stream would be, or would be expected to be, beneficial. Thus, individuals who have a disease or condition that involves reduced or impaired insulin secretion and/or release may benefit from the compounds detailed herein, or pharmaceutically acceptable salts thereof. Such indications include, but are not limited to type 2 diabetes, glucose intolerance and metabolic syndrome. An individual who has a disease or condition that involves reduced or impaired insulin secretion and/or release may experience one or more beneficial or desirable results upon administration of an adrenergic receptor $\alpha_{2A}$ antagonist provided herein, or pharmaceutically acceptable salt thereof. In one aspect, the beneficial or desirable result is a reduction in the individual's blood glucose level for a period of time (e.g., about any one of 6, 12, 24 or 48 hours or more) following administration of the compound or pharmaceutically acceptable salt thereof. In another aspect, the beneficial or desirable result is an increase in glucose metabolism for a period of time (e.g., about any one of 6, 12, 24 or 48 hours or more) following administration of the compound or pharmaceutically acceptable salt thereof.

Compounds that are inverse agonists of the adrenergic receptor $\alpha_{2A}$ may stimulate islet cell release of insulin even in the absence of sympathetic stimulation of the adrenergic receptor $\alpha_{2A}$ with epinephrine and/or norepinephrine. Inverse agonists of the adrenergic receptor $\alpha_{2A}$ provided herein are thus expected to find use in therapy, particularly in indications in which stimulation of islet cell release of insulin would be, or would be expected to be, beneficial. Individuals who have a disease or condition responsive to inhibition of the adrenergic receptor $\alpha_{2A}$ may benefit from the compounds detailed herein, or pharmaceutically acceptable salts thereof. Such indications include, but are not limited to type 2 diabetes, metabolic syndrome, and glucose intolerance.

In one aspect, compounds are provided that do not bind appreciably any one or more of the histamine, dopamine and serotonin receptors. In any of the methods detailed herein, in one variation the individual does not have a cognitive disorder, psychotic disorder, neurotransmitter-mediated disorder and/or neuronal disorder. As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI). As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression. As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

The adrenergic receptor $\alpha_{2A}$ antagonists provided herein may also be administered in combination with an insulin sensitizer, and as such find use in therapy for treating indications in which increasing in an individual's insulin secretion and/or insulin release into the blood stream would be, or would be expected to be, beneficial, provided that the therapy also promotes insulin responsiveness to glucose. In one aspect, where the adrenergic receptor $\alpha_{2A}$ antagonists provided herein may be administered in combination with another anti-diabetic drug, such as an insulin sensitizer, the beneficial or desirable result of which is a reduction in the individual's blood glucose levels for a period of time (e.g., about any one of 6, 12, 24 or 48 hours or more) following administration of the compound or pharmaceutically acceptable salt thereof. In a particular variation, such a therapy may include an adrenergic receptor $\alpha_{2A}$ antagonist provided herein and a second agent that reduces, or is expected to reduce, blood pressure and an insulin sensitizer. In a further variation, such a therapy may include an adrenergic receptor $\alpha_{2A}$ antagonist provided herein and a second agent that (i) is an agent that reduces, or is expected to reduce, blood pressure; (ii) is an agent that is an insulin sensitizer or (iii) is an agent that induces no or reduced (in number and/or severity) hypoglycemic episodes.

Methods

Methods of using the compounds detailed herein, or pharmaceutical salts thereof, to increase an individual's ability to secrete insulin and/or to release insulin into the blood stream are provided. In any of the methods detailed herein, the method may comprise the step of administering an adrenergic receptor $\alpha_{2A}$ antagonist, or pharmaceutically acceptable salt thereof, to an individual in need thereof. In one aspect, the adrenergic receptor $\alpha_{2A}$ antagonists of the methods also bind to and are antagonists of one or more of the adrenergic receptors $\alpha_{2B}$, $\alpha_{1B}$ and $\alpha_{1D}$. In one variation, a method of increasing insulin secretion and/or release into the blood stream in an individual in need thereof is provided, wherein the method comprises administering to an individual in need thereof a compound that binds to and is an antagonists of the adrenergic receptor $\alpha_{2A}$. In another variation, a method of increasing insulin secretion and/or release into the blood stream in an individual in need thereof is provided, wherein the method comprises administering to an individual in need thereof a compound that binds to and is an antagonists of the adrenergic receptor $\alpha_{2A}$, wherein the compound either (a) also binds to and is an antagonist of the adrenergic receptor $\alpha_{2B}$ or (b) is administered in conjunction with a second agent that reduces, or is expected to reduce, blood pressure in the individual. In some variations, methods of using the compounds detailed herein to increase an individual's ability to secrete insulin and/or release insulin into the blood stream while reducing or eliminating an increase in the individual's blood pressure due to antagonizing the adrenergic receptor $\alpha_{2A}$ are thus provided. Methods of using the compounds detailed herein to promote an individual's ability to metabolize glucose while reducing or eliminating an increase in the individual's blood pressure due to antagonizing the adrenergic receptor $\alpha_{2A}$ are also provided. It is understood that in methods of promoting an individual's ability to metabolize glucose, the method in one variation may employ administration of both an adrenergic receptor $\alpha_{2A}$ antagonist and an insulin sensitizer. The compounds or pharmaceutical salts thereof may also find use in treating a disease or condition that is, or is expected to be, responsive to an increase in an individual's ability to secrete insulin and/or release of insulin into the blood stream. Individuals to be treated in such methods in one variation have a reduced or impaired ability to secrete insulin and/or release insulin into the blood stream. The compounds as provided herein may also be used in a method of delaying the onset and/or development of a disease or condition associated with reduced or impaired ability to secrete insulin and/or release insulin into the blood stream, comprising administering a compound as provided herein, or a pharmaceutical salt thereof, to an individual who is at risk of developing a disease or condition associated with reduced or impaired ability to secrete insulin and/or release insulin into the blood stream. The compounds as provided herein may also be used in a method of delaying the onset and/or development of a disease or condition associated with reduced or impaired ability to metabolize glucose, comprising administering an adrenergic receptor $\alpha_{2A}$ antagonist as provided herein, or a pharmaceutical salt thereof, to an individual who is at risk of developing a disease or condition associated with reduced or impaired ability to metabolize glucose. The individual may be an adult, child or teen who has or is at risk of developing type 2 diabetes, glucose intolerance or metabolic syndrome.

Further provided herein are methods of using an adrenergic receptor $\alpha_{2A}$ antagonist, or a pharmaceutically acceptable salt thereof, in combination with an insulin sensitizer to promote insulin responsiveness and increase an individual's ability to secrete insulin and/or to release insulin into the blood stream. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In one variation, a method of promoting insulin responsiveness and increasing insulin secretion and/or release into the blood stream in an individual in need thereof is provided, wherein the method comprises administering to an individual in need thereof an insulin sensitizer and an adrenergic receptor $\alpha_{2A}$ antagonist. In another variation, a method of promoting insulin responsiveness and increasing insulin secretion and/or release into the blood stream in an individual in need thereof is provided, wherein the method comprises administering to an individual in need thereof an insulin sensitizer and a compound that binds to and is an antagonists of the adrenergic receptor $\alpha_{2A}$, wherein the compound either (a) also binds to and is an antagonist of the adrenergic receptor $\alpha_{2B}$ or (b) is administered in conjunction with a second agent that reduces, or is expected to reduce, blood pressure in the individual. In a particular variation, a method of promoting insulin responsiveness and increasing insulin secretion and/or release into the blood stream in an individual in need thereof is provided, wherein the method comprises administering to an individual in need thereof an insulin sensitizer and an adrenergic receptor $\alpha_{2A}$ antagonist that also binds to and is an antagonist of one or more of the adrenergic receptors $\alpha_{2B}$, $\alpha_{1B}$ and $\alpha_{1D}$ In some embodiments, the method comprises administering any of the compounds detailed herein in combination with an insulin sensitizer.

In one aspect, a method of treating type 2 diabetes is provided, where the method comprises administering to an individual in need thereof a compound detailed herein, such as an adrenergic receptor $\alpha_{2A}$ antagonist detailed herein. In one aspect, the compound binds to and is an adrenergic receptor $\alpha_{2A}$ antagonist. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating type 2 diabetes is provided, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in an individual. Individuals to be treated in such methods in one variation have type 2 diabetes. The compounds as provided herein may also be used in a method of delaying the onset and/or development of type 2 diabetes, comprising administering an adrenergic receptor $\alpha_{2A}$ antagonist, or pharmaceutically acceptable salt thereof, to an individual who has one or more risk factors associated with developing type 2 diabetes. In one variation, the compounds as provided herein are used in a method of delaying the onset and/or development of type 2 diabetes; and inducing extra-pancreatic effects such as reducing hepatic glucose production via glycogenolysis or gluconeogenesis or both, comprising administering an adrenergic receptor $\alpha_{2A}$ antagonist, or pharmaceutically acceptable salt thereof, to an individual such as an individual who has one or more risk factors associated with developing type 2 diabetes. In one variation, compounds provided herein may (i) have an extra-pancreatic effect and/or (ii) prevent or lower hepatic glucose production.

Risk factors may include gender, race, ethnicity, age, family history, weight and/or lifestyle. For example, certain races and ethnicities (e.g., Blacks, Hispanics, Native Americans and Asians (which as used herein includes individuals of the continent of Asia, such as Indians and Chinese) and individuals of such descent) are more likely to develop type 2 diabetes. Being overweight (e.g., having a body mass index>25) is also a risk factor for type 2 diabetes, with higher amount of fatty tissue also correlating with higher resistance of cells to insulin. Inactivity, which can lead to weight gain, is also a risk factor for type 2 diabetes (physical activity helps not only to control an individual's weight, but also utilizes glucose as energy and makes cells more sensitive to insulin). Family history is often a risk factor for many diseases, including type 2 diabetes, where the risk of developing type 2 diabetes increases if a parent or sibling has type 2 diabetes. The risk of developing type 2 diabetes also increases with age, especially after age 45, which may also correlate with a tendency to exercise less, lose muscle mass and gain weight with age. However, as obesity rates rise in children and young adults, type 2 diabetes is increasing common in these individuals and children and young adults who are overweight and/or sedentary are also at risk of developing type 2 diabetes. Being pre-diabetic, in which an individual's blood sugar level is higher than normal, but not high enough to be classified as type 2 diabetes, if left untreated, often progresses to type 2 diabetes. Other risk factors associated with type 2 diabetes include: a woman who has had gestational diabetes, gave birth to a baby weighing more than 9 pounds or has a history of polycystic ovary disease (PCOS); an individual who has metabolic syndrome; an individual who has hypertension; an individual who has a high-density lipoprotein (HDL) value under 35 mg/dL (milligrams per deciliter) and/or a triglyceride level over 250 mg/dL; and an individual with a history of vascular disease, such as stroke. Individuals who have more than one risk factor are particularly susceptible to developing type 2 diabetes.

In one aspect, a method of treating glucose intolerance is provided, where the method comprises administering to an individual in need thereof an adrenergic receptor $\alpha_{2A}$ antagonist, or pharmaceutically acceptable salt thereof. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating glucose intolerance is provided, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in the individual. The compounds as provided herein may also be used in a method of delaying the onset and/or development of glucose intolerance, comprising administering a compound as provided herein to an individual who has one or more risk factors associated with developing glucose intolerance. A method of reducing blood glucose levels in an individual in need thereof is also provided, the method comprising administering an adrenergic receptor $\alpha_{2A}$ antagonist, or pharmaceutically acceptable salt thereof, to the individual. A method of enhancing glucose metabolism in an individual in need thereof is also provided, the method comprising administering an adrenergic receptor $\alpha_{2A}$ antagonist, or pharmaceutically acceptable salt thereof, to the individual.

Further provided are methods of using the compounds detailed herein, or pharmaceutical salts thereof, to regulate blood glucose levels in an individual, for example, an individual experiencing hyperglycemia and/or undesirable fluctuation in blood glucose levels.

In some embodiments, provided is a method of regulating blood glucose levels in an individual in need thereof, where the method comprises administering to an individual in need thereof an adrenergic receptor $\alpha_{2A}$ antagonist. In some embodiments, administration of an adrenergic receptor $\alpha_{2A}$ antagonist reduces the blood glucose levels in an individual (e.g., a hyperglycemic individual). In some embodiments, administration of an adrenergic receptor $\alpha_{2A}$ antagonist stabilizes the blood glucose levels in an individual (e.g., an individual experiencing undesirable fluctuations in blood glucose levels). In some embodiments, administration of an adrenergic receptor $\alpha_{2A}$ antagonist reduces and stabilizes the blood glucose levels in an individual. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, provided is a method of regulating (e.g., reducing and/or stabilizing) blood glucose levels in an individual in need thereof, where the method comprises administering to an individual in need thereof a compound as provided herein, wherein the compound binds to and is an antagonist of the adrenergic receptor $\alpha_{2A}$ and wherein the compound either (a) also binds to and is an antagonist of the adrenergic receptor $\alpha_{2B}$ or (b) is administered in conjunction with a second agent that reduces, or is expected to reduce, blood pressure in an individual. In some embodiments, the adrenergic receptor $\alpha_{2A}$ antagonist described herein may also be an inverse agonist of the adrenergic receptor $\alpha_{2A}$.

In some embodiments, provided is a method of reducing blood glucose level in an individual in need thereof, comprises administering to an individual in need thereof an adrenergic receptor $\alpha_{2A}$ antagonist, wherein the blood glucose level is reduced to a desirable level. The adrenergic receptor $\alpha_{2A}$ antagonist may be administered alone or in combination with other agents such as an agent that reduces blood pressure in the individual. In some embodiments, the blood glucose level is reduced by about 10%, about 20%, about 30%, about 40%, about 50%, about 60%, or about 70%, provided that the reduction in glucose level does not result in hypoglycemia. In some embodiments, the blood glucose level is reduced by at least about 10%, at least about 20%, at least about 30%, at least about 40%, at least about 50%, or at least about 60%, provided that the reduction in glucose level does not result in hypoglycemia. In some embodiments, the blood glucose level is reduced by less than about 10%, between about 10% and about 30%, between about 30% and about 50%, between about 10% and about 50%, between about 50% and about 70%, between about 30% and about 70%, between about 20% and about 40%, between about 40% and about 60%, or between about 20% and about 60%, provided that the reduction in glucose level does not result in hypoglycemia. The reduction of blood glucose level occurs over a period of time after administration of the adrenergic receptor $\alpha_{2A}$ antagonist. In some embodiments, the reduction of blood glucose occurs within about 15 minutes after administration of the compound or pharmaceutically acceptable salt thereof. In some embodiments, the reduction of blood glucose occurs within about 30 minutes, within about 1 hour, or within about 2 hours after administration of the adrenergic receptor $\alpha_{2A}$ antagonist. In some embodiments, the reduction of blood glucose occurs at about 15 minutes or more, at about 30 minutes or more, at about 1 hour or more, or at about 2 hours or more after administration of the adrenergic receptor $\alpha_{2A}$ antagonist. In some embodiments, the method results in a reduction in the individual's blood glucose level by any of the amount described herein for a period of time (e.g., about any one of 0.5, 1, 2, 3, 6, 12, 24 or 48 hours or more) following administration of the compound or pharmaceutically acceptable salt thereof. In some embodiments, the method results in a reduction in the individual's blood glucose level by any of the amount described herein for a period of about 1 hour, about 2 hours, about 3 hours, about 6 hours, about 12 hours, or about 24 hours or more following administration of the compound or pharmaceutically acceptable salt thereof.

The blood glucose levels in an individual can be measured by methods known in the art, such as by a calorimetric method or by using a device (e.g., a glucose meter). A blood glucose level in the range of about 80 to 120 mg/dL pre-meal and about 100 to 140 mg/dL post-meal is considered desirable in healthy human beings. A blood glucose level at above the desirable level is considered hyperglycemic, such as that in diabetic patients. The blood glucose level in a mildly diabetic human is about 100 to 200 mg/dL. The blood glucose level in a moderately diabetic human is about 200 to 350 mg/dL. The blood glucose level in a severely diabetic human is above 400 mg/dL. A blood glucose level at below the desirable level is considered hypoglycemic, e.g., at below 60 to 80 mg/dL. The blood glucose levels may be measured at a single time point. However, a more accurate measurement requires an average over multiple time points or an area under the curve (AUC) over a period of time (e.g., 2 to 3 hours). The blood glucose level over a past period of about 2-3 months may be established by measuring the glycosylated hemoglobin (HbA1c) level in the blood. HbA1c is a useful way to monitor a patient's overall response to diabetes treatment over time. The HbA1c in a healthy human being is about 5%. It is desirable for a diabetic patient to keep the HbA1c level below about 7%. Provided is a method of reducing blood glucose level in an individual having an HbA1c level of above about 7%, comprises administering to the individual an adrenergic receptor $\alpha_{2A}$ antagonist, wherein the HbA1c level is reduced to below about 7% following administration of the compound or pharmaceutically acceptable salt thereof. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$.

In one aspect, a method of treating metabolic syndrome is provided, where the method comprises administering to an individual in need thereof a compound detailed herein, such as an adrenergic receptor $\alpha_{2A}$ antagonist detailed herein. In one aspect, the compound binds to and is an adrenergic receptor $\alpha_{2A}$ antagonist. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, a method of treating metabolic syndrome is provided, where the method comprises administering to an individual in need thereof a compound as provided herein, wherein the compound binds to and is an antagonist of the adrenergic receptor $\alpha_{2A}$, and wherein the compound either (a) also binds to and is an antagonist of the adrenergic receptor $\alpha_{2B}$ or (b) is administered in conjunction with a second agent that reduces, or is expected to reduce, blood pressure in an individual. The compounds as provided herein may also be used in a method of delaying the onset and/or development of metabolic syndrome, comprising administering a compound as provided herein to an individual who has one or more risk factors associated with developing metabolic syndrome. In a particular variation of the methods relating to metabolic syndrome, the adrenergic receptor $\alpha_{2A}$ antagonist is administered to an individual in conjunction with an insulin sensitizer.

As is understood by those of skill in the art, metabolic syndrome is a cluster of conditions, which may include increased blood pressure, excess body fat around the waist, abnormal cholesterol levels and elevated insulin levels due to insulin resistance whereby cells have a diminished ability to respond to insulin and the pancreas compensates by secreting more insulin leading to high insulin levels in blood. According to the American Heart Association and the National Heart, Lung, and Blood Institute, metabolic syndrome is present if an individual has three or more of the following signs: blood pressure equal to or higher than 130/85 mm Hg; fasting blood sugar (glucose) equal to or higher than 100 mg/dL; large waist circumference, which for men is 40 inches or more and for women is 35 inches or more; low HDL cholesterol, which for men is under 40 mg/dL and for women is under 50 mg/dL; and triglycerides equal to or higher than 150 mg/dL.

Treatment of metabolic syndrome requires a careful and well-balanced approach to account for both treatment of elevated insulin levels and high blood pressure. Thus, it is desirable in the context of treating metabolic syndrome that a compound that is an antagonist of the adrenergic receptor $\alpha_{2A}$ is also an antagonist of the adrenergic receptor $\alpha_{2B}$ and/or $\alpha_{1B}$ and/or $\alpha_{1D}$ to reduce blood pressure. Alternatively, an adrenergic receptor $\alpha_{2A}$ antagonist that does not also antagonize the adrenergic receptor $\alpha_{2B}$ and/or $\alpha_{1B}$ may be administered in conjunction with a second agent that reduces, or is expected to reduce blood pressure in an individual. In one aspect, provided is a method of regulating (e.g., reducing and/or stabilizing) blood glucose levels and reducing the blood pressure in an individual in need thereof (e.g., an individual experiencing metabolic syndrome, or an individual with hypertension who is also suffering from obesity and/or type 2 diabetes), where the method comprises administering to an individual in need thereof an adrenergic receptor $\alpha_{2A}$ antagonist. In one aspect, the adrenergic receptor $\alpha_{2A}$ antagonist also binds to and is an antagonist of one or more of the adrenergic receptors $\alpha_{2B}$, $\alpha_{1B}$ and $\alpha_{1D}$. In another aspect, provided a method of regulating (e.g., reducing and/or stabilizing) blood glucose levels and reducing the blood pressure in an individual in need thereof, where the method comprises administering to an individual in need thereof a compound as provided herein, wherein the compound binds to and is an antagonist of the adrenergic receptor $\alpha_{2A}$, and wherein the compound either (a) also binds to and is an antagonist of the adrenergic receptor $\alpha_{2B}$ or (b) is administered in conjunction with a second agent that reduces, or is expected to reduce, blood pressure in an individual. In some embodiments, the compound is an antagonist and an inverse agonist of the adrenergic receptor $\alpha_{2A}$.

Risk factors associated with developing metabolic syndrome include: more than one parent or sibling who has type 2 diabetes, individuals with high blood pressure and/or cardiovascular disease; individuals who are obese or overweight (e.g., individual's having a body mass index above 25); individuals who have more fat around their waist than around their hips (an apple shape); age greater than 40 years (although it is understood that children and young adults, particularly those who are overweight and/or sedentary, may also be at risk for developing metabolic syndrome); a woman who had gestational diabetes when pregnant or who has a history of polycystic ovary syndrome (PCOS); individuals who are pre-diabetic and individuals of Latino, Black, Asian or Native American ethnicity.

Further provided herein are methods of determining if an individual suffering from glucose intolerance (e.g., an individual testing negative in a glucose tolerance test) has (i) reduced or impaired insulin secretion or (ii) has reduced or impaired responsiveness to insulin, the method comprising administering a compound provided herein to the individual and testing the individual in a glucose tolerance test, wherein an increase in insulin levels after glucose challenge (the glucose tolerance test) indicates that the individual has reduced or impaired insulin secretion; or wherein insufficient increases in insulin levels indicates that the individual has reduced or impaired responsiveness to insulin.

Provided herein are methods of assessing whether an individual is likely to be responsive to a compound that promotes an increase in insulin secretion and/or release (e.g., an adrenergic receptor $\alpha_{2A}$ antagonist, or pharmaceutically acceptable salt thereof), administered either alone or in conjunction with an insulin sensitizer. In one aspect of such a method, an individual who has failed a glucose tolerance test (e.g., an individual whose glucose levels do not return to normal levels following glucose challenge and/or whose insulin levels are not sufficiently elevated in response to administration of glucose, as measured by methods and as assessed by standards known in the art), is administered glucose following administration of an adrenergic receptor $\alpha_{2A}$ antagonist, or pharmaceutically acceptable salt thereof, and their insulin levels are then assessed. In one embodiment of such methods, the adrenergic receptor $\alpha_{2A}$ antagonist is administered to the individual about any one of 5, 10, 15, 30 and 60 minutes or more or between about 5 and about 15 or between about 5 and about 30 or between about 5 and about 60 or between about 15 and about 30 or between about 30 and about 60 minutes prior to administration of glucose. If such an individual, after administration of glucose and an adrenergic receptor $\alpha_{2A}$ antagonist, or pharmaceutically acceptable salt thereof, exhibits an increase in insulin levels, the individual may be an individual who is responsive to a compound that promotes an increase in insulin secretion and/or release (e.g., an adrenergic receptor $\alpha_{2A}$ antagonist, or pharmaceutically acceptable salt thereof). If such an individual exhibits an increase in insulin levels, but the individual's glucose levels do not decrease, then the individual may be an individual who is responsive to a compound that can increase insulin secretion and/or release (including but not limited to an adrenergic receptor $\alpha_{2A}$ antagonist, or pharmaceutically acceptable salt thereof), used in conjunction with an insulin sensitizer. Sufficient levels of insulin increase and/or glucose decrease are known by those of skill in the art. Thus, a method of assessing whether an individual suffering from glucose intolerance (e.g., an individual who has failed (e.g., within the last 6 months, 3 months, 1 month, 2 weeks or 1 week) a glucose tolerance test administered in the absence of an adrenergic receptor $\alpha_{2A}$ antagonist) is more likely to be responsive or less likely to be responsive to a therapy that can increase insulin secretion and/or release (including but not limited to an adrenergic receptor $\alpha_{2A}$ antagonist, or pharmaceutically acceptable salt thereof), is provided, the method comprising administering an adrenergic receptor $\alpha_{2A}$ antagonist, or pharmaceutically acceptable salt thereof, to the individual and testing the individual in a glucose tolerance test, wherein an increase in insulin levels after glucose challenge (the glucose tolerance test) indicates that the individual is more likely to be responsive to said therapy, and wherein a reduced or insignificant or no increase in insulin levels indicates that the individual is less likely to be responsive to said therapy.

Also provided herein are methods of selecting an individual suffering from glucose intolerance (e.g., an individual who has failed a glucose tolerance test) for a therapy comprising a compound which increases insulin secretion and/or release (e.g. an adrenergic receptor $\alpha_{2A}$ antagonist) based on the levels of insulin and/or glucose of the individual following a glucose tolerance test in which the individual is administered an adrenergic receptor $\alpha_{2A}$ antagonist prior to glucose challenge, wherein an increase in insulin levels after glucose challenge and/or failure of the individual's glucose levels to return to normal selects the individual for said therapy. Thus, a method of selecting an individual for therapy comprising a compound that increases insulin secretion and/or release is provided (e.g., an adrenergic receptor $\alpha_{2A}$ antagonist), the method comprising the steps of (i) administering an adrenergic receptor $\alpha_{2A}$ antagonist to an individual who has failed (e.g., within the last 6 months, 3 months, 1 month, 2 weeks or 1 week) a glucose tolerance test administered in the absence of an adrenergic receptor $\alpha_{2A}$ antagonist; (2) administering a glucose tolerance test in which glucose is administered after the administration of the adrenergic receptor $\alpha_{2A}$ antagonist; and (3) correlating the results of the glucose tolerance test administered in conjunction with the administration of the adrenergic receptor $\alpha_{2A}$ antagonist to the individual (e.g., where glucose is administered about any one of 5, 15, 30, 60 or more minutes following administration of the adrenergic receptor $\alpha_{2A}$ antagonist) with whether the individual is more or less likely to be responsive to an adrenergic receptor $\alpha_{2A}$ antagonist, either alone, or in conjunction with an insulin sensitizer; and (4) selecting an individual who is more likely to be responsive to a compound that increases insulin secretion and/or release (e.g., an adrenergic receptor $\alpha_{2A}$ antagonist for adrenergic receptor $\alpha_{2A}$ antagonist therapy). An individual so selected may then be administered a compound that increases insulin secretion and/or release (e.g., an adrenergic receptor $\alpha_{2A}$ antagonist for adrenergic receptor $\alpha_{2A}$ antagonist therapy). In one aspect, the individual is selected for therapy if their insulin levels increase in response to the glucose tolerance test administered in conjunction with the administration of the adrenergic receptor $\alpha_{2A}$ antagonist. If such an individual also exhibits a normal reduction in glucose levels, the individual may be selected for monotherapy with a compound that increases insulin secretion and/or release (e.g., an adrenergic receptor $\alpha_{2A}$ antagonist). However, if such an individual does not exhibit a normal reduction in glucose levels, the individual may be selected for therapy with a compound that increases insulin secretion and/or release (e.g., an adrenergic receptor $\alpha_{2A}$ antagonist) in conjunction with an insulin sensitizer. Individuals so selected may then be administered a compound that increases insulin secretion and/or release (e.g., an adrenergic receptor $\alpha_{2A}$ antagonist), either alone or in conjunction with an insulin sensitizer. Methods of monitoring the treatment of an individual for glucose intolerance are also provided.

Also provided herein are methods of treating an individual suffering from a disease or condition which is, or is expected to be, responsive to an increase in insulin secretion and/or release, the method comprising (i) determining insulin levels of an individual in a glucose tolerance test after administration of an adrenergic receptor $\alpha_{2A}$ antagonist and (ii) administering a compound that increases insulin secretion and/or release (e.g., an adrenergic receptor $\alpha_{2A}$ antagonist) to an individual having an increase in insulin levels after the glucose tolerance test. In one aspect of such a method, the individual has failed (e.g., recently failed) a glucose tolerance test administered in the absence of an adrenergic receptor $\alpha_{2A}$ antagonist and the individual's insulin levels increase in response to a glucose tolerance test which employed administration of glucose and an adrenergic receptor $\alpha_{2A}$ antagonist.

In any of the methods employing a glucose tolerance test in conjunction with an adrenergic receptor $\alpha_{2A}$ antagonist, in one variation, if the individual's insulin does not increase in response to a glucose challenge in conjunction with an adrenergic receptor $\alpha_{2A}$ antagonist, the individual may have type 2 diabetes with a defect in insulin secretion. Therefore, also provided are methods of identifying individuals who may have type 2 diabetes with a defect in insulin secretion.

Some genetic polymorphisms of the adrenergic receptor $\alpha_{2A}$ gene associate with high blood glucose and can be used to screen for patients who respond to an adrenergic receptor $\alpha_{2A}$ antagonist with an increase in insulin secretion and a decrease in blood glucose. For example the DNA polymorphism Rs553668 located in the 3' UTR region of adrenergic receptor $\alpha_{2A}$ associates with overexpression of the adrenergic receptor $\alpha_{2A}$, reduced insulin secretion, and increased type 2 diabetes risk (Rosengren et al., *Science* 327:217 (2010) and Talmud et al., *Diabetologia* 54:1710 (2011)). Human pancreatic islets from Rs553668 allele carriers exhibited reduced granule docking and secreted less insulin in response to glucose. Individuals with elevated blood glucose would be screened for the polymorphism. Individuals heterozygous or homozygous for this polymorphism would be anticipated to respond to treatment with an adrenergic receptor $\alpha_{2A}$ antagonist. Other DNA polymorphisms may also be used to identify individuals with elevated blood sugar that would respond to an adrenergic receptor $\alpha_{2A}$ antagonist; for example Rs7911129, Rs1971596, Rs602618, and Rs2203616. Thus provided herein is a method of selecting an individual for therapy comprising a compound that (i) increases insulin secretion and/or release, and/or (ii) regulates blood glucose (e.g., an adrenergic receptor $\alpha_{2A}$ antagonist), the method comprising screening the individual for polymorphisms of the adrenergic receptor $\alpha_{2A}$ gene associate with high blood glucose, such as one or more of the DNA polymorphisms Rs553668, Rs7911129, Rs1971596, Rs602618 and Rs2203616.

Also provided is a method of regulating (e.g., reducing and/or stabilizing) blood glucose levels in an individual, the method comprises the steps of (i) screening the individual for genetic polymorphisms of the adrenergic receptor $\alpha_{2A}$ gene associate with high blood glucose; and (ii) administering to the individual carrying one or more genetic polymorphisms of the adrenergic receptor $\alpha_{2A}$ gene associated with high blood glucose an adrenergic receptor $\alpha_{2A}$ antagonist. In one variation, provided is a method of increasing insulin serration and/or release into the blood stream in an individual, the method comprises the steps of (i) screening the individual for genetic polymorphisms of the adrenergic receptor $\alpha_{2A}$ gene associate with high blood glucose; and (ii) administering to the individual carrying one or more genetic polymorphisms of the adrenergic receptor $\alpha_{2A}$ gene associated with high blood glucose an adrenergic receptor $\alpha_{2A}$ antagonist. Further provided are methods of treating type 2 diabetes, glucose intolerance and/or metabolic syndrome, where the method comprises administering to an individual in need thereof an adrenergic receptor $\alpha_{2A}$ antagonist, wherein the individual carries one or more genetic polymorphisms of the adrenergic receptor $\alpha_{2A}$ gene associated with high blood glucose, such as one or more of the DNA polymorphisms Rs553668, Rs7911129, Rs1971596, Rs602618 and Rs2203616. In some embodiments, the adrenergic receptor $\alpha_{2A}$ antagonist also binds to and is an antagonist of one or more of the adrenergic receptors $\alpha_{2B}$, $\alpha_{1B}$ and $\alpha_{1D}$. In some embodiments, the adrenergic receptor $\alpha_{2A}$ antagonist also binds to and is an antagonist of the adrenergic receptors $\alpha_{2B}$. In some embodiments, the method of regulating blood glucose levels, increasing insulin seretion and/or release into the blood stream, or treating type 2 diabetes, glucose intolerance and/or metabolic syndrome, further comprises administering to the individual a second agent that reduces, or is expected to reduce, blood pressure in an individual.

Compounds described herein showing adrenergic receptors $\alpha_{2A}$ and adrenergic receptor $\alpha_{2B}$ antagonist activity may find particular use in patients with fatty liver or/and obesity or/and hypertension with type-2 diabetes associated with glucose intolerance; and super-added with polymorphisms in the adrenergic receptor $\alpha_{2A}$ gene.

Cell Viability and Mitochondrial Health

Methods of promoting cellular viability by promoting mitochondrial health are provided, the methods comprising contacting the cell with a compound detailed herein. The methods are applicable to various cells, such as neuronal and non-neuronal cells. In one variation, the cell is a non-neuronal cell, such as a renal or cardiac cell (e.g., myocardial muscle cell). In one aspect, methods of promoting cellular viability are provided wherein the cell is one whose viability would be, or would be expected to be, promoted by nutrient influx and/or oxygenation. Methods of promoting cellular viability in a cell experiencing, or exhibiting symptoms of, mitochondrial stress are also provided.

Methods of treating a disease or condition that is, or is expected to be, responsive to promoting mitochondrial health and cell viability are also described, the methods comprising administering to an individual in need thereof an effective amount of a compound provided herein. In one variation, the disease or condition is one which is associated with dysfunction of mitochondria in a non-neuronal cell. In a particular variation, the disease or condition is one which is associated with dysfunction of mitochondria in a renal or cardiac cell (e.g., myocardial muscle cell). In another variation, the disease or condition is one which would benefit from cellular (e.g., renal or cardiac) nutrient influx and/or oxygenation.

Thus, individuals who have a disease or condition that is associated with, or believed to be associated with, mitochondrial dysfunction may benefit from the compounds detailed herein, or pharmaceutically acceptable salts thereof. An individual who has a disease or condition that is associated with mitochondrial dysfunction should experience one or more beneficial or desirable results upon administration of an effective amount of a compound provided herein, or pharmaceutically acceptable salt thereof. In one aspect, the beneficial or desirable result is an increase in nutrient influx and/or oxygenation of a cell. In another aspect, the beneficial or desirable result is a reduction in the number and/or severity of symptoms associated with a disease or condition that is associated with mitochondrial dysfunction.

In one variation, a method of treating a renal or cardiac condition is provided, comprising administering to an individual in need thereof a compound as detailed herein. Such conditions include, but are not limited to, renal failure, such as acute renal failure and chronic renal failure, coronary (e.g., myocardial) ischemia, heart failure, such as acute and chronic congestive heart failure (including the muscle fatigue associated with these conditions), and coronary artery disease. Methods of treating other diseases and conditions are also described, such as methods of treating sleep apnea, acute respiratory distress syndrome (adult and infant) and peripheral vascular disease. The compounds as provided herein may also be used in a method of delaying the onset and/or development of a disease or condition associated with mitochondrial dysfunction, comprising administering a compound as provided herein, or a pharmaceutical salt thereof, to an individual who is at risk of developing a disease or condition associated with mitochondrial dysfunction.

Compounds that do not bind appreciably to neurotransmitter receptors but nevertheless enhance mitochondrial function, e.g., when administered to cells in the setting of mitochondrial stress (e.g., excess intracellular calcium), may be used in the methods herein to promote cell survival. In one aspect, the compounds exhibit the ability to enhance mitochondrial function by protecting against cell death mediated by mitochondrial dysfunction in an assay detailed herein. Thus, it is understood and clearly conveyed that enhancing mitochondrial function includes protecting a cell against cell death mediated by mitochondrial dysfunction. The compounds may also be assessed in assays known in the art.

It is understood and clearly conveyed that the binding and activity profiles detailed herein (e.g., in the disclosure above) in one variation apply to the formulae provided herein (e.g., the formulae for use in the methods). In one aspect, compounds of the invention are of the formulae (IA), (IB), (IA1), (IA2), (IA3), (A1), (A2), (A3), (A4), (A5), (B1), (B2), (B3), (B4), (B5), (B6), (B7), (B8), (B9), (B10), (B11), (J-1), (J-2), (J-3), (J-4), (J-5), (J-1a), (J-2a), (J-3a), (J-4a), (J-5a), (K-1), (K-2), (K-3), (K-4), (K-5), (K-1a), (K-2a), (K-3a), (K-4a) and (K-5a).

Compounds of the Invention

Compounds according to the invention are detailed herein, including in the Brief Summary of the Invention and elsewhere. The invention includes the use of all of the compounds described herein, including any and all stereoisomers, including geometric isomers (cis/trans or E/Z isomers), tautomers, salts and solvates of the compounds described herein, as well as methods of making such compounds.

In one aspect, compounds of the formula (IA) are provided:

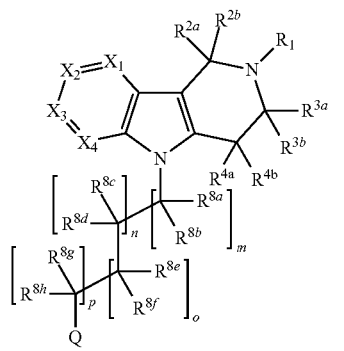

(IA)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$CH$_2$—) moiety or a propylene (—CH$_2$CH$_2$CH$_2$—) moiety, or $R^{4a}$ and $R^{2a}$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)aryl, —S(O)aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$, where present, is independently H, hydroxyl, alkoxy, acyloxy, thiol, —S-alkyl, —S-aryl, —S-aralkyl, —S(O)-alkyl, —S(O)-aryl, —S(O)aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —CR$^9$═CR$^{10a}$R$^{10b}$ or of the structure:

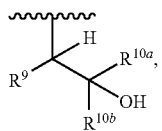

wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety.

In one embodiment, a compound of formula (IA) is provided where the Q group is of the formula —CR$^9$═CR$^{10a}$R$^{10b}$, wherein R$^9$, R$^{10a}$ and R$^{10b}$ are as defined above.

In another embodiment, a compound of formula (IA) is provided where the Q group is of the structure:

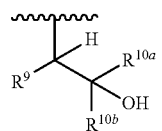

wherein R$^9$, R$^{10a}$ and R$^{10b}$ are as defined above.

In one variation, provided is a compound of the formula (IA) where at least one of X$^1$, X$^2$, X$^3$ and X$^4$ is N. In another variation, one of X$^1$, X$^2$ and X$^3$ is N. In one variation, X$^1$ is N and each X$^2$, X$^3$ and X$^4$ is independently CH or CR$^6$. In another variation, X$^2$ is N and each X$^1$, X$^3$ and X$^4$ is independently CH or CR$^6$. In yet another variation, X$^3$ is N and each X$^1$, X$^2$ and X$^4$ is independently CH or CR$^6$. In yet another variation, X$^4$ is N and each X$^1$, X$^2$ and X$^3$ is independently CH or CR$^6$. In another variation, two of X$^1$, X$^2$, X$^3$ and X$^4$ is N. In one variation, each X$^1$ and X$^3$ is N, and X$^2$ and X$^4$ is CH or CR$^6$. In another variation, each X$^2$ and X$^4$ is N, and X$^1$ and X$^3$ is CH or CR$^6$. In another variation, each X$^1$ and X$^4$ is N, and X$^2$ and X$^3$ is CH or CR$^6$.

In another aspect of the invention, compounds of the formula (IB) are provided:

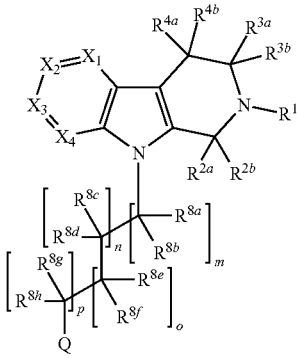

(IB)

or a salt or solvate thereof; wherein:

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or R$^1$ and R$^{2a}$ are taken together to form a propylene (—CH$_2$CH$_2$CH$_2$—) moiety or a butylene (—CH$_2$CH$_2$CH$_2$CH$_2$—) moiety, or R$^1$ and R$^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^{4a}$ are taken together to form an ethylene (—CH$_2$CH$_2$—) moiety or a propylene (—CH$_2$CH$_2$CH$_2$—) moiety;

each R$^{2a}$ and R$^{2b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$CH$_2$—) moiety or a propylene (—CH$_2$CH$_2$CH$_2$—) moiety, or R$^{2a}$ and R$^{4a}$ are taken together to form a methylene (—CH$_2$—) moiety or an ethylene (—CH$_2$CH$_2$—) moiety;

each R$^{3a}$ and R$^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;

each R$^{4a}$ and R$^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;

each m, n, o and p is independently 0 or 1;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)aryl, —S(O)aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$—C cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —$CR^9$=$CR^{10a}R^{10b}$ or of the structure:

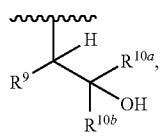

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In a particular embodiment, provided is a compound of formula (IB) where the Q group is of the formula —$CR^9$=$CR^{10a}R^{10b}$, wherein $R^9$, $R^{10a}$ and $R^{10b}$ are as defined above.

In another embodiment, provided is a compound of formula (IB) where the Q group is of the structure:

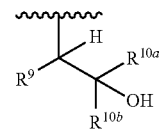

wherein $R^9$, $R^{10a}$ and $R^{10b}$ are as defined above.

In one variation, provided is a compound of the formula (IB) where at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

In another aspect, the invention provides a method of treating a cognitive disorder, psychotic disorder, neurotransmitter-mediated disorder or a neuronal disorder in an individual comprising administering to an individual in need thereof an effective amount of a compound of any formula detailed herein, such as a compound of formulae (IA), (IA1), (IA2), (IA3), (A1), (A2), (A3), (A4), (A5), (IB), (B1), (B2), (B3), (B4), (B5), (B6), (B7), (B8), (B9), (B10), (B11), (J-1), (J-2), (J-3), (J-4), (J-5), (J-1a), (J-2a), (J-3a), (J-4a), (J-5a), (K-1), (K-2), (K-3), (K-4), (K-5), (K-1a), (K-2a), (K-3a), (K-4a) and (K-5a).

In one variation, compounds of formulae (IA) or (IB), or variations herein, are provided, wherein the chain comprising $R^{8a}$, $R^{8b}$, $R^{8c}$, $R^{8d}$, $R^{8e}$, $R^{8f}$, $R^{8g}$, $R^{8h}$ and Q is selected from the following structures:

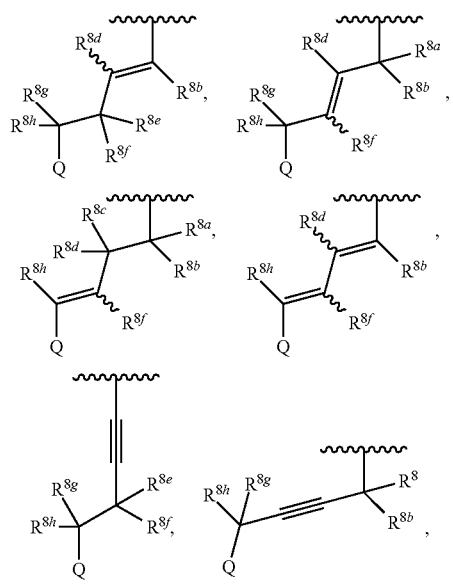

-continued

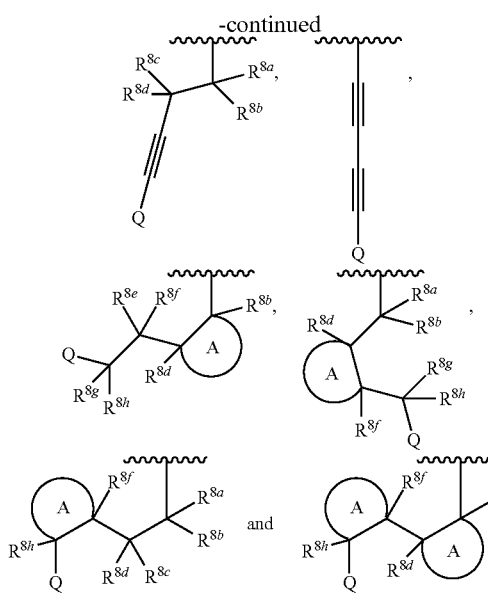

or a salt or solvate thereof, wherein $R^{8a}$, $R^{8b}$, $R^{8c}$, $R^{8d}$, $R^{8e}$, $R^{8f}$, $R^{8g}$, $R^{8h}$ and Q are defined as for formula (IA) or (IB) and ring A comprises a substituted or unsubstituted $C_3$-$C_8$ cycloalkyl, substituted or unsubstituted $C_3$-$C_8$ cycloalkenyl, or substituted or unsubstituted heterocyclyl group.

In another variation, compounds of formulae (IA) or (IB) are provided, or any variation herein, wherein the chain comprising $R^{8a}$, $R^{8b}$, $R^{8c}$, $R^{8d}$, $R^{8e}$, $R^{8f}$, $R^{8g}$, $R^{8h}$ and Q is selected from the following structures:

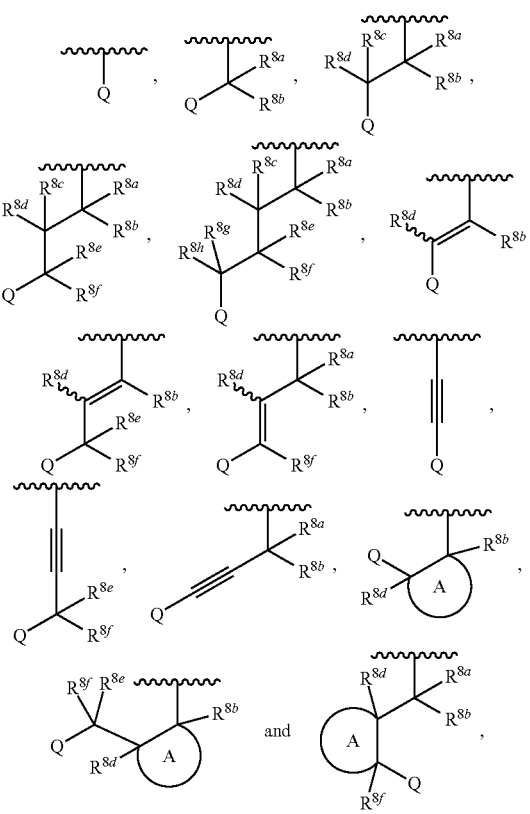

or a salt or solvate thereof, wherein $R^{8a}$, $R^{8b}$, $R^{8c}$, $R^{8d}$, $R^{8e}$, $R^{8f}$, $R^{8g}$, $R^{8h}$ and Q are defined as for formula (IA) or (IB) and ring A comprises a substituted or unsubstituted $C_3$-$C_8$ cycloalkyl, substituted or unsubstituted $C_3$-$C_8$ cycloalkenyl, or substituted or unsubstituted heterocyclyl group. In a particular variation, when o and p are each 0, the chain comprising $R^{8a}$, $R^{8b}$, $R^{8c}$, $R^{8d}$ and Q is selected from the following structures:

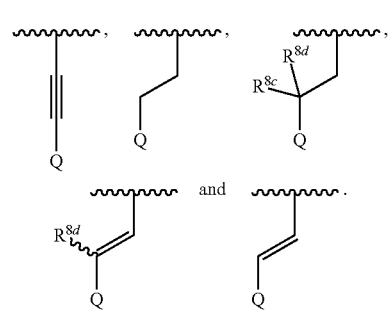

In a particular variation, where ring A depicted above comprises a substituted or unsubstituted $C_3$-$C_8$ cycloalkenyl, the double-bond of the cycloalkenyl ring is at a position other than in the linear chain. For example, if the carbon atoms bearing $R^{8a}$ and $R^{8c}$ are part of a substituted or unsubstituted $C_3$-$C_8$ cycloalkenyl ring, e.g., a ring A depicted above, then the carbon atoms bearing $R^{8a}$ and $R^{8c}$ are connected by a single bond.

In one variation, the compound is of formulae (IA) or (IB), or any variation herein, where at least one of $X^1$-$X^4$ is $CR^6$ where $R^6$ is chloro. In such variation, $X^2$ is $CR^6$ where $R^6$ is chloro. In another variation, $X^2$ is $CR^6$, and $X^1$ and $X^3$ are each CH.

In specific variations, compounds of formula (IA) have the structure:

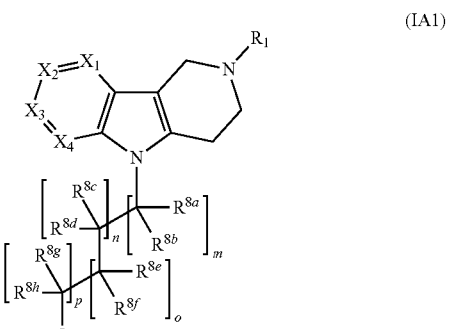

(IA1)

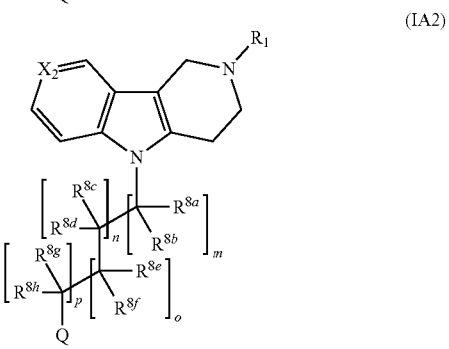

(IA2)

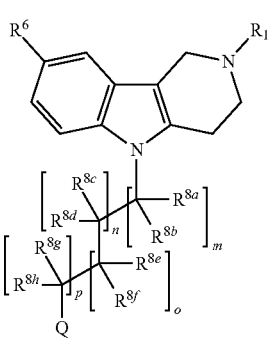

(IA3)

or a salt or solvate thereof, wherein $R^1$, $R^6$, $X^1$, $X^2$, $X^3$, $X^4$, $R^{8(a-h)}$, m, n, o, p and Q are defined as for formula (IA) and, where applicable, any variation thereof detailed herein. That is, variations of formula (IA) detailed throughout, where applicable, apply equally to any of formulae (IA1) to (IA3) the same as if each and every variation were specifically and individually listed for formulae (IA1) to (IA3). Pharmaceutically acceptable salts of compounds of formulae (IA1) to (IA3) are also provided.

In some variations of formula (IA1), at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

In one variation of formula (IA2), $X^2$ is CH or $CR^6$ where $R^6$ is halo or substituted or unsubstituted $C_1$-$C_8$ alkyl. In a particular variation of formula (IA2), $X^2$ is CR where $R^6$ is halo (e.g., chloro). In another particular variation of formula (IA2), $X^2$ is $CR^6$ where $R^6$ is unsubstituted $C_1$-$C_8$ alkyl (e.g., methyl). In a particular variation of formula (IA2), $X^2$ is CH.

In one variation, compounds of the formula (IA3) are provided, or a salt or solvate thereof, where $R^1$ is a substituted or unsubstituted $C_1$-$C_8$ alkyl, and $R^6$ is H, halo, trifluoromethyl, a $C_1$-$C_8$ unsubstituted alkyl or a substituted amino. In one variation of formula (IA3), $R^1$ is an unsubstituted $C_1$-$C_8$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (IA3), $R^1$ is —$CH_3$, —$CH_2CH_2F$, —$CH_2CF_3$, or —$CH_2CH_2C(CH_3)_2OH$. In another variation of formula (IA3), $R^6$ is H, halo, methyl, trifluoromethyl, or a substituted amino of the formula —N(H)($C_1$-$C_8$ unsubstituted alkyl). When $R^6$ is a halo (e.g., fluoro or chloro), in one aspect $R^6$ is chloro. In one variation of formula (IA3), $R^6$ is H, methyl or chloro. In one variation of formula (IA3), $R^6$ is methyl or chloro. When $R^6$ is a substituted amino of the formula —N(H)($C_1$-$C_8$ unsubstituted alkyl), in one aspect $C_1$-$C_8$ unsubstituted alkyl is a linear $C_1$-$C_8$ unsubstituted alkyl such as methyl or ethyl. In a particular variation of formula (IA3), $R^6$ is —N(H)($CH_3$). It is understood that any $R^1$ for formula (IA3) may be combined with any $R^6$ of formula (IA3) the same as if each and every combination were specifically and individually listed. For example, compounds of the formula (IA3) are provided where $R^1$ is —$CH_3$, —$CH_2CH_2F$, —$CH_2CF_3$, or —$CH_2CH_2C(CH_3)_2OH$ and $R^6$ is H, chloro, fluoro, methyl, trifluoromethyl, or —N(H)($CH_3$). Likewise, compounds of the formula (IA3) are provided where $R^1$ is methyl and $R^6$ is H, halo, methyl or a substituted amino of the formula —N(H)($C_1$-$C_8$ unsubstituted alkyl). In one such aspect, compounds of the formula (IA3) are provided where $R^1$ is methyl and $R^6$ is H, halo or methyl. In one such aspect, compounds of the formula (IA3) are provided where $R^1$ is methyl and $R^6$ is halo (e.g., fluoro or chloro), trifluoromethyl, or methyl.

All variations referring to the formulae herein, such as formulae (IA), (IA1), (IA2) and (IA3), where applicable, may apply to formula (IB) the same as if each and every variation were specifically and individually listed.

In specific variations, compounds of formula (IA) have the structure:

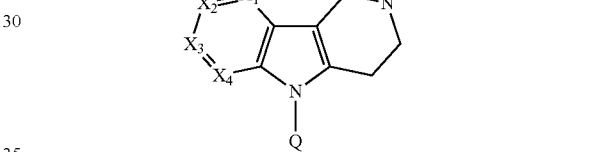

(A1)

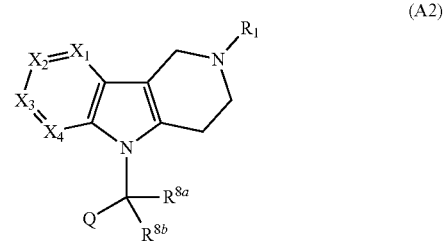

(A2)

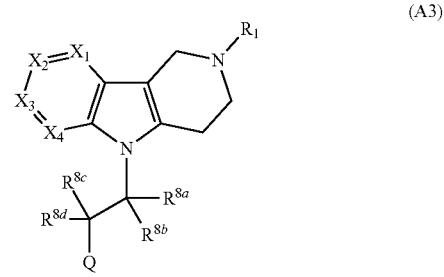

(A3)

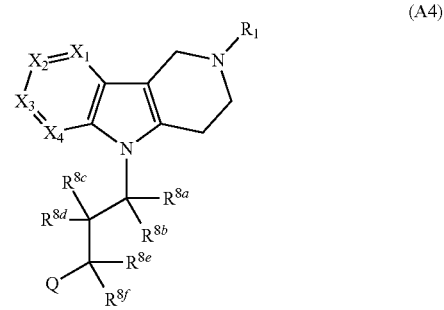

(A4)

-continued

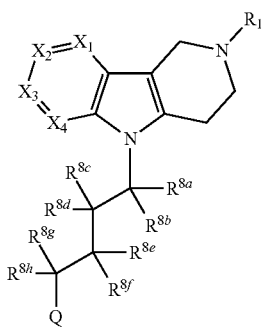
(A5)

or a salt or solvate thereof; wherein $R^1$, $X^1$, $X^2$, $X^3$, $X^4$, $R^{8(a-h)}$ and Q, where present, are defined herein and, where applicable, any variation thereof detailed herein. That is, variations of the formula (IA) detailed throughout, where applicable, apply equally to any of formulae (A1) to (A5) the same as if each and every variation were specifically and individually listed for formulae (A1) to (A5). In one aspect of this invention, at least one of $X^1$, $X^2$, $X^3$ and $X^4$ is N. In another aspect of this invention, at least two of $X^1$, $X^2$, $X^3$ and $X^4$ are N. In another aspect of this variation, both $X^1$ and $X^3$ are N, and $X^2$ is $CR^6$, where $R^6$ is as defined herein. In another aspect of this variation, both $X^2$ and $X^4$ are N. In another aspect of this variation, both $X^1$ and $X^4$ are N, and $X^2$ is $CR^6$, where $R^6$ is as defined herein. Pharmaceutically acceptable salts of compounds of formulae (A1) to (A5) are also provided.

All variations referring to formula (IA), such as formulae (A1) to (A5), where applicable, may apply equally to formula (IB), the same as if each and every variation were specifically and individually listed.

In another variation, compounds of formula (IA) have the structure:

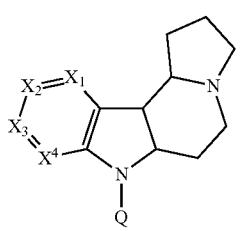
(B1)

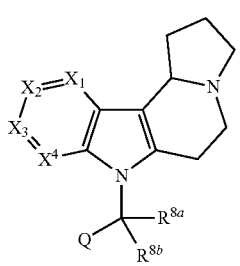
(B2)

-continued

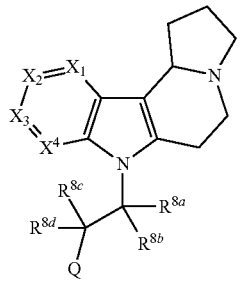
(B3)

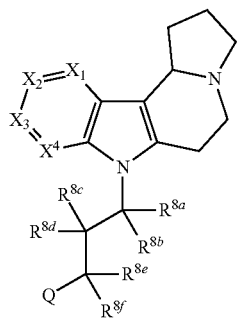
(B4)

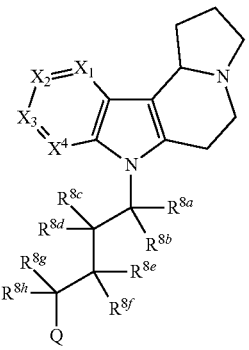
(B5)

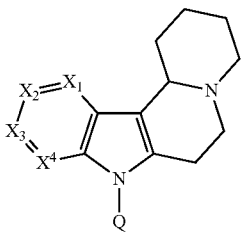
(B6)

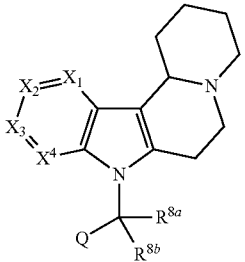
(B7)

(B8)

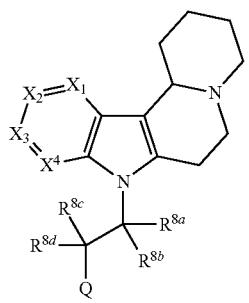

(B9)

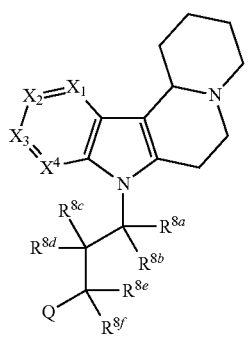

(B10)

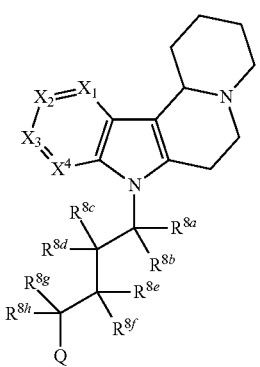

or a salt or solvate thereof; wherein $X^1$, $X^2$, $X^3$, $X^4$, $R^{8(a-h)}$ and Q, where present, are defined herein and, where applicable, any variation thereof detailed herein. That is, variations of the formula (IA) detailed throughout, where applicable, apply equally to any of formulae (B1) to (B11) the same as if each and every variation were specifically and individually listed for formulae (B1) to (B11). In one embodiment, compounds of the formula (IA) are provided wherein the compounds are of the formula (B1) to (B11) except that, instead of $R^1$ of formula (IA) being taken together with $R^{2a}$ of formula (IA) to provide compounds of the formula (B1) to (B11), $R^1$ is taken together with $R^{3a}$ to form a propylene moiety or a butylene moiety. In another embodiment, compounds of the formula (IA) are provided wherein the compounds are of the formula (B1) to (B11) except that, instead of $R^1$ of formula (IA) being taken together with $R^{2a}$ of formula (IA) to provide compounds of the formula (B1) to (B11), $R^1$ is taken together with $R^{4a}$ to form an ethylene moiety or a propylene moiety. In a further embodiment, compounds of the formula (IA) are provided wherein the compounds are of the formula (B1) to (B11) except that, instead of $R^1$ of formula (IA) being taken together with $R^{2a}$ of formula (IA) to provide compounds of the formula (B1) to (B11), $R^{2a}$ and $R^{3a}$ are taken together to form an ethylene moiety or a propylene moiety. In still a further embodiment, compounds of the formula (IA) are provided wherein the compounds are of the formula (B1) to (B10) except that, instead of $R^1$ of formula (IA) being taken together with $R^{2a}$ of formula (IA) to provide compounds of the formula (B1) to (B10), $R^{2a}$ and $R^{4a}$ are taken together to form a methylene moiety or an ethylene moiety. In yet another embodiment, compounds of the formula (IA) are provided wherein the compounds are of the formula (B1) to (B10) except that, instead of $R^1$ of formula (IA) being taken together with $R^{2a}$ of formula (IA) to provide compounds of the formula (B1) to (B10), $R^{3a}$ and $R^{4a}$ are taken together to form a propylene moiety or a butylene moiety. Variations detailed throughout, where applicable, apply to such formulae the same as if each and every variation were specifically and individually listed. Pharmaceutically acceptable salts of such formulae are also provided. In one aspect of this invention, at least one of $X^1$, $X^2$, $X^3$ and $X^4$ is N. In another aspect of this invention, at least two of $X^1$, $X^2$, $X^3$ and $X^4$ are N. In another aspect of this variation, both $X^1$ and $X^3$ are N, and $X^2$ is $CR^6$, where $R^6$ is as defined herein. In another aspect of this variation, both $X^2$ and $X^4$ are N. In another aspect of this variation, both $X^1$ and $X^4$ are N, and $X^2$ is $CR^6$, where $R^6$ is as defined herein. Pharmaceutically acceptable salts of compounds of formulae (B1) to (B11) are also provided.

In another aspect, compounds of the formula (IA) are provided where $X^1$, $X^3$ and $X^4$ are each CH; $X^2$ is $CR^6$; $R^{2b}$, $R^{4a}$, $R^{4b}$ and $R^9$ are each H and the compounds are of the formula (B11):

(B11)

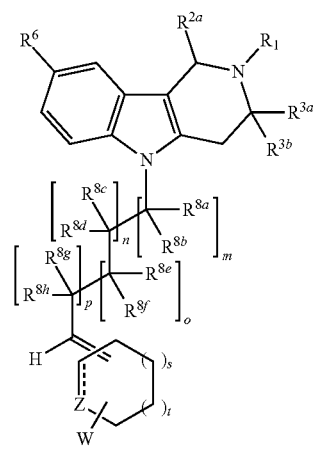

or a salt of solvate thereof, where $R^{8a}$, $R^{8b}$, $R^{8c}$, $R^{8d}$, $R^{8e}$, $R^{8f}$, $R^{8g}$, $R^{8h}$, m, n, o and p are as defined for formula (IA), and wherein:

$R^6$ is selected from the group consisting of a substituted or unsubstituted $C_1$-$C_8$ alkyl, a substituted or unsubstituted $C_3$-$C_7$ cycloalkyl, halo, cyano and trifluoromethyl;

$R^1$ is either (a) selected from the group consisting of H, a substituted or unsubstituted $C_1$-$C_8$ alkyl, a substituted or unsubstituted $C_3$-$C_7$ cycloalkyl, and an alkaryl, wherein the alkaryl is bound to the parent structure via the alkyl portion of the moiety; or (b) is taken together with $R^{2a}$ or $R^{3a}$ to form a propylene or butylene moiety;

$R^{2a}$ is (a) H or an unsubstituted $C_1$-$C_8$ alkyl; (b) taken together with $R^1$ to form a propylene or butylene moiety; or (c) is taken together with $R^{3a}$ to form an ethylene moiety;

$R^{3a}$ and $R^{3b}$ are: (a) independently H or an unsubstituted $C_1$-$C_8$ alkyl or (b) $R^{3b}$ is H and $R^{3a}$ is taken together with $R^1$ to form a propylene or butylene moiety; or (c) $R^{3b}$ is H and $R^{3a}$ is taken together with $R^{2a}$ to form an ethylene moiety;

Z is $CH_2$, O, S, NH, N—$CH_3$ or $CHCH_3$ and the Z-containing ring is bound to the parent structure at any available ring position;

the bond indicated with ---- is a single or double bond;

s and t are independently 0 or 1; and

W is H or is a substituted or unsubstituted aryl, a substituted or unsubstituted cycloalkyl or a substituted or unsubstituted heteroaryl group fused to the Z-containing ring at two adjacent ring positions.

In one aspect of formula (B11), $R^6$ is a substituted or unsubstituted $C_1$-$C_8$ alkyl or halo. In another aspect of formula (B11), $R^1$ is unsubstituted $C_1$-$C_8$ alkyl. In a further aspect, $R^6$ is a substituted or unsubstituted $C_1$-$C_8$ alkyl or halo and $R^1$ is an unsubstituted $C_1$-$C_8$alkyl. In still another aspect, $R^6$ is methyl, fluoromethyl or chloro and $R^1$ is methyl. In any such aspect, the compounds of formula (B11) may be defined by any one or more (where applicable) of the following structural features: (i) Z is $CH^2$; (ii) W is H; (iii) W is an unsubstituted aryl or heteroaryl ring fused to the Z-containing ring; (iv) Z is a substituted or unsubstituted pyridyl moiety; (v) t is 0; (vi) t is 1; and (vii) s and t are both 1; (viii) Z is N or O.

All variations referring to formula (IA), such as formulae (B1) to (B11) and variations thereof, where applicable, may apply to formula (IB), the same as if each and every variation were specifically and individually listed.

In some variations, provided is a compound of any one of the formulae (A1) to (A5) and (B1) to (B10), where at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

The invention also embraces compounds of formulae (J-1) to (J-5):

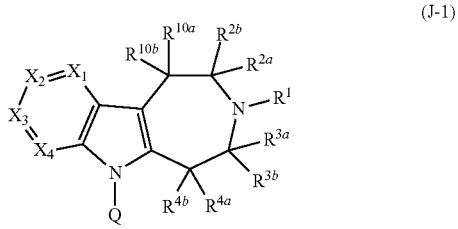
(J-1)

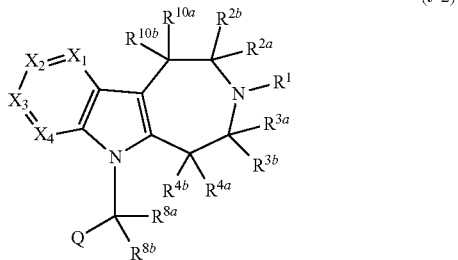
(J-2)

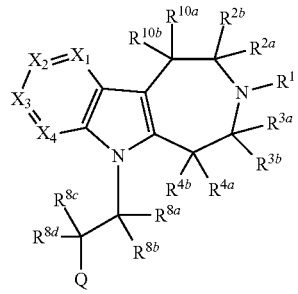
(J-3)

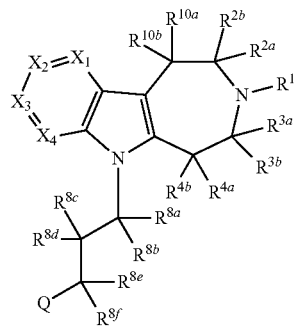
(J-4)

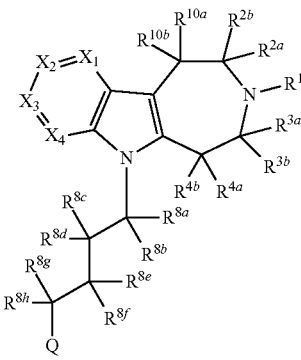
(J-5)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $X^1$, $X^2$, $X^3$ and $X^4$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl; and Q is a group of the formula $CR^9$=$CR^{10a}R^{10b}$ or of the structure:

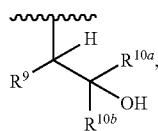

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In some embodiments, compounds of formulae (J-1) to (J-5) are provided where the Q group is of the formula —$CR^9$=$CR^{10a}R^{10b}$, wherein $R^9$, $R^{10a}$ and $R^{10b}$ are as defined above.

In other embodiments, compounds of formulae (J-1) to (J-5) are provided where the Q group is of the structure:

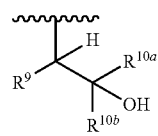

wherein $R^9$, $R^{10a}$ and $R^{10b}$ are as defined above.

In a particular embodiment, compounds formulae (J-1) to (J-5) are provided where at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

In a particular variation, compounds of formulae (J-1) to (J-5) have the structure:

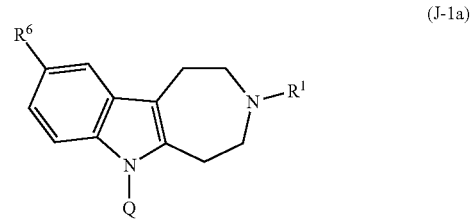
(J-1a)

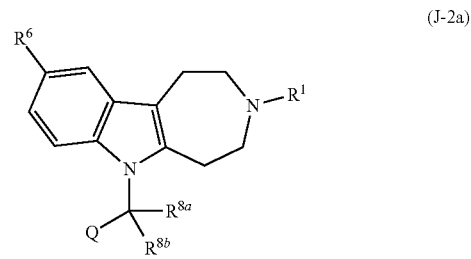
(J-2a)

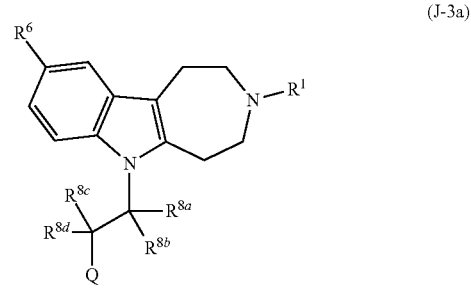
(J-3a)

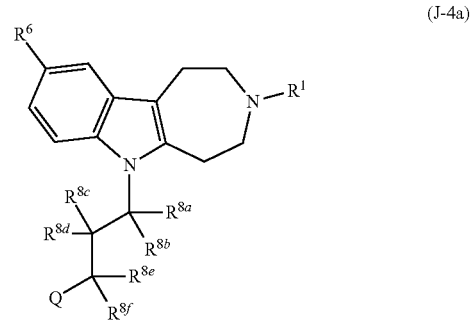
(J-4a)

-continued (J-5a)

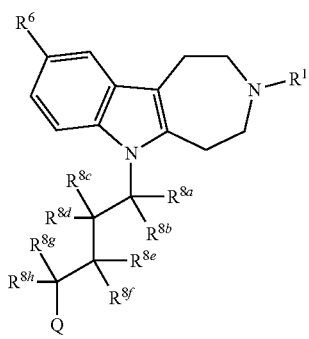

or a salt or solvate thereof, wherein $R^1$, $R^6$, $R^{8a}$, $R^{8b}$, $R^{8c}$, $R^{8d}$, $R^{8e}$, $R^{8f}$, $R^{8g}$ and $R^{8h}$, where present, and Q are defined as for formulae (J-1) to (J-5) and, where applicable, any variation thereof detailed herein. That is, variations of formulae (J-1) to (J-5) detailed throughout, where applicable, apply to formulae (J-1a) to (J-5a) the same as if each and every variation were specifically and individually listed for formulae (J-1a) to (J-5a). Pharmaceutically acceptable salts of compounds of formulae (J-1a) to (J-5a) are also provided.

The invention also embraces compounds of formulae (K-1) to (K-5):

(K-1)

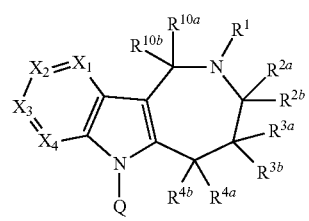

(K-2)

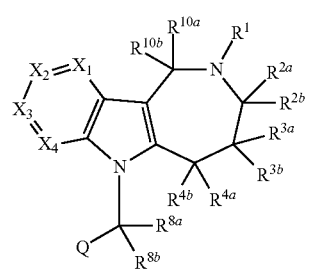

(K-3)

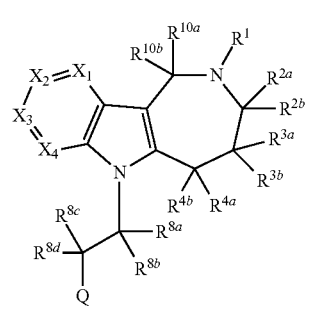

(K-4)

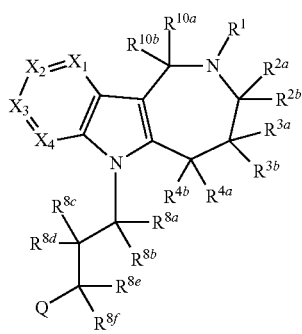

(K-5)

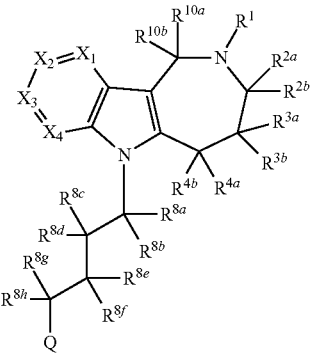

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $X^1$, $X^2$, $X^3$ and $X^4$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl; and Q is a group of the formula —$CR^9$=$CR^{10a}R^{10b}$ or of the structure of:

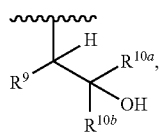

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

In some embodiments, compounds of formulae (K-1) to (K-5) are provided where the Q group is of the formula —$CR^9$=$CR^{10a}R^{10b}$, wherein $R^9$, $R^{10a}$ and $R^{10b}$ are as defined above.

In other embodiments, compounds of formulae (K-1) to (K-5) are provided where the Q group is of the structure:

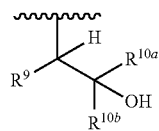

wherein $R^9$, $R^{10a}$ and $R^{10b}$ are as defined above.

In a particular embodiment, compounds formulae (K-1) to (K-5) are provided where at least one of $X^1$, $X^2$, $X^3$ and $X^4$ is N. In another variation, one of $X^1$, $X^2$ and $X^3$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is CH or $CR^6$. In another variation, each $X^2$ and $X^4$ is N, and $X^1$ and $X^3$ is CH or $CR^6$. In another variation, each $X^1$ and $X^4$ is N, and $X^2$ and $X^3$ is CH or $CR^6$.

In a particular embodiment, compounds of formulae (K-1) to (K-5) are provided wherein the ring comprising $X^1$, $X^2$ and $X^3$ is a phenyl, pyridyl, pyrimidinyl or pyrazinyl ring, optionally substituted with 0-2 $R^6$ groups (i.e., $(R^6)_n$ where n is 0, 1 or 2). In some such embodiments, n is 1 or 2 and each $R^6$ is independently halo, methyl or $CF_3$.

In particular variation, compounds of formulae (K-1) to (K-5) have the structure:

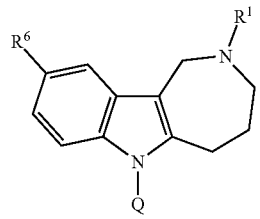
(K-1a)

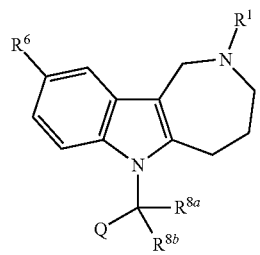
(K-2a)

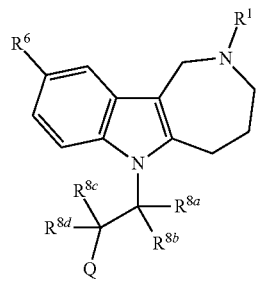
(K-3a)

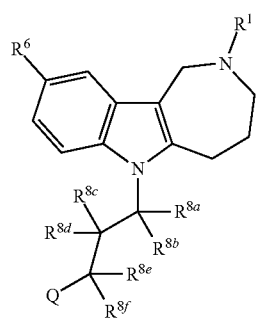
(K-4a)

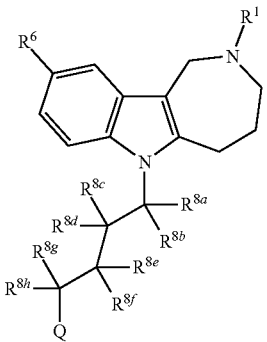
(K-5a)

or a salt or solvate thereof, wherein $R^1$, $R^6$, $R^{8a}$, $R^{8b}$, $R^{8c}$, $R_{8d}$, $R^{8e}$, $R^{8f}$, $R^{8g}$ and $R^{8h}$, where present, and Q are defined as for formulae (K-1) to (K-5) and, where applicable, any variation thereof detailed herein. That is, variations of formulae (K-1) to (K-5) detailed throughout, where applicable, apply to formulae (K-1a) to (K-5a) the same as if each and every variation were specifically and individually listed for formulae (K-1a) to (K-5a). Pharmaceutically acceptable salts of compounds of formulae (K-1a) to (K-5a) are also provided.

In certain embodiments, compounds are provided where $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In specific embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl. In more specific embodiments, $R^1$ is an unsubstituted $C_1$-$C_8$ alkyl such as methyl and cyclopropyl.

In certain embodiments, compounds are provided wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy. In more specific embodiments, $R^1$ is a sulfonyl such as —$SO_2$-alkyl, —$SO_2$-aryl and —$SO_2$-aralkyl.

In certain embodiments, compounds of formulae (IA) or (IB), or any variation herein, are provided where $R^1$ is selected from the following moieties:

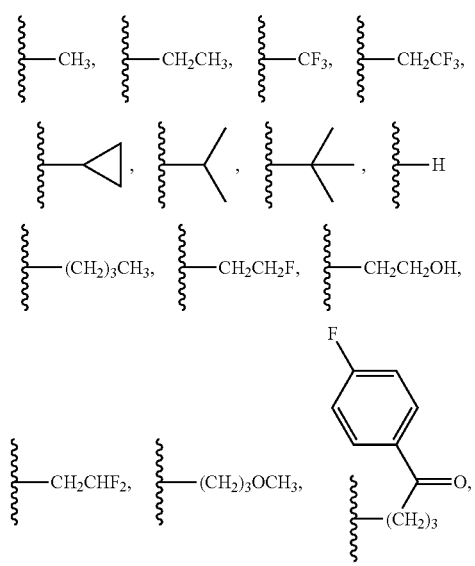

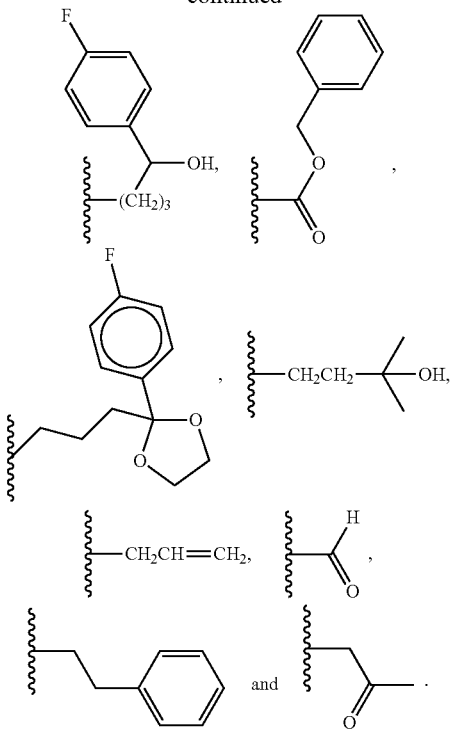

In certain embodiments, compounds are provided where each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{2a}$ and $R^{2b}$ is independently H, methyl, fluoro or $R^{2a}$ and $R^{2b}$ are taken together to form a carbonyl moiety. In a specific embodiment, $R^{2a}$ and $R^{2b}$ are both H.

In certain embodiments, compounds are provided where each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety. In specific embodiments, each $R^{3a}$ and R is independently H or fluoro. In another specific embodiment, $R^{3a}$ and $R^{3b}$ are both H. In a further specific embodiment, $R^{3a}$ and $R^{3b}$ are both H and $R^{2a}$ and $R^{2b}$ are both H.

In certain embodiments, compounds are provided where each $R^{4a}$ and $R^{4b}$ is independently H, substituted or unsubstituted $C_1$-$C_8$ alkyl, halo, cyano, hydroxyl, alkoxy, nitro or $R^{4a}$ and $R^{4b}$ are taken together to form a carbonyl moiety. In specific embodiments, each $R^{4a}$ and $R^{4b}$ is independently H, halo, hydroxyl or methyl or $R^{4a}$ and $R^{4b}$ are taken together to form a carbonyl moiety. In another specific embodiment, $R^{4a}$ and $R^{4b}$ are both H. In a further specific embodiment, $R^{4a}$ and $R^{4b}$ are both H and $R^{2a}$, $R^{2b}$, $R^{3a}$ and $R^{3b}$ are each H.

In certain embodiments, compounds are provided where each $X^1$, $X^2$, $X^3$ and $X^4$ is independently N, CH or $CR^6$. In certain embodiments, each $X^1$, $X^2$, $X^3$ and $X^4$ is CH or $CR^6$, such that the ring comprising $X^1$, $X^2$, $X^3$, and $X^4$ is an optionally substituted phenyl ring. In specific embodiments, $X^2$ is $CR^6$ where $R^6$ is halo or alkyl and $X^1$, $X^3$ and $X^4$ are each CH. In other embodiments, one of $X^1$, $X^2$, $X^3$ and $X^4$ is N, and the others are CH or $CR^6$, such that the ring is an optionally substituted pyridine ring. In further embodiments, two of $X^1$, $X^2$, $X^3$ and $X^4$ are N, and the other is CH or $CR^6$, such that the ring is an optionally substituted pyrimidine or pyrazine ring.

In certain embodiments, compounds are provided where each $R^6$, where present, is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In one variation, at least one of $X^1$-$X^4$ is $CR^6$ where $R^6$ is halo. In a particular variation, one of $X^1$-$X^4$ is $CR^6$ where $R^6$ is chloro and the others are CH. In a specific variation, $X^1$, $X^3$ and $X^4$ are each CH and $X^2$ is $CR^6$ where $R^6$ is chloro.

In certain embodiments, compounds are provided where each $R^6$, where present, is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl. In further embodiments, each $R^6$ is independently hydroxyl, halo, $C_1$-$C_4$ perhaloalkyl, substituted or unsubstituted $C_1$-$C_4$ alkyl, substituted or unsubstituted aryl, substituted or unsubstituted heteroaryl, or $C_1$-$C_4$ alkoxy; or in still a further variation, each $R^6$ is independently halo, unsubstituted $C_1$-$C_4$ alkyl or $C_1$-$C_4$ perhaloalkyl.

In specific embodiments, the ring comprising $X^1$-$X^4$ is a phenyl, pyridyl, pyrimidinyl or pyrazinyl ring, optionally substituted with 0-2 $R^6$ groups (i.e., $(R^6)_n$ where n is 0, 1 or 2). In some such embodiments, n is 1 or 2 and each $R^6$ is independently halo, methyl or $CF_3$.

In some embodiments of formulae (IA) or (IB), or any variation herein, $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; and each $R^{4a}$ and $R^{4b}$ is independently H, halo, hydroxyl or methyl or $R^{4a}$ and $R^{4b}$ are taken together to form a carbonyl moiety. In particular variations of formulae (IA) or (IB), or any variation herein, $R^1$ is an unsubstituted $C_1$-$C_8$ alkyl and $R^{2a}$, $R^{2b}$, $R^{3a}$, $R^{3b}$, $R^{4a}$ and $R^{4b}$ are each H.

In particular embodiments of the formula (IA) or (IB), or any variation herein, each $X^1$, $X^2$, $X^3$ and $X^4$ is CH or $CR^6$. In other embodiments, the compound is of the formula (IA) or (IB), or any variation herein, where at least one of $X^1$, $X^2$, $X^3$ and $X^4$ is N. Another variation provides a compound of the formula (IA) or (IB), or any variation herein, where at least two of $X^1$, $X^2$, $X^3$ and $X^4$ are N. A further variation provides a compound of the formula (IA) or (IB), or any variation herein, where two of $X^1$, $X^2$, $X^3$ and $X^4$ are N and one of $X^1$, $X^2$, $X^3$ and $X^4$ is CH or $CR^6$. Compounds of the formula (IA) or (IB), or any variation herein, where one of $X^1$, $X^2$, $X^3$ and $X^4$ is N and two of $X^1$, $X^2$, $X^3$ and $X^4$ are CH or $CR^6$ are also embraced by this invention.

In another variation, compounds of the invention are provided wherein the ring comprising $X^1$-$X^4$ is an aromatic moiety selected from the following structures:

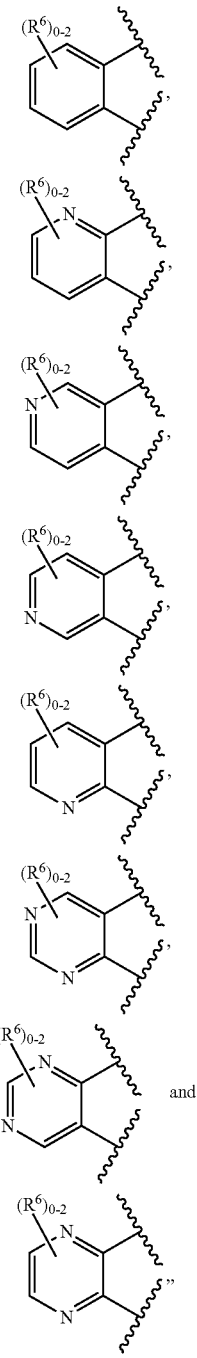

where each $R^6$ is as defined for formula (IA) or (IB). In a particular variation, each $R^6$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^6$ is independently halo, unsubstituted $C_1$-$C_4$ alkyl, $C_1$-$C_4$ perhaloalkyl, or $C_1$-$C_4$ alkoxy.

In still a further variation, compounds of the invention are provided wherein the ring comprising $X^1$-$X^4$ is an aromatic moiety selected from the following structures:

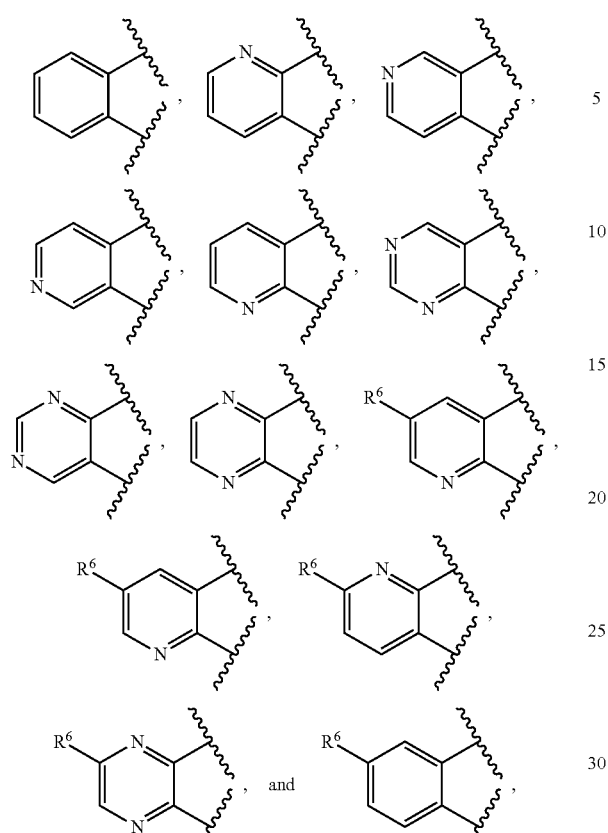

wherein $R^6$ is as defined in formula (IA) or (IB); or in a particular variation, where $R^6$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^6$ is independently halo, unsubstituted $C_1$-$C_4$ alkyl, $C_1$-$C_4$ perhaloalkyl, or $C_1$-$C_4$ alkoxy.

In a further variation, compounds of the invention are provided wherein the ring comprising $X^1$-$X^4$ is an aromatic moiety selected from the following structures:

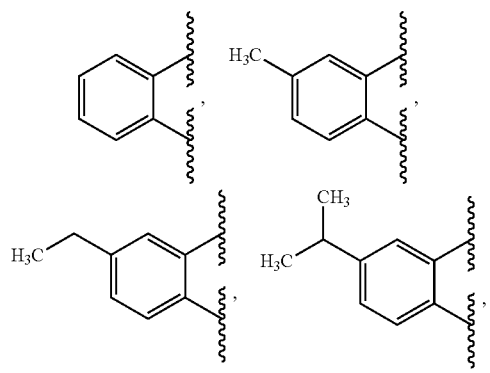

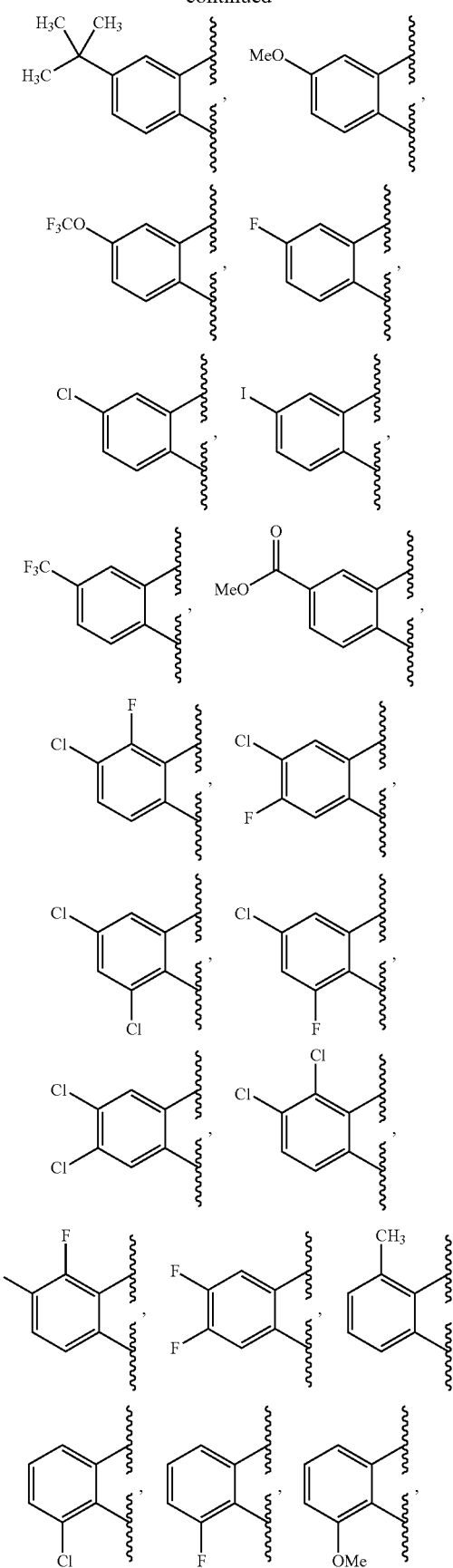

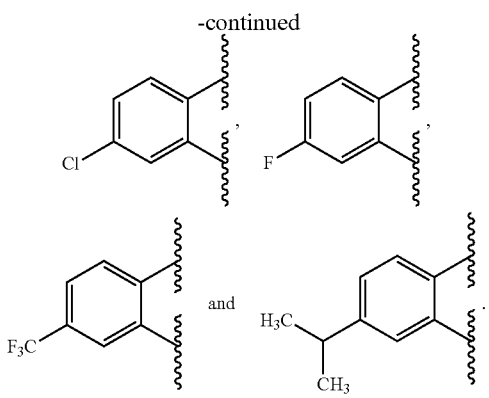

Any formula detailed herein, where applicable, may in one variation have $X^1$, $X^2$, $X^3$ and $X^4$ taken together to provide an aromatic moiety detailed herein above. It is understood that by "where applicable" it is intended that in one variation such $X^1$, $X^2$, $X^3$ and $X^4$ groups are taken together to provide a moiety hereinabove if the formula encompasses such a structure. For example, if a given formula does not encompass structures wherein $X^1$, $X^2$, $X^3$ and $X^4$ groups are taken together provide a pyridyl moiety, then a pyridyl moiety as detailed hereinabove is not applicable to that particular formula, but remains applicable to formulae that do encompass structures where $X^1$, $X^2$, $X^3$ and $X^4$ groups are taken together provide a pyridyl moiety.

In another embodiment, compounds of the invention are provided wherein $X^1$-$X^4$ are as defined in formula (IA) or (IB) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, compounds of the invention are provided wherein $X^1$-$X^4$ are as defined in formula (IA) or (IB) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, compounds of the invention are provided wherein $X^1$-$X^4$ are as defined in formula (IA) or (IB) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is provided where $X^1$-$X^4$ and $R^1$ are as defined herein or as detailed in any variation herein, where $R^{2a}$ and $R^{2b}$ are independently H, substituted or unsubstituted $C_1$-$C_8$ alkyl, halo, cyano, nitro or $R^{2a}$ and $R^{3b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is provided where $X^1$-$X^4$ and $R^1$ are as defined herein or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is provided where $X^1$-$X^4$ and $R^1$ are as defined herein or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention where $X^1$-$X^4$ and R are as defined herein or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety.

The invention further embraces compounds of the invention according to formula (IA) or (IB), or any variation herein, where $X^1$-$X^4$ and $R^1$ are as defined in formula (IA) or (IB) or as detailed in any variation herein, where each $R^{2a}$, $R^{2b}$, $R^{3a}$ and $R^{3b}$ is H. In one variation, compounds of the invention are provided where $X^1$-$X^4$ and $R^1$ are as defined in formula (IA) or (IB) or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety.

In still another variation, compounds of the invention are provided where $X^1$-$X^4$ and $R^1$ are as defined in formula (IA) or (IB) or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety. In another variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety.

The invention also embraces compounds according to formula (IA) or (IB), or any variation herein, where $X^1$-$X^4$, $R^1$, $R^{2a}$, $R^{2b}$, $R^{3a}$ and $R^{3b}$ are as defined in formula (IA) or (IB) or as detailed in any variation herein, where each $R^{4a}$ and $R^{4b}$ is independently H, halo, an unsubstituted $C_1$-$C_8$ alkyl, hydroxyl or $R^{4a}$ and $R^{4b}$ are taken together to form a carbonyl moiety. Also embraced are compounds according to formula (IA) or (IB), or any variation herein, where $X^1$-$X^4$, $R^1$, $R^{2a}$, $R^{2b}$, $R^{3a}$ and $R^{3b}$ are as defined in formula (IA) or (IB) or as detailed in any variation herein, where each $R^{4a}$ and $R^{4b}$ is independently H, halo, an unsubstituted $C_1$-$C_4$ alkyl, hydroxyl or $R^{4a}$ and $R^{4b}$ are taken together to form a carbonyl moiety. In another variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where each $R^{4a}$ and $R^{4b}$ is independently H, bromo, methyl, hydroxyl or $R^{4a}$ and $R^{4b}$ are taken together to form a carbonyl moiety.

In yet another variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where at least one of $R^{4a}$ and $R^{4b}$ is an unsubstituted $C_1$-$C_8$ alkyl, hydroxyl, halo or $R^{4a}$ and $R^{4b}$ are taken together to form a carbonyl moiety. In still a further variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where at least one of $R^{4a}$ and $R^{4b}$ is methyl, bromo, hydroxyl or $R^{4a}$ and $R^{4b}$ are taken together to form a carbonyl moiety.

In another variation, compounds of the invention are provided where $X^1$-$X^4$, $R^1$, $R^2$, $R^{2b}$, $R^{3a}$ and $R^{3b}$ are as defined in formula (IA) or (IB) or as detailed in any variation herein, where both $R^{4a}$ and $R^{4b}$ are methyl. In another variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where $R^{4a}$ and $R^{4b}$ are taken together to form a carbonyl moiety. In another variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where $R^{4a}$ is H and $R^{4b}$ is methyl. In another variation, compounds of the invention are provided where $X^1$-$X^4$, $R^1$, $R^{2a}$, $R^{2b}$, $R^{3a}$ and $R^{3b}$ are as defined in formula (IA) or (IB) or as detailed in any variation herein, where $R^{4a}$ is H and $R^{4b}$ is bromo.

When any carbon of the preceding formulae bearing $R^{2a}$ and $R^{2b}$, or $R^{3a}$ and $R^{3b}$, or $R^{4a}$ and $R^{4b}$, or $R^9$, or $R^{10a}$ and $R^{10b}$ is optically active, it may be in the (R)- or (S)-configuration and compositions comprising substantially pure (R) or (S) compound or mixtures thereof in any amount are embraced by this invention.

In one variation, compounds of the invention are provided wherein the ring comprising N, $R^{2a}$, $R^{2b}$, $R^{3a}$, $R^{3b}$, $R^{4a}$ and $R^{4b}$ is a moiety selected from the following structures:

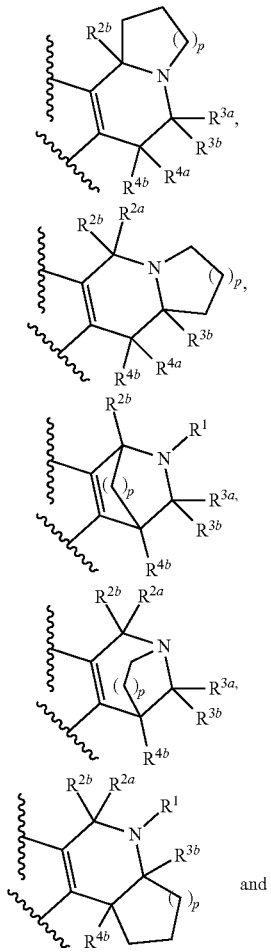

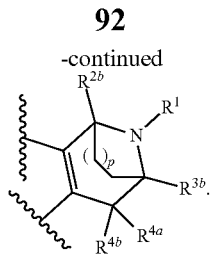

wherein $R^1$, $R^{2a}$, $R^{2b}$, $R^{3a}$, $R^{3b}$, $R^{4a}$ and $R^{4b}$ are as defined for formula (IA) or (IB), and p is 1 or 2.

In another variation, compounds of the invention are provided wherein the ring comprising N, $R^{2a}$, $R^{2b}$, $R^{3a}$, $R^{3b}$, $R^{4a}$ and $R^{4b}$ is a moiety selected from the following structures:

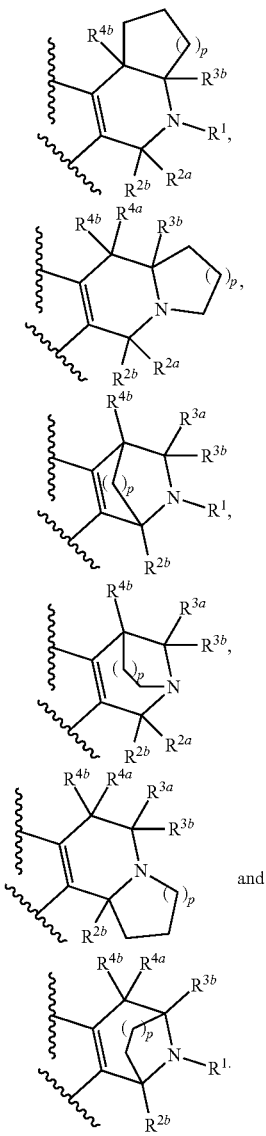

wherein $R^1$, $R^{2a}$, $R^{2b}$, $R^{3a}$, $R^{3b}$, $R^{4a}$ and $R^{4b}$ are as defined for formula (IA) or (IB), and p is 1 or 2.

In another variation, compounds of the invention are provided wherein the ring comprising N, $R^{2a}$, $R^{2b}$, $R^{3a}$, $R^{3b}$, $R^{4a}$ and $R^{4b}$ is a moiety selected from the following structures:

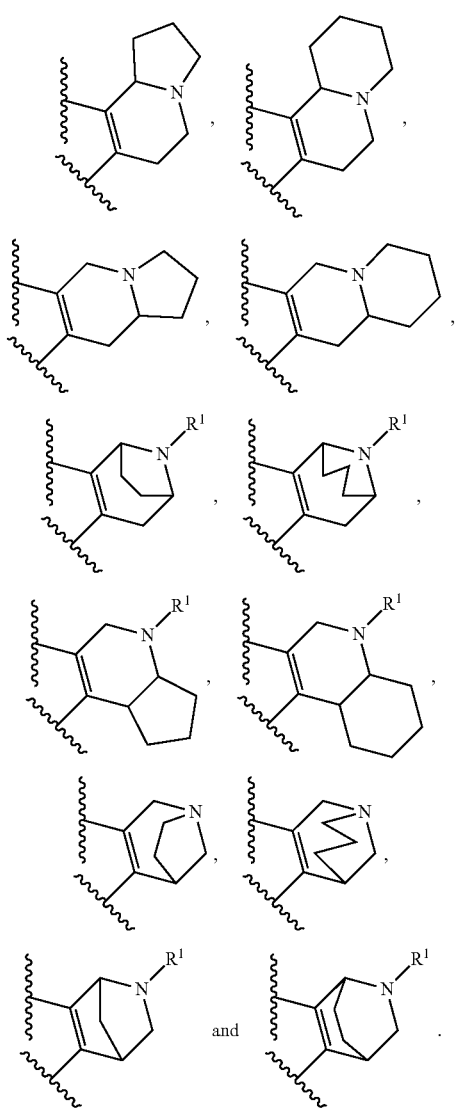

In another variation, compounds of the invention are provided wherein the ring comprising N, $R^{2a}$, $R^{2b}$, $R^{3a}$, $R^{3b}$, $R^{4a}$ and $R^{4b}$ is a moiety selected from the following structures:

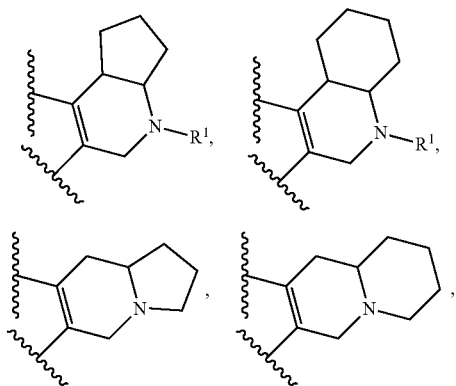

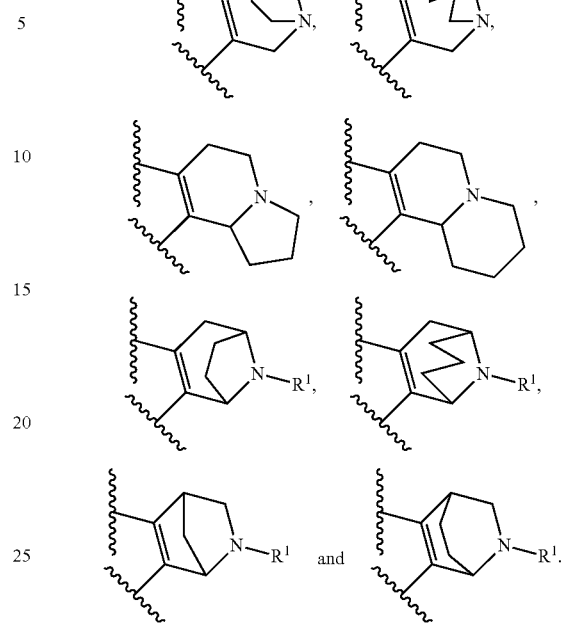

In any one of the variations of compounds of the formulae described herein, all stereoisomers are intended. For example, the ring can be either or

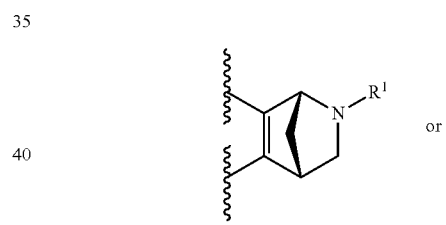

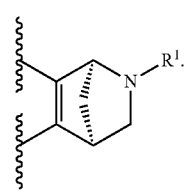

Where more than one stereocenter is present, it is understood that all such stereoisomers are intended. For example, a compound having two stereocenters may be present in the (S),(S); (S),(R); (R),(R); and (R),(S) forms. Compositions comprising a single stereoisomer or mixtures of more than one stereoisomer are also intended. Compositions comprising a mixture of stereoisomers in any ratio are embraced, including mixtures of two or more stereochemical forms of a compound of the invention in any ratio, such that racemic, non-racemic, enantioenriched and scalemic mixtures of a compound are embraced.

In some embodiments, the ring comprising N, $R^{2a}$, $R^{2b}$, $R^{3a}$, $R^{3b}$, $R^{4a}$ and $R^{4b}$ is a moiety selected from the following structures:

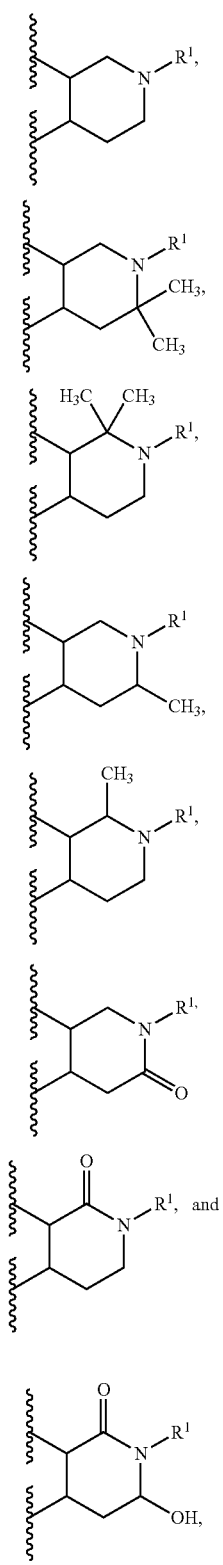

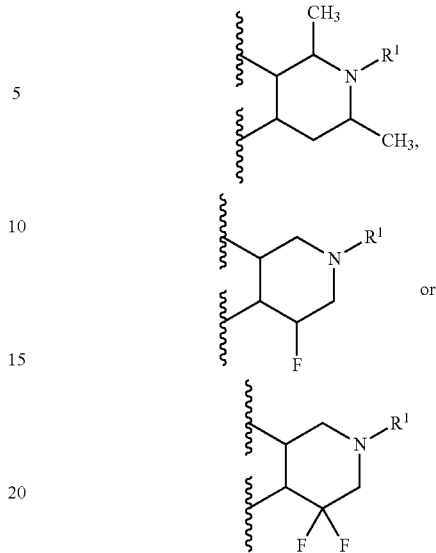

where $R^1$ is as defined for formula (IA) or (IB) or any particular variation detailed herein. Any formula detailed herein, where applicable, may in one variation have a ring according to the structures above.

Compounds according to any formulae detailed herein, such as formulae (IA) or (IB), or any variation of the foregoing, where applicable, in one variation is provided where m, n, o, p, $R^{8a}$, $R^{8b}$, $R^{8c}$, $R^{8d}$, $R^{8e}$, $R^{8f}$, $R^g$ and $R^h$, if present and where applicable, are taken together to form a moiety selected from the group consisting of the structures:

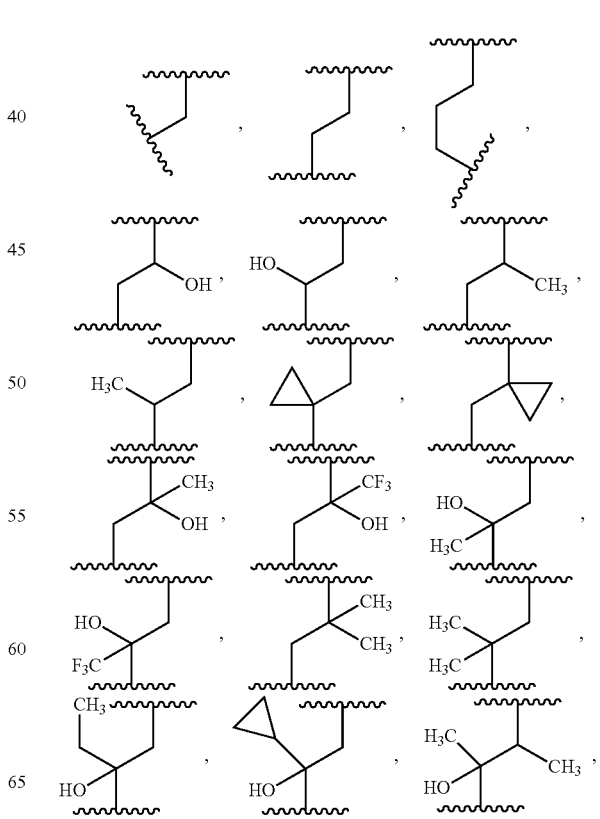

where $R^1$ in the structures above is as defined for formula (IA) or (IB) or any particular variation detailed herein. In some embodiments, the ring comprising N, $R^{2a}$, $R^{2b}$, $R^{3a}$, $R^{3b}$, $R^{4a}$ and $R^{4b}$ is a moiety selected from the following structures:

-continued

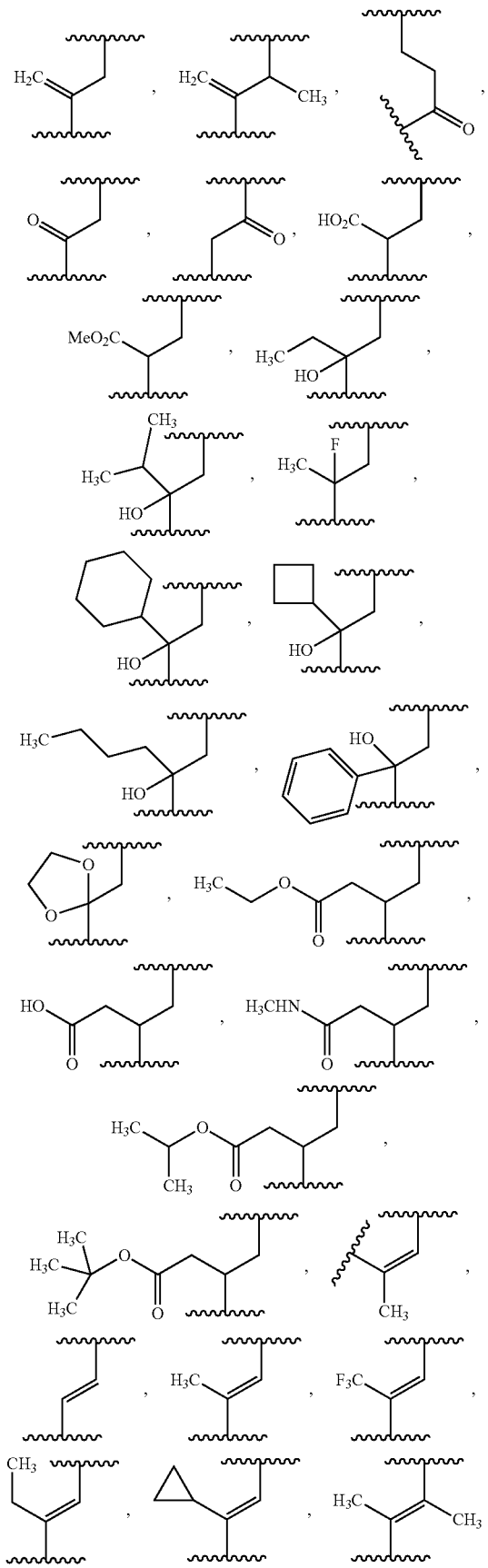

-continued

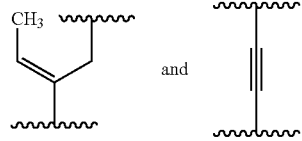

When the above structures are applied to the formulae herein, such as formulae (IA) or (IB) or any variation thereof, it is understood that m, n, o, p, and $R^{8(a-h)}$ where applicable are taken together to form the foregoing moieties, including but not limited to, the structures of this paragraph. Likewise, any formula detailed herein, where applicable, may in one variation have m, n, o, p, and $R^{8(a-h)}$, if present, taken together to form a moiety as detailed herein above, including but not limited to, the structures of this paragraph. It is understood that by "where applicable" it is intended that in one variation such m, n, o, p, and $R^{8(a-h)}$ groups, if present, are taken together to provide a moiety hereinabove if the formula encompasses such a structure. For example, if a given formula does not encompass structures wherein m, n, o, p, and $R^{8(a-h)}$ groups, if present, are taken together to provide a —CH$_2$CH$_2$— moiety, then a —CH$_2$CH$_2$— moiety as detailed hereinabove is not applicable to that particular formula, but remains applicable to formulae that do encompass structures where m, n, o, p, and $R^{8(a-h)}$ groups, if present, are taken together to provide a —CH$_2$CH$_2$— moiety.

In one aspect, at least one of $R^{8(a-h)}$ is a $C_1$-$C_8$ alkyl substituted with a carbonylalkoxy, carboxyl or acylamino moiety.

Compounds according to any formulae detailed herein, such formulae (IA) or (IB), or any variation of the foregoing, where applicable, in one variation are provided where one or more of $R^{8(a-h)}$ and the carbon to which it is attached, together with a vicinal $R^8$ and the carbon to which it is attached, form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

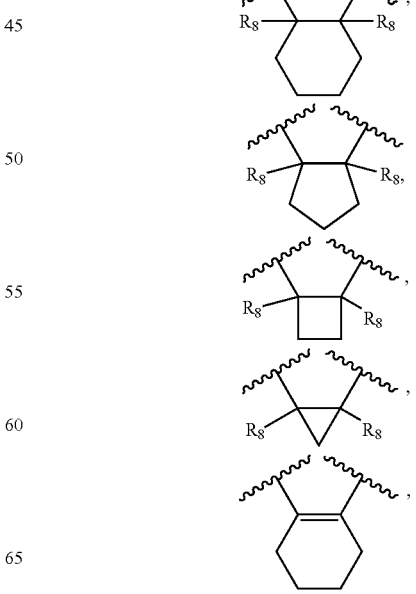

In another variation, any double bond, if present in the cycloalkenyl ring, may also be present at any location in the ring, where chemically feasible, as exemplified above for the cyclopropenyl moiety.
In one variation, a compound of the invention is provided where Q is a moiety selected from the structures:
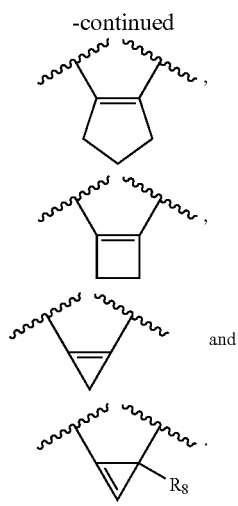
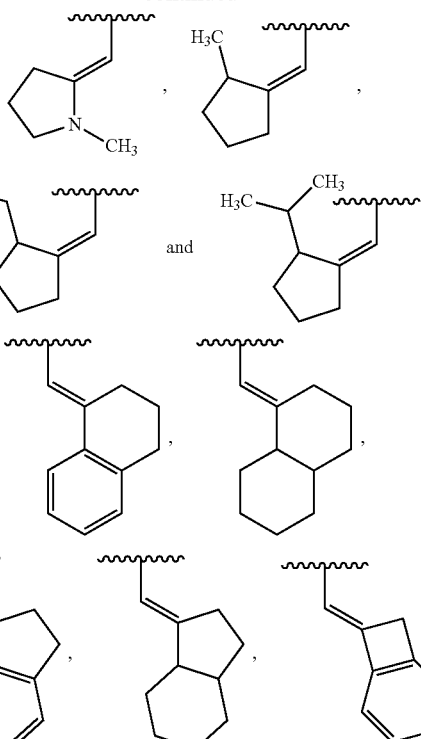

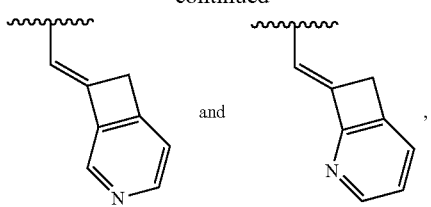

and geometric isomers thereof.

In another variation, a compound of the invention is provided where Q is a moiety selected from the structures:

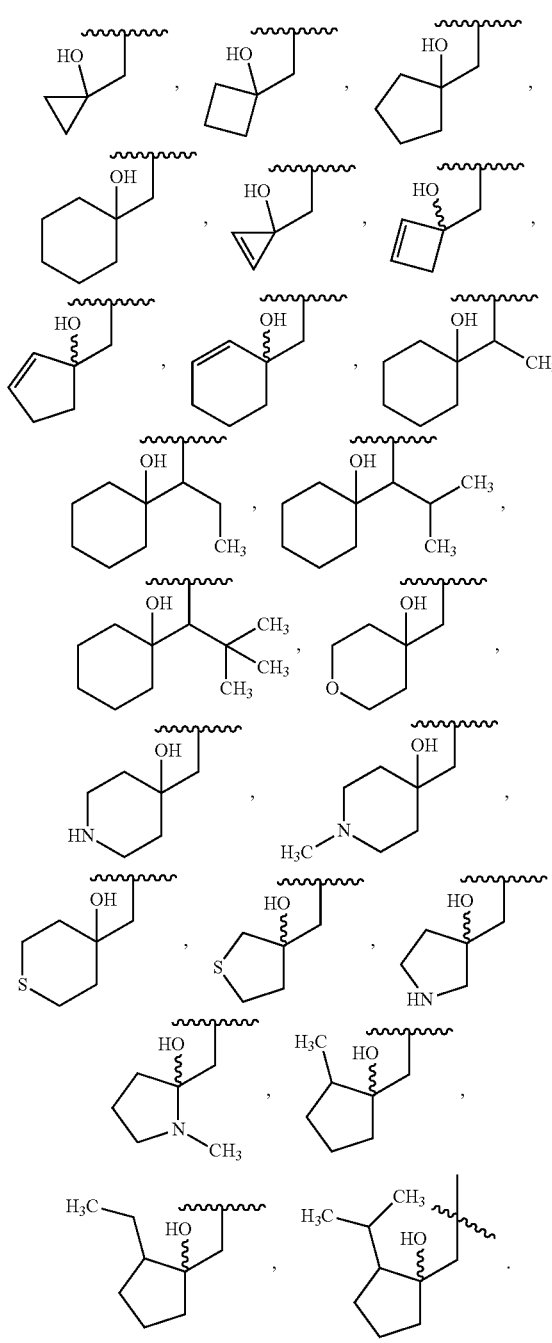

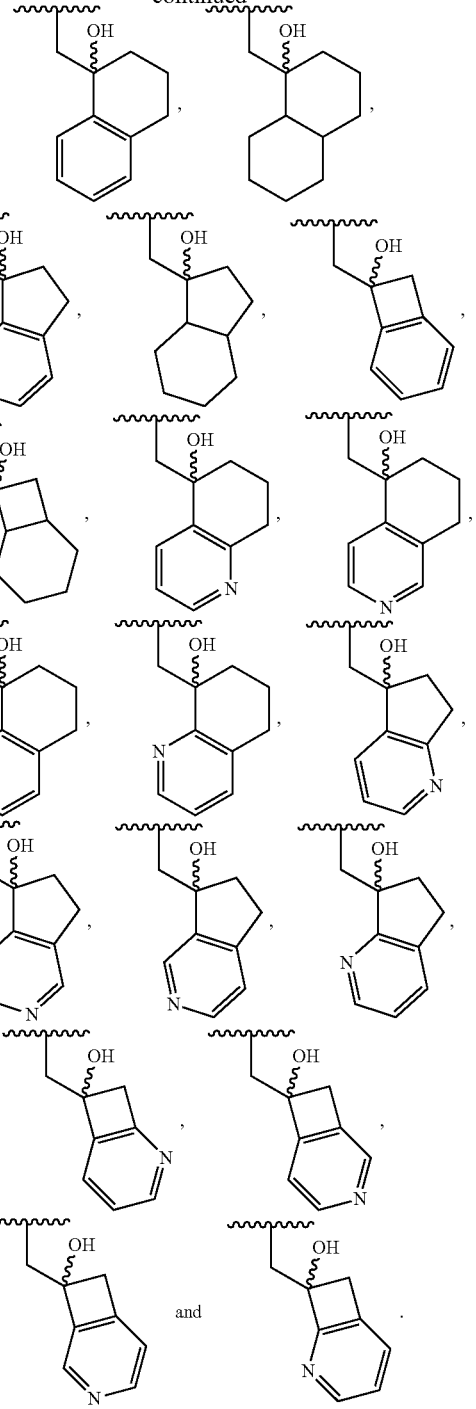

In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is provided where $R^1$ is a substituted or unsubstituted $C_1$-$C_8$ alkyl; each $R^{2a}$, $R^{2b}$, $R^{3a}$ and $R^{3b}$ is independently H or halo; each $R^6$ is independently halo, $C_1$-$C_8$ perhaloalkyl, or substituted or unsubstituted $C_1$-$C_8$ alkyl. The invention also embraces a compound of the formulae (IA) or (IB), or any variation herein where $R^1$ is a methyl; at least one of $X^1$-$X^4$ is $CR^6$, and each $R^6$ is independently halo, methyl or trifluoromethyl. The invention embraces compounds where each Q in any variation detailed is independently substituted with at least one carbonyl, hydroxymethyl, methyl or hydroxyl group, to the extent such substituent makes chemical sense.

In a particular variation, a compound is provided where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; each $R^6$ is independently halo or a substituted or unsubstituted $C_1$-$C_8$ alkyl; each $R^{4a}$ and $R^{4b}$ is independently H, halo, a substituted or unsubstituted $C_1$-$C_8$ alkyl, hydroxyl, alkoxy or $R^{4a}$ and $R^{4b}$ are taken together to form a carbonyl moiety, provided that at least one of $R^{4a}$ and $R^{4b}$ is other than H. In yet another aspect of this variation, $X^1$, $X^2$ and $X^3$ are CH or $CR^6$ and each $R^6$ is independently halo or methyl.

The embodiments and variations described herein are suitable for compounds of any formulae detailed herein, where applicable. For instance, all variations referring to the formula (IA) detailed herein, such as formulae (IA1), (IA2), (IA3), (A1), (A2), (A3), (A4), (A5), (IB), (B1), (B2), (B3), (B4), (B5), (B6), (B7), (B8), (B9), (B10) and (B11), where applicable, may apply to formulae (IB), (J-1), (J-2), (J-3), (J-4), (J-5), (J-1a), (J-2a), (J-3a), (J-4a), (J-5a), (K-1), (K-2), (K-3), (K-4), (K-5), (K-1a), (K-2a), (K-3a), (K-4a) and (K-5a) the same as if each and every variation were specifically and individually listed. In another instance, all variations referring to the formulae herein, such as formulae (IA), (IA1), (IA2) and (IA3), where applicable, may apply to formula (A1), (A2), (A3), (A4), (A5), (IB), (B1), (B2), (B3), (B4), (B5), (B6), (B7), (B8), (B9), (B10), (B11), (J-1), (J-2), (J-3), (J-4), (J-5), (J-1a), (J-2a), (J-3a), (J-4a), (J-5a), (K-1), (K-2), (K-3), (K-4), (K-5), (K-1a), (K-2a), (K-3a), (K-4a) and (K-5a) the same as if each and every variation were specifically and individually listed.

In one embodiment, the invention relates to Compounds described in Tables 1 and 2, and uses thereof.

In another embodiment, the invention relates to Compound Nos. i-1, i-2, i-3, i-4, i-5, i-6, i-7, i-8, i-10, i-11, i-11a, i-11b, i-12, i-12a, i-12b, i-12c, i-12d, i-13, i-13a, i-13b, i-14, i-14a, i-14b, i-14c, i-14d, i-15, i-15a, i-15b, i-16, i-16a, i-16b, i-16c, i-16d, i-17, i-17a, i-17b, i-18, i-19, i-19a, i-19b, i-19c, i-19d, i-20, i-20a, i-20b, i-21, i-22, i-22a, i-22b, i-22c, i-22d, i-23, i-24, i-24a, i-24b, i-24c, i-24d, i-25, i-26, i-27, i-28, i-29, i-30, i-31, i-32, i-33, i-34, i-35, i-36, i-37, i-38, i-39, i-40, i-41, i-42, i-43, i-44, i-45, i-46, i-47, i-48. i-49, i-50, i-51, i-52, i-53, i-54, i-55, i-56, i-57, i-58, i-59, i-59a, i-59b, i-60, i-60a, i-60b, i-61, i-61a, i-61b, i-62, i-62a, i-62b, i-63, i-63a, i-63b, i-64, i-64a, i-64b, i-65, i-65a, i-65b, i-66, i-66a, i-67, i-67a, i-67b, i-68, i-68a, i-68b, i-69, i-69a, i-69b, i-70, i-70b, i-71, i-72, i-73, i-74, i-75, i-76, i-77, i-78, i-79, i-80, i-80a, i-80b, i-81, i-81a, i-81b, i-82, i-82a, i-82b, i-83, i-83a, i-83b, i-84, i-84a, i-84b, i-85, i-86, i-86a, i-86b, i-87, i-87a, i-87b, i-88, i-88a, i-88b, i-89, i-90, i-90a, i-90b, i-91, i-91a, i-91b, i-92, i-93, i-93a, i-93b, i-94, i-94a, i-94b, i-95, i-95a, i-95b, i-96, i-96a, i-96b, i-97, i-97a, i-97b, i-98, i-99, i-100, i-101, i-102, i-102a, i-102b, i-102c, i-102d, i-103, i-104, i-105, i-106, i-107, i-108, i-109, i-110, i-111, i-112, ii-1, ii-2, ii-2a, ii-2b, ii-4, ii-5, ii-6, ii-7, ii-8, ii-10, ii-11, ii-11a, ii-11b, ii-12, ii-12a, ii-12b, ii-12c, ii-12d, ii-13, ii-13a, ii-13b, ii-13c, ii-13d, ii-14, ii-14a, ii-14b, ii-14c, ii-14d, ii-14e, ii-14f, ii-14g, ii-14h, ii-15, ii-15a, ii-15b, ii-16, ii-16a, ii-16b, ii-16c, ii-16d, ii-16e, ii-16f, ii-16g, ii-16h, ii-17, ii-17a, ii-17b, ii-18, ii-19, ii-19a, ii-19b, ii-19c, ii-19d, ii-20, ii-20a, ii-20b, ii-21, ii-22, ii-22a, ii-22b, ii-22c, ii-22d, ii-22e, ii-22f, ii-22g, ii-22h, ii-23, ii-23a, ii-23b, ii-24, ii-24a, ii-24b, ii-24c, ii-24d, ii-24e, ii-24f, ii-24g, ii-24h, ii-25, ii-25a, ii-25b, ii-26, ii-27, ii-27a, ii-27b, ii-28, ii-28a, ii-28b, ii-29, ii-29a, ii-29b, ii-30, ii-30a, ii-30b, ii-31, ii-31a, ii-31b, ii-32, ii-32a, ii-32b, ii-33, ii-33a, ii-33b, ii-34, ii-34a, ii-34b, ii-35, ii-35a, ii-35b, ii-36, ii-36a, ii-36b, ii-37, ii-37a, ii-37b, ii-38, ii-38a, ii-38b, ii-39, ii-39a, ii-39b, ii-40, ii-40a, ii-40b, ii-41, ii-41a, ii-41b, ii-42, ii-42a, ii-42b, ii-43, ii-43a, ii-43b, ii-43c, ii-43d, ii-44, ii-44a, ii-44b, ii-44c, ii-44d, ii-45, ii-45a, ii-45b, ii-45c, ii-45d, ii-46, ii-46a, ii-46b, ii-46c, ii-46d, ii-47, ii-47a, ii-47b, ii-47c, ii-47d, ii-48, ii-48a, ii-48b, ii-48c, ii-48d, ii-49, ii-49a, ii-49b, ii-50, ii-50a, ii-50b, ii-51, ii-51a, ii-51b, ii-52, ii-52a, ii-52b, ii-53, ii-53a, ii-53b, ii-54, ii-54a, ii-54b, ii-54c, ii-54d, ii-55, ii-55a, ii-55b, ii-55c, ii-55d, ii-56, ii-56a, ii-56b, ii-56c, ii-56d, ii-57, ii-57a, ii-57b, ii-57c, ii-57d, ii-58, ii-58a, ii-58b, ii-58c, ii-58d, ii-59, ii-59a, ii-59b, ii-59c, ii-59d, ii-59e, ii-59f, ii-59g, ii-59h, ii-60, ii-60a, ii-60b, ii-60c, ii-60d, ii-61, ii-61a, ii-61b, ii-61c, ii-61d, ii-62, ii-62a, ii-62b, ii-62c, ii-62d, ii-63, ii-63a, ii-63b, ii-63c, ii-63d, ii-64, ii-64a, ii-64b, ii-64c, ii-64d, ii-65, ii-65a, ii-65b, ii-65c, ii-65d, ii-66, ii-66a, ii-66b, ii-66c, ii-66d, ii-67, ii-67a, ii-67b, ii-67c, ii-67d, ii-68, ii-68a, ii-8b, ii-68c, ii-68d, ii-69, ii-69a, ii-69b, ii-69c, ii-69d, ii-70, ii-70a, ii-70b, ii-70c, ii-70d, ii-71, ii-71a, ii-71b, ii-72, ii-72a, ii-72b, ii-73, ii-73a, ii-73b, ii-74, ii-74a, ii-74b, ii-75, ii-75a, ii-75b, ii-76, ii-76a, ii-76b, ii-77, ii-77a, ii-77b, ii-78, ii-78a, ii-78b, ii-79, ii-79a, ii-79b, ii-80, ii-80a, ii-80b, ii-80c, ii-80d, ii-81, ii-81a, ii-81b, ii-81c, ii-81d, ii-82, ii-82a, ii-82b, ii-82c, ii-82d, ii-83, ii-83a, ii-83b, ii-83c, ii-83d, ii-84, ii-84a, ii-84b, ii-84c, ii-84d, ii-85, ii-85a, ii-85b, ii-86, ii-86a, ii-86b, ii-86c, ii-86d, ii-87, ii-87a, ii-87b, ii-87c, ii-87d, ii-88, ii-88a, ii-88b, ii-88c, ii-88d, ii-89, ii-89a, ii-89b, ii-90, ii-90a, ii-90b, ii-90c, ii-90d, ii-91, ii-91a, ii-91b, ii-91c, ii-91d, ii-92, ii-92a, ii-92b, ii-93, ii-93a, ii-93b, ii-93c, ii-93d, ii-94, ii-94a, ii-94b, ii-94c, ii-94d, ii-95, ii-95a, ii-95b, ii-95c, ii-95d, ii-96, ii-96a, ii-96b, ii-96c, ii-96d, ii-97, ii-97a, ii-97b, ii-97c, ii-97d, ii-98, ii-98a, ii-98b, ii-99, ii-99a, ii-99b, ii-100, ii-100a, ii-100b, ii-101, ii-102, ii-102a, ii-102b, ii-102c, ii-102d, ii-102e, ii-102f, ii-102g, ii-102h, ii-103, ii-103a, ii-103b, ii-104, ii-104a, ii-104b, ii-105, ii-105a, ii-105b, ii-106, ii-106a, ii-106b, ii-107, ii-107a, ii-107b, ii-108, ii-108a, ii-108b, ii-109, ii-109a, ii-109b, ii-110, ii-110a, ii-110b, ii-111, ii-111a, ii-111b, ii-112, ii-112a, ii-112b, ii-113, ii-113a and ii-113b, and uses thereof.

In another embodiment, the invention relates to Compound Nos. i-1, i-2, i-3, ii-2, ii-2a, ii-2b, ii-74, ii-74a, ii-74b, ii-111, ii-111a, ii-111b, ii-112, ii-112a, ii-112b, ii-113, ii-113a and ii-113b, and uses thereof.

In one embodiment, the invention embraces compounds detailed herein provided that the compound is other than dimebon and metabolites of dimebon. In another embodiment, the invention embraces dimebon or a salt thereof for uses detailed herein. In another embodiment, the invention embraces a dimebon metabolite or salt thereof for uses detailed herein, such as use in therapy, e.g., to increase insulin secretion and treat diseases or conditions that are, or are expected to be, responsive to an increase in insulin production, or to treat type 2 diabetes.

The embodiments and variations described herein are suitable for compounds of any formulae detailed herein, where applicable.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, the composition of "substantially pure" compound contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a cognitive disorder, psychotic disorder, neurotransmitter-mediated disorder or a neuronal disorder.

Articles of manufacture comprising a compound of the invention, or a salt or solvate thereof, in a suitable container are provided. The container may be a vial, jar, ampoule and the like.

In one embodiment, the invention embraces compounds detailed herein provided that the compound is other than dimebon and metabolites of dimebon. In another embodiment, the invention embraces dimebon or a salt thereof for uses detailed herein. In another embodiment, the invention embraces a dimebon metabolite or salt thereof for uses detailed herein, such as use in therapy, e.g., to (i) reduce blood pressure and/or (ii) promote renal blood flow and/or (iii) decrease or inhibit sodium reabsorption.

The embodiments and variations described herein are suitable for compounds of any formulae detailed herein, where applicable.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. For example, when a 2-hydroxypyridyl moiety is depicted, the corresponding 2-pyridone tautomer is also intended. The tautomeric forms specifically depicted may or may not be the predominant forms in solution or when used according to the methods described herein.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a disease or condition for which a reduction in blood pressure and/or promoting renal blood flow and/or inhibiting or decreasing sodium reabsorption is expected to be or is beneficial.

Articles of manufacture comprising a compound of the invention, or a salt or solvate thereof, in a suitable container are provided. The container may be a vial, jar, ampoule and the like.

In one aspect, a compounds detailed herein as provided herein exhibits the ability to cross the blood-brain barrier. In another aspect, a compounds detailed herein as provided herein is not able to cross the blood-brain barrier. In one aspect, a compounds detailed herein as provided herein exerts its therapeutic effect in the brain only. In one aspect, a compounds detailed herein as provided herein exerts its therapeutic effect in the periphery only. In one aspect, a compounds detailed herein as provided herein exerts its therapeutic effect both in the brain and peripherally. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

Blood brain barrier permeability can be measured in rodents or dog by administering the compound orally or intravenously, recovering a blood and brain tissue sample at different time points and comparing how much compound is in each sample. Blood fraction is typically processed to plasma for determination of compound content. Brain exposure can be described from the ratio of brain to plasma levels of drug. In one variation, a compound that poorly crosses the blood brain barrier has a brain to plasma ratio of compound of about 0.1 or less. In another variation, the compound has a brain to plasma ratio of about 0.2 or less, about 0.3 or less, about 0.4 or less, about 0.5 or less, about 0.8 or less, or about 1.0 or less.

Preferably, the compounds detailed herein are orally bioavailable. However, the compounds may also be formulated for parenteral (e.g., intravenous) administration. In some settings, parenteral administration of an adrenergic receptor $\alpha_{2B}$ antagonists (e.g., selective adrenergic receptor $\alpha_{2B}$ antagonist) may be desired. For example, intra-renal delivery may offer treatment options for acute and chronic renal failure, end stage renal failure and acute decompensated congestive heart failure. Parenteral formulation may be preferred in the treatment of hypertensive urgency and emergency. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., reducing the blood pressure of an individual, promoting renal blood flow and/or decreasing or inhibiting sodium reabsorption.

Methods as provided herein may comprise administering to an individual a pharmacological composition that contains an effective amount of a compound and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Compositions comprising a compound provided herein are also described. In one variation, the composition comprises a compound and a pharmaceutically acceptable carrier or excipient. In another variation, a composition of substantially pure compound is provided.

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for any one or more of the following uses: treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention also provides compositions (including pharmacological compositions) as described herein for the use in treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption and other methods described herein.

In one aspect, compounds provided herein may have any one or more of the following beneficial effects on an individual: (1) reduce arterial blood pressure (e.g., in an individual with hypertension, certain forms of heart failure and/or renal failure); (2) reduce pulse pressure (e.g., in an individual with hypertension, certain forms of heart failure and/or renal failure); (3) tachycardia-preserved baroreceptor activity (e.g., in an individual whose systolic blood pressure is expected to or does fall in response to an $\alpha_{2B}$ antagonist), which may suggest a lack of orthostatic hypotension; and (4) bradycardia-reduced cardiac work load and added reduction on blood pressure reduction by further reducing cardiac output (e.g., in an individual who has been administered a therapy that is an $\alpha_{2B}$ and $\alpha_{1B}$ mixed antagonist).

The invention also provides compositions (including pharmacological compositions) as described herein for the use in treating, preventing, and/or delaying the onset and/or development of diabetes type 2 and/or a disease or condition which is responsive, or expected to be responsive, to an increase in insulin secretion and other methods described herein.

Representative compounds of the invention are shown in Tables 1 and 2.

TABLE 1

Representative Compounds of the Invention

| Compound No. | Structure |
|---|---|
| i-1 | 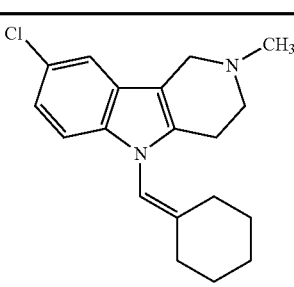 |

TABLE 1-continued
Representative Compounds of the Invention
| Compound No. | Structure |
|---|---|
| i-2 | 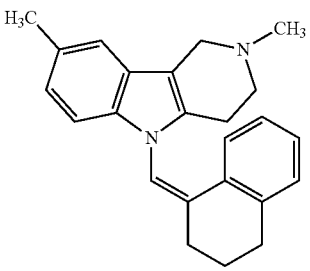 [SMILES: Cc1ccc2c(c1)c1c(n2/C=C2/CCCc3ccccc32)CCN(C)C1] |
| i-3 | 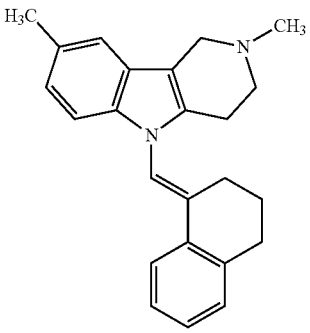 |
| i-4 | 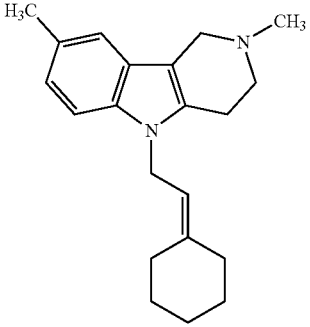 |
| i-5 | 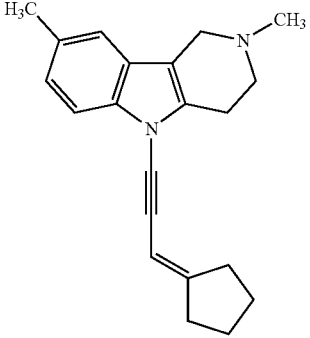 |
| i-6 | 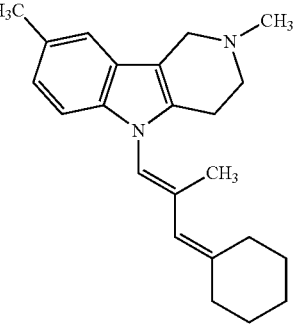 |
| i-7 | 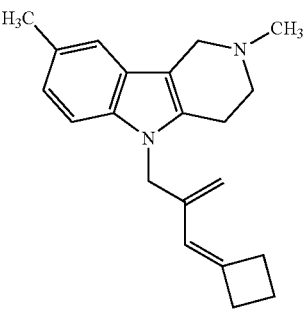 |
| i-8 | 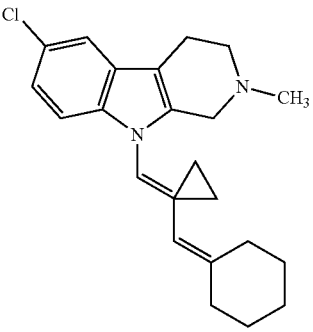 |
| i-10 | 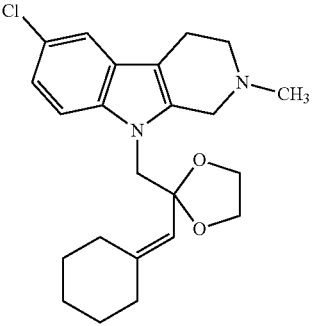 [SMILES: CN1CCc2c(n(CC3(C=C4CCCCC4)OCCO3)c3ccc(Cl)cc23)C1] |

TABLE 1-continued
Representative Compounds of the Invention
| Compound No. | Structure |
|---|---|
| i-11<br>i-11a (isomer 1)<br>i-11b (isomer 2) | 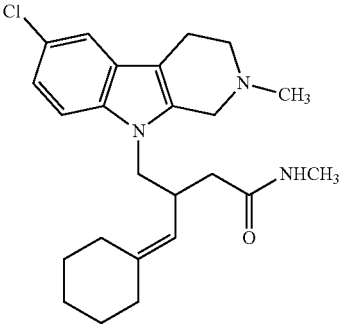 [SMILES: CNC(=O)CC(C=C1CCCCC1)Cn1c2c(c3cc(Cl)ccc31)CCN(C)C2] |
| i-12<br>i-12a (isomer 1)<br>i-12b (isomer 2)<br>i-12c (isomer 3)<br>i-12d (isomer 4) | 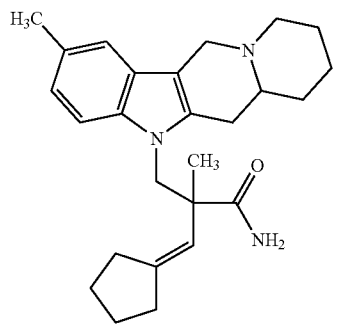 [SMILES: Cc1ccc2c(c1)c1c(n2CC(C)(C=C2CCCC2)C(N)=O)CC2CCCCN2C1] |
| i-13<br>i-13a (isomer 1)<br>i-13b (isomer 2) | 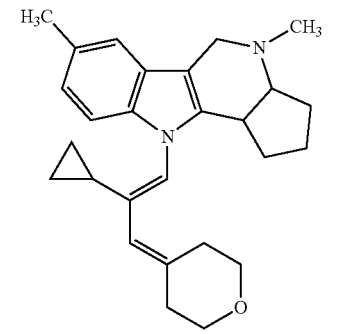 [SMILES: Cc1ccc2c(c1)c1c(n2/C=C(/C=C2CCOCC2)C2CC2)C2CCCC2N(C)C1] |
| i-14<br>i-14a (isomer 1)<br>i-14b (isomer 2)<br>i-14c (isomer 3)<br>i-14d (isomer 4) | 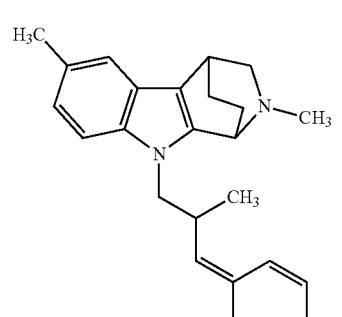 |
| i-15<br>i-15a (isomer 1)<br>i-15b (isomer 2) | 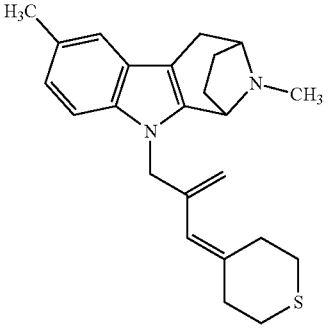 [SMILES: C=C(C=C1CCSCC1)Cn1c2c(c3cc(C)ccc31)CC1CCC2N1C] |
| i-16<br>i-16a (isomer 1)<br>i-16b (isomer 2)<br>i-16c (isomer 3)<br>i-16d (isomer 4) | 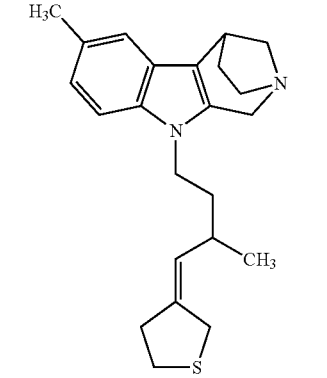 [SMILES: Cc1ccc2c(c1)c1c(n2CCC(C)/C=C2/CCSC2)CN2CCC1C2] |
| i-17<br>i-17a (isomer 1)<br>i-17b (isomer 2) | 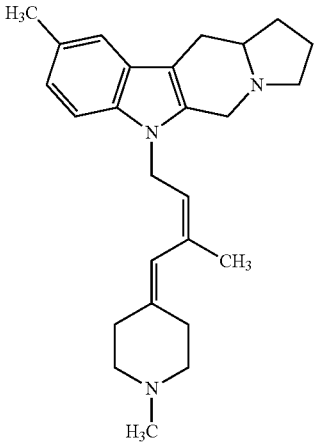 [SMILES: C/C(C=C1CCN(C)CC1)=C/Cn1c2c(c3cc(C)ccc31)CC1CCCN1C2] |
| i-18 | 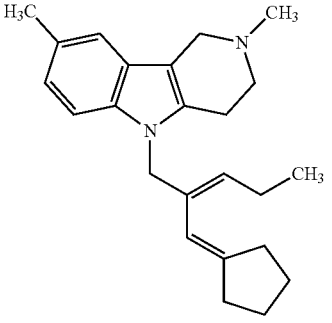 [SMILES: CC/C=C(\C=C1CCCC1)Cn1c2c(c3cc(C)ccc31)CN(C)CC2] |

TABLE 1-continued

Representative Compounds of the Invention

| Compound No. | Structure |
|---|---|
| i-19<br>i-19a (isomer 1)<br>i-19b (isomer 2)<br>i-19c (isomer 3)<br>i-19d (isomer 4) | (structure) |
| i-20<br>i-20a (isomer 1)<br>i-20b (isomer 2) | (structure) |
| i-21 | (structure) |
| i-22<br>i-22a (isomer 1)<br>i-22b (isomer 2)<br>i-22c (isomer 3)<br>i-22d (isomer 4) | (structure) |
| i-23 | (structure) |
| i-24<br>i-24a (isomer 1)<br>i-24b (isomer 2)<br>i-24c (isomer 3)<br>i-24d (isomer 4) | (structure) |
| i-25 | (structure) |
| i-26 | (structure) |
| i-27 | (structure) |

TABLE 1-continued

Representative Compounds of the Invention

| Compound No. | Structure |
|---|---|
| i-28 | 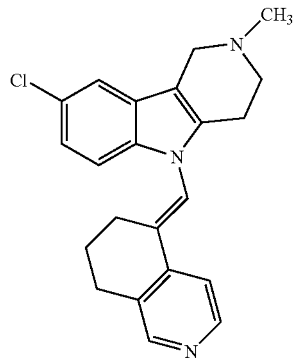 [SMILES: CN1CCc2c(c3cc(Cl)ccc3n2/C=C2\CCCc3cnccc32)C1] |
| i-29 | 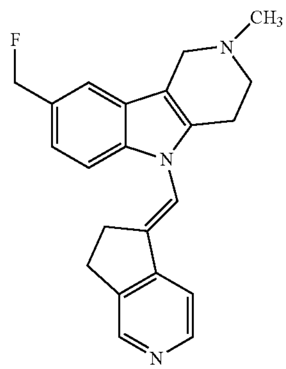 [SMILES: CN1CCc2c(c3cc(CF)ccc3n2/C=C2\CCc3cnccc32)C1] |
| i-30 | 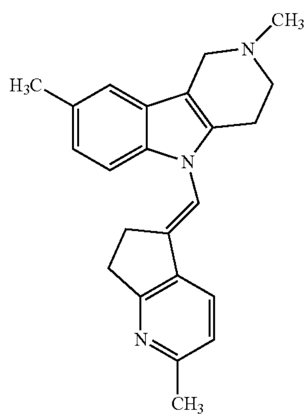 |
| i-31 | 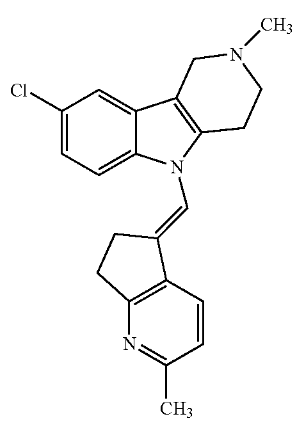 [SMILES: Cc1ccc2c(n1)CC/C2=C\n1c2c(c3cc(Cl)ccc31)CN(C)CC2] |
| i-32 | |
| i-33 | |
| i-34 | |
| i-35 | |

TABLE 1-continued
Representative Compounds of the Invention
| Compound No. | Structure |
|---|---|
| i-36 | 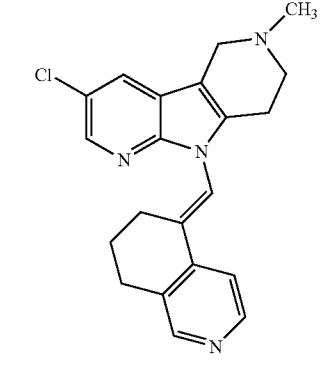 [SMILES: CN1CCc2c(c3cc(Cl)cnc3n2/C=C2\CCCc3cnccc32)C1] |
| i-37 | 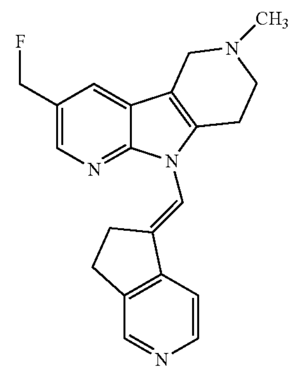 [SMILES: CN1CCc2c(c3cc(CF)cnc3n2/C=C2\CCc3cnccc32)C1] |
| i-38 | 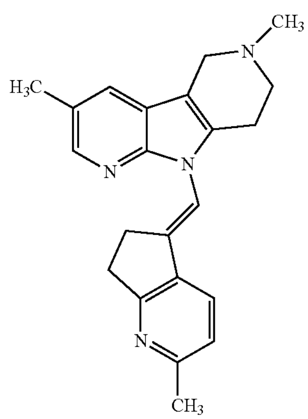 |
| i-39 | 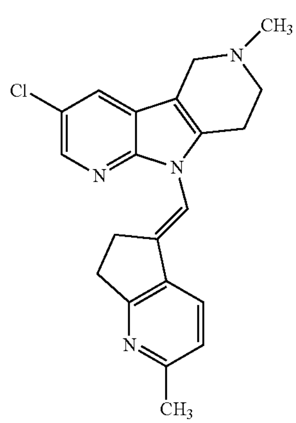 |
| i-40 | 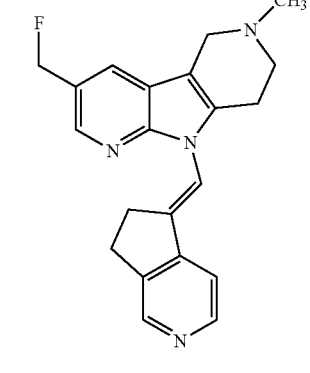 |
| i-41 | |
| i-42 | |
| i-43 | |

TABLE 1-continued
Representative Compounds of the Invention
| Compound No. | Structure |
|---|---|
| i-44 | 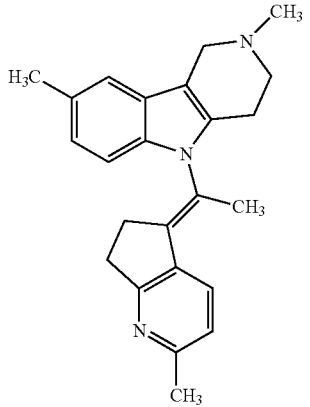 |
| i-45 | 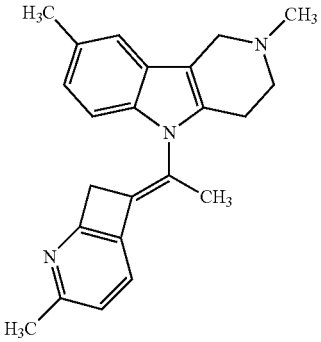 |
| i-46 | 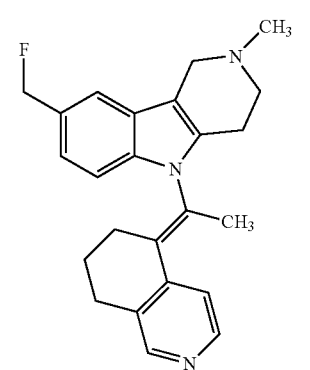 [SMILES: C/C(=C1/CCCc2cnccc21)n1c2c(c3cc(CF)ccc31)CN(C)CC2] |
| i-47 | 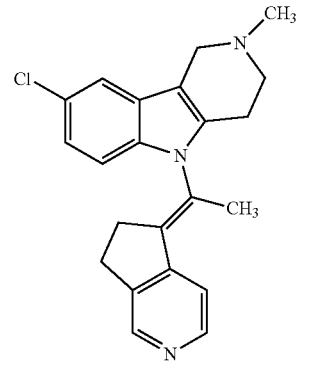 [SMILES: C/C(=C1/CCc2cnccc21)n1c2c(c3cc(Cl)ccc31)CN(C)CC2] |
| i-48 | 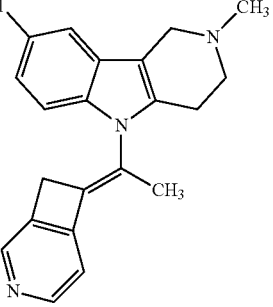 |
| i-49 | 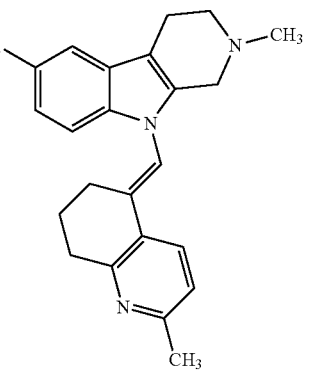 |
| i-50 | 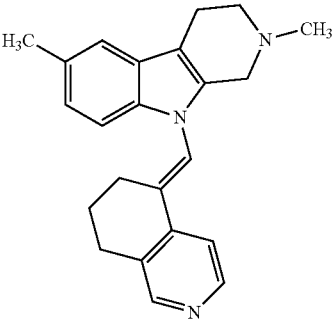 |
| i-51 | 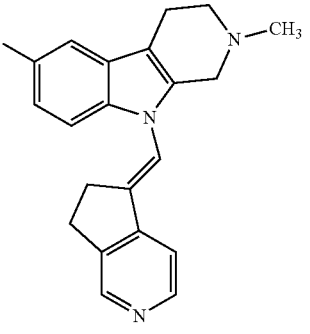 |

TABLE 1-continued

Representative Compounds of the Invention

| Compound No. | Structure |
|---|---|
| i-52 | 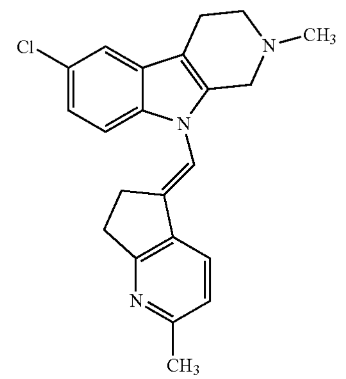 [SMILES: Cc1ccc2c(n1)CC/C2=C\n1c2c(c3cc(Cl)ccc31)CCN(C)C2] |
| i-53 | 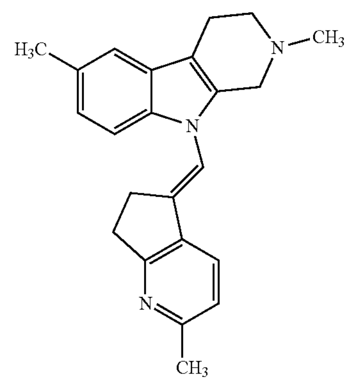 |
| i-54 | 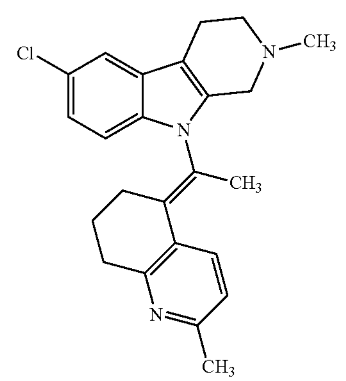 [SMILES: C/C(=C1/CCCc2nc(C)ccc21)n1c2c(c3cc(Cl)ccc31)CCN(C)C2] |
| i-55 | 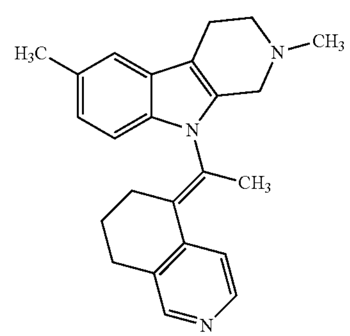 |
| i-56 | |
| i-57 | |
| i-58 | |
| i-59
i-59a (isomer 1)
i-59b (isomer 2) | |

TABLE 1-continued

Representative Compounds of the Invention

| Compound No. | Structure |
|---|---|
| i-60<br>i-60a (isomer 1)<br>i-60b (isomer 2) | 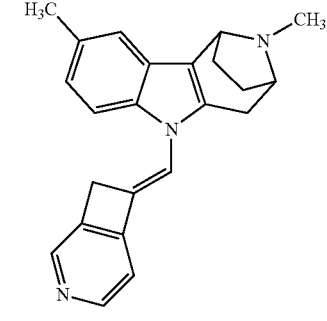 |
| i-61<br>i-61a (isomer 1)<br>i-61b (isomer 2) | 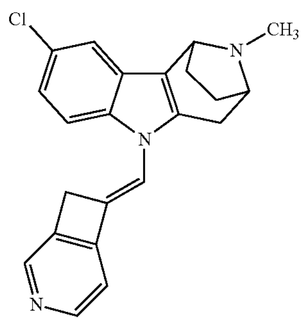 [SMILES: CN1C2CCC1c1c(n(/C=C3\Cc4cnccc43)c3ccc(Cl)cc13)C2] |
| i-62<br>i-62a (isomer 1)<br>i-62b (isomer 2) | 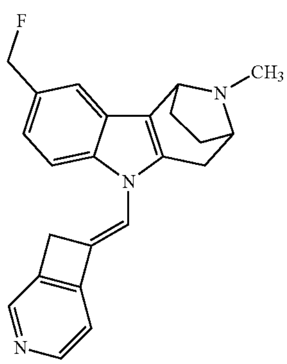 [SMILES: CN1C2CCC1c1c(n(/C=C3\Cc4cnccc43)c3ccc(CF)cc13)C2] |
| i-63<br>i-63a (isomer 1)<br>i-63b (isomer 2) | 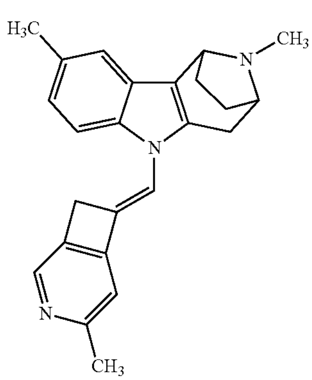 |

TABLE 1-continued

Representative Compounds of the Invention

| Compound No. | Structure |
|---|---|
| i-64<br>i-64a (isomer 1)<br>i-64b (isomer 2) | 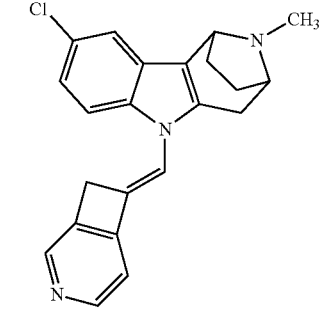 |
| i-65<br>i-65a (isomer 1)<br>i-65b (isomer 2) | 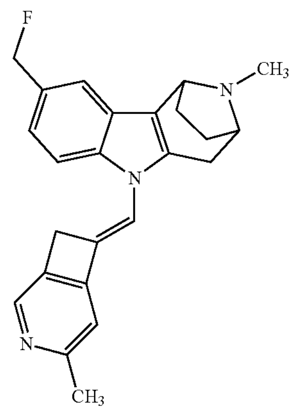 [SMILES: Cc1cc2c(cn1)C/C2=C\n1c2c(c3cc(CF)ccc31)C1CCC(C2)N1C] |
| i-66<br>i-66a (isomer 1)<br>i-66b (isomer 2) | 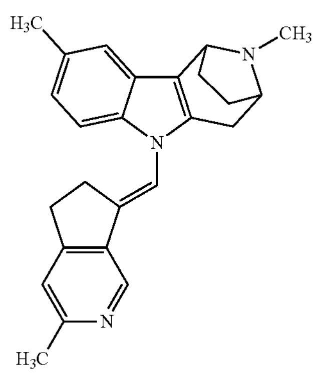 |
| i-67<br>i-67a (isomer 1)<br>i-67b (isomer 2) | 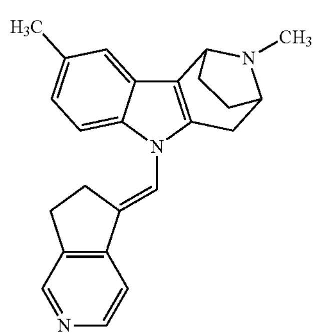 |

TABLE 1-continued
Representative Compounds of the Invention
| Compound No. | Structure |
|---|---|
| i-68<br>i-68a (isomer 1)<br>i-68b (isomer 2) | 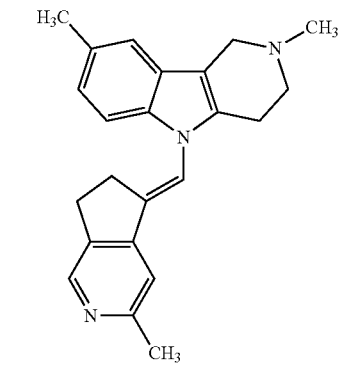 |
| i-69<br>i-69a (isomer 1)<br>i-69b (isomer 2) | 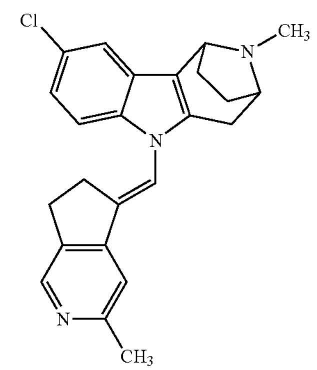 [SMILES: Cc1cc2c(cn1)CC/C2=C\n1c2c(c3cc(Cl)ccc31)C1CCC(C2)N1C] |
| i-70<br>i-70a (isomer 1)<br>i-70b (isomer 2) | 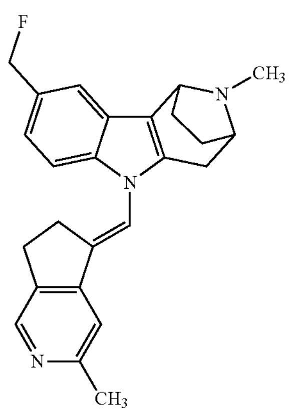 [SMILES: Cc1cc2c(cn1)CC/C2=C\n1c2c(c3cc(CF)ccc31)C1CCC(C2)N1C] |
| i-71 | 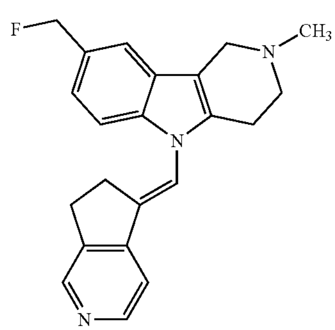 [SMILES: CN1CCc2c(c3cc(CF)ccc3n2/C=C2\CCc3cnccc32)C1] |
TABLE 1-continued
Representative Compounds of the Invention
| Compound No. | Structure |
|---|---|
| i-72 | 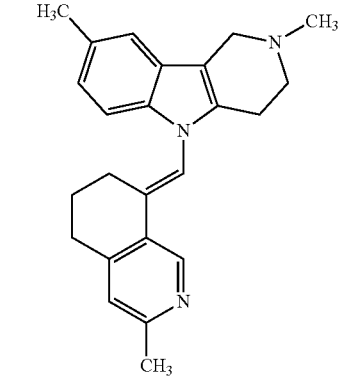 |
| i-73 | |
| i-74 | |
| i-75 | |

TABLE 1-continued
Representative Compounds of the Invention
| Compound No. | Structure |
|---|---|
| i-76 | 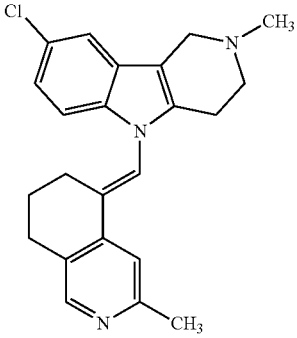 [SMILES: Cc1cc2c(cn1)CCC/C2=C\n1c2c(c3cc(Cl)ccc31)CN(C)CC2] |
| i-77 | 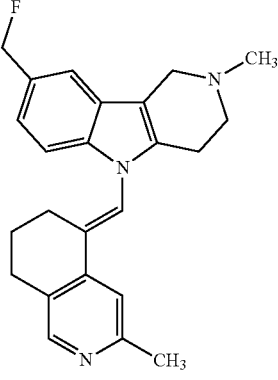 [SMILES: Cc1cc2c(cn1)CCC/C2=C\n1c2c(c3cc(CF)ccc31)CN(C)CC2] |
| i-78 | 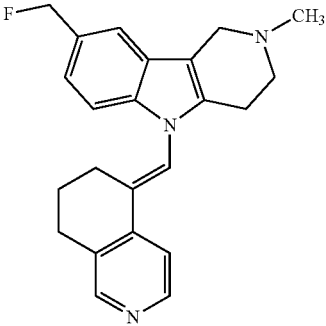 [SMILES: CN1CCc2c(c3cc(CF)ccc3n2/C=C2\CCCc3cnccc32)C1] |
| i-79 | 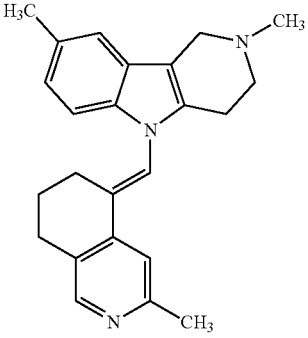 |
| i-80<br>i-80a (isomer 1)<br>i-80b (isomer 2) | 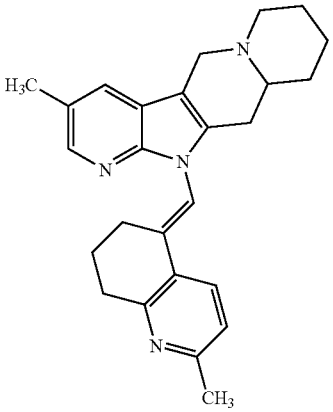 [SMILES: Cc1cnc2c(c1)c1c(n2/C=C2\CCCc3nc(C)ccc32)CC2CCCCN2C1] |
| i-81<br>i-81a (isomer 1)<br>i-81b (isomer 2) | 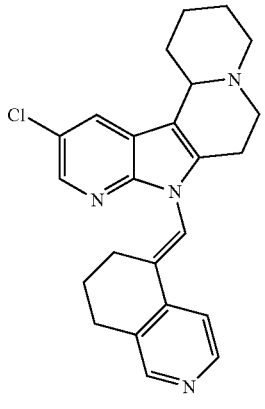 [SMILES: Clc1cnc2c(c1)c1c(n2/C=C2\CCCc3cnccc32)CCN2CCCCC12] |
| i-82<br>i-82a (isomer 1)<br>i-82b (isomer 2) | 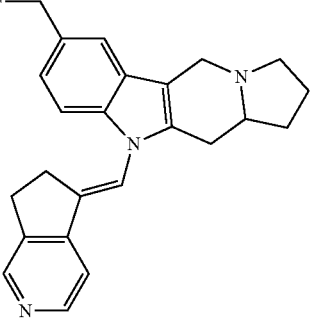 |
| i-83<br>i-83a (isomer 1)<br>i-83b (isomer 2) | 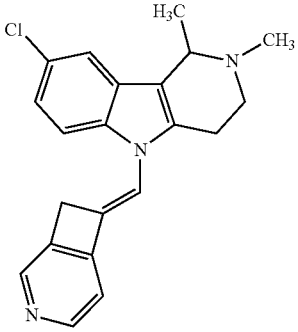 [SMILES: CC1c2c(n(/C=C3\Cc4cnccc43)c3ccc(Cl)cc23)CCN1C] |

TABLE 1-continued

Representative Compounds of the Invention

| Compound No. | Structure |
|---|---|
| i-84<br>i-84a (isomer 1)<br>i-84b (isomer 2) | 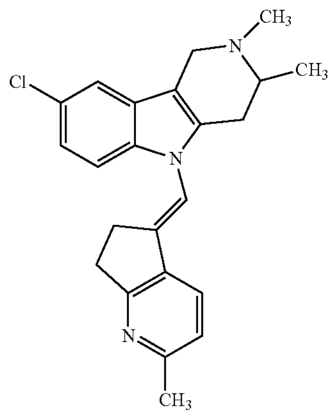 [SMILES: Cc1ccc2c(n1)CC/C2=C\n1c2c(c3cc(Cl)ccc31)CN(C)C(C)C2] |
| i-85 | 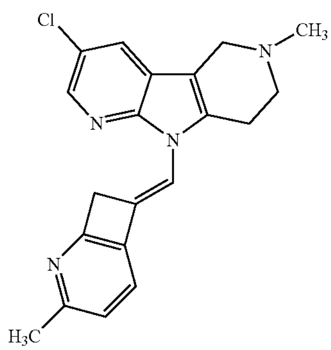 |
| i-86a<br>i-86a (isomer 1)<br>i-86b (isomer 2) | 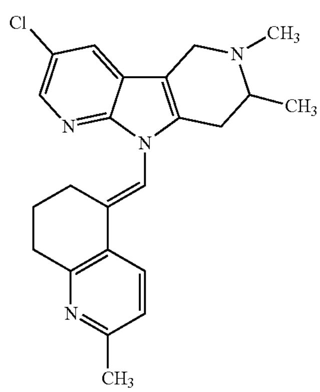 |
| i-87<br>i-87a (isomer 1)<br>i-87b (isomer 2) | 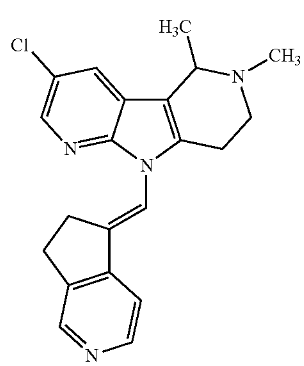 [SMILES: CC1c2c(n(/C=C3\CCc4cnccc43)c3ncc(Cl)cc23)CCN1C] |
| i-88<br>i-88a (isomer 1)<br>i-88b (isomer 2) | |
| i-89 | |
| i-90<br>i-90a (isomer 1)<br>i-90b (isomer 2) | |
| i-91<br>i-91a (isomer 1)<br>i-91b (isomer 2) | |

TABLE 1-continued
Representative Compounds of the Invention
| Compound No. | Structure |
|---|---|
| i-92 | 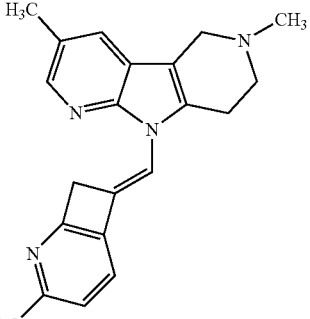 |
| i-93<br>i-93a (isomer 1)<br>i-93b (isomer 2) | 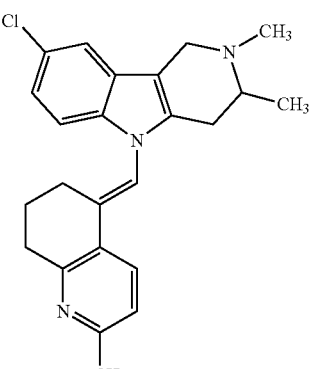 |
| i-94<br>i-94a (isomer 1)<br>i-94b (isomer 2) | 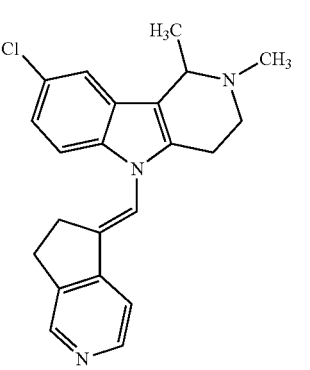 |
| i-95<br>i-95a (isomer 1)<br>i-95b (isomer 2) | 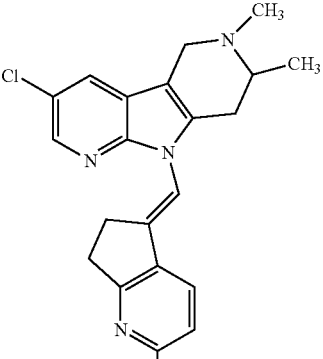 |
| i-96<br>i-96a (isomer 1)<br>i-96b (isomer 2) | 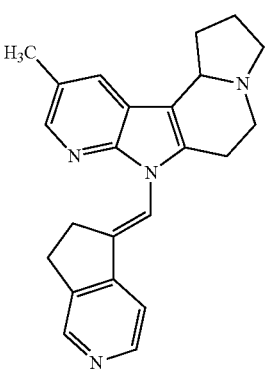 [SMILES: Cc1ccc2c(c1)c1c(n2/C=C2\CCc3cnccc32)CCN2CCCC12] |
| i-97<br>i-97a (isomer 1)<br>i-97b (isomer 2) | 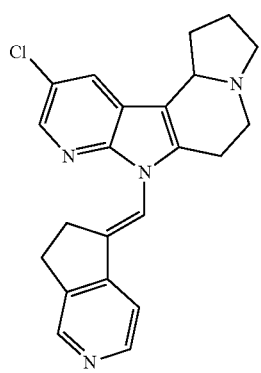 [SMILES: Clc1cnc2c(c1)c1c(n2/C=C2\CCc3cnccc32)CCN2CCCC12] |
| i-98 | 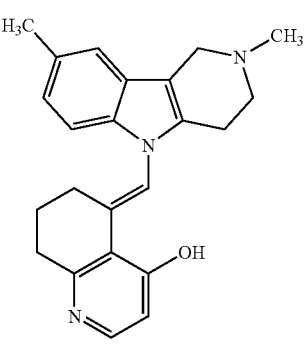 |
| i-99 | 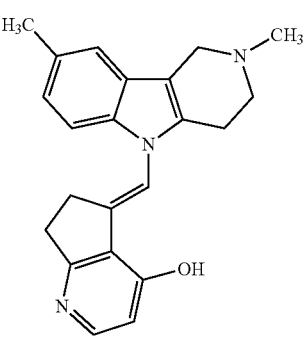 |

TABLE 1-continued

Representative Compounds of the Invention

| Compound No. | Structure |
|---|---|
| i-100 | 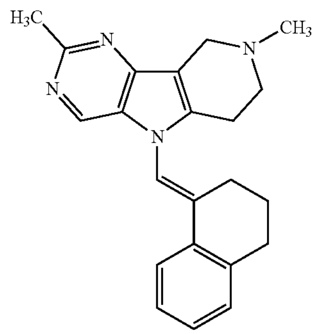 |
| i-101 | 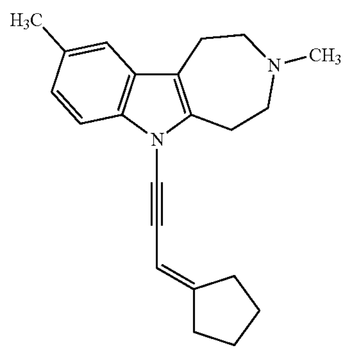 |
| i-102<br>i-102a (isomer 1)<br>i-102b (isomer 2)<br>i-102c (isomer 3)<br>i-102d (isomer 4) | 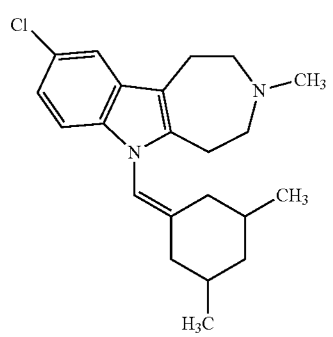 [SMILES: CC1CC(=Cn2c3c(c4cc(Cl)ccc42)CCN(C)CC3)CC(C)C1] |
| i-103 | 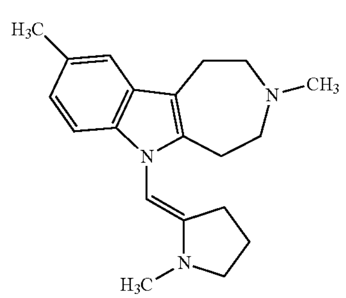 |
| i-104 | |
| i-105 | |
| i-106 | |
| i-107 | |

TABLE 1-continued
Representative Compounds of the Invention
| Compound No. | Structure |
|---|---|
| i-108 | 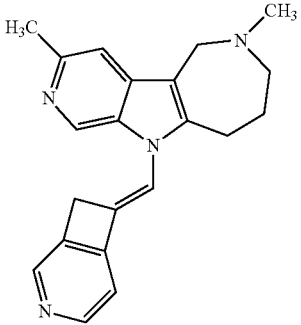 |
| i-109 | 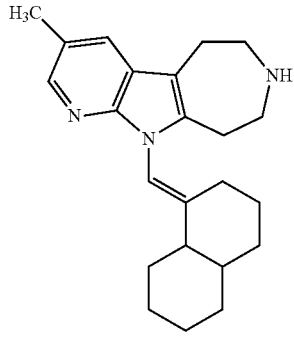 [SMILES: Cc1cnc2c(c1)c1c(n2/C=C2\CCCC3CCCCC23)CCNCC1] |
| i-110 | 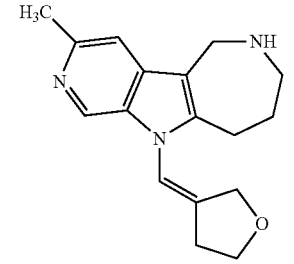 [SMILES: Cc1cc2c3c(n(/C=C4/CCOC4)c2cn1)CCCNC3] |
| i-111 | 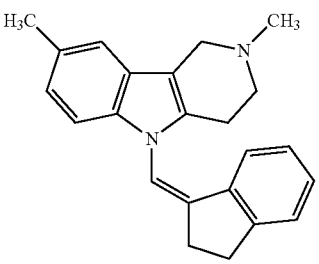 [SMILES: Cc1ccc2c(c1)c1c(n2/C=C2/CCc3ccccc32)CCN(C)C1] |
| i-112 | 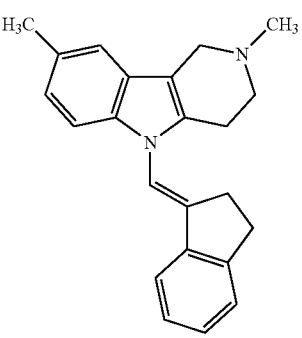 |
TABLE 2
Representative Compounds of the Invention
| Compound No. | Structure |
|---|---|
| ii-1 | 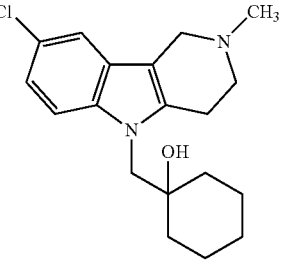 |
| ii-2<br>ii-2a (isomer 1)<br>ii-2b (isomer 2) | 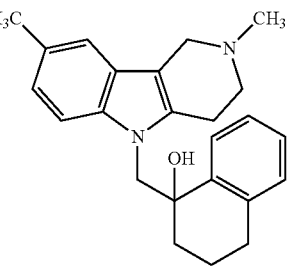 |
| ii-4 | 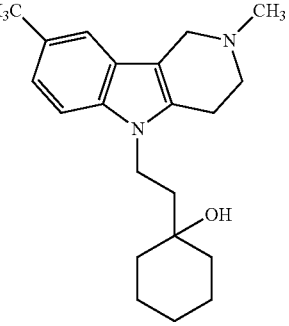 |
| ii-5 | 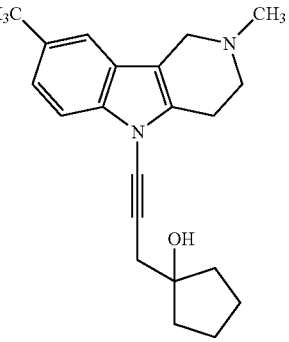 |
| ii-6 | 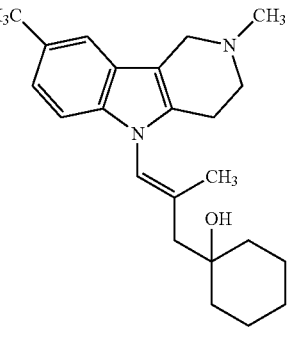 |

TABLE 2-continued

Representative Compounds of the Invention

| Compound No. | Structure |
|---|---|
| ii-7 | 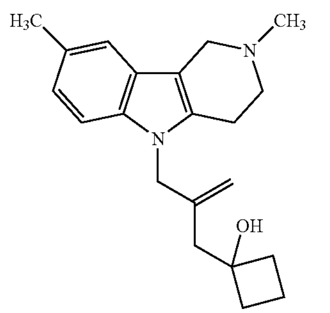 [SMILES: C=C(Cn1c2c(c3cc(C)ccc31)CN(C)CC2)CC1(O)CCC1] |
| ii-8 | 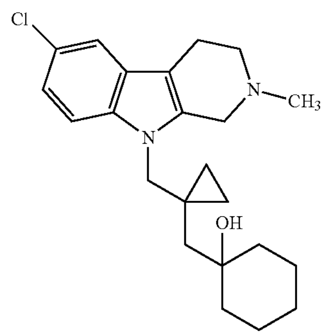 [SMILES: CN1CCc2c(n(CC3(CC4(O)CCCCC4)CC3)c3ccc(Cl)cc23)C1] |
| ii-10 | 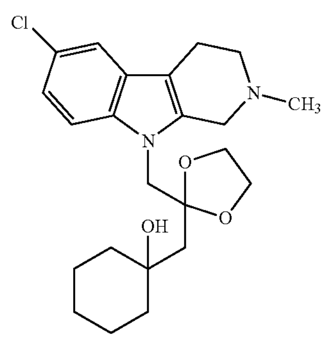 [SMILES: CN1CCc2c(n(CC3(CC4(O)CCCCC4)OCCO3)c3ccc(Cl)cc23)C1] |
| ii-11<br>ii-11a (isomer 1)<br>ii-11b (isomer 2) | 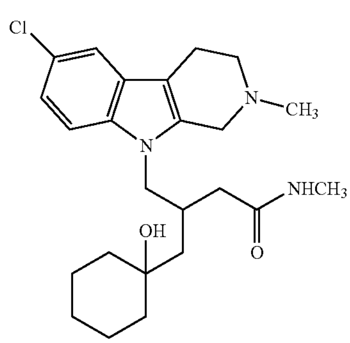 [SMILES: CNC(=O)CC(Cn1c2c(c3cc(Cl)ccc31)CCN(C)C2)CC1(O)CCCCC1] |
| ii-12<br>ii-12a (isomer 1)<br>ii-12b (isomer 2)<br>ii-12c (isomer 3)<br>ii-12d (isomer 4) | |
| ii-13<br>ii-13a (isomer 1)<br>ii-13b (isomer 2)<br>ii-13c (isomer 3)<br>ii-13d (isomer 4) | |
| ii-14<br>ii-14a (isomer 1)<br>ii-14b (isomer 2)<br>ii-14c (isomer 3)<br>ii-14d (isomer 4)<br>ii-14e (isomer 5)<br>ii-14f (isomer 6)<br>ii-14g (isomer 7)<br>ii-14h (isomer 8) | |
| ii-15<br>ii-15a (isomer 1)<br>ii-15b (isomer 2) | |

TABLE 2-continued

Representative Compounds of the Invention

| Compound No. | Structure |
|---|---|
| ii-16<br>ii-16a (isomer 1)<br>ii-16b (isomer 2)<br>ii-16c (isomer 3)<br>ii-16d (isomer 4)<br>ii-16e (isomer 5)<br>ii-16f (isomer 6)<br>ii-16g (isomer 7)<br>ii-16h (isomer 8) | |
| ii-17<br>ii-17a (isomer 1)<br>ii-17b (isomer 2) | |
| ii-18 | |
| ii-19<br>ii-19a (isomer 1)<br>ii-19b (isomer 2)<br>ii-19c (isomer 3)<br>ii-19d (isomer 4) | |
| ii-20<br>ii-20a (isomer 1)<br>ii-20b (isomer 2) | 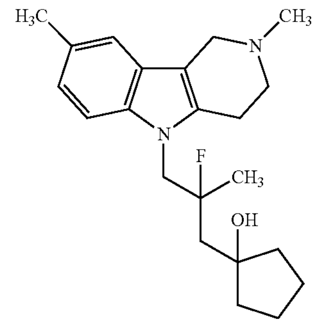 [SMILES: Cc1ccc2c(c1)c1c(n2CC(C)(F)CC2(O)CCCC2)CCN(C)C1] |
| ii-21 | 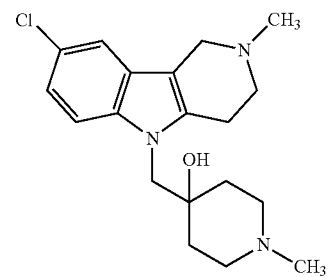 [SMILES: CN1CCC(O)(Cn2c3c(c4cc(Cl)ccc42)CN(C)CC3)CC1] |
| ii-22<br>ii-22a (isomer 1)<br>ii-22b (isomer 2)<br>ii-22c (isomer 3)<br>ii-22d (isomer 4)<br>ii-22e (isomer 5)<br>ii-22f (isomer 6)<br>ii-22g (isomer 7)<br>ii-22h (isomer 8) | 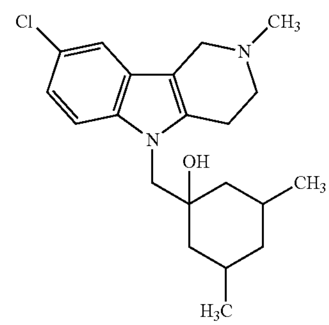 [SMILES: CC1CC(C)CC(O)(Cn2c3c(c4cc(Cl)ccc42)CN(C)CC3)C1] |
| ii-23<br>ii-23a (isomer 1)<br>ii-23b (isomer 2) | 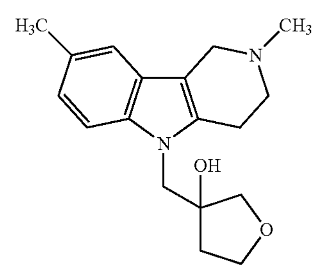 |
| ii-24<br>ii-24a (isomer 1)<br>ii-24b (isomer 2)<br>ii-24c (isomer 3)<br>ii-24d (isomer 4)<br>ii-24e (isomer 5)<br>ii-24f (isomer 6)<br>ii-24g (isomer 7)<br>ii-24h (isomer 8) | 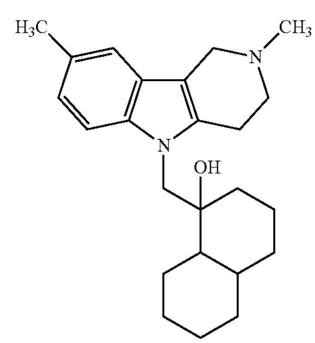 |

TABLE 2-continued
Representative Compounds of the Invention
| Compound No. | Structure |
|---|---|
| ii-25<br>ii-25a (isomer 1)<br>ii-25b (isomer 2) | 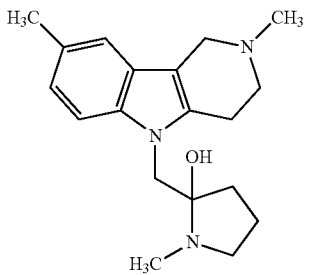 |
| ii-26 | 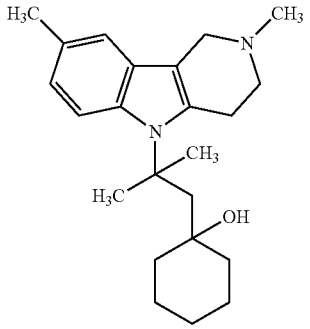 |
| ii-27<br>ii-27a (isomer 1)<br>ii-27b (isomer 2) | 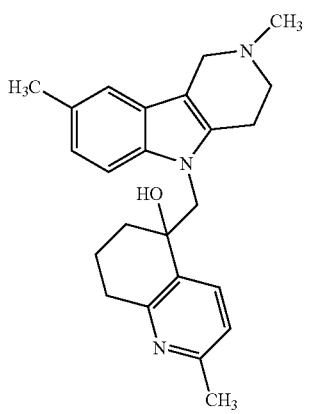 |
| ii-28<br>ii-28a (isomer 1)<br>ii-28b (isomer 2) | 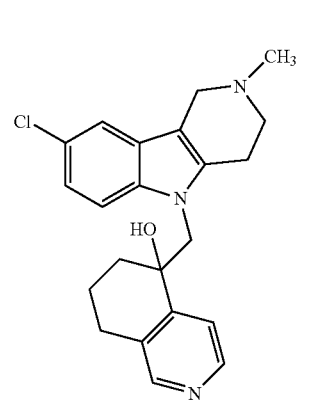 [SMILES: CN1CCc2c(c3cc(Cl)ccc3n2CC2(O)CCCc3cnccc32)C1] |
| ii-29<br>ii-29a (isomer 1)<br>ii-29b (isomer 2) | 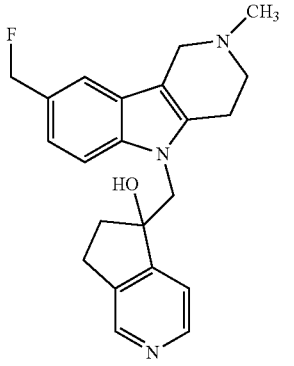 [SMILES: CN1CCc2c(c3cc(CF)ccc3n2CC2(O)CCc3cnccc32)C1] |
| ii-30<br>ii-30a (isomer 1)<br>ii-30b (isomer 2) | 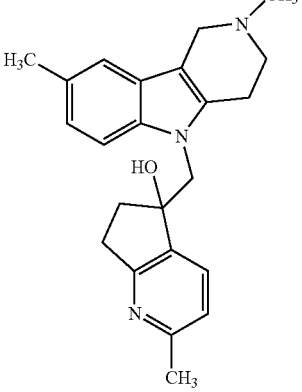 |
| ii-31<br>ii-31a (isomer 1)<br>ii-31b (isomer 2) | 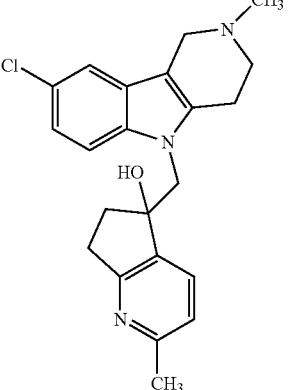 |
| ii-32<br>ii-32a (isomer 1)<br>ii-32b (isomer 2) | 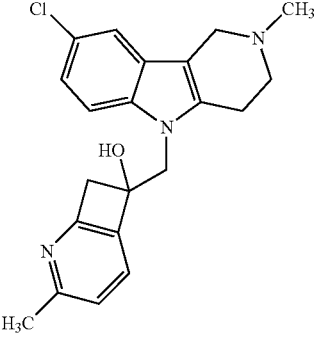 |

TABLE 2-continued
Representative Compounds of the Invention
| Compound No. | Structure |
|---|---|
| ii-33<br>ii-33a (isomer 1)<br>ii-33b (isomer 2) | 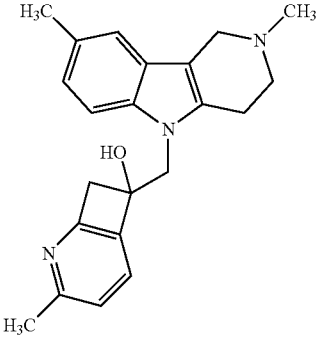 |
| ii-34<br>ii-34a (isomer 1)<br>ii-34b (isomer 2) | 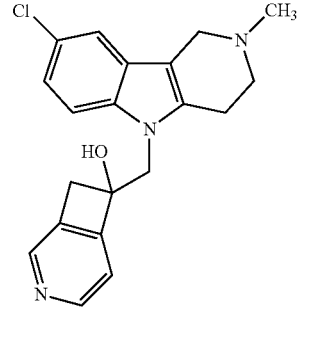 [SMILES: CN1CCc2c(c3cc(Cl)ccc3n2CC2(O)Cc3cnccc32)C1] |
| ii-35<br>ii-35a (isomer 1)<br>ii-35b (isomer 2) | 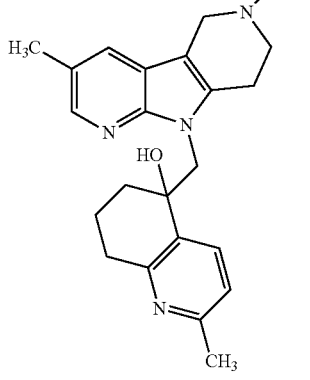 |
| ii-36<br>ii-36a (isomer 1)<br>ii-36b (isomer 2) | 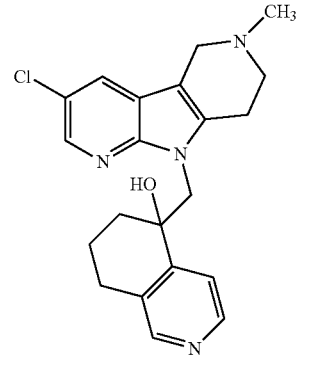 [SMILES: CN1CCc2c(c3cc(Cl)cnc3n2CC2(O)CCCc3cnccc32)C1] |
| ii-37<br>ii-37a (isomer 1)<br>ii-37b (isomer 2) | 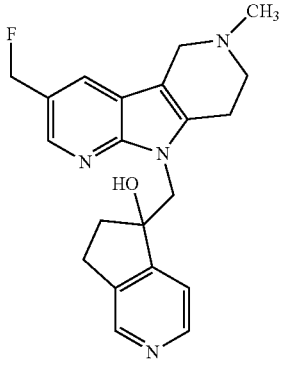 [SMILES: CN1CCc2c(c3cc(CF)cnc3n2CC2(O)CCc3cnccc32)C1] |
| ii-38<br>ii-38a (isomer 1)<br>ii-38b (isomer 2) | 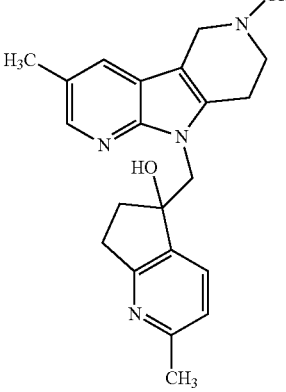 |
| ii-39<br>ii-39a (isomer 1)<br>ii-39b (isomer 2) | 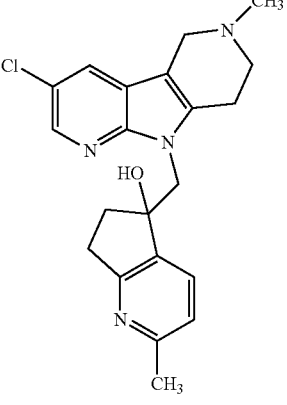 |
| ii-40<br>ii-40a (isomer 1)<br>ii-40b (isomer 2) | 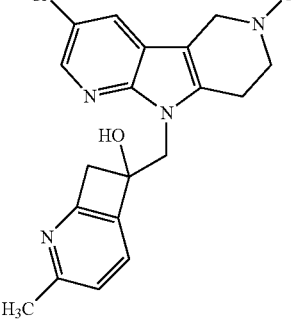 |

TABLE 2-continued

Representative Compounds of the Invention

| Compound No. | Structure |
|---|---|
| ii-41<br>ii-41a (isomer 1)<br>ii-41b (isomer 2) | (structure) |
| ii-42<br>ii-42a (isomer 1)<br>ii-42b (isomer 2) | (structure) |
| ii-43<br>ii-43a (isomer 1)<br>ii-43b (isomer 2)<br>ii-43c (isomer 3)<br>ii-43d (isomer 4) | (structure) |
| ii-44<br>ii-44a (isomer 1)<br>ii-44b (isomer 2)<br>ii-44c (isomer 3)<br>ii-44d (isomer 4) | (structure) |
| ii-45<br>ii-45a (isomer 1)<br>ii-45b (isomer 2)<br>ii-45c (isomer 3)<br>ii-45d (isomer 4) | (structure) |
| ii-46<br>ii-46a (isomer 1)<br>ii-46b (isomer 2)<br>ii-46c (isomer 3)<br>ii-46d (isomer 4) | (structure) |
| ii-47<br>ii-47a (isomer 1)<br>ii-47b (isomer 2)<br>ii-47c (isomer 3)<br>ii-47d (isomer 4) | (structure) |
| ii-48<br>ii-48a (isomer 1)<br>ii-48b (isomer 2)<br>ii-48c (isomer 3)<br>ii-48d (isomer 4) | (structure) |

TABLE 2-continued

Representative Compounds of the Invention

| Compound No. | Structure |
|---|---|
| ii-49<br>ii-49a (isomer 1)<br>ii-49b (isomer 2) | 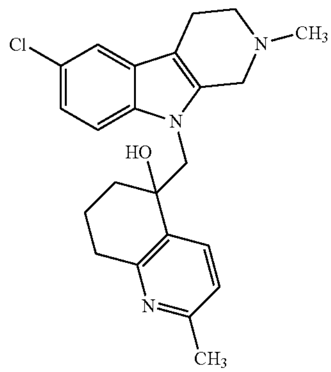 [SMILES: Cc1ccc2c(n1)CCCC2(O)Cn1c2c(c3cc(Cl)ccc31)CCN(C)C2] |
| ii-50<br>ii-50a (isomer 1)<br>ii-50b (isomer 2) | 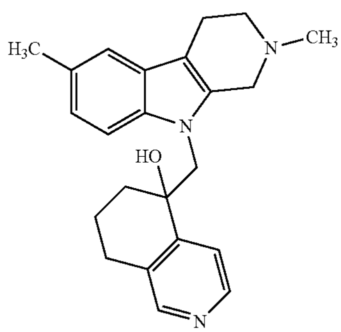 |
| ii-51<br>ii-51a (isomer 1)<br>ii-51b (isomer 2) | 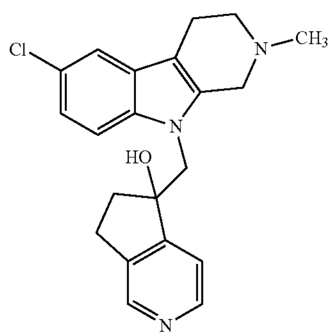 [SMILES: CN1CCc2c(n(CC3(O)CCc4cnccc43)c3ccc(Cl)cc23)C1] |
| ii-52<br>ii-52a (isomer 1)<br>ii-52b (isomer 2) | 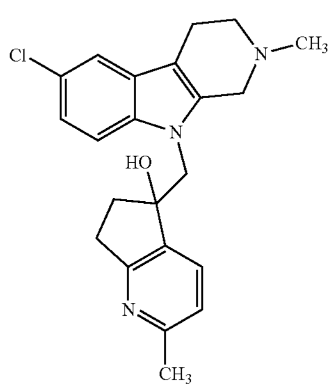 [SMILES: Cc1ccc2c(n1)CCC2(O)Cn1c2c(c3cc(Cl)ccc31)CCN(C)C2] |
| ii-53<br>ii-53a (isomer 1)<br>ii-53b (isomer 2) | 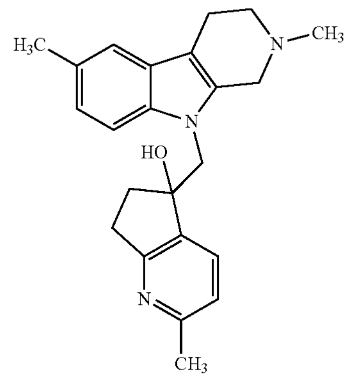 |
| ii-54<br>ii-54a (isomer 1)<br>ii-54b (isomer 2)<br>ii-54c (isomer 3)<br>ii-54d (isomer 4) | 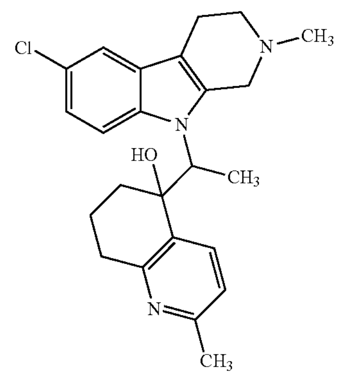 [SMILES: Cc1ccc2c(n1)CCCC2(O)C(C)n1c2c(c3cc(Cl)ccc31)CCN(C)C2] |
| ii-55<br>ii-55a (isomer 1)<br>ii-55b (isomer 2)<br>ii-55c (isomer 3)<br>ii-55d (isomer 4) | 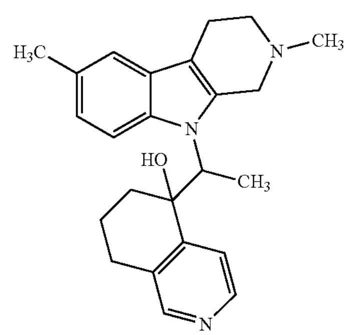 |
| ii-56<br>ii-56a (isomer 1)<br>ii-56b (isomer 2)<br>ii-56c (isomer 3)<br>ii-56d (isomer 4) | 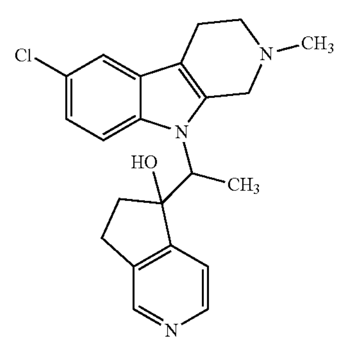 [SMILES: CC(n1c2c(c3cc(Cl)ccc31)CCN(C)C2)C1(O)CCc2cnccc21] |

TABLE 2-continued

Representative Compounds of the Invention

| Compound No. | Structure |
|---|---|
| ii-57<br>ii-57a (isomer 1)<br>ii-57b (isomer 2)<br>ii-57c (isomer 3)<br>ii-57d (isomer 4) | *structure* |
| ii-58<br>ii-58a (isomer 1)<br>ii-58b (isomer 2)<br>ii-58c (isomer 3)<br>ii-58d (isomer 4) | *structure* |
| ii-59<br>ii-59a (isomer 1)<br>ii-59b (isomer 2)<br>ii-59c (isomer 3)<br>ii-59d (isomer 4) | *structure* |
| ii-60<br>ii-60a (isomer 1)<br>ii-60b (isomer 2)<br>ii-60c (isomer 3)<br>ii-60d (isomer 4) | *structure* |
| ii-61<br>ii-61a (isomer 1)<br>ii-61b (isomer 2)<br>ii-61c (isomer 3)<br>ii-61d (isomer 4) | *structure* |
| ii-62<br>ii-62a (isomer 1)<br>ii-62b (isomer 2)<br>ii-62c (isomer 3)<br>ii-62d (isomer 4) | *structure* |
| ii-63<br>ii-63a (isomer 1)<br>ii-63b (isomer 2)<br>ii-63c (isomer 3)<br>ii-63d (isomer 4) | *structure* |
| ii-64<br>ii-64a (isomer 1)<br>ii-64b (isomer 2)<br>ii-64c (isomer 3)<br>ii-64d (isomer 4) | *structure* |

TABLE 2-continued

Representative Compounds of the Invention

| Compound No. | Structure |
|---|---|
| ii-65<br>ii-65a (isomer 1)<br>ii-65b (isomer 2)<br>ii-65c (isomer 3)<br>ii-65d (isomer 4) | 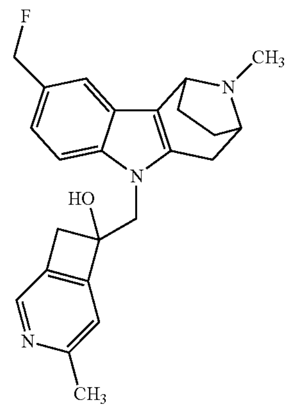 [SMILES: Cc1cc2c(cn1)CC2(O)Cn1c2c(c3cc(CF)ccc31)C1CCC(C2)N1C] |
| ii-66<br>ii-66a (isomer 1)<br>ii-66b (isomer 2)<br>ii-66c (isomer 3)<br>ii-66d (isomer 4) | 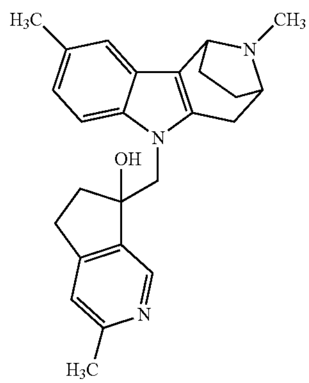 |
| ii-67<br>ii-67a (isomer 1)<br>ii-67b (isomer 2)<br>ii-67c (isomer 3)<br>ii-67d (isomer 4) | 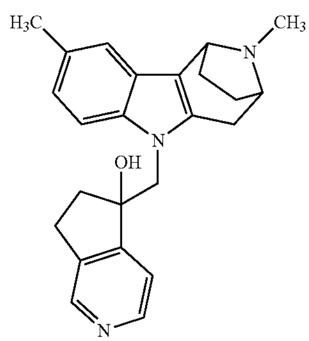 |
| ii-68<br>ii-68a (isomer 1)<br>ii-68b (isomer 2)<br>ii-68c (isomer 3)<br>ii-68d (isomer 4) | 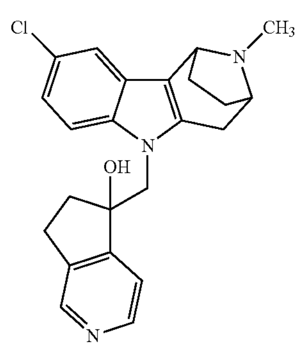 [SMILES: CN1C2CCC1c1c(n(CC3(O)CCc4cnccc43)c3ccc(Cl)cc13)C2] |
| ii-69<br>ii-69a (isomer 1)<br>ii-69b (isomer 2)<br>ii-69c (isomer 3)<br>ii-69d (isomer 4) | |
| ii-70<br>ii-70a (isomer 1)<br>ii-70b (isomer 2)<br>ii-70c (isomer 3)<br>ii-70d (isomer 4) | |
| ii-71<br>ii-71a (isomer 1)<br>ii-71b (isomer 2) | |
| ii-72<br>ii-72a (isomer 1)<br>ii-72b (isomer 2) | |

TABLE 2-continued

Representative Compounds of the Invention

| Compound No. | Structure |
|---|---|
| ii-73<br>ii-73a (isomer 1)<br>ii-73b (isomer 2) | (structure) |
| ii-74<br>ii-74a (isomer 1)<br>ii-74b (isomer 2) | (structure) |
| ii-75<br>ii-75a (isomer 1)<br>ii-75b (isomer 2) | (structure) |
| ii-76<br>ii-76a (isomer 1)<br>ii-76b (isomer 2) | (structure) |
| ii-77<br>ii-77a (isomer 1)<br>ii-77b (isomer 2) | (structure) |
| ii-78<br>ii-78a (isomer 1)<br>ii-78b (isomer 2) | (structure) |
| ii-79<br>ii-79a (isomer 1)<br>ii-79b (isomer 2) | (structure) |
| ii-80<br>ii-80a (isomer 1)<br>ii-80b (isomer 2)<br>ii-80c (isomer 3)<br>ii-80d (isomer 4) | (structure) |

TABLE 2-continued

Representative Compounds of the Invention

| Compound No. | Structure |
|---|---|
| ii-81<br>ii-81a (isomer 1)<br>ii-81b (isomer 2)<br>ii-81c (isomer 3)<br>ii-81d (isomer 4) | 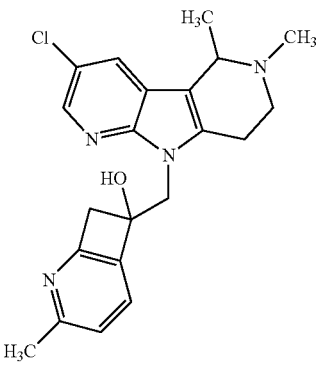 |
| ii-82<br>ii-82a (isomer 1)<br>ii-82b (isomer 2)<br>ii-82c (isomer 3)<br>ii-82d (isomer 4) | 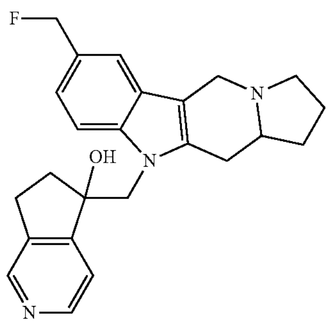 [SMILES: OC1(Cn2c3c(c4cc(CF)ccc42)CN2CCCC2C3)CCc2cnccc21] |
| ii-83<br>ii-83a (isomer 1)<br>ii-83b (isomer 2)<br>ii-83c (isomer 3)<br>ii-83d (isomer 4) | 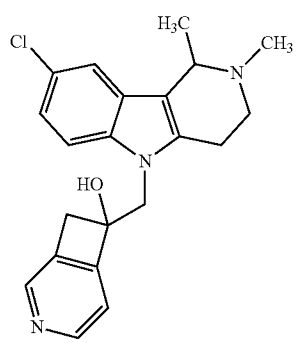 [SMILES: CC1c2c(n(CC3(O)Cc4cnccc43)c3ccc(Cl)cc23)CCN1C] |
| ii-84<br>ii-84a (isomer 1)<br>ii-84b (isomer 2)<br>ii-84c (isomer 3)<br>ii-84d (isomer 4) | 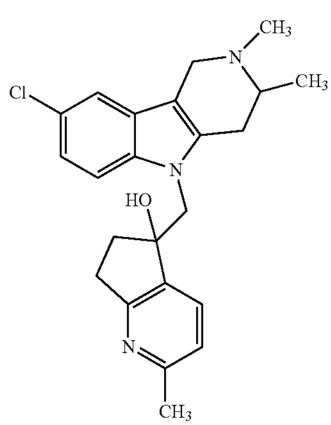 [SMILES: Cc1ccc2c(n1)CCC2(O)Cn1c2c(c3cc(Cl)ccc31)CN(C)C(C)C2] |

TABLE 2-continued

Representative Compounds of the Invention

| Compound No. | Structure |
|---|---|
| ii-85<br>ii-85a (isomer 1)<br>ii-85b (isomer 2) | 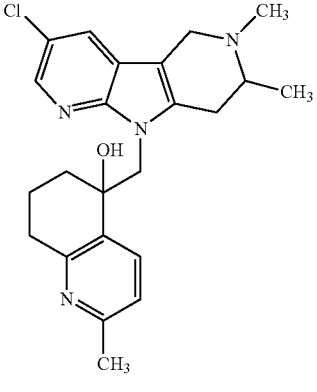 |
| ii-86<br>ii-86a (isomer 1)<br>ii-86b (isomer 2)<br>ii-86c (isomer 3)<br>ii-86d (isomer 4) | 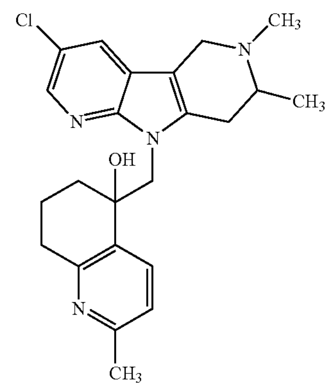 |
| ii-87<br>ii-87a (isomer 1)<br>ii-87b (isomer 2)<br>ii-87c (isomer 3)<br>ii-87d (isomer 4) | 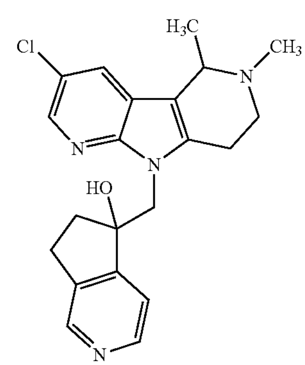 [SMILES: CC1c2c(n(CC3(O)CCc4cnccc43)c3ncc(Cl)cc23)CCN1C] |
| ii-88<br>ii-88a (isomer 1)<br>ii-88b (isomer 2)<br>ii-88c (isomer 3)<br>ii-88d (isomer 4) | 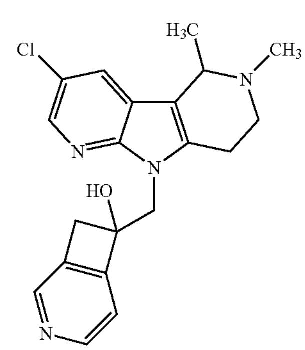 [SMILES: CC1c2c(n(CC3(O)Cc4cnccc43)c3ncc(Cl)cc23)CCN1C] |

TABLE 2-continued

Representative Compounds of the Invention

| Compound No. | Structure |
|---|---|
| ii-89<br>ii-89a (isomer 1)<br>ii-89b (isomer 2) | 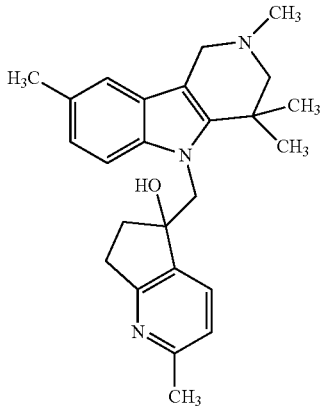 |
| ii-90<br>ii-90a (isomer 1)<br>ii-90b (isomer 2)<br>ii-90c (isomer 3)<br>ii-90d (isomer 4) | 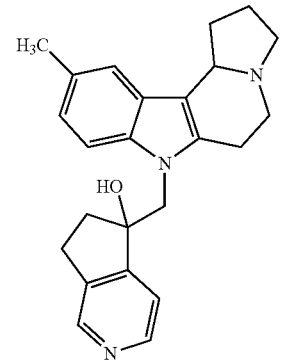 [SMILES: Cc1ccc2c(c1)c1c(n2CC2(O)CCc3cnccc32)CCN2CCCC12] |
| ii-91<br>ii-91a (isomer 1)<br>ii-91b (isomer 2)<br>ii-91c (isomer 3)<br>ii-91d (isomer 4) | 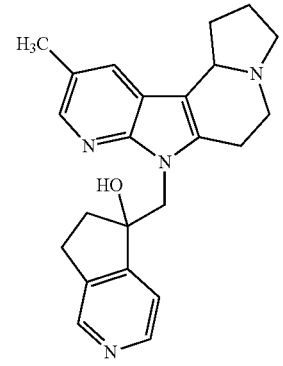 [SMILES: Cc1cnc2c(c1)c1c(n2CC2(O)CCc3cnccc32)CCN2CCCC12] |
| ii-92<br>ii-92a (isomer 1)<br>ii-92b (isomer 2) | 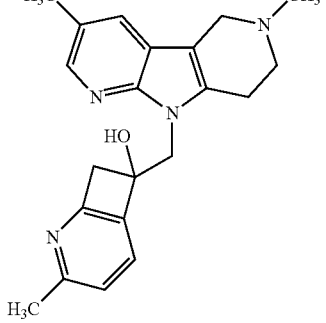 |
| ii-93<br>ii-93a (isomer 1)<br>ii-93b (isomer 2)<br>ii-93c (isomer 3)<br>ii-93d (isomer 4) | 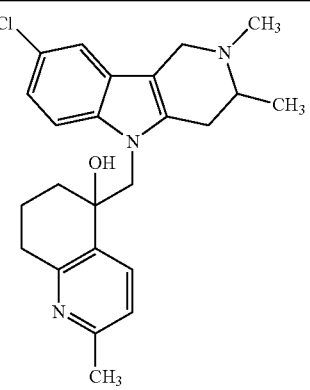 |
| ii-94<br>ii-94a (isomer 1)<br>ii-94b (isomer 2)<br>ii-94c (isomer 3)<br>ii-94d (isomer 4) | 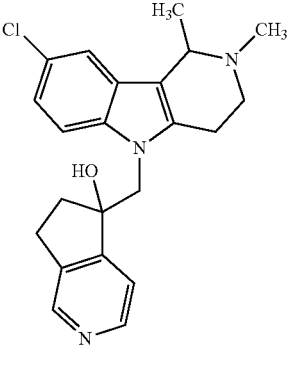 [SMILES: CC1c2c(n(CC3(O)CCc4cnccc43)c3ccc(Cl)cc23)CCN1C] |
| ii-95<br>ii-95a (isomer 1)<br>ii-95b (isomer 2)<br>ii-95c (isomer 3)<br>ii-95d (isomer 4) | 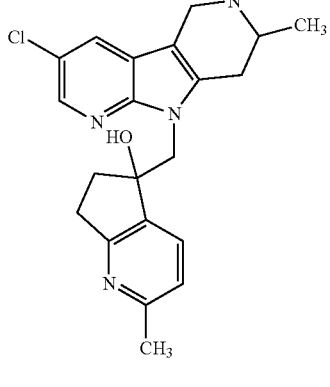 |
| ii-96<br>ii-96a (isomer 1)<br>ii-96b (isomer 2)<br>ii-96c (isomer 3)<br>ii-96d (isomer 4) | 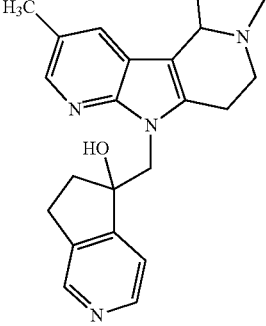 |

TABLE 2-continued

Representative Compounds of the Invention

| Compound No. | Structure |
|---|---|
| ii-97<br>ii-97a (isomer 1)<br>ii-97b (isomer 2)<br>ii-97c (isomer 3)<br>ii-97d (isomer 4) | 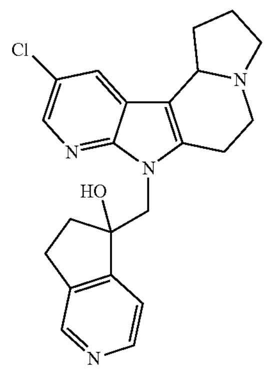 [SMILES: OC1(Cn2c3c(c4cc(Cl)cnc42)C2CCCN2CC3)CCc2cnccc21] |
| ii-98<br>ii-98a (isomer 1)<br>ii-98b (isomer 2) | 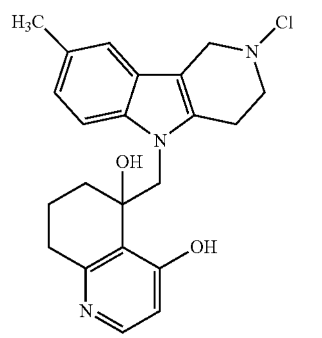 [SMILES: Cc1ccc2c(c1)c1c(n2CC2(O)CCCc3nccc(O)c32)CCN(Cl)C1] |
| ii-99<br>ii-99a (isomer 1)<br>ii-99b (isomer 2) | 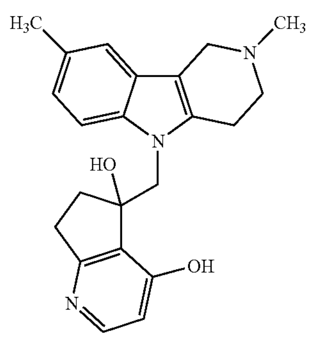 |
| ii-100<br>ii-100a (isomer 1)<br>ii-100b (isomer 2) | 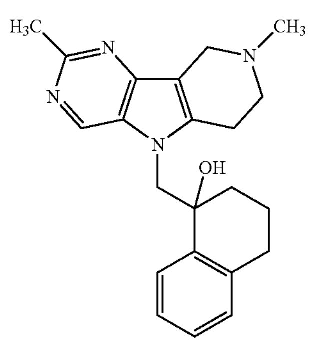 |
| ii-101 | |
| ii-102<br>ii-102a (isomer 1)<br>ii-102b (isomer 2)<br>ii-102c (isomer 3)<br>ii-102d (isomer 4)<br>ii-102e (isomer 5)<br>ii-102f (isomer 6)<br>ii-102g (isomer 7)<br>ii-102h (isomer 8) | |
| ii-103<br>ii-103a (isomer 1)<br>ii-103b (isomer 2) | |
| ii-104<br>ii-104a (isomer 1)<br>ii-104b (isomer 2) | |

TABLE 2-continued

Representative Compounds of the Invention

| Compound No. | Structure |
|---|---|
| ii-105<br>ii-105a (isomer 1)<br>ii-105b (isomer 2) | |
| ii-106<br>ii-106a (isomer 1)<br>ii-106b (isomer 2) | |
| ii-107<br>ii-107a (isomer 1)<br>ii-107b (isomer 2) | |
| ii-108<br>ii-108a (isomer 1)<br>ii-108b (isomer 2) | |
| ii-109<br>ii-109a (isomer 1)<br>ii-109b (isomer 2) | 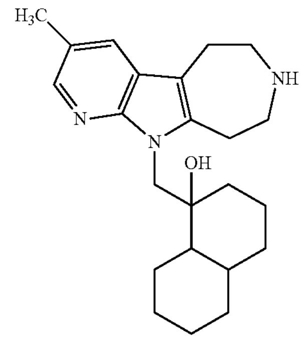 [SMILES: Cc1cnc2c(c1)c1c(n2CC2(O)CCCC3CCCCC32)CCNCC1] |
| ii-110<br>ii-110a (isomer 1)<br>ii-110b (isomer 2) | 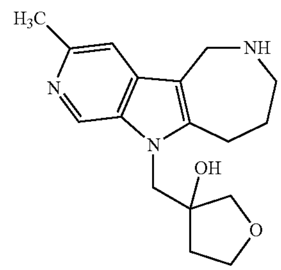 [SMILES: Cc1cc2c3c(n(CC4(O)CCOC4)c2cn1)CCCNC3] |
| ii-111<br>ii-111a (isomer 1)<br>ii-111b (isomer 2) | 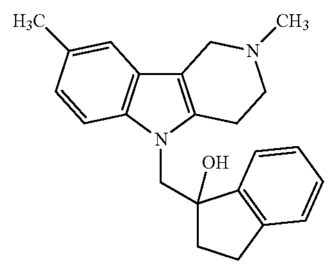 [SMILES: Cc1ccc2c(c1)c1c(n2CC2(O)CCc3ccccc32)CCN(C)C1] |
| ii-112<br>ii-112a (isomer 1)<br>ii-112b (isomer 2) | 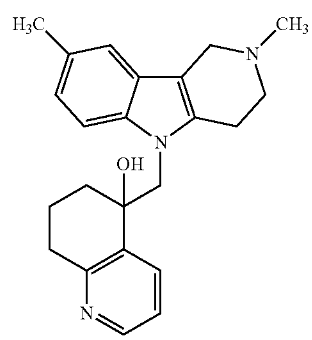 |
| ii-113<br>ii-113a (isomer 1)<br>ii-113b (isomer 2) | 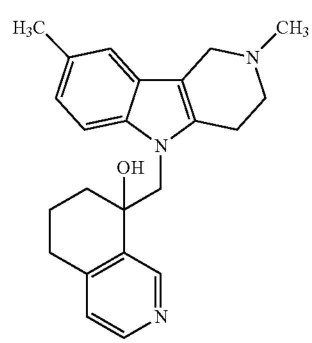 |

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., 5-$HT_{2A}$, 5-$HT_{2C}$, 5-$HT_6$ and 5-$HT_7$), inhibition of binding of a ligand to a dopamine receptor (e.g., $D_{2L}$), and inhibition of binding of a ligand to a histamine receptor (e.g., $H_1$, $H_2$ and $H_3$); agonist/antagonist activity to a serotonin receptor (e.g., 5-$HT_{2A}$, 5-$HT_6$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic dysfunction/hypofunction; efficacy in a preclinical model of attention impulsivity and executive function, and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85% and about 95% or between about 90% and about 100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g., $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$, $H_3$). In one variation, a compound of the invention inhibits binding of a ligand to at least one receptor and as many as eleven as detailed herein (e.g., $\alpha_{1D}$, $\alpha_{2A}$, $\alpha_{2B}$, 5-$HT_{2A}$, 5-$HT_{2C}$, 5-$HT_6$, 5-$HT_7$, $D_2$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor 5-$HT_{2A}$, serotonin receptor 5-$HT_6$, dopamine receptor $D_{2L}$, dopamine receptor $D_{2S}$ and histamine receptor $H_1$) as measured in the assays described herein. In one variation, agonist response of serotonin receptor 5-$HT_{2A}$ is inhibited by compounds of the invention by at least about any one of 50%, 60%, 70%, 80%, 90%, 100%, 110%, 120%, 130%, 140%, 150% as determined in a suitable assay such as the assay described herein.

In one variation, a compound of the invention displays the above described neurotransmitter receptor binding profile, e.g. inhibits binding of a ligand to at least one receptor and as many as eleven as detailed herein and further stimulates neurite outgrowth, e.g., as measured by the assays described herein. Certain compounds of the invention showed activity in neurite outgrowth assays using primary neurons in culture. Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neuronal disorders include ADHD. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, and in preclinical models of attention/impulsivity and executive function, e.g. shows pro-cognitive effects in a preclinical model of memory dysfunction. Compounds of the invention have been shown to be effective in a preclinical model of memory dysfunction associated with cholinergic hypofunction (see relevant Examples). As $H_1$ antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-$HT_6$ antagonist may have cognition-enhancing effects as serotonin acting through this receptor may impair memory.

In another variation, a compound of the invention inhibits binding of a ligand to at least one and as many as eleven receptors as detailed herein, further shows efficacy in a preclinical model of memory dysfunction associated with cholinergic dysfunction/hypofunction, e.g. shows pro-cognitive effects in a preclinical model of memory dysfunction, in preclinical models of attention/impulsivity and executive function, and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction, e.g. shows pro-cognitive effects in a preclinical model of memory dysfunction, and in preclinical models of attention/impulsivity and executive function, and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction, e.g. shows pro-cognitive effects in a preclinical model of memory dysfunction, in preclinical models of attention/impulsivity and executive function, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, e.g., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and in preclinical models of attention/impulsivity and executive function, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In a further variation, a compound of the invention inhibits binding of a ligand to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In one aspect, compounds of the invention inhibit binding of a ligand to adrenergic receptors $\alpha_{1D}$, $\alpha_{2A}$, $\alpha_{2B}$ and inhibit binding of a ligand to serotonin receptor 5-$HT_6$. In another variation, compounds of the invention inhibit binding of a ligand to adrenergic receptors $\alpha_{1D}$, $\alpha_{2A}$, $\alpha_{2B}$, to serotonin receptor 5-$HT_6$ and to any one or more of the following receptors: serotonin receptor 5-$HT_7$, 5-$HT_{2A}$ and 5-$HT_{2C}$. In another variation, compounds of the invention inhibit binding of a ligand to adrenergic receptors $\alpha_{1D}$, $\alpha_{2A}$, $\alpha_{2B}$, to serotonin receptor 5-$HT_6$ and to any one or more of the following receptors: serotonin receptor 5-$HT_7$, 5-$HT_{2A}$ and 5-$HT_{2C}$ and further show weak inhibition of binding of a ligand to histamine receptor $H_1$ and/or $H_2$. In one variation, compounds of the invention that also display strong inhibition of binding of a ligand to the serotonin receptor 5-$HT_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-$HT_6$ and further show weak inhibition of binding of a ligand to histamine receptor $H_1$ and/or $H_2$. Weak inhibition of binding of a ligand to the histamine $H_1$ receptor is permitted as agonists of this receptor have been implicated in stimulating memory as well as weight gain. In one variation, binding to histamine receptor $H_1$ is inhibited by less than about 80%. In another variation, binding of a ligand to histamine receptor $H_1$ is inhibited by less than about any of 75%, 70%, 65%, 60%, 55%, or 50% as determined by a suitable assay known in the art such as the assays described herein.

In another variation, compounds of the invention inhibit binding of a ligand to a dopamine receptor $D_2$. In another variation, compounds of the invention inhibit binding of a ligand to dopamine receptor $D_{2L}$. In another variation, compounds of the invention inhibit binding of a ligand to dopamine receptor $D_2$ and to serotonin receptor 5-$HT_{2A}$. In another variation, compounds of the invention inhibit binding of a ligand to dopamine receptor $D_{2L}$ and to serotonin receptor 5-$HT_{2A}$. In another variation, compounds of the invention inhibit binding of a ligand to histamine receptor $H_1$. In certain aspects, compounds of the invention further show one or more of the following properties: strong inhibition of binding of a ligand to the serotonin 5-$HT_7$ receptor, strong inhibition of binding of a ligand to the serotonin 5-$HT_{2A}$ receptor, strong inhibition of binding of a ligand to the serotonin 5-$HT_{2C}$ receptor, weak inhibition of binding of a ligand to the histamine $H_1$ receptor, weak inhibition of binding of ligands to the histamine $H_2$ receptor, and antagonist activity to serotonin receptor 5-$HT_{2A}$.

In one variation, compounds of the invention show any of the receptor binding aspects detailed herein and further display agonist/antagonist activity to one or more of the following receptors: serotonin receptor 5-$HT_{2A}$, serotonin receptor 5-$HT_6$, dopamine receptor $D_{2L}$, dopamine receptor $D_{2S}$ and histamine receptor $H_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction, such as enhancement of memory retention and reduction of memory impairment and in preclinical models of attention/impulsivity and executive function. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-$HT_{2A}$, 5-$HT_6$, dopamine receptor $D_{2L}$, dopamine receptor $D_{2S}$ and histamine receptor $H_1$), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors $\alpha_{1D}$, $\alpha_{2A}$, $\alpha_{2B}$, serotonin receptor 5-$HT_6$ and a dopamine receptor $D_2$ by at least about 80% as determined in a suitable assay known in the art such as the assays described herein. In one variation binding is inhibited by at least about 80% as measured in a suitable assay such as the assays described herein. In some aspects, compounds of the invention inhibit binding of a ligand to adrenergic receptors $\alpha_{1D}$, $\alpha_{2A}$, $\alpha_{2B}$, serotonin receptor 5-$HT_6$ and dopamine receptor $D_{2L}$ by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95% or between about 90% and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity and several compounds of the invention have been shown to be effective in a preclinical model of schizophrenia (see relevant Examples). In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In one variation, cognitive disorder as used herein includes and intends disorders that contain a cognitive component, such as psychotic disorders (e.g., schizophrenia) containing a cognitive component (e.g., CIAS). In one variation, cognitive disorder includes ADHD. In another aspect, the compounds described herein may be used to treat, prevent, delay the onset and/or delay the development of a psychotic disorder. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, methods of improving at least one cognitive and/or psychotic symptom associated with schizophrenia are provided. In one aspect, methods of improving cognition in an individual who has or is suspected of having CIAS are provided. In a particular aspect, methods of treating schizophrenia are provided wherein the treatment provides for an improvement in one or more negative symptom and/or one or more positive symptom and/or one or more disorganized symptom of schizophrenia. In yet another aspect, the compounds described herein may be used to treat, prevent, delay the onset and/or delay the development of a neurotransmitter-mediated disorders disorder. In one aspect, a neurotransmitter-mediated disorder includes ADHD. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis, depression and ADHD. In one variation, depression as used herein includes and intends treatment-resistant depression, depression related to a psychotic disorder, or depression related to a bipolar disorder. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects. In a particular variation, a method of treating schizophrenia is provided, wherein the treatment provides an improvement in at least one cognitive function, such as an improvement in a cognitive function in an individual who has or is suspected of having CIAS. In a further variation, a method of treating schizophrenia is provided wherein the method reduces psychotic effects associated with schizophrenia. In one embodiment, a method of treating schizophrenia is provided wherein the method improves the negative symptoms of schizophrenia in an individual in need thereof. In one embodiment, a method of treating schizophrenia is provided wherein the method improves the positive symptoms of schizophrenia in an individual in need thereof. In a further variation, a method of treating schizophrenia is provided wherein the method both improves cognitive function and reduces psychotic effects in an individual in need thereof. A method of improving one or more negative, positive and disorganized symptoms of schizophrenia is also provided, where the method entails administering a compound as detailed herein, or a pharmaceutically acceptable salt thereof, to an individual in need of such improvement. In one variation, a method of improving at least one negative symptom of schizophrenia is provided, where the method entails administering a compound as detailed herein, or a pharmaceutically acceptable salt thereof, to an individual in need of such improvement. In another variation, a method of improving at least one negative and at least one positive symptom of schizophrenia is provided, where the method entails administering a compound as detailed herein, or a pharmaceutically acceptable salt thereof, to an individual in need of such improvement. In yet another variation, a method of improving at least one negative and at least one disorganized symptom of schizophrenia is also provided, where the method entails administering a compound as detailed herein, or a pharmaceutically acceptable salt thereof, to an individual in need of such improvement. In still another variation, a method of improving at least one positive and at least one disorganized symptom of schizophrenia is also provided, where the method entails administering a compound as detailed herein, or a pharmaceutically acceptable salt thereof, to an individual in need of such improvement. In still a further variation, a method of improving at least one negative, at least one positive and at least one disorganized symptom of schizophrenia is provided, where the method entails administering a compound as detailed herein, or a pharmaceutically acceptable salt thereof, to an individual in need of such improvement.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-HT$_{2A}$, 5-HT$_6$, 5-HT$_7$, histamine receptor H$_1$ and/or H$_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-HT$_6$ receptor is expected to be or is beneficial for the cognitive disorders, psychotic disorders, neurotransmitter-mediated disorders and/or neuronal disorders. In some variations, modulation of adrenergic receptor amu, $\alpha_{2A}$, $\alpha_{2B}$, and a serotonin receptor 5-HT$_6$ receptor and modulation of one or more of the following receptors serotonin 5-HT$_7$, 5-HT$_{2A}$, 5-HT$_{2C}$ and histamine H$_1$ and H$_2$ is expected to be or is beneficial for the cognitive disorders, psychotic disorders, neurotransmitter-mediated disorders and/or neuronal disorders. In some variations, modulation of a dopamine receptor D$_2$ is expected to be or is beneficial for the cognitive disorders, psychotic disorders, neurotransmitter-mediated disorders and/or neuronal disorders. In some variations, modulation of dopamine receptor D$_{2L}$ is expected to be or is beneficial for the cognitive disorders, psychotic disorders, neurotransmitter-mediated disorders and/or neuronal disorders. In some variations, modulation of a dopamine receptor D$_2$ is expected to be or is beneficial for the cognitive disorders, psychotic disorders, neurotransmitter-mediated disorders and/or neuronal disorders. In certain variations, modulation of a dopamine D$_{2L}$ receptor and serotonin receptor 5-HT$_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{2B}$, serotonin receptor 5-HT$_{2A}$, 5-HT$_6$, 5-HT$_7$, histamine receptor H$_1$ and/or H$_2$ is desirable or expected to be desirable to improve cognitive functions. In some variations modulation of $\alpha_{1D}$, $\alpha_{2A}$, $\alpha_{2B}$ adrenergic receptors and a serotonin 5-HT$_6$ receptor is desirable or expected to be desirable to improve cognitive functions. In some variations, modulation of $\alpha_{1D}$, $\alpha_{2A}$, $\alpha_{2B}$ adrenergic receptors and serotonin receptor 5-HT$_6$ and modulation of one or more of the following receptors: serotonin receptor 5-HT$_7$, 5-HT$_{2A}$, 5-HT$_{2C}$ and histamine receptor H$_1$ and H$_2$, is desirable or expected to be desirable to improve cognitive functions. In another aspect, the invention encompasses methods to reduce psychotic effects by administering a compound of the invention to an individual in need thereof. In some embodiments, modulation of a dopamine D$_2$ receptor is expected to be or is desirable to reduce psychotic effects. In some embodiments, modulation of a dopamine D$_{2L}$ receptor is expected to be or is desirable to reduce psychotic effects. In some embodiments, modulation of a dopamine D$_2$ receptor and a serotonin 5-HT$_{2A}$ receptor is expected to be or is desirable to reduce psychotic effects. In some embodiments, modulation of a dopamine D$_{2L}$ receptor and a serotonin 5-HT$_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 μM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-HT$_6$ receptor. In some variations, the aminergic G protein-coupled receptor is a $\alpha_{1D}$, $\alpha_{2A}$, $\alpha_{2B}$ adrenergic receptor and a serotonin 5-HT$_6$ and 5-HT$_7$ receptor. In some variations, the aminergic G protein-coupled receptor is a $\alpha_{1D}$, $\alpha_{2A}$, $\alpha_{2B}$ adrenergic receptor, a serotonin 5-HT$_6$ and one or more of the following receptors: serotonin 5-HT$_7$, 5-HT$_{2A}$ and 5-HT$_{2C}$ and histamine H$_1$ and H$_2$ receptor. In some variations, the aminergic G protein-coupled receptor is a dopamine D$_2$ receptor. In some variations, the aminergic G protein-coupled receptor is a dopamine D$_{2L}$ receptor. In some variations, the aminergic G protein-coupled receptor is a dopamine D$_2$ receptor and a serotonin 5-HT$_{2A}$ receptor. In some variations, the aminergic G protein-coupled receptor is a dopamine D$_{2L}$ receptor and a serotonin 5-HT$_{2A}$ receptor. In some variations, the aminergic G protein-coupled receptor is a histamine H$_1$ receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Protocol for Chiral Preparative HPLC Separation of Racemic Compounds

For chiral separations, samples were dissolved in MeOH and EtOH according to the solubility of sample and filtered through 0.22μ PTFE filters. The columns used were CHIRALPAK-AD; 20*250 mm, 10μ and CHIRALCEL-ODH; 20*250 mm, 5μ. A flow rate of 12 mL/min-17 mL/min was used according to the resolution. Alkanes such as n-Pentane, Hexane and Heptane (40%-95%) and alcohols such as EtOH, Isopropyl alcohol and t-Butanol (5%-60%) were used as mobile phase. In some cases alcohol combinations i.e., (EtOH+MeOH), (EtOH+IPA), (IPA+MeOH), (t-Butanol+ MeOH), (t-Butanol+EtOH) were used instead of a single alcohol. Diethyl amine (up to 0.3%) was used as modifier in the mobile phase.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

Compounds detailed herein may be prepared by those of skill in the art by referral to General Methods and Examples described in published PCT applications WO2009/055828 (see e.g., General Methods 1-24 and Examples 1-325), WO2010/127177 (General Methods 1-3 and Examples 1-58), WO2009/120720 (General Methods 1-15C and Examples 1-134), WO2009/120717 (General Methods 1-17 and Examples 1-134), WO2010/051501 (General Methods 1-10 and Examples 1-450) and WO2010/051503 (General Methods 1-15 and Examples 1-111), WO2011/019417 (General Methods 1-9 and Examples 1-10), WO2011/038164 (General Methods 1-19), WO2011/038162 (General Methods 1-21 and Examples 1-6), WO2011/038163 (General Methods 1-19 and Examples 1-49) and WO2011/038161 (General Methods 1-15B and Examples 1-22). The PCT publications described above are incorporated herein by reference in their entireties.

Exemplified routes to synthesizing particular compounds of the invention are shown below as General Methods 1 to 4.

General Method 1

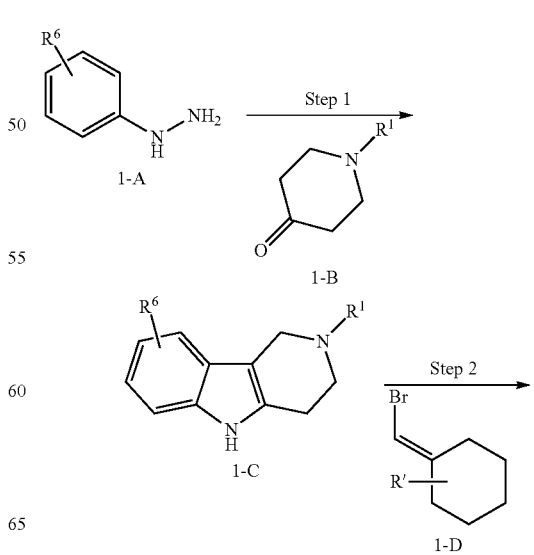

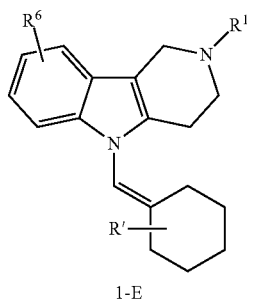

1-E

Heating of appropriately substituted hydrazine 1-A with appropriately substituted piperidone 1-B in acid provides the cyclized carboline 1-C which, upon subjecting to coupling conditions with vinyl halide 1-D yields the desired alkylidene product 1-E.

General Method 2

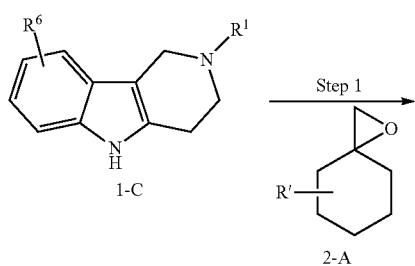

2-A

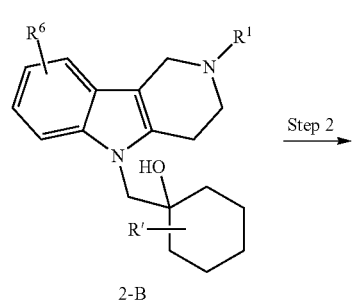

2-B

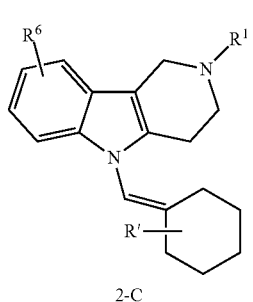

2-C

Base-mediated treatment of the carboline 1-C from General Method 1 with appropriately substituted oxirane 2-A yields the coupled alcohol intermediate 2-B which, upon dehydration in acid, yields the alkylidene product 2-C.

General Method 3

Preparation of N-Methyl and N-Ethyl 9-Chloro-1,2,3,4,5,6-hexhydroazepino[4,3-b]indole

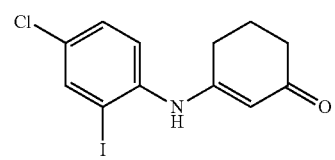 [SMILES: O=C1C=C(Nc2ccc(Cl)cc2I)CCC1]

A mixture of 4-chloro-2-iodoaniline (0.5 g, 1.97 mmol), 1,3-cyclohexanedione (0.22 g, 1.96 mmol) and p-toluenesulfonic acid monohydrate (catalytic) in toluene (6 mL) were heated to reflux for 2 h. The reaction was cooled and EtOAc (50 mL) was added and the organic phase was washed with water (20 mL) and brine (20 mL), dried over sodium sulfate, filtered and evaporated to give a brown solid, which was purified by column chromatography [Silica, eluent: EtOAc: hexane to give 3-(4-chloro-2-iodophenylamino)cyclohex-2-enone as a yellow solid (0.55 g, 80%).

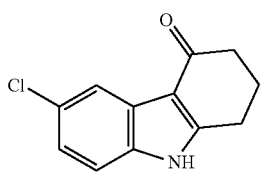 [SMILES: O=C1CCCc2[nH]c3ccc(Cl)cc3c21]

A mixture of 3-(4-chloro-2-iodo-phenylamino)-cyclohex-2-enone (0.5 g, 1.44 mmol), cuprous iodide (27.4 mg, 0.14 mmol), L-proline (33.12 mg, 0.29 mmol) and potassium hydroxide (0.32 g, 5.70 mmol) in DMSO (6 mL) were heated to 90° C. for 24 h. The reaction was cooled and poured into water. The aqueous phase was extracted with EtOAc (3×50 mL). The combined organic phase was washed with brine (25 mL), dried over magnesium sulfate, filtered and the solvent removed under reduced pressure to give a dark brown solid. This was recrystallized using acetonitrile water to give a brown solid (0.17 g, 54%). mp 281-282° C.

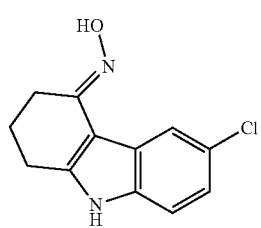 [SMILES: O/N=C1\CCCc2[nH]c3ccc(Cl)cc3c21]

A solution of 6-chloro-2,3-dihydro-1H-carbazol-4(9H)-one (500 mg, 2.27 mmol), hydroxylamine hydrochloride (238 mg, 3.41 mmol) and NaOAc (280 mg, 3.41 mmol) in EtOH:water (4.5:2 mL) was heated to reflux (125° C.) for 5 h. The reaction mixture was concentrated to dryness. Water was added to the residue and the solid filtered, dried under vacuum to yield the title compound.

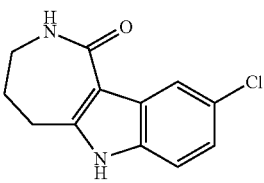 [SMILES: O=C1NCCCc2[nH]c3ccc(Cl)cc3c21]

6-Chloro-2,3-dihydro-1H-carbazol-4(9H)-one oxime (4.39 g, 18.71 mMol) and polyphosphoric acid (119 g) was heated together at 120° C. for 20 min. After cooling to RT, ice-water mixture was added to hydrolyze the mixture and stirred for 2 h. The mixture was filtered and washed with NH₄OH (40 ml) followed by water. The resultant solid was dissolved in MeOH and filtered. The methanolic solution was concentrated to yield 4.7 g of crude as a brown solid. The crude product was purified by flash column chromatography over silica-gel (230-400 mesh) using EtOAc/Hexane followed by MeOH/EtOAc, the product eluting at 2-10% MeOH/EA. Yield: 2.1g (47.8%).

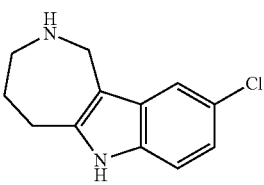 [SMILES: Clc1ccc2[nH]c3c(c2c1)CNCCC3]

To an ice-cooled stirred suspension of Lithium aluminum hydride (486 mg, 12.8 mmol) in dry THF (29 mL) was added dropwise a solution of 9-chloro-2,3,4,5-tetrahydroazepino[4,3-b]indol-1(6H)-one (380 mg, 1.62 mmol) in dry THF (20 mL), and the reaction mixture heated to reflux for 15 h (89° C.). The reaction mixture was cooled to RT, quenched with water (3 mL), and 15% NaOH solution (6 mL) and water (9 mL), and then diluted with THF. The reaction mixture was filtered through Celite and the filtrate concentrated under reduced pressure to yield the title compound.

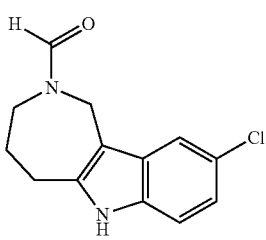

A solution of 9-chloro-1,2,3,4,5,6-hexahydroazepino[4,3-b]indole (360 mg, 1.6 mmol) in THF (1 mL) was added dropwise to ethyl formate (1 mL). The reaction mixture was stirred at RT for 30 min, followed by heating to reflux for 14 h. The solvent was removed under reduced pressure to yield the title compound.

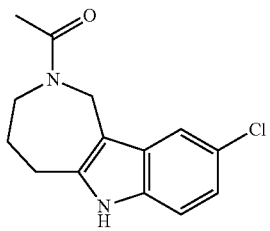 [SMILES: CC(=O)N1CCCc2[nH]c3ccc(Cl)cc3c2C1]

A solution of 9-chloro-1,2,3,4,5,6-hexahydroazepino[4,3-b]indole (360 mg, 1.6 mmol) was stirred in acetic anhydride for 12 h. The solvent was removed under reduced pressure to yield the title compound.

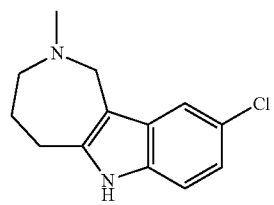 [SMILES: CN1CCCc2[nH]c3ccc(Cl)cc3c2C1]

A solution of 9-chloro-1,2,3,4,5,6-hexahydroazepino[4,3-b]indole (12.3 g, 55.9 mmol) in ethyl formate (369 mL) was stirred at 55° C. for 2 h. The progress of reaction was monitored by TLC. The reaction mixture was concentrated under reduced pressure and the crude product (13.5 g) was used for the next step without purification. To a stirred suspension of lithium aluminum hydride (4.13 g, 108.8 mmol) in dry THF (405 mL) was added portionwise 9-chloro-3,4,5,6-tetrahydroazepino[4,3-b]indole-2(1H)-carbaldehyde (13.5 g) and the mixture heated to reflux for 2 h. The progress of reaction was monitored by TLC. The reaction was quenched with saturated aqueous sodium sulfate solution at 0° C., and the mixture filtered. The filtrate was dried over anhydrous sodium sulfate and evaporated to dryness. The residue was washed with diethyl ether to yield the title compound (9.7 g). ¹H NMR (DMSO) δ (ppm): 11.02 (s, 1H, D₂O exchangeable), 7.45 (s, 1H), 7.25-7.22 (d, 1H), 6.98-6.95 (d, 1H), 3.72 (s, 2H), 2.90-2.80 (m, 4H), 2.30 (s, 3H), 1.82-1.77 (m, 2H).

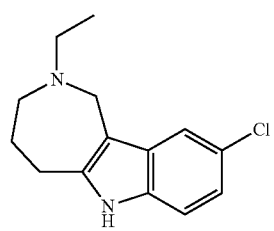 [SMILES: CCN1CCCc2[nH]c3ccc(Cl)cc3c2C1]

To an ice-cooled stirred suspension of lithium aluminum hydride (390 mg, 10.09 mmol) in 1,4-dioxane (15 mL) was added portionwise 1-(9-chloro-4,5-dihydroazepino[4,3-b]indol-2(1H,3H,6H)-yl)ethanone (300 mg, 1.14 mmol), and the reaction mixture heated to reflux for 6 h. The reaction mixture was quenched with water (1 mL), 15% aq. NaOH solution (3 mL) and water (3 mL), and extracted with warm EtOAc (3×50 mL). The combined organic extract was concentrated and the residue purified by silica gel (230-400 mesh) flash column chromatography (100% EtOAc) to yield the title compound (115 mg).

General Method 4

Preparation of 2,9-dimethyl-1,2,3,4,5,6-hexahydroazepino[4,3-b]indole

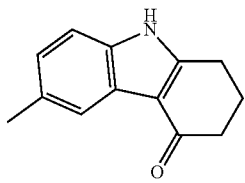

To a solution of p-tolylhydrazine hydrochloride (7.5 g, 47.2 mmol) in 1,4-dioxane:conc. H₂SO₄ (225:16.5 mL) was added cyclohexane-1,3-dione (4.42 g, 39.4 mmol), and the mixture heated to reflux for 16 h (85-90° C.). The reaction mixture was cooled to RT, basified with 15% aqueous KOH (pH 10) and extracted with EtOAc. The organic layer was washed twice with brine, dried over anhydrous sodium sulfate and concentrated under reduced pressure to yield the title compound (7.7 g, crude).

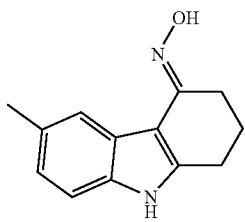 [SMILES: Cc1ccc2[nH]c3c(c2c1)/C(=N/O)CCC3]

A solution of 2,3-dihydro-6-methyl-1H-carbazol-4(9H)-one (5.8 g, 19.1 mmol), hydroxylamine hydrochloride (3.0 g, 43.6 mmol) and NaOAc (3.58 g, 43.6 mmol) in EtOH:water (58:25.3 mL) was heated to reflux (125° C.) for 5 h. The reaction mixture was concentrated to dryness. Water was added to the residue and the solid filtered, dried under vacuum to yield title compound.

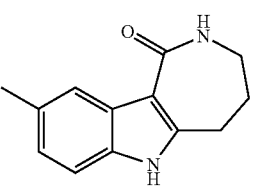 [SMILES: Cc1ccc2[nH]c3c(c2c1)C(=O)NCCC3]

To a preheated (105° C.) solution of polyphosphoric acid (225 g) was added powdered 6-methyl-2,3-dihydro-1H-carbazol-4(9H)-one oxime (10 g) under nitrogen and heating continued for 15 min. The reaction mixture was cooled to and to it was added crushed ice water. The crystallized solid obtained was collected by filtration. The solid was washed with water and then by dilute ammonium hydroxide, then dried under vacuum to obtain the desired product (8 g, crude product).

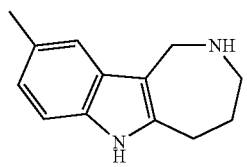

Lithium aluminum hydride (3 g, 78.95 mmol) was placed in 1,4-dioxane (100 mL) under inert atmosphere and 9-methyl-2,3,4,5-tetrahydroazepino[4,3-b]indol-1 (6H)-one (3 g, 14.018 mmol) was added, and the mixture heated to reflux for 15 h. The reaction was monitored by TLC. The reaction was quenched with saturated aqueous sodium sulfate at 0° C., and the reaction mixture filtered. The filtrate was dried over anhydrous sodium sulfate and evaporated to dryness to afford solid, which was washed with water followed by EtOAc, and dried to afford 1.25 g of the title compound.

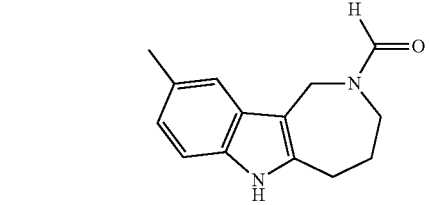 [SMILES: Cc1ccc2[nH]c3c(c2c1)CN(C=O)CCC3]

9-Methyl-1,2,3,4,5,6-hexahydroazepino[4,3-b]indole (0.25 g, 1.25 mmol) was taken in ethyl formate (18 mL, 227 mmol) and stirred at 55° C. for 3 h. The reaction was monitored by TLC. The reaction mixture was evaporated under reduced pressure and used for the next step without purification (0.2 g).

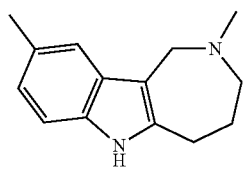 [SMILES: Cc1ccc2[nH]c3c(c2c1)CN(C)CCC3]

To a stirred suspension of lithium aluminum hydride (2 g, 52.63 mmol) in dry THF (150 mL) was added portionwise 9-methyl-3,4,5,6-tetrahydroazepino[4,3-b]indole-2(1H)-carbaldehyde (5.9 g, 25.87 mmol) and the reaction mixture stirred at 55° C. for 2 h. The progress of reaction was monitored by TLC. The reaction mixture was quenched with saturated sodium aqueous sulfate solution at 0° C. and then filtered. The filtrate was dried over anhydrous sodium sulfate and evaporated to dryness to afford the title compound (5.2 g).
¹H NMR (DMSO) δ (ppm): 7.12-7.05 (m, 2H), 6.80-6.6.76 (d, 1H), 3.65 (s, 2H), 2.90-2.80 (m, 4H), 2.34 (s, 3H), 2.26 (s, 3H), 1.80-1.72 (m, 2H).

One or more of the General Methods detailed above may be adapted or combined as required by those of skill in the art to make compounds detailed herein. Particular examples of each of the General Methods are provided in the Examples below. For instance, compounds i-1, i-2, i-3 were prepared according to Examples 1-3 respectively.

The following Examples are provided to illustrate but not to limit the invention.

All references disclosed herein are incorporated by reference in their entireties.

EXAMPLES

Example 1

Preparation of Compound No. i-1

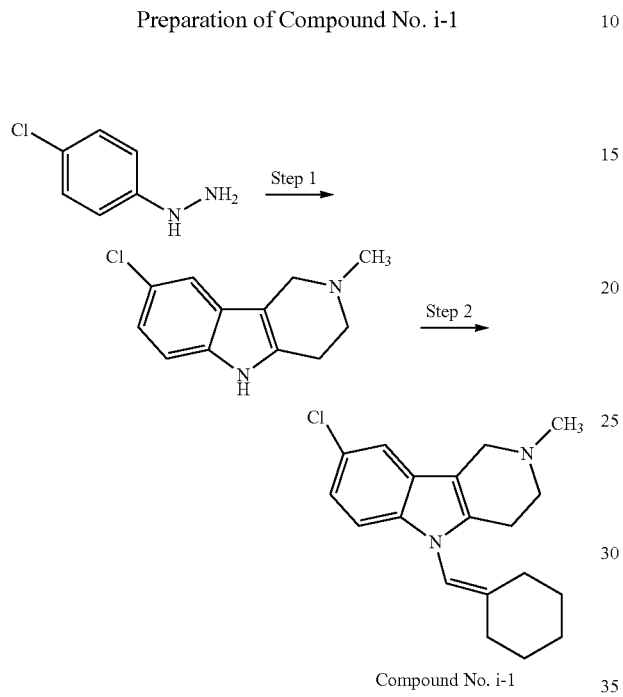

Compound No. i-1

Step 1:

To a solution of 4-chlorophenyl hydrazine hydrochloride (30 g, 167.59 mmol) in dioxane (300 mL) were added 1-methyl-4-piperidone (28 mL, 234.63 mmol) and sulfuric acid (14.4 mL) dropwise. The reaction mixture was stirred at 80° C. for 3 h. The dioxane layer was decanted and the residue basified with 10% aqueous KOH solution. The resulting solid was filtered and washed with water (2 L) and finally with hexane (500 mL). The product was dried under vacuum at RT to yield the desired compound as a light brown solid (30 g). $^1$H NMR (Freebase, CDCl$_3$) δ (ppm): 7.40 (s, 1H), 7.20-7.10 (d, 1H), 7.10-7.00 (d, 1H), 3.60 (s, 2H), 2.90 (s, 4H), 2.60 (s, 3H).

Step 2:

To a solution of 8-chloro-2,3,4,5-tetrahydro-2-methyl-1H-pyrido[4,3-b]indole (110 mg, 0.5 mmol), K$_3$PO$_4$ (212.4 mg, 1 mmol), copper (I) iodide (9.5 mg, 0.05 mmol) and L-proline (11.51 mg. 0.1 mmol) in DMF (3 mL) was added dropwise a solution of (bromomethylene)cyclohexane (105 mg, 0.6 mmol) in DMF (2 mL). The reaction mixture was degassed using nitrogen and stirred at 85° C. overnight. Water was added to the reaction mixture and the inorganic matter was filtered. The filtrate was concentrated under reduced pressure to afford crude material, which was purified by column chromatography using silica (100-200) and 0-3% MeOH-DCM to yield Compound No. i-1 (160 mg). $^1$H NMR (HCl salt, CD$_3$OD) δ (ppm): 7.50 (s, 1H), 7.18 (m, 2H), 6.38 (s, 1H), 4.70 (m, 1H), 4.50 (m, 1H), 3.85 (m, 1H), 3.60 (m, 1H), 3.15 (s, 3H), 3.10 (m, 2H), 2.40 (m, 2H), 1.94 (m, 2H), 1.75 (m, 2H), 1.65 (m, 2H), 1.50 (m, 2H).

Example 2

Preparation of Compound No. i-2

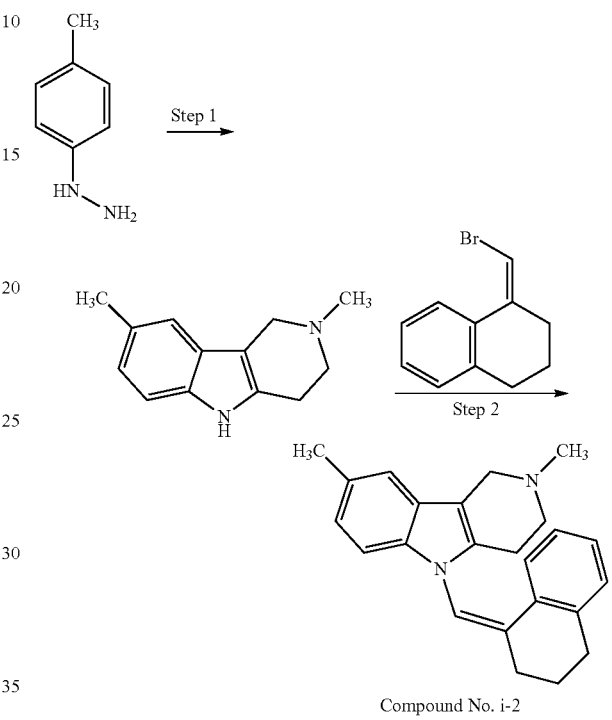

Compound No. i-2

Step 1:

To a solution of p-tolyl hydrazine hydrochloride (6.0 g, 37 mmol) in dioxane (60 mL) was added sulfuric acid (2 mL). After stirring for 5 min, N-methyl piperidone (5.03 g, 41 mmol) was added and stirring continued at 80° C. for 2 h. The reaction mixture was concentrated under reduced pressure to ~20 mL and basified with 10% aqueous KOH solution (to pH 10). The reaction mixture was extracted with EtOAc (3×300 mL). The organic layer was dried over anhydrous sodium sulfate and concentrated under reduced pressure to yield the desired compound as a brown solid (4.0 g). $^1$H NMR (Freebase, DMSO) δ (ppm): 7.2 (d, 1H), 7.15 (s, 1H), 6.95 (d, 1H), 4.5 (m, 1H), 4.2 (m, 1H), 3.6 (m, 1H), 3.2 (m, 1H), 3.0 (m, 2H), 2.9 (s, 3H), 2.4 (s, 3H).

Step 2:

To a solution of 2,8-dimethyl-2,3,4,5-tetrahydro-1H-pyrido[4,3-b]indole (0.224 g, 1.12 mmol), CuI (21 mg, 0.112 mmol), L-proline (25 mg, 0.224 mmol) and K$_3$PO$_4$ (0.477 g, 2.24 mmol) in DMF (10 mL) was slowly added (Z)-1-(bromomethylene)-1,2,3,4-tetrahydronaphthalene (0.3 g, 1.34 mmol) under inert atmosphere. The reaction mixture was stirred at 80° C. for 14 h. The reaction mixture was cooled to RT and extracted with EtOAc (3×200 mL). The organic layer was dried over anhydrous sodium sulfate and concentrated under reduced pressure to afford crude material, which was purified by column chromatography using 4% MeOH-DCM to yield Compound No. A2 (325 mg). $^1$H NMR (TFA salt, CD$_3$OD) δ (ppm): 7.22 (s, 1H), 7.18 (d, 2H), 7.1 (dd, 1H), 7.0 (d, 1H), 6.7 (d, 2H), 6.4 (m, 1H), 4.62 (m, 1H), 4.39m, 1H), 3.62 (m, 1H), 3.4 (m, 1H), 2.9-3.1 (m, 5H), 2.5-2.77 (m, 3H), 2.4 (m, 4H), 1.98-2.19 (m, 2H).

Example 3

Preparation of Compound No. i-3

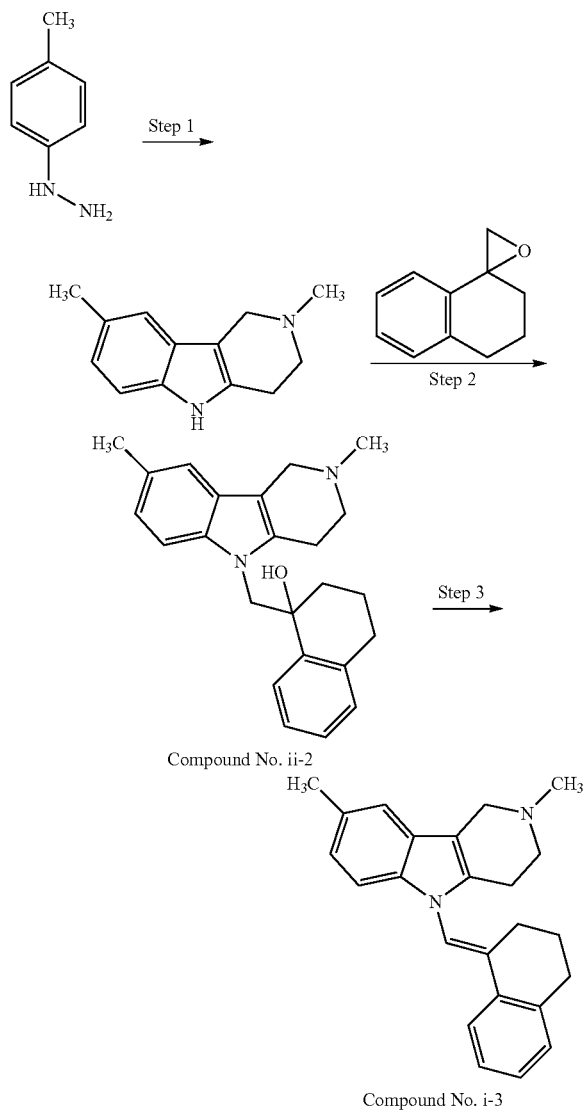

Compound No. i-3

Step 1:

To a solution of p-tolyl hydrazine hydrochloride (6.0 g, 37 mmol) in dioxane (60 mL) was added sulfuric acid (2 mL). After stirring for 5 min, N-methyl piperidone (5.03 g, 41 mmol) was added and stirring continued at 80° C. for 2 h. The reaction mixture was concentrated under reduced pressure to ~20 mL and basified with 10% aqueous KOH solution (to pH 10). The reaction mixture was extracted with EtOAc (3×300 mL). The organic layer was dried over anhydrous sodium sulfate and concentrated under reduced pressure to yield the desired compound as a brown solid (4.0 g). $^1$H NMR (Freebase, DMSO) δ (ppm): 7.2 (d, 1H), 7.15 (s, 1H), 6.95 (d, 1H), 4.5 (m, 1H), 4.2 (m, 1H), 3.6 (m, 1H), 3.2 (m, 1H), 3.0 (m, 2H), 2.9 (s, 3H), 2.4 (s, 3H).

Step 2:

To a stirred solution of NaH (0.186 g, 70.3 mmol) in DMF was added 2,8-dimethyl-2,3,4,5-tetrahydro-1H-pyrido[4,3-b]indole (0.5 g, 28.1 mmol) in portions at RT. After stirring for 15 min, 3,4-dihydro-2H-spiro[naphthalene-1,2'-oxirane] (0.9 g, 56.25 mmol) was added dropwise into the reaction mixture and stirring continued at RT overnight. The reaction mixture was quenched with ice water, extracted with EtOAc and washed with brine. The organic layer was dried over anhydrous sodium sulfate and concentrated under reduced pressure to afford crude material, which was purified by washing with 20% acetone-hexane to yield Compound No. ii-2. $^1$H NMR (TFA salt, DMSO) δ (ppm): 9.90 (bs, 1H), 7.20 (dd, 1H), 7.14-7.04 (m, 4H), 7.0 (m, 1H), 6.90 (d, 1H), 5.30 (d, 1H), 4.60 (m, 1H), 4.30 (m, 2H), 3.70 (m, 2H), 3.0 (m, 2H), 2.95 (s, 3H), 2.70 (m, 2H), 2.38 (s, 3H), 2.02-1.80 (m, 4H).

Step 3:

A solution of 1-((2,8-dimethyl-3,4-dihydro-1H-pyrido[4,3-b]indol-5(2H)-yl)methyl)-1,2,3,4-tetrahydro naphthalen-1-ol (2 g, 5.55 mmol) (enantiomers B2a and B2b) in 25% aq. sulfuric acid was stirred at 80° C. for 4 h. The reaction mixture was cooled to RT, basified with 2N sodium hydroxide and extracted with EtOAc. The organic layer was dried over anhydrous sodium sulfate and concentrated under reduced pressure to yield Compound No. i-3 (1.2 g). $^1$H NMR (TFA salt, CD$_3$OD) δ (ppm): 7.8 (d, 1H), 7.3 (s, 1H), 7.2-7.29 (m, 4H), 7.02-7.17 (dd, 2H), 4.7 (d, 1H), 4.4 (d, 1H), 3.81 (m, 1H), 3.6 (m, 1H), 3.07-3.17 (m, 5H), 2.83 (t, 2H), 2.41 (s, 3H), 2.24 (t, 2H), 1.8 (m, 2H).

Example 4

Preparation of Compound Nos. ii-74, ii-74a and ii-74b

To a solution of 2,3,4,5-tetrahydro-2,8-dimethyl-1H-pyrido[4,3-b]indole (1.4 g, 7 mmol) in DMF (7 mL) was added NaH (840 mg, 21 mmol). After stirring for 10 min at RT, a solution of 5-epoxide-tetrahydroisoquinoline (1.5 g, 9.3 mmol) in DMF (1 mL) was added into the reaction mixture, which was stirred at RT for 16 h. The progress of reaction was monitored by TLC, LCMS and NMR. The reaction mixture was quenched with ice-water and extracted with EtOAc. The organic layer was washed with water, dried over anhydrous sodium sulfate and concentrated under reduced pressure to yield the crude product, which was purified by reverse phase HPLC to give racemic Compound No. ii-74, followed by chiral preparative HPLC to obtain Compound Nos. ii-74a and ii-74b. $^1$H NMR (freebase, CDCl$_3$) δ (ppm): 8.4 (s, 1H), 8.29 (d, 1H), 7.24 (m, 1H), 7.18 (s, 1H), 7.08 (s, 1H), 6.96 (d, 1H), 4.23 (dd, 2H), 2.87 (m, 4H), 2.61 (bs, 4H), 2.43 (s, 3H), 2.17 (d, 2H), 2.03 (m, 3H), 1.75 (t, 2H).

Example 5

Preparation of Compound Nos. ii-111, ii-111a and ii-111b

To solution of 2,3,4,5-tetrahydro-2,8-dimethyl-1H-pyrido[4,3-b]indole (1.0 g, 5 mmol) in DMF (7 mL) was added NaH (60%, 600 mg, 15 mmol). After stirring for 5 min at RT, a solution of indanone epoxide (1.2 g, 7.5 mmol) in DMF (4 mL) was added into the reaction mixture, which was stirred at 60° C. for 26 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The residue was crystallized with EtOH-ether to yield Compound No. ii-111 (370 mg) which was separated by chiral preparative HPLC to obtain Compound Nos. ii-111a and ii-111b. $^1$H NMR (freebase, CDCl$_3$) δ (ppm): 7.21 (m, 2H), 7.1 (s, 1H), 7.05 (d, 1H), 7.0 (m, 1H), 6.85 (d, 1H), 6.76 (d, 1H), 4.25 (d, 1H), 4.1 (d, 1H), 3.6 (d, 1H), 2.9 (m, 3H), 2.7 (m, 2H), 2.5 (m, 2H), 2.5 (s, 3H), 2.45 (s. 3H), 2.2 (d, 1H), 2.05 (m 1H).

Example 6

Preparation of Compound Nos. ii-112, ii-112a and ii-112b

To a solution of 2,3,4,5-tetrahydro-2,8-dimethyl-1H-pyrido[4,3-b]indole (400 mg, 2 mmol) in DMF (5 mL) was added NaH (60% suspension, 240 mg, 6 mmol). After stirring for 10 min at RT, a solution of 7',8'-dihydro-6'H-spiro[oxirane-2,5'-quinoline](483 mg, 3 mmol) in DMF (1 mL) was added into the reaction mixture, which was stirred at RT for 16 h. The reaction mixture was quenched with ice-water and extracted with EtOAc. The organic layer was washed with water, dried over anhydrous sodium sulfate and concentrated under reduced pressure to yield Compound No. B112, which was purified by reverse phase HPLC followed by chiral semi preparative HPLC to provide Compound Nos. ii-112a and ii-112b. $^1$H NMR (freebase, CDCl$_3$) δ (ppm): 8.2 (d, 1H), 6.8 (s, 1H), 6.7 (s, 1H), 6.6 (d, 1H), 6.4 (bs, 1H), 5.9 (bs, 1H), 4.2 (d, 1H), 4.1 (d, 1H), 3.3 (bs, 1H), 3.1 (d, 1H), 3.0 (m, 3H), 2.8 (m, 1H), 2.6 (d, 1H), 2.41 (t, 1H), 2.4 (s, 3H), 2.35 (s, 3H), 2.2 (d, 1H), 2.18 (m, 2H), 1.9 (t, 1H).

Example 7

Preparation of Compound Nos. ii-113, ii-113a and ii-113b

To a solution of 2,3,4,5-tetrahydro-2,8-dimethyl-1H-pyrido[4,3-b]indole (300 mg, 1.5 mmol) in DMF (4 mL) was added NaH (180 mg, 4.5 mmol). After stirring at RT for 15 min, the epoxide (483 mg, 3 mmol) was added into the reaction mixture, which was stirred at RT for 12 h. The progress of reaction was monitored by TLC and LCMS. The reaction mixture was quenched with ice-water and extracted with EtOAc (3×50 mL). The organic layer was washed with water (4×50 mL), dried over anhydrous sodium sulfate and concentrated under reduced pressure. The residue was purified by reverse phase HPLC to yield Compound No. ii-113 (186 mg) which was separated by chiral preparative HPLC to obtain Compound Nos. ii-113a and ii-113b. $^1$H NMR (freebase, CDCl$_3$) δ (ppm): 8.33 (s, 1H), 7.85 (bs, 1H), 7.04 (s, 1H), 6.85 (m, 3H), 4.14 (dd, 2H), 3.55 (bs, 2H), 2.98 (m, 3H), 2.86 (m, 1H), 2.68 (m, 2H), 2.49 (s, 3H), 2.38 (s, 3H), 2.13 (d, 1H), 1.99 (m, 2H), 1.74 (m, 2H).

Example B1

Determination of the Ability of Compounds of the Invention to Bind a Histamine Receptor Histamine H$_1$ To evaluate in radioligand binding assays the activity of compounds of the invention, human recombinant histamine H1 receptor expressed in Chinese hamster ovary (CHO) K1 cells (De Backer, M. et al, Biochem. Biophys. Res. Comm. 197(3):1601, 1993) in a modified Tris-HCl buffer (50 mM Tris-HCl, pH 7.4, 2 mM MgCl$_2$, 100 mM NaCl, 250 mM Sucrose) was used. Compounds of the invention were incubated with 1.2 nM [$^3$H]Pyrilamine for 180 min at 25° C. Non-specific binding was estimated in the presence of 1 µM Pyrilamine. Receptor proteins were filtered and washed, the filters were then counted to determine [$^3$H]Pyrilamine specifically bound. Compounds were screened at 1 µM or lower, using 1% DMSO as vehicle. Biochemical assay results are presented as the percent inhibition of specific binding in Table 3.

Histamine H$_2$

To evaluate in radioligand binding assays the activity of compounds of the invention, human recombinant histamine H2 receptor expressed in Chinese hamster ovary (CHO) K1 cells (Ruat, M., Proc. Natl. Acad. Sci. USA. 87(5):1658, 1990) in a 50 mM Phosphate buffer, pH 7.4 is used. Compounds of the invention are incubated with 0.1 nM [$^{125}$I] Aminopotentidine for 120 min at 25° C. Non-specific binding is estimated in the presence of 3 µM Tiotidine. Receptor proteins are filtered and washed, the filters are then counted to determine [$^{125}$I]Aminopotentidine specifically bound. Compounds are screened at 1 µM or lower, using 1% DMSO as vehicle. Compounds of the invention are tested in this biochemical assay and percent inhibition of specific binding is determined.

Histamine H$_3$

To evaluate in radioligand binding assays the activity of compounds of the invention, human recombinant histamine H$_3$ receptor expressed in Chinese hamster ovary (CHO) K1 cells (Krueger, K. et al. J. Pharmacol. Exp. Ther. 314(1):271, 2005; Yanai, K. et al, Jpn. J. Pharmacol. 65(2):107, 1994; Zhu, Y. et al, Mol. Pharmacol. 59(3):434, 2001) in a modified Tris-HCl buffer (50 mM Tris-HCl, pH 7.4, 5 mM MgCl$_2$, 0.1% BSA) is used. Compounds of invention are incubated with 0.4 nM [$^3$H]Nα-Methylhistamine for 12 min at 25° C. Non-specific binding is estimated in the presence of 1 µM R(-)-α-Methylhistamine. Receptor proteins are filtered and washed, the filters are then counted to determine [$^3$H]R(-)-α-Methylhistamine specifically bound. Compounds are screened at 1 µM or lower, using 1% DMSO as vehicle. Compounds of the invention are tested in this biochemical assay and percent inhibition of specific binding is determined.

Example B2

Determination of the Ability of Compounds of the Invention to Bind a Imidazoline I2 Receptor Central Imidazoline I$_2$ To evaluate in radioligand binding assays the activity of compounds of the invention, rat central imidazoline I$_2$ receptor obtained from Wistar Rat cerebral cortex (Brown, C. et al, Br. J. Pharmacol. 99:803, 1990) in a modified Tris-HCl buffer (50 mM Tris-HCl buffer, pH 7.4, 0.5 mM EDTA) is used. Compounds of the invention are incubated with 2 nM [$^3$H] Idazoxan for 30 min at 25° C. Non-specific binding is estimated in the presence of 1 µM Idazoxan. Receptor proteins are filtered and washed, the filters are then counted to determine [$^3$H]Idazoxan specifically bound. Compounds are screened at 1 µM or lower, using 1% DMSO as vehicle. Compounds of the invention are tested in this biochemical assay and percent inhibition of specific binding is determined.

TABLE 3

Binding data (Percentage inhibition)

| Compound No. | Histamine H$_1$ (1 µM) | Compound No. | Histamine H$_1$ (0.1 µM) |
|---|---|---|---|
| i-1 | 100 | i-2 | 28 |
| ii-2 | 36 | i-3 | 32 |
| | | ii-74a | 1 |
| | | ii-74b | 11 |
| | | ii-112a | 4 |
| | | ii-112b | 13 |
| | | ii-113a | 13 |
| | | ii-113b | 6 |

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds of the invention were screened at 1 µM or lower, using 1% DMSO as vehicle. Biochemical assay results are presented as the percent inhibition of specific binding in Table 3.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. et al, Biochem. Biophys. Res. Commun. 186:760, 1992; Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds were screened at 1 µM or lower, using 1% DMSO as vehicle. Biochemical assay results are presented as the percent inhibition of specific binding in Table 3.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. et al, Br. J. Pharmacol. 115(6):981, 1995) in a 50 mM Tris-HCl buffer, pH 7.4, was used. Compounds of invention were incubated with 0.6 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds were screened at 1 µM or lower, using 1% DMSO as vehicle. Biochemical assay results are presented as the percent inhibition of specific binding in Table 3.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min at 25° C. MK-912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 3.

Adrenergic $\alpha_{2B}$

To evaluate in radioligand binding assays the activity of compounds of the invention, human recombinant adrenergic $\alpha_{2B}$ receptor expressed in Chinese hamster ovary (CHO) KI cells (Uhlen, S. et al, Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H]Rauwolscine for 60 min at 25° C. Non-specific binding was estimated in the presence of 10 µM Prazosin. Receptor proteins were filtered and washed, the filters were then counted to determine [$^3$H]Rauwolscine specifically bound. Compounds were screened at 1 µM or lower, using 1% DMSO as vehicle. Biochemical assay results are presented as the percent inhibition of specific binding in Table 3.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of the invention were incubated with 1 nM [$^3$H]MK-912 for 60 min at 25° C. Non-specific binding was estimated in the presence of 10 M WB-4101. Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 3.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. et al, Proc. Natl. Acad. Sci. USA. 86:9762, 1989; Hayes, G. et al, Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 min at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 4.

TABLE 4

Percentage inhibition of ligand binding to aminergic G protein-coupled receptors by compounds of the invention

| Compound No. | Adrenergic 0.1 μM | | | | | | Adrenergic 0.03 μM | Dopamine (1 μM) |
|---|---|---|---|---|---|---|---|---|
| | $\alpha_{1A}$ | $\alpha_{1B}$ | $\alpha_{1D}$ | $\alpha_{2A}$ | $\alpha_{2B}$ | $\alpha_{2C}$ | $\alpha_{2B}$ | $D_{2L}$ |
| i-1 | — | — | — | — | — | — | — | 93 |
| i-2 | 51 | 85 | 86 | 98 | 81 | 90 | — | 47 |
| i-3 | 18 | 66 | 43 | 92 | 57 | 72 | — | 49 |
| ii-2 | — | — | — | — | — | — | — | 47 |
| ii-2a | — | 92 | — | 42 | — | — | 50 | — |
| ii-2b | — | 5 | — | 12 | — | — | 34 | — |
| ii-74a | — | 12 | — | 14 | — | — | 22 | — |
| ii-74b | — | 83 | — | 12 | — | — | 69 | — |
| ii-111a | — | 94 | — | 45 | — | — | 76 | — |
| ii-111b | — | 51 | — | 22 | — | — | 0 | — |
| ii-112a | — | 79 | — | 15 | — | — | 58 | — |
| ii-112b | — | 14 | — | 4 | — | — | 40 | — |
| ii-113a | — | 5 | — | 9 | — | — | 23 | — |
| ii-113b | — | 82 | — | 8 | — | — | 68 | — |

Example B5

Determination of the Ability of Compounds of the Invention to Bind a Serotonin Receptor Serotonin (5-Hydroxytryptamine) 5-HT$_{1A}$ To evaluate in radioligand binding assays the activity of compounds of the invention, human recombinant serotonin (5-Hydroxytryptamine) 5-HT$_{1A}$ receptor expressed in Chinese hamster ovary (CHO) K1 cells (Martin, G. et al, Neuropharmacol. 33:261, 1994; May J. et al, J. Pharmacol. Exp. Ther. 306(1):301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H]8-OH-DPAT for 60 min at 25° C. Non-specific binding is estimated in the presence of 10 μM Metergoline. Receptor proteins are filtered and washed, the filters are then counted to determine [$^3$H]8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{1B}$

To evaluate in radioligand binding assays the activity of compounds of the invention, serotonin (5-Hydroxytryptamine) 5-HT$_{1B}$ receptor from Wistar Rat cerebral cortex (Hoyer et al, Eur. J. Pharmacol. 118:1, 1985; Pazos et al, Eur. J. Pharmacol. 106:531, 1985) in a modified Tris-HCl buffer (50 mM Tris-HCl, pH 7.4, 154 mM NaCl, 10 μM Pargyline, 30 μM Isoprenaline) is used. Compounds of invention are incubated with 10 μM [$^{125}$I]Cyanopindolol for 90 min at 37° C. Non-specific binding is estimated in the presence of 10 μM Serotonin (5-HT). Receptor proteins are filtered and washed, the filters are counted to determine [$^{125}$I]Cyanopindolol specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO) K1 cells (Bonhaus, D. et al, Br. J. Pharmacol. 115:622, 1995; Saucier, C. et al, J. Neurochem. 68:1998, 1997) in a 50 mM Tris-HCl buffer, pH 7.4, was used. Compounds of the invention were incubated with 0.5 nM [$^3$H]Ketanserin for 60 min at 25° C. Non-specific binding was estimated in the presence of 1 μM Mianserin. Receptor proteins were filtered and washed, the filters were then counted to determine [$^3$H]Ketanserin specifically bound. Compounds were screened at 1 μM or lower, using 1% DMSO as vehicle. Biochemical assay results are presented as the percent inhibition of specific binding in Table 5.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO) K1 cells (Bonhaus, D. et al, Br. J. Pharmacol. 115:622, 1995) in a modified Tris-HCl buffer (50 mM Tris-HCl, pH 7.4, 4 mM CaCl$_2$, 0.1% Ascorbic Acid) is used. Compounds of invention are incubated with 1.2 nM [$^3$H]Lysergic acid diethylamide (LSD) for 60 min at 37° C. Non-specific binding is estimated in the presence of 10 μM Serotonin (5-HT). Receptor proteins are filtered and washed, the filters are then counted to determine [$^3$H]LSD specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO) K1 cells (Wolf, W. et al, J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^3$H]Mesulergine for 60 min at 25° C. Non-specific binding was estimated in the presence of 1 μM Mianserin. Receptor proteins were filtered and washed, the filters were then counted to determine [$^3$H]Mesulergine specifically bound. Compounds were screened at 1 μM or lower, using 1% DMSO as vehicle. Biochemical assay results are presented as the percent inhibition of specific binding in Table 5.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller, K. et al, Synapse 11:58, 1992; Boess, F. et al, Neuropharmacology 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^3$H]GR-65630 for 60 min at 25° C. Non-specific binding is estimated in the presence of 10 μM MDL-72222. Receptor proteins are filtered and washed, the filters are then counted to determine [$^3$H]GR-65630 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman, C. et al, Br. J. Pharmacol. 109:618, 1993) in a 50 mM Tris-HCl, pH 7.4, is used. Compounds of invention are incubated with 0.7 nM [$^3$H]GR-113808 for 30 min at 25° C. Non-specific binding is estimated in the presence of 30 μM Serotonin (5-HT). Receptor proteins are filtered and washed, the filters are counted to determine [$^3$H]GR-113808 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO) K1 cells (Rees, S. et al, FEBS Lett. 355:242, 1994) in a modified Tris-HCl buffer (50 mM Tris-HCl, pH 7.4, 10 mM MgCl$_2$, 0.5 mM EDTA) was used. Compounds of the invention were incubated with 1.7 nM [$^3$H]Lysergic acid diethylamide (LSD) for 60 min at 37° C. Non-specific binding was estimated in the presence of 100 µM Serotonin (5-HT). Receptor proteins were filtered and washed, the filters were counted to determine [$^3$H]LSD specifically bound. Compounds were screened at 1 µM or lower, using 1% DMSO as vehicle. Biochemical assay results are presented as the percent inhibition of specific binding in Table 5.

Serotonin (5-Hydroxytryptamine) 5-HT$_6$

To evaluate in radioligand binding assays the activity of compounds of the invention, human recombinant serotonin (5-Hydroxytryptamine) 5-HT$_6$ receptor expressed in human HeLa cells (Monsma, F. Jr. et al, Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 min at 37° C. Non-specific binding was estimated in the presence of 5 µM Serotonin (5-HT). Receptor proteins were filtered and washed, the filters were then counted to determine [3H]LSD specifically bound. Compounds were screened at 1 µM or lower, using 1% DMSO as vehicle. Biochemical assay results are presented as the percent inhibition of specific binding in Table 5.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. et al, J. Pharmacol. Exp. Ther. 268:1403, 1994; Shen, Y. et al, J. Biol. Chem. 268:18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [$^3$H]Lysergic acid diethylamide (LSD) for 2h at 25° C. Non-specific binding was estimated in the presence of 10 µM Serotonin (5-HT). Receptor proteins were filtered and washed, the filters were then counted to determine [$^3$H]LSD specifically bound. Compounds were screened at 1 M or lower, using 1% DMSO as vehicle. Biochemical assay results are presented as the percent inhibition of specific binding in Table 5.

TABLE 5

Percentage inhibition of ligand binding to aminergic G protein-coupled receptors by compounds of the invention

| Compound No. | Serotonin (0.1 µM) | | | | |
| --- | --- | --- | --- | --- | --- |
| | 5-HT$_{2A}$ | 5-HT$_{2C}$ | 5-HT$_{5A}$ | 5-HT$_6$ | 5-HT$_7$ |
| i-1 | 94 | 98 | — | 91 | 81 |
| i-2 | 99 | 100 | 101 | 102 | 97 |
| i-3 | 100 | 100 | 91 | 83 | 96 |
| ii-2 | 89 | 86 | — | 86 | 77 |
| ii-74a | — | 28 | — | — | — |
| ii-74b | — | 53 | — | — | — |
| ii-112a | — | 42 | — | — | — |
| ii-112b | — | 37 | — | — | — |

TABLE 5-continued

Percentage inhibition of ligand binding to aminergic G protein-coupled receptors by compounds of the invention

| Compound No. | Serotonin (0.1 µM) | | | | |
| --- | --- | --- | --- | --- | --- |
| | 5-HT$_{2A}$ | 5-HT$_{2C}$ | 5-HT$_{5A}$ | 5-HT$_6$ | 5-HT$_7$ |
| ii-113a | — | 37 | — | — | — |
| ii-133b | — | 58 | — | — | — |

Example B6

Determination of Serotonin (5-Hydroxytryptamine) 5-HT$_{2A}$ or 5-HT$_7$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman et al., Eur. J. Pharmacol. 414:23-30, 2001) or human recombinant serotonin 5-HT$_7$ receptor expressed in CHO cells (Adham et al, J. Pharmacol. Exp. Ther. 287:508-514, 1998) is used. Cells are suspended in DMEM buffer, and distributed in microplates. For the 5-HT$_{2A}$ assay, a cytoplasmic calcium fluorescent indicator which varies proportionally to the free cytosolic Ca$^{2+}$ ion concentration is mixed with probenecid in HBSS buffer complemented with 20 mM Hepes (pH 7.4), added into each well and equilibrated with the cells for 30 min at 37° C. followed by 30 min at 22° C. For the 5-HT$_7$ assay, the reaction product is cAMP, detected by HTRF.

To measure 5-HT$_{2A}$ agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells. The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer is followed by the addition of 3 nM 5-HT (5-HT$_{2A}$), 100 nM 5-HT (5-HT$_7$) or HBSS buffer (basal control) prior the fluorescence measurements. The results are expressed as a percent inhibition of the control response to 3 nM 5-HT. The standard reference antagonist is ketanserin (5-HT$_{2A}$) or mesulergine (5-HT$_7$), which is tested in each experiment at several concentrations to generate a concentration-response curve from which its IC$_{50}$ value is calculated. Compounds are screened at 3 µM or lower, using DMSO as vehicle.

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R. et al, J. Neurochem. 66:47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 µM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 µM 5-HT. Following incubation, the cells are lysed and the fluorescence acceptor (D2-labeled cAMP) and fluorescence donor (anti-cAMP antibody labeled with europium cryptate) are added. After 60 min at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 µM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor ($D_2$-labeled cAMP) and fluorescence donor (anti-cAMP antibody labeled with europium cryptate) are added.

After 60 min at room temperature, the fluorescence transfer is measured as mentioned above. The results are expressed as a percent inhibition of the control response to 100 nM 5-HT. The standard reference antagonist is methiothepin.

Example B8

Determination of Dopamine $D_{2L}$ Antagonist Activity of Compounds

To determine for agonist or antagonist activity of compounds of the invention in functional assays, human recombinant dopamine $D_{2L}$ receptor stably expressed in Chinese hamster ovary (CHO) cells (Senogles, S. et al, J. Biol. Chem. 265(8):4507, 1990) is used. Compounds of the invention are pre-incubated with the membranes (0.1 mg/mL) and 10 mM GDP in modified HEPES buffer (20 mM HEPES, pH 7.4, 100 mM NaCl, 10 mM $MgCl_2$, 1 mM DTT, 1 mM EDTA) for 20 min and Scintillation Proximity Assay (SPA) beads are added for another 60 min at 30° C. The reaction is initiated by 0.3 nM [$^{35}$S]GTPγS for an additional 15 min incubation period. Increase of [$^{35}$S]GTPγS binding by 50% or more (350%) relative to the 1 mM dopamine response by compounds of the invention indicates possible dopamine $D_{2L}$ receptor agonist's activity. Inhibition of a 10 µM dopamine-induced increase of [$^{35}$S]GTPγS binding response by 50% or more (350%) by compounds of the invention indicates receptor antagonist activity. Compounds are screened at 3 µM or lower, using 0.4% DMSO as vehicle. Assay results are presented as the percent response of specific binding.

Example B9

Determination of Dopamine $D_{2S}$ Antagonist Activity of Compounds of the Invention To determine for agonist or antagonist activity of compounds of the invention in functional assays, human recombinant dopamine $D_{2S}$ receptor stably expressed in Chinese hamster ovary (CHO) cells (Gilliland, S. et al, Naunyn-Schmiedeberg's Archives of Pharmacology 361:498, 2000) is used. Compounds of the invention are pre-incubated with the membranes (0.05 mg/mL) and 3 µM GDP in modified HEPES buffer (20 mM HEPES, pH 7.4, 100 mM NaCl, 10 mM $MgCl_2$, 1 mM DTT, 1 mM EDTA) for 20 min and Scintillation Proximity Assay (SPA) beads are then added for another 60 min at 30° C. The reaction is initiated by 0.3 nM [$^{35}$S]GTPγS for an additional 30 min incubation period. Increase of [$^{35}$S]GTPγS binding by 50 percent or more (350%) relative to the 100 µM dopamine response by compounds of the invention indicates possible dopamine $D_{2S}$ receptor agonist's activity. Inhibition of a 3 µM dopamine-induced increase of [$^{35}$S]GTPγS binding response by 50 percent or more (350%) by compounds of the invention indicates receptor antagonist activity. Compounds are screened at 3 µM or lower, using 0.4% DMSO as vehicle. Assay results are presented as the percent response of specific binding.

Example B10

Determination for Agonist or Antagonist Activity of Compounds of the Invention in a Histamine $H_1$ Functional Assay To determine for agonist or antagonist activity of compounds of the invention in functional assays, human recombinant Histamine $H_1$ receptor expressed in human embryonic kidney (HEK-293) cells (Miller, T. et al, J. Biomol. Screen. 4: 249-258, 1999) is used. Cells are suspended in DMEM buffer, and then distributed in microplates. A cytoplasmic calcium fluorescent indicator-which varies proportionally to the free cytosolic $Ca^{2+}$ ion concentration is mixed with probenecid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B11

Determination of Binding Activity of Compounds of the Invention at the 5-$HT_{1B}$ Receptor with a Radioligand Binding Competition Assay To determine the binding activity at the human recombinant serotonin 5-$HT_{1B}$ receptor of compounds of the invention, CHO-K1 cell line expressing the human 5-$HT_{1B}$ recombinant receptor is amplified to prepare membranes used for the radioligand binding assay throughout the study. Radioligand binding competition on 5-HT$_{1B}$ is performed by adding successively in the wells of a 96 well plate (Master Block, Greiner, 786201) 50 µL of test compounds or reference ligand (5-HT, Sigma, H-9523) at increasing concentrations (diluted in binding buffer: 50 mM Tris pH 7.4, 12.5 mM MgCl$_2$, 0.1% Ascorbic Acid, 1 mM EDTA, pH 7.4), 25 µL [$^3$H]5-CT (Amersham, TRK1038, diluted in assay buffer for a final concentration of 0.6 nM) and 25 µL 5-HT1B membrane extracts (7 µg/well). Non specific binding is determined by co-incubation with 200-fold excess of 5-HT. The plate is incubated 60 min at 25° C. in a water bath and then filtered over GF/B filters (Perkin Elmer, 6005177, presoaked in 0.5% PEI for 2h at room temperature) with a Filtration unit (Perkin Elmer). The filters are washed 3× with 0.5 mL of ice-cold washing buffer (50 mM Tris pH 7.4), 50 µL Microscint 20 (Packard) is added and the plate is incubated 15 min on an orbital shaker and then counted with a TopCount™ for 1 min/well.

On each day of experimentation and prior to the testing of compounds, the reference compound is tested at several concentrations in duplicate (n=2) to obtain a dose-response curve and an estimated IC$_{50}$ value. The reference value thus obtained for the test is compared to a historical value obtained from the same receptor and used to validate the experimental session. A session is considered as valid only if the reference value is found to be within a 0.5 logs interval from the historical value. For replicate determinations, the maximum variability tolerated in the test is of +/−20% around the average of the replicates.

Compounds are tested for binding activity in the radioligand binding competition assay on human 5-HT$_{1B}$ receptor, at one concentration 5 µM, in duplicate. Dose-response data from test compounds are analyzed with XLfit (IDBS) software using nonlinear regression applied to a sigmoidal dose-response model.

Example B12

Functional Activity on Recombinant Dopamine D$_{2L}$ and Serotonin 5-HT$_{2A}$ Receptors Using Aequorin, cAMP and GTPγS Functional Assays To study the functional activity of compounds of the invention on the human recombinant dopamine D$_{2L}$ with Aequorin, GTPγS and cAMP functional assays and on the human recombinant serotonin 5-HT$_{2A}$ receptor with Aequorin, CHO-K1 cell lines expressing D$_{2L}$ or 5-HT$_{2A}$ recombinant receptor, mitochondrial apoaequorin and Gα16 are used for the Aequorin assay. CHO-K1 cell line expressing the recombinant D$_{2L}$ receptor is used for the cAMP assay and is amplified to prepare membranes used for the GTPγS assay.

Aequorin Assay Procedure:

Aequorin dopamine D$_{2L}$ (FAST-0101A) or serotonin 5-HT$_{2A}$ (FAST-0505A) cells, grown 18h prior to the test in media without antibiotics, are detached by gentle flushing with PBS-EDTA (5 mM EDTA), recovered by centrifugation and resuspended in "assay buffer" (DMEM/HAM's F12 with HEPES, without phenol red+0.1% BSA protease free). Cells are incubated at RT for at least 4h with Coelenterazine h (Molecular Probes). Dose response curves with reference compounds are performed before testing the compounds of the invention. D$_{2L}$ reference agonist and antagonist are quinpirol (Tocris, 1061) and haloperidol (Tocris, 0931), respectively. 5-HT$_{2A}$ reference agonist and antagonist are α-methyl-5-HT (Sigma, M-110) and ketanserin (Tocris, 908), respectively. For agonist testing, 50 µL of cell suspension are injected on 50 µL of test compound or reference agonist plated in a 96-well plate. The resulting emission of light is recorded using the Hamamatsu Functional Drug Screening System 6000 (FDSS 6000). Following an incubation of 15 min after the first injection, 100 µL of reference agonist at a concentration corresponding to its EC$_{80}$ is injected on the 100 µL of the mixture of cell suspension and test compound, for antagonist testing. The resulting emission of light is recorded using the same luminometer as for agonist testing. To standardize the emission of recorded light (determination of the "100% signal") across plates and across different experiments, some of the wells contain 100 µM digitonin or a saturating concentration of ATP (20 µM). Plates also contain the reference agonist at a concentration equivalent to the EC$_{100}$ and EC$_{80}$ obtained during the test validation. Compounds are tested for agonist & antagonist activity at the human dopamine D$_{2L}$ receptor (FAST-0101A) and serotonin 5-HT$_{2A}$ receptor (FAST-0505A) at the following nanomolar concentrations, in duplicate: Agonist (nM): 10, 30, 100, 300, 1000, 3000, 10000, and 30000; Antagonist (nM): 5, 15, 50, 150, 500, 1500, 5000, and 15000.

cAMP Assay Procedure:

D$_{2L}$ CHO-K1 cells (FAST-0101C), grown to mid-log phase in culture media without antibiotics, are detached with PBS-EDTA (5 mM EDTA), centrifuged and resuspended in assay buffer (KRH, 1 mM IBMX) at a concentration of 2.1×10$^5$ cells/mL. The test is performed in 96 well plates. For agonist testing, 12 µL of cells (2,500 cells/well) are mixed with 6 µL of increasing concentrations of test compound or reference agonist and 6 µL of Forskolin 10 µM final concentration (Calbiochem, cat n° 344270). For antagonist testing, 12 µL of cells (2,500 cells/well) are mixed with 6 µL of test compound or reference antagonist at increasing concentrations. After incubation of 10 min at room temperature, 6 µL of a mix of Forskolin 10 µM final concentration and the reference agonist at a final concentration corresponding to the EC$_{80}$ are added. The plates are then incubated for 30 min at room temperature. During the incubation, the anti-cAMP cryptate antibody (K) and the cAMP-D2 (D2) are prepared according to the manufacturer specifications (HTRF kit from Cis-Bio International (cat n° 62AM2PEB). 12 µL of cAMP-D$_2$ solution followed by 12 µL of K solution are added to each well. The plate is then covered by a top-seal and incubated for at least 1h at room temperature. The plate is then read on the Rubystar and data are analyzed by non-linear regression using a single site model. Compounds are tested for antagonist activity at the human dopamine D$_{2L}$ receptor (FAST-0101C) at the following nanomolar concentrations, in duplicate: Antagonist (nM): 5, 15, 50, 150, 500, 1500, 5000, and 15000.

GTPγS Assay Procedure:

Assay buffer [20 mM HEPES pH 7.4; 100 mM NaCl, 10 µg/mL saponin, 30 mM MgCl$_2$]; Membranes [Recombinant CHO-K1-D$_{2L}$ membrane extracts thawed on ice and diluted in assay buffer to give 1 mg/mL (10 µg/10 µL) and kept on ice]; GDP [diluted in assay buffer to give 3 µM final concentration]; Beads [PVT-WGA (Amersham, RPNQ0001), diluted in assay buffer at 25 mg/mL (0.25 mg/10 µL)]; GTPγ$^{35}$S [(PerkinElmer NEG030X), diluted in assay buffer to give 0.1 nM final concentration]; Ligand [Quinpirol (Tocris, 1061) as reference agonist and haloperidol (Tocris, 0931) as reference antagonist, diluted in assay buffer]. Membranes are mixed with GDP (volume:volume) and incubated for at least 15 min on ice. In parallel, GTPγ[$^{35}$S] is mixed with the beads (volume:volume) just before starting the reaction. For agonist testing, the following reagents are successively added in the wells of an Optiplate (Perkin Elmer): 50 µL of test or reference ligand, 20 µL of the membranes:GDP mix, 10 µL of assay buffer and 20 µL of the GTPγ[$^{35}$S]:beads mix. For antagonist testing, the following reagents are successively added in the wells of an Optiplate (Perkin Elmer): 50 µL of test or reference ligand, 20 µL of the membranes:GDP mix, and then after an incubation of 15 min at room temperature, 10 µL of reference agonist at historical $EC_{80}$ concentration and 20 µL of the GTPγ[$^{35}$S]:beads mix. The plates are covered with a top seal, mixed on an orbital shaker for 2 min, and then incubated for 1h at room temperature. Then the plates are centrifuged for 10 min at 2000 rpm, incubated at RT 1 h and counted for 1 min/well with a Perkin Elmer TopCount reader. Compounds are tested for antagonist activity at the human dopamine $D_{2L}$ receptor (FAST-0101G) at the following nanomolar concentrations, in duplicate: Antagonist (nM): 5, 15, 50, 150, 500, 1500, 5000, and 15000.

Example B13

Increase of Neurite Outgrowth of Neurons that are Cultured with Compounds of the Invention Neurite Outgrowth in Cortical Neurons Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 min with a pipette in Dulbecco's Modified Eagle Media ("DMEM"; Gibco) with 10% Fetal Bovine Serum ("FBS") (Gibco) and centrifuged at 350×g for 10 min at RT. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue is cut to small pieces. The cells are separated by 15-min incubation with DNase and papain. The cells are collected by centrifugation (1500 rpm, 5 min). The tissue is triturated with a pipette and the cells are plated using the micro-islet protocol (20,000 cells in 25 µL medium) on poly-L-lysine coated 48 wells, in MEM supplemented with 2 mM glutamine, 0.1 µg/mL gentamicin, 10% heat-inactivated fetal bovine serum (FBS-HI) and 10% heat-inactivated horse serum (HS-HI). After the cells attach to the well, 250 µL medium is added to the wells. 4h after plating, the medium is changed to fresh medium (MEM with supplements and 5% HS-HI) containing test compound at 0.5, 5 and 50 nM concentrations. As positive controls BDNF (50, 100 and/or 150 ng/mL), and/or NGF (50 ng/mL and/or 100 ng/mL) are used. After 2 days in vitro, the cell's conditioned media are collected from plates before fixing the cells. The media samples are centrifuged 13,000 rpm 3 min to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48h at +4° C., washed with PBS and incubated with secondary antibody goat anti-rabbit IgG conjugated to Alexa Fluor568 (1:200, A111036, Molecular Probes) for 2h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software. The number of wells per compound concentration used is 6 (n=6). All data are presented as mean±standard deviation (SD) or standard error of mean (SEM), and differences are considered to be statistically significant at the $p<0.05$ level. Statistical analysis is performed using StatsDirect statistical software. Differences between group means are analyzed by using 1-way-ANOVA followed by Dunnet's test (comparison to the vehicle treated group).

Example B14

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic short term memory. Ennaceur, A., and Delacour, J. (1988), Behav. Brain Res. 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C. et al, Neurosci. Letts. 170:117-120, 1994; and Bartolini, L. et al, Biochem. Behav. 53:277-283, 1996.

Male Sprague-Dawley rats between six and seven weeks old, weighing between 220-300 grams are obtained from Centre d'Elevage (Rue Janvier, B. P. 55, Le Genest-Saint-Isle 53940, France). The animals are housed in groups of 2 to 4 in polypropylene cages (with a floor area of 1032 cm$^2$) under standard conditions: at RT (22±2° C.), under a 12h light/12h dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for 3 min in the presence of two objects (habituation). Animals to be tested are placed in the experimental room at least 30 min before testing.

Novel object recognition test is comprised of two trials separated by an interval of 120 min or 24h. When agents that disrupt memory such as the cholinergic antagonist scopolamine are used an inter-trial interval of 120 min is preferred. Alternatively a 24h inter-trial interval is used when studying effect of natural forgetting on novel object recognition task. During the first, or acquisition, trial ($T_1$), rats are placed in the arena, where two identical objects have been previously placed. The time required for each animal to complete 15 sec of object exploration is determined, with a cut-off time of 4 min. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for 3 min., and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 sec of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) is evaluated. The % of animals in each group with $T_{Novel} - T_{Familiar}$ greater than or equal to 5 sec is also derived; described as % of good learners.

Animals not meeting a minimal level of object exploration are excluded from the study as having naturally low levels of spontaneous exploration. Thus, only rats exploring the objects for at least five sec ($T_{Novel} + T_{Familiar} > 5$ sec) are included in the study.

Animals are randomly assigned to groups of 14. Compounds of the invention and controls are administered to animals the groups as follows: Solutions of compounds are prepared freshly each day at a concentration of 0.25 mg/mL using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil is administered (e.g., intraperitoneally) 40 minutes before the acquisition trial (T1). Scopolamine is administered (e.g., intraperitoneally) 30 minutes before the acquisition trial (T1). Vehicle (purified water) or test compound is administered (e.g., by gavage) 25 minutes before the acquisition trial (T1), 5 min after scopolamine challenge. The volume of administration is 5 mL/kg body weight for compounds administered intraperitoneally, and 10 mL/kg for compounds administered orally.

Recognition scores and % of good learners for compounds of the invention are determined.

Example B15

Use of an In Vivo Model to Determine the Ability of Compounds to Treat, Prevent and/or Delay the Onset and/or the Development of Schizophrenia (Hyperactivity in PCP Treated Animals)

In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al, Science 277:953-955, 1997; and Piercey et al, Life Sci. 43(4):375-385, 1988. Standard experimental protocols may be employed in this or in other animal models. One protocol involves PCP-induced hyperactivity.

Male C57B1/6J mice from Jackson Laboratories (Bar Harbor, Me.) are used. Mice are received at 6-weeks of age. Upon receipt, mice are assigned unique identification numbers (tail marked) and are group housed with 4 mice/cage in OPTIMICE ventilated cages. All animals remain housed in groups of 4 during the remainder of the study. All mice are acclimated to the colony room for at least 2 weeks prior to testing and are subsequently tested at an average age of 8 weeks of age. During the period of acclimation, mice are examined on a regular basis, handled, and weighed to assure adequate health and suitability. Animals are maintained on a 12h/12h light/dark cycle. The RT is maintained between 20 and 23° C. with a relative humidity maintained between 30% and 70%. Food and water are provided ad libitum for the duration of the study. In each test, animals are randomly assigned across treatment groups.

The following compounds are used for this study: 1) Compound of the invention (0.03, 0.1, 0.3, 1, 3, 10 & 30 mg/kg) is dissolved in 5% PEG-200 in sterile water and administered p.o. 30 min prior to PCP injection; 2) Clozapine (1.0 mg/kg) is dissolved in 10% DMSO and administered i.p. 30 min prior to phencyclidine (PCP) injection; 3) PCP (5.0 mg/kg) is dissolved in sterile water and administered i.p. immediately before the 60 min test. All compounds are administered at a dose volume of 10 mL/kg.

The open filed (OF) test assesses locomotor behavior to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moves whereas rearing activity is measured from vertical beam breaks. Mice (10 to 12 animals per treatment group) are brought to the activity experimental room for at least 1 h acclimation to the experimental room conditions prior to testing. Eight animals are tested in each run. Mice are administered vehicle (e.g., 10% DMSO or 5% PEG200 and 1% Tween 80), Compound of the invention, clozapine (positive control, 1 mg/kg ip) and placed in the OF chambers for 30 min following which they are injected with either water or PCP and placed back in the OF chambers for a 60-min session. At the end of each OF test session the OF chambers are thoroughly cleaned.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fall above or below 2 standard deviations from the mean are removed from the final analyses. An effect is considered significant if $p<0.05$.

Example B16

Use of an In Vivo Model to Determine the Ability of Compounds to Treat, Prevent and/or Delay the Onset and/or the Development of Schizophrenia (Hyperactivity in Amphetamine Treated Animals)

Male mice (various strains, e.g., C57Bl/6J) from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12h/12h light/dark cycle. The RT is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglas square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1h acclimation prior to start of treatment. Animals are administered with vehicle, haloperidol (positive control, 0.1 mg/kg ip) or compound of the invention and placed in the OF. The time of administration of test compound to each animal is recorded. Baseline activity is recorded for 30 min following which mice receive amphetamine (4 mg/kg) or water and are placed back in the OF chambers for a 60-min session. At the end of each open field test session the OF chambers are thoroughly cleaned.

Typically ten to twelve mice are tested in each group. Test compound doses typically range from 0.01 mg/kg to 60 mg/kg.

Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B17

Use of the In Vivo Conditioned Avoidance Response (CAR) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

The effects of compounds of the invention, at concentrations including 0.1, 0.3, 1, 3, 10 and 20 mg/kg, p.o., in the conditioned avoidance response model are assessed in the male Wistar rat. Risperidone (0.3 mg/kg, s.c.) is used in the present study as a positive reference compound.

For each testing session, animals are first placed for a 4-min habituation period in a shuttlebox with an electrified grid floor. Then, rats are submitted to 30 trials spaced by intertrial intervals varying at random between 20 and 30 sec. Each trial consists of a 10-sec light stimulus (conditioned stimulus, CS) followed by a 10-sec electric foot shock (unconditioned stimulus, US) in presence of the light presented in the compartment where the rat is located. If the animal moves to the other compartment during the initial 10-sec of the trial, the light is terminated (no shock is delivered) and the response is recorded as an avoidance response. If the rat changes compartment during the foot shock, the light and the shock are terminated and the response is recorded as an unconditioned response. If the rat does not change compartment during the 10-sec light period (CS) and during the 10-sec shock+light period (US+CS), an escape failure is recorded. If a response is made during an intertrial interval, the response is recorded as an intertrial crossing. Training is performed 5 days per week with one session of 30 trials per day, until rats reach the performance criterion of 80% of avoidance response on at least two consecutive daily sessions. Once the performance criterion is reached, each animal is sequentially administered with vehicle (15% HPBCD, p.o.), compound of the invention (0.1, 0.3, 1, 3, 10 and 20 mg/kg, p.o.) and risperidone (0.3 mg/kg, s.c.). A minimal wash-out period of 48h is allowed between 2 treatments. During the wash-out period, animals are trained until they recover an avoidance performance of at least 80%.

Statistical analysis is performed using a Friedman two-way ANOVA by ranks followed by the Wilcoxon matched-pairs signed-ranks test to test each dose of the test compound administered versus vehicle control treated rats.

Example B18

An Animal Model of the Negative Symptoms of Schizophrenia: Subchronic PCP-Induced Social Interaction Deficits Phencyclidine (PCP) administered to humans as well to experimental animals induces full-spectrum of schizophrenia symptoms, including negative symptoms and cognitive deficits. A major symptom of schizophrenia is considered to be social isolation/withdrawal as part of the cluster of negative symptoms. Subchronic treatment with PCP in rats leads to the development of clear signs of social withdrawal as measured by deficits in the interaction time with a cage intruder rat.

Male Sprague Dawley rats (~150 g on arrival) from Harlan (Indiana) are used in this study. Upon receipt, rats are group housed in OPTI rats ventilated cages. Rats are housed in groups of 2-3/cage for the remainder of the study. During the period of acclimation, rats are examined on a regular basis, handled, and weighed to assure adequate health and suitability. Rats are maintained on a 12h/12h light/dark cycle with the light on at 7:00 a.m. The RT is maintained between 20 and 23° C. with a relative humidity maintained between 30% and 70%. Chow and water are provided ad libitum for the duration of the study. Animals are randomly assigned across treatment groups and balanced by age. Animals are not disturbed between test days.

The following compounds are used. 1) Compound of the invention (0.3, 1 and 3 mg/kg; p.o.) is dissolved in 3% Tween and PBS and administered 30 min prior to test; 2) PCP (2 mg/kg; s.c.) is dissolved in saline and administered twice daily for 5 days prior to test day; 3) Clozapine (2.5 mg/kg; i.p.) is dissolved in 5% PEG:5% Tween 80 in saline and administered 30 min prior to test. All compounds are administered at a dose volume of 1 mL/kg.

For 5 days prior to test, rats are injected twice daily with either PCP (2 mg/kg; s.c) or saline (s.c). On day 6 and following a 30 min pretreatment with vehicle, clozapine or Compound of the invention, a pair of rats, unfamiliar to each other, receiving the same treatment are placed in a white plexiglas open field arena (24"×17"×8") and allowed to interact with each other for 6 min. Social interactions ('SI') include: sniffing the other rat; grooming the other rat; climbing over or under or around the other rat; following the other rat; or exploring the ano-genital area of the other rat. Passive contact and aggressive contact are not considered a measure of social interaction. The time the rats spend interacting with each other during the 6 min test is recorded by a trained observer. The social interaction chambers are thoroughly cleaned between the different rats.

Data are analyzed by analysis of variance (ANOVA) followed by post-hoc analysis (e.g., Fischer, Dunnett) when appropriate. An effect is considered significant if $p<0.05$.

Example B19

An Animal Model of Extrapyramidal Syndrome (EPS): Measurement of Catalepsy in the Mouse Bar Test Antipsychotic drugs are known to induce extrapyramidal syndrome (EPS) in animals and in humans. An animal model considered to be predictive of EPS is the mouse bar test, which measures cataleptic responses to pharmacological agents.

Male C57B1I6J mice from Jackson Laboratories (Bar Harbor, Me.) are used. Mice are received at 6-weeks of age. Upon receipt, mice are assigned unique identification numbers (tail marked) and are group housed with 4 mice/cage in OptiMICE ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12h/12h light/dark cycle. The RT is maintained between 20 and 23° C. with a relative humidity maintained between 30% and 70%. Chow and water are provided ad libitum for the duration of the study. In each test, animals are randomly assigned across treatment groups.

The following compounds are used for this study. 1) Compound of the invention (0.03, 0.1, 0.3, 1, 3, 10, 30 mg/kg) is dissolved in 3% Tween in PBS and administered orally at a dose volume of 10 mL/kg; 2) Haloperidol (2 mg/kg) is dissolved in 10% DMSO and administered i.p. at a dose volume of 10 mL/kg.

The front paws of a mouse are placed on a horizontal metal bar raised 2" above a Plexiglas platform and time is recorded for up to 30 sec per trial. The test ends when the animal's front paws return to the platform or after 30 sec. The test is repeated three times and the average of the three trials is reported as the intensity index of catalepsy. Antipsychotic agents such as haloperidol cause rigidity as a side effect. Animals treated with haloperidol will hold on to the bar without moving for several minutes. Mice are brought to the activity experimental room for at least 1 h acclimation to the experimental room conditions prior to testing. Following injection of either vehicle, Compound of the invention, or haloperidol, catalepsy is assessed at 3 time points: 30 min, 1 h and 3h. At the end of each trial, the apparatus is thoroughly cleaned with 70% ethanol.

Data are analyzed by analysis of variance (ANOVA) followed by post-hoc comparisons with Fisher Tests when appropriate. An effect is considered significant if $p<0.05$.

Example B20

Use of the 5-Choice Serial Reaction Task to Determine the Ability of Compounds to Enhance Attention/Vigilance and Reduce Impulsivity Attention and impulsivity are characteristic of several disease states. The continuous performance test (CPT), used in humans, is capable of detecting attention deficits in a number of disorders, including attention deficit hyperactivity disorder, schizophrenia and mild cognitive impairment. The preclinical analogue of the CPT is the 5-choice serial reaction time task (5CSRTT). In this operant-based test, rats are required to be attentive and withhold responding while they monitor 5 apertures for the appearance of a brief stimulus light in one of the apertures. The brief illumination of the stimulus light in the 5CSRTT is analogous to the appearance of the "correct" letters in the CPT in humans. Upon observing the stimulus light, the rat must nose-poke in the corresponding aperture to receive a food reward. The 5CSRTT allows the measurement of similar behavioral responses as the CPT, including accuracy, speed of responding, impulsive and compulsive responding. In this study, drug tests are performed under altered test parameters which result in increased premature responding. This premature responding is hypothesized to indicate impulsivity, e.g., a failure to withhold an inappropriate response, and has been shown to be sensitive to atomoxetine.

Thirteen male Long-Evans rats (275-300 g) are obtained from Harlan Laboratories, Indianapolis, Ind. At the time of testing for the current study, the rats are approximately 16-18 months old. Upon arrival, the rats are assigned unique identification numbers (tail marked). Rats are single-housed in OptiRAT cages and acclimated for 7 days prior to commencing a food-restriction regimen: rats are held at 85% of age-matched free-feeding control bodyweights, receiving approximately 10-20 g of rat chow daily. Water is provided ad libitum, except during testing. Animals are maintained in a 12h/12h light/dark cycle (lights on at 0700 EST) with RT maintained at 22±2° C. and the relative humidity maintained at approximately 50%. All animals are examined, handled and weighed prior to initiation of the study to assure adequate health and suitability and to minimize non-specific stress associated with testing. The 5CSRTT sessions are performed during the animal's light cycle phase. All experiments and procedures are approved by the Institutional Animal Care and Use Committee of PsychoGenics, Inc.

The apparatus consists of 10 aluminum and Plexiglas chambers with grid floors (width 31.5 cm, depth 25.0 cm, height 33.0 cm), housed in sound-attenuating cabinets. Each cabinet is fitted with a low-level noise extractor fan which also helped to mask external noise. The left wall of each chamber is concavely curved with 5 apertures evenly spaced, located approximately 2.5 cm from the floor. Each aperture contains a standard 3 W LED to serve as stimulus lights. The opposite wall contains a food magazine, located approximately 3.0 cm from the floor. Each chamber is illuminated with a 3 W house-light located in the center of the ceiling panel. After each test session the apparatus is cleaned with 70% ethanol.

The following compounds are used for this study. 1) Compound of the invention is dissolved in saline, and administered p.o. at 0.1, 0.3 and 1.0 mg/kg, 30 min prior to testing at 1 mL/kg body weight; 2) The reference compound atomoxetine (1.0 mg/kg) is dissolved in saline and administered i.p. 30 min prior to testing at 1 mL/kg body weight.

Training: Animals are trained to monitor the five apertures for stimulus light illumination. Each session is initiated by the illumination of the house light, and the delivery of a food reward into the magazine. The first trial begins when the rat opens the magazine to obtain the food pellet. After the inter-trial interval (ITI) one of the stimulus lights is illuminated for 500 msec. The rat must nose-poke in the illuminated aperture either during or within 5 sec of stimulus light illumination. Such a response is defined as a correct response, and is rewarded with delivery of a food pellet. Collection of the pellet initiates the next trial. A nose-poke response in a non-illuminated aperture (incorrect response) or a nose-poke after the 5 sec limited hold (missed trial) results in termination of the trial with extinction of the house-light and imposition of a time-out period.

Testing: After acquisition of the 5CSRTT with a high level of accuracy (at least 75% correct, at least 50 trials completed per session), drug testing begins. Animals are treated with test compound (various doses, appropriate vehicle), vehicle and positive control (atomoxetine 1 mg/kg ip). During drug test sessions, the ITI is varied between 10, 7, 5 or 4 sec in duration, presented in groups of 4 trials (each of which contains 1 trial at each ITI duration in a randomized order). The session ends when 60 min have elapsed. All rats receive all drug treatments, according to a randomized-order within-subjects design. Drug tests are performed on Wednesdays and Fridays of each week, only when rats perform at least 75% correct trials for a minimum of 50 trials in the previous test session.

Measures obtained during the test sessions are: (1) percent correct, defined as the number of correct trials×100, divided by the total number of correct and incorrect trials, (2) missed trials, defined as responding beyond the 5 sec limited hold or failing to respond, (3) correct latency, defined as the time taken to make a correct response after the illumination of the stimulus, (4) magazine latency, defined as the time taken to enter the magazine to collect the food pellet after making a correct response, (5) premature responding, defined as the total number of nose-poke responses made during the ITI, and (6) preservative responding, defined as the total number of additional responses emitted after the initial nose-poke.

Example B21

An Animal Model to Test the Anxiolytic Effects of Compounds Using the Elevated Plus Maze (EPM) Test This study aims to test the anxiolytic properties of compounds of the invention using the elevated plus maze (EPM) test in C57Bl/6J mice.

Male C57Bl/6J mice from Jackson Laboratories (Bar Harbor, Me.) are used for the open field study. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for approximately 2 week prior to testing and are subsequently tested at an average age of 8 weeks of age. During the period of acclimation, mice and rats are examined on a regular basis, handled, and weighed to assure adequate health and suitability. Animals are maintained on a 12h/12h light/dark cycle. The RT is maintained between 20 and 23° C. with a relative humidity maintained between 30% and 70%. Chow and water are provided ad libitum for the duration of the study. In each test, animals are randomly assigned across treatment groups. All animals are euthanized after the completion of the study.

The following compounds are used for this study: 1) Compound of the invention (0.03, 0.1 and 1 mg/kg) is dissolved in 5% PEG200/$H_2O$ and administered orally at a dose volume of 10 mL/kg 30 min prior to test; 2) Diazepam (2.5 mg/kg) is dissolved in 45% hydroxypropyl-β-cyclodextrin and administered orally at a dose volume of 10 mL/kg 30 min prior to test.

The elevated plus maze test assesses anxiety. The maze (Hamilton Kinder) consists of two closed arms (14.5 h×5 w×35 l cm) and two open arms (6 w×35 l cm) forming a cross, with a square center platform (6×6 cm). All visible surfaces are made of black acrylic. Each arm of the maze is placed on a support column 56 cm above the floor. Antistatic black vinyl curtains (7' tall) surround the EPM to make a 5'×5" enclosure. Animals are brought to acclimate to the experimental room at least 1 h before the test. Mice are placed in the center of the elevated plus maze facing the closed arm for a 5-min run. All animals are tested once. The time spent, distance traveled and entries in each arm are automatically recorded by the computer. The EPM is thoroughly cleaned after each mouse.

Data are analyzed using analysis of variance (ANOVA) followed by Fisher's LSD post hoc analysis when appropriate. An effect is considered significant if $p<0.05$.

Example B22

Cell Culture and Cell Viability Assay

SH-SY5Y cells cultured in DMEM/F12 media supplemented with 10% FBS are seeded in 96-well microplates at 150,000 cells/$cm^2$. After 24 h, cells are depleted from FBS and kept in culture for 24 h before the experiment. Cells are then treated with 4-Br-A23187 (2 μM), hydrogen peroxide (300 μM) or the mitochondrial toxin rotenone (25 μM) in the presence of vehicle or Test compound of the Invention for 24 h. Cell death is determined by measurements of LDH release according to the Cytotoxicity Detection KitPlus (Roche, Mannheim, Germany). Cell viability is determined by measuring the capacity of cells to metabolize MTS tetrazolium (MTS) according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA). Test compounds are screened at 10 nM, using DMSO as vehicle. Assay results for the experiments with hydrogen peroxide are presented as the LDH release (cell death) of untreated cells (control), hydrogen peroxide-treated cells (vehicle), and co-incubation of hydrogen peroxide with Compounds of the Invention treated cells normalized to the vehicle. This assay assesses the ability of the test compounds to protect against cell death that is mediated by mitochondrial dysfunction. In the assay, the calcium ionophore 4-Br-A23187 is used to challenge the cells, causing calcium levels to rise in mitochondria, which leads to depolarization and cell death. Test compounds are assessed for their ability to prevent cell death in response to challenge with 4-Br-A23187.

Assay results for the experiments with Br-A23187 are presented as the MTS reduction capacity (cell viability) of untreated cells (control), 4-Br-A23187-treated cells (vehicle), and co-incubation of Br-A23187 with Compounds of the Invention treated cells and using p-trifluoromethoxyphenylhydrazone (FCCP) at 10 µM for 30 min as a control.

Example B23

Cell Culture and Cell Viability Assay

Cell Culture

SH-SY5Y cells stably transfected with a doxycycline-inducible wild-type α-synuclein (α-syn) gene along with control SH-SY5Y cells over-expressing the β-galactosidase (β-gal) gene (a gift from L. Stefanis, Division of Basic Neurosciences, Biomedical Research Foundation of the Academy of Athens, Athens, Greece) are cultured as described by Vekrellis et al. (Vekrellis K, Xilouri M, Emmanouilidou E, Stefanis L. (2009). Inducible over-expression of α-syn in human neuronal cells leads to caspase-dependent non-apoptotic death. J Neurochem 109, 1348-1362). In accordance with this method, cells are cultured and maintained in RPMI 1640, 10% fetal bovine serum supplemented with 250 µg/mL G418 and 50 µg/mL Hygromycin B. Expression of α-syn is switched off in stock cultures with doxycycline (2 g/mL). For experimental procedures, cells are plated at ($4$-$8\times10^4$ cells/cm$^2$) and differentiated in absence of doxycycline and in the presence of 20 µM all-trans retinoic acid (RA) (Sigma, St Louis, Mo., USA).

Viability Assay

Cells are cultured in 96-well plates. After 24 h, cells are treated with RA and Compounds of Invention at 0.1 and 10 nM in the absence of doxycycline. Culture medium with RA and drugs is fully replaced after 7 days. Cell viability is measured by the release of lactate dehydrogenase (LDH) from necrotic cells into the culture medium and by measuring the capacity of cells to metabolize MTS tetrazolium (MTS) after 14 days in culture. LDH leakage is assessed according to the Cytotoxicity Detection KitPlus (Roche, Mannheim, Germany) and MTS reduction is assessed by the CellTiter 960 AQueous One Solution Cell Proliferation assay (Promega Corporation, Madison, Wis., USA).

Assay results for the experiments with α-syn over-expression are presented as the MTS reduction capacity (cell viability) of control cells (+ dox), cells over-expressing α-syn (- dox), and cells over-expressing α-syn incubated with Compounds of the Invention at 0.1 nM or 10 nM Immunoblotting of α-synuclein and α-synuclein Aggregates Cells stably expressing α-synuclein are cultured in 6-well plates at a density of $4\times10^4$ cells/cm$^2$ cells per well. Cells are differentiated and treated with Compound of the Invention at 10 nM in absence of dox after 24 h of plating. Drug treatments are repeated after 7 days in freshly prepared medium containing RA. After 14 days, cells are washed twice with cold PBS and lysed in lysis buffer containing 1% Triton X-100, 20 mM HEPES, 150 mM NaCl, 10% glycerol, 1 mM EGTA, 1.5 mM MgCl$_2$, 1 mM PMSF pH 7.4, and 1× protease inhibitor mixture (Roche, Mannheim, Germany). Lysates are homogenized and subjected to four successive freeze-thaw cycles to disrupt membranes. Triton soluble fractions and triton insoluble pellets are obtained by ultracentrifugation at 100,000×g for 30 min at 4° C. The concentration of protein in each fraction is determined by BCA assay (Thermo Scientific). Samples from total, soluble and triton insoluble fractions, are boiled in 1× sample buffer (20 mM Tris, 1% glycerol, 180 mM 3-mercaptoethanol, 0.003% bromophenol blue, and 2% SDS, pH 6.8), loaded on 12% SDS-PAGE gels, and transferred to polyvinylidene difluoride (PVDF) membranes (0.2 µM-pore immobilon Biorad). Membranes are blocked in 1×TBS-Tween (20 mM Tris, pH 7.4, 150 mM NaCl, and 0.2% Tween 20) containing 5% milk for 1 h and incubated overnight at 4° C. with the following primary antibodies in blocking solution at the indicated dilutions: monoclonal anti-α-synuclein α-syn-1 (1:1000; BD Transduction Laboratories). (Perrin, R. J., Payton, J. E., Barnett, D. H., Wraight, C. L., Woods, W. S., Ye, L., and George, J. M. (2003). Epitope mapping and specificity of the anti-α-synuclein monoclonal antibody Syn-1 in mouse brain and cultured cell lines. Neurosci Lett 349, 133-135), and monoclonal vimentin (1:1000; BD PharMingen). Primary antibodies are detected with secondary anti-mouse antibodies conjugated to HRP (1:5000).

Isolation of RNA and RT-Quantitative PCR (RT-qPCR)

SH-SY5Y cells stably over-expressing α-syn are treated with Compound of the Invention (10 nM). Total RNA from these cells as well as control cells not treated with Compound is extracted using the E.Z.N.A RNA extraction Kit (OMEGAbiotek, Norcross, Ga.). 1 µg of RNA is reverse transcribed to cDNA using the M-Mulv reverse transcriptase enzyme (Promega Corporation, Madison, Wis., USA). RT-qPCR of cDNA templates is carried out using TAQMAN probes for human α-synuclein (Hs00240906_M1) and TAQMAN masterMix (Applied Biosystems) and a Mx3005P real-time PCR system (Agilent Technologies Inc., Santa Clara, Calif.). Levels of alpha-tubulin mRNA are used to normalize the amounts of total RNA between samples. Fold changes are calculated as described by (Pfaffl, M. W. (2001). A new mathematical model for relative quantification in real-time RT-PCR. Nucleic Acids Res 29, e45).

Example B24

Functional Activity on Recombinant Adrenergic $\alpha_{1B}$, Adrenergic $\alpha_{2A}$, Adrenergic $\alpha_{2B}$ and Adrenergic $\alpha_{1D}$ Receptors Using Aequorin and GTPγS Functional Assays To study the functional activity of compounds of the invention on the human recombinant adrenergic $\alpha_{2B}$, adrenergic $\alpha_{2A}$, adrenergic $\alpha_{1B}$ or adrenergic $\alpha_{1D}$ with Aequorin functional assays and on the human recombinant adrenergic $\alpha_{2B}$ receptor with GTPγS assay, CHO-K1 cell lines expressing adrenergic $\alpha_{2B}$, adrenergic $\alpha_{2A}$, adrenergic $\alpha_{1B}$ or adrenergic $\alpha_{1D}$ recombinant receptor, mitochondrial apoaequorin and Gα16 are used for the Aequorin assay. CHO-K1 cell line expressing the recombinant $\alpha_{2B}$ receptor is amplified to prepare membranes used for the GTPγS assay.

The following reference agonists are used as both the reference ligand in agonist mode and as the agonist that needs to be inhibited in antagonist mode.

| Assay | $\alpha_{1B}$ (aeq) | $\alpha_{1D}$ (aeq) | $\alpha_{2A}$ (aeq) | $\alpha_{2B}$ (aeq) | $\alpha_{2B}$ (GTPgS) |
|---|---|---|---|---|---|
| Agonist ligand | Cirazoline | Cirazoline | UK 14304 | Oxymetazoline | Guanfacine |

Aequorin Assay Procedure:

Aequorin adrenergic $\alpha_{1B}$ (FAST-008A), adrenergic $\alpha_{2A}$ (FAST-006A) or adrenergic $\alpha_{2B}$ (FAST-007A) cells are grown 18h prior to the test in media without antibiotics. They are then detached by gentle flushing with PBS-EDTA (5 mM EDTA), recovered by centrifugation and re-suspended in "assay buffer" (DMEM/HAM's F12 with HEPES+0.1% BSA protease free). Cells are incubated at RT for at least 4h with Coelenterazine h (Molecular Probes). Dose response curves with reference compounds are performed before testing the compounds of the invention. The $\alpha_{1B}$ reference agonist and antagonist are cirazoline and quinazoline, respectively. The $\alpha_{2A}$ reference agonist and antagonist are UK14, 304 and rauwolscine, respectively. The $\alpha_{2B}$ reference agonist and antagonist are oxymetazoline and rauwolscine, respectively.

For agonist testing, 50 μL of cell suspension are injected on 50 μL of test compound or reference agonist plated in a 96-well plate. The resulting emission of light is recorded using the Hamamatsu Functional Drug Screening System 6000 (FDSS 6000). For antagonist testing, following an incubation of 15 min. after the first injection, 100 μL of reference agonist at a concentration corresponding to its $EC_{80}$ is injected on the 100 μL of the mixture of cell suspension and test compound. The resulting emission of light is recorded using the same luminometer as for agonist testing. To standardize the emission of recorded light (determination of the "100% signal") across plates and across different experiments, some of the wells contained 100 μM digitonin or a saturating concentration of ATP (20 μM). Plates also contained the reference agonist at a concentration equivalent to the $EC_{80}$ obtained during the test validation.

Agonist activity of test compound is expressed as a percentage of the activity of the reference agonist at its $EC_{100}$ concentration. Antagonist activity of test compound is expressed as a percentage of the inhibition of reference agonist activity at its $EC_{80}$ concentration.

Test compounds are tested for agonist & antagonist activity at the human adrenergic $\alpha_{1B}$ (FAST-008A), adrenergic $\alpha_{2A}$ (FAST-006A) or adrenergic $\alpha_{2B}$ (FAST-007A) at the following nanomolar concentrations, in duplicate: Agonist (nM): 0.3, 1, 3, 10, 30, 100, 300, 1000, 3000, 10000; Antagonist (nM): 0.15, 0.5, 1.5, 5, 15, 50, 150, 500, 1500, and 5000.

GTPγS Assay Procedure:

The procedure is carried out with the following: assay buffer [20 mM HEPES pH 7.4; 100 mM NaCl, 10 μg/mL saponin, 1 mM $MgCl_2$]; membranes [Recombinant CHO-K1-adrenergic $\alpha_{2B}$ membrane extracts thawed on ice and diluted in assay buffer to give 10 μg/well and kept on ice]; GDP [diluted in assay buffer to give 3 μM final concentration]; beads [PVT-WGA (Amersham, RPNQ0001), diluted in assay buffer at 0.5 mg/well]; GTPγ$^{35}$S [(PerkinElmer NEG030X), diluted in assay buffer to give 0.1 nM final concentration]; ligand [Guanfacine (Tocris, 1030) as reference agonist and Rauwolscine (Tocris, 891) as reference antagonist, diluted in assay buffer]. Membranes are mixed with GDP (volume:volume) and incubated for at least 15 min. on ice. In parallel, GTPγ[$^{35}$S] is mixed with the beads (volume:volume) just before starting the reaction.

For agonist testing, the following reagents are successively added in the wells of an Optiplate (Perkin Elmer): 50 μL of test or reference ligand, 20 μL of the membranes:GDP mix, 10 μL of assay buffer and 20 μL of the GTPγ[$^{35}$S]:beads mix. For antagonist testing, the following reagents are successively added in the wells of an Optiplate (Perkin Elmer): 50 μL of test or reference ligand, 20 μL of the membranes:GDP mix, and then after an incubation of 15 min. at RT, 10 μL of reference ligand at historical $EC_{80}$ concentration and 20 μL of the GTPγ[$^{35}$S]:beads mix.

The plates are covered with a top seal, mixed on an orbital shaker for 2 min, and then incubated for 1 h at RT. Then the plates are centrifuged for 10 min. at 2000 rpm, incubated at RT 4h and counted for 1 min/well with a Perkin Elmer Top-Count reader.

Test compounds are tested for antagonist activity at the human adrenergic $\alpha_{2B}$ receptor (FAST-007G) (Figure 4) at the following nanomolar concentrations, in duplicate: Agonist and antagonist (nM): 0.3, 1, 3, 10, 30, 100, 300, 1000, 3000, and 10000.

Inverse Agonist Activity

SPA 35S-GTPgS and Radioligand Binding experiments are conducted with Euroscreen membrane preparations. Test compound is tested for inverse agonist activity at the human Adrenergic a2A receptor using GTPg35S binding functional assay (FAST-006G) in dose-response and in duplicates.

Example B25

$\alpha_{2B}$ Pharmacology: Studies in Spontaneously Hypertensive Rat (SHR) Model of Hypertension Male spontaneously hypertensive rats (SHR), approximately 3 months of age and weighting approximately 250 grams are utilized. Free access to standard lab chow for rats and reverse osmosis (RO) water is granted. All aspects of this work, including housing, experimentation and disposal of animals are performed in general accordance with the Guide for the Care and Use of Laboratory Animals (National Academy Press, Washington, D. C., 1996).

The animals are anaesthetized with sodium pentobarbital (50 mg/kg IP). The left carotid artery when compound dosed orally (PO) or subcutaneously (SC); and both left carotid and femoral artery when compound dosed intravenous (i.v.) are cannulated with a polyethylene catheter (38 cm in length; PE60, Portex, Ltd.) connected with a polyurethane tubing (12 cm in length; PU-40, Cat. #BB520-40, Scientific Commodities, Inc.), which is tunneled under the skin and exited through the nape of the neck. The arterial cannula is connected to a pressure transducer through a swivel system, allowing free roaming during continuous recording of mean arterial pressure and heart rate. The animals are housed individually with food and water freely available during recovery. On the following day, the arterial cannula is connected via a Statham (P 23×L) pressure transducer to a NEC/San-Ei amplifier and data acquisition and analysis system (Power Lab 8/SP) for direct mean arterial pressure and heart rate measurements.

The test compounds, dissolved in sterile saline, are administered subcutaneously (SC) or orally (PO), or by intravenous (i.v.) bolus administration in two minutes or the escalating doses of compound administration in every 30 minutes, with each dose and its strength delivered over 2 minutes as shown in the respective figures; the internal standard phentolamine is given by oral gavage. The control group received vehicle alone. Immediately before (−10 min and −5 min) and at 15 min, 30 min, 1 hr, 1.5 hr, 2 hr, 2.5 hr, 3 hr, 3.5 hr, and 4 hr post-dosing, systolic pressure blood pressure values are recorded. Effect of the test compounds on blood pressure is determined.

Example B26

$\alpha_{2B}$ Pharmacology: Studies in Healthy Dogs and Dexmedetomidine (DEX) Induced Beagle Dog Model of Hypertension These studies are conducted in both acute and chronic modes.

Four adult beagle dogs of both sex and weighted around 10 kg are chosen for the acute studies after a preliminary qualitative electrocardiogram/ECG, clinical pathology and physical examination. Upon arrival at the laboratory, the dogs are weighed and acclimated for a period of one week. Lab Diet certified canine diet #5007, PMI Nutrition International Inc is made available ad libitum to all dogs except during fasting periods. The dogs are surgically implanted with a pressure transducer equipped telemetry transmitter under sodium pentobarbitone anesthesia. The transmitter assembly is secured internally, and the fluid-filled catheter is placed into an appropriate artery.

In the acute studies, the test compounds at different doses is administered by oral gavage, 30 minutes prior to intravenous dexmedetomidine (5 g/kg) challenge. Dexmedetomidine administration is enabled by prior placement of a peripheral intravenous line. The same four dogs are received all four treatments in the order noted in the table below, with at least a 3-day washout period between treatments.

In another acute study, the test agent is administered a dose of 6 mg/kg by oral gavage to 4 healthy dogs; and the blood pressure monitored for a period of 4 hours.

For the chronic study mode (see Table B9), the test compound at 3 doses is administered by oral gavage once on day 1 and then twice/day on days 2 to 14, and finally once on day 15. The dexmedetomidine is administered on day −4 to check its effectiveness in inducing blood pressure, and once following the morning dose of test compound or vehicle on days 2, 7 and 14. Blood pressure and heart rate data are collected 1 h prior and 4h post-morning dose on days 1, 2, 7, 14 and 15 to allow the appropriate data comparisons. Blood aliquots are saved at 4h post-morning dose for exposure determination.

TABLE B9

Chronic dosing sequence and study design for test compound

| Test Compound - 30 minute Pretreatment (mg/kg, p.o.) with b.i.d. regimen for 14 days | Dexmedetomidine Challenge (µg/kg, i.v.) | Number of Dogs |
| --- | --- | --- |
| 0 | 5 | 6 |
| 6 | 5 | 6 |
| 18 | 5 | 6 |

| | | | Day | | |
| --- | --- | --- | --- | --- | --- |
| | −4 | 1 | 2 | 7 | 14 | 15 |
| Compound dosed on | — | am | am/pm | from day 2 am/pm | to day 14 am/pm | Am |
| DEX* | am | — | Am | am | Am | — |

*DEX administered 30 min following am dose of test compound.

In both acute and chronic studies, dogs are weighed before dosing. Cardiovascular evaluations at each dose of test compound are collected with animals gently restrained in a sling. Dogs are placed in the sling at least 1 hour prior to dose administration, and after at least 30 minutes of stable baseline data collection. The dogs are monitored continuously for 3-4 hours subsequent to test compound administration and summarized in 5-minute bins. The systolic blood pressure is collected. Data is reported as mean±SEM or mean.

In acute studies, oral administration of test compound dose-dependently reduced systolic blood pressure in both healthy and dexmedetomidine induced dogs that are tested in the acute mode.

Adrenergic receptors $\alpha_{2B}$ and $\alpha_{2A}$ mixed inhibitor's pharmacology—Studies in Spontaneously Hypertensive Rat (SHR) Model of Hypertension: Similar to dosing regimen for selective antagonists of adrenergic receptor $\alpha_{2B}$, the mixed inhibitors is dosed orally (PO) or intravenous (i.v bolus or escalating doses) to SHR rats. A compound that is an adrenergic receptor $\alpha_{2B}$ antagonist also showing adrenergic receptor $\alpha_{2A}$ antagonist and/or inverse agonist activity can be useful for reducing blood pressure in an individual with hypertension who is also suffering from metabolic syndrome.

Example B27

Peripheral and Central Effects of Test Compound on Blood Pressure in Conscious Rabbits Four adult New Zealand White rabbits of both sexes are chosen for these studies. The experiments are conducted in accordance with the Australian code of Practice for the Care and use of Animals for Scientific Purposes and approval is sought from the Animal Experimental Committee of Alfred Hospital, Baker IDI, Melbourne, Australia. The conscious rabbits are implanted with an intravenous catheter in marginal ear vein or by centrally by intracisternal catheter interfaced to a pressure transducer connected to a suitable recorder. To unveil peripheral effects of test compound, two sets of acute studies are conducted in rabbits. In the first set of studies, test compound is dosed to rabbit intravenously for a dose-response study with cumulative doses starting 0 (Ringer's Lock solution as a vehicle), 0.1, 0.3, 1, 3.2 and 10 mg/kg where each dose is tested on a separate day. A single intravenous bolus dose at 3 mg/kg is given and a time-course study is conducted in the second set of studies. Systolic, diastolic, mean and diastolic blood pressures are recorded in both the studies. Data collections are made for 3 hours in the second set of studies. Heart rate (HR) is derived electronically using an algorithm to determine HR from pulse interval. In a separate set of studies, Clonidine (positive control) is tested where all experimental procedures including dose-regimen are identical to that of the studies with test compound.

The mean arterial pressure responses to test compound are dose-dependent in the dose-response study with cumulative doses Under similar conditions, Clonidine produces a maximum drop of arterial blood pressure of −6 mmHg before the blood pressure reversed back.

The cardiovascular effects of intracranial administration of test compound are tested in rabbits. Test compound is administered by infusion directly into the brain with the cannula delivering the compound placed directly into the 4th ventrical of the brain. Several doses are tested for cardiovascular effects, including effects on blood pressure and heart rate, following direct brain infusion. The blood pressure effects following intravenous and ventricular infusion provides the effect of the compound on the peripheral and central nervous systems respectively.

Example B28

Renal Effects of Test Compound in Conscious Rabbits

The long duration of blood pressure effect of Compounds of the invention results in a reduction in blood volume that can result from diuresis and/or the movement of fluid from the vascular space to the extravascular space. The effect of test compound on hematocrit levels is measured, compounds that reduce blood volume increase hematocrit. Characterization of the effect of $\alpha_{2B}$ antagonists on renal function is determined by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

Example B29

Insulin Secretion Ability—In Vitro

Islet Isolation and In-Vitro Insulin Release from Rat Islets:
Rat isolated pancreatic islets are prepared from rat pancreas by collagenase digestion. After digestion, islets are hand-picked and incubated in a humidified atmosphere with RPMI 1640 tissue culture medium supplemented with 10% (vol/vol) fetal bovine serum and penicillin/streptomycin [Carter J D, Dula S B, Corbin K L, Wu R, Nunemaker C S. (2009) "A practical guide to rodent islet isolation and assessment." Biol. Proced. Online 11(1): 3-31]. In-vitro insulin secretion is measured in static incubations. Prior to experiments, islets are preincubated for 1 hour at 37° C. in a Krebs-Ringer bicarbonate buffer composed of 120 mM NaCl, 25 mM NaHCO$_3$, 5 mM KCl, 1 mM MgCl$_2$, 2.5 mM CaCl$_2$, 2.8 mM glucose and 0.5% bovine serum albumin. The medium is gassed with 100% CO$_2$ for 15 minutes to obtain constant pH. Next, groups of 15 islets are incubated in 1 mL for 60 minutes at 37° C. in Krebs-Ringer buffered solution supplemented with glucose (2.8 mM as low glucose or 20 mM as high glucose), test compound, clonidine, yohimbine or norepinephrine as indicated. Immediately after incubation, an aliquot of the medium is removed for analysis of insulin content by ELISA (Mercodia). FIGS. 6 and 7 show a dose-proportional increase in insulin release in the presence of Compound 129d, in competition with either norepinephrine or clonidine.

Example B30

Insulin Secretion Ability—In Vitro

To demonstrate the insulin secretion ability and/or glucose lowering effect of compounds of the invention several animal models are used, including clonidine (an $\alpha_{2A}$ agonist) induced, norepinephrine (a natural ligand of $\alpha 2A$) induced, glucose induced, and spontaneous (no agonist) rat (normal Wistar rats or spontaneously hypertensive rats with obesity (SHR.OB)) models of hyperglycemia and norepinephrine induced and spontaneous (no agonist) obese mouse (ob/ob) models of hyperglycemia. These models and their pathophysiology are reported in e.g., Kuhn C. M. et al., *Pharmacol. Biochem. Behav.* 26:491-495 (1987); Velliquette R. A. and Ernsberger P, *J. Pharmacol. Exp. Ther.* 306:646-657 (2003); Rosengren A. H., et al., *Science,* 327:217-220 (2010); Chen B., et al., *Exp. Biol. Med.,* 236:309-414 (2011); and Saperstein R., et al., *Metabolism,* 39:445-451 (1990). To rule out the possible hypoglycemic effects, nonnoglycemic rats are used. Male or female 16 week old spontaneously hypertensive obese rats (SHR.OB), 10 week old male Wistar rats and 10 week old male ob/ob mice are utilized in these studies. Free access to standard lab chow and reverse osmosis (RO) water is supplied to all rats. All aspects of this work, including housing and feeding, experimentation and disposal of animals are performed in general accordance with the Guide for the Care and Use of Laboratory Animals (National Academy Press, Washington, D. C., 1996).

Effect of Test Compound on Blood Glucose Levels in Clonidine Induced Rat Models of Hyperglycemia:
In separate studies, six hour fasted SHR.OB or Wistar rats are randomized according to their baseline blood glucose levels and divided into several groups with an "n" of 4 for group depending on the experimental design. All the experimental agents are dissolved in sterile saline or appropriate solvents and administered sub-cutaneously (SC), oral (PO) or intra-peritoneal (IP) as indicated. The vehicle group received saline alone via SC route. Test compound at doses of 0 (vehicle), 6 mg/kg and 18 mg/kg in SHR.OB rats; and 0 (vehicle), 5 mg/kg and 15 mg/kg to Wistar rats are administered via SC route at -30 minutes. Hyperglycemia is induced in both SHR.OB and Wistar rats with clonidine at a dose of 0.05 mg/kg via PO route at 0 min. At all the study points, blood glucose levels are measured by one touch glucose meter (Lifescan, Milpitas, Calif.). The tip of the tail is snipped by sharp scissors and gently squeezed for a drop of blood. The glucose strip is inserted in the slot of the hand-held glucose meter and a drop of blood is added to the strip. Within 20 seconds, the device determined the blood glucose levels. Blood glucose levels are recorded at -30, 0, 15, 30, 60 and 120 minutes.

Effect of Test Compound on Blood Glucose and Serum Insulin Levels in Norepinephrine Induced Rat Models of Hyperglycemia:
All experimental conditions and experimental procedures are identical to that of clonidine induced rat models of hyperglycemia in SHR.OB and Wistar rats except norepinephrine is given in the place of clonidine at a dose of 1 mg/kg via IP route; and test compound is tested at a single dose, 15 or 18 mg/kg via SC route. In further studies, both blood glucose and serum insulin levels are measured in the same study at 10 or 30 mg/kg SC doses of test compound.

Effect of Test Compound on Blood Glucose and Serum Insulin Levels in Norepinephrine Induced Ob/Ob Mouse Model Hyperglycemia:
Studies with ob/ob mice, all experimental procedures are identical to that of norepinephrine induced rat models of hyperglycemia and test compound is tested via SC route at a dose of 30 mg/kg. Number of mice used per group per time point are 3.

Effect of Test Compound on Blood Glucose and Serum Insulin Levels in Ob/Ob Mouse Model Spontaneous Hyperglycemia with No Norephinephrine:
All experimental procedures are identical to that of studies conducted in ob/ob mice where norepinephrine is not given at 0 minutes; and test compound at a dose of 30 mg/kg via SC route is dosed at -30 minutes. Number of mice used per group and each time point are 3.

Effect of test compound on blood glucose and serum insulin levels in glucose induced (oral glucose tolerance test—OGTT) rat SHR.OB model of hyperglycemia:
All experimental procedures are identical to that of norepinephrine induced hyperglycemia in SHR.OB rats except glucose is given in the place of norepinephrine at 0 minutes at a dose of 6 g/kg via oral route as reported by Chen et al, *Exp. Biol. Med.,* 236:309-414 (2011). Number of rats used per group are 8.

When administered via SC route to SHR.OB or Wistar rats, test compound markedly reduced blood glucose levels by 30 minutes after the clonidine or norepinephrine challenge and the effect is evident throughout the entire study period. Identical effects on blood glucose levels are found in norepinephrine induced hyperglycemic ob/ob mice. These effects are dose-dependent and obvious. The glucose lowering effect of test compound is robust in $\alpha_{2A}$ agonized SHR.OB rats, which is an animal model of metabolic syndrome, when compared to Wistar rats. In agreement with the reduction in blood glucose levels, the test compound proportionally increased insulin secretion in all these models. It also found that test compound lowers blood glucose levels even in the absence of norepinephrine where ob/ob mice are spontaneously (moderately) hyperglycemic; and it proportionally enhanced insulin secretions. Intriguingly, test compound promoted insulin secretions but not reduced blood glucose levels at higher dose in a OGTT test conducted in SHR.OB rats, suggesting that its role is obvious in insulin secretion but may not improve insulin sensitivity in this particular model.

Effect of Test Compound on Blood Glucose Levels in Normoglycemic Rats:

In addition to the studies with rat models of hyperglycemia, the effect of test compound at high dose (18 mg/kg, SC) on blood glucose levels is also tested in normoglycemic SHR.OB rats, which is an animal model of metabolic syndrome. This is to rule out possible hypoglycemic effects in normoglycemic rats. The experimental protocol in this study is identical to that of the other studies except that the rats are normoglycemic and did not get clonidine or norepinephrine at 0 minutes.

Test compound markedly prevented clonidine/norepinephrine induced hyperglycemia, suggesting the compound can prevent or halt hepatic glucose production via blocking gluconeogenesis or glycogenolysis or both which is an extra-pancreatic effect.

Test compound potentiated nateglinide/meglitinides induced insulin release in pancreatic beta cell in-vitro model. This discovery suggests that it may be used in combination with another anti-diabetic agent such as secretagogues, sensitizers or/and others agents.

Example B31

Blood Pressure Lowering Ability In Vivo

To demonstrate the blood pressure lowering effect of a test compound, male spontaneously hypertensive rats (SHR) are used. SHR rats are anaesthetized with sodium pentobarbital (50 mg/kg IP). The left carotid artery cannulated with a polyethylene catheter (38 cm in length; PE60, Portex, Ltd.) connected with a polyurethane tubing (12 cm in length; PU-40, Cat. #BB520-40, Scientific Commodities, Inc.), which is tunneled under the skin and exited through the nape of the neck. The arterial cannula is connected to a pressure transducer through a swivel system, allowing free roaming during continuous recording of mean arterial pressure and heart rate. The animals are housed individually with food and water freely available during recovery. On the following day, the arterial cannula is connected via a Statham (P 23×L) pressure transducer to a NEC/San-Ei amplifier and data acquisition and analysis system (PowerLab 8/SP) for direct mean arterial pressure and heart rate measurements. To determine the effect of test compound on systolic blood pressure, oral or i.v. bolus or i.v. escalating doses of compound administration in every 30 minutes is performed and systolic blood pressure is monitored at various time points, baseline data is collected during 0 to 120 minutes time points; test compound is dosed at 120 minutes; and compound effect is monitored from 120 minutes to 255 minutes.

When test compound is tested oral (10 mg/kg) or i.v., bolus (1 mg/kg) or i.v., escalating doses (1, 3, 10 and 30 mg/kg/iv for every 30 minutes), its systolic blood pressure lowering effects are robust which suggests that test compound is a promising agent for the management of a pathological condition where type-2 diabetes or obesity or metabolic syndrome is clustered with hypertension.

Example B32

Synergistic Studies with Other Secretagogue Drugs

Similar to the methods mentioned in the earlier section (Insulin Secreation Ability in vitro), male Sprague Dawley rats are anesthetized with a mixture of ketamine and xilazine (1:1) and their abdominal walls are cut open. Ten milliliter Hank's buffer saline containing collagenase (2 mg/ml) is injected into the common bile duct of the rat. The pancreas swollen with the digestion solution is quickly excised and immersed into a plastic culture bottle with solution for 12 minutes-14 minutes incubation at 37° C. The digested suspension obtained is washed with Hank's buffer complement with 0.2% bovine serum albumin. Islets are obtained from a rat by gradient centrifugation (Histopaque-1077). After, islets are cultured for 24 hours in RPMI medium and collected for tests. Different secretagogue drugs like sulfonylureas (nateglinide, a meglitinide class) or sulfonylureas (glibenclamide, a second generation sulfonylureas or glimepiride, a third generation sulfonylurea) are tested with Test compound and found synergism (Figure 8, Figure 23 and Figure 24).

Test Compound Blocks pERK1/2:

For Western blotting, whole-cell extracts, cells are washed with ice-cold PBS and lysate with lysis buffer and collected by scraping. The protein concentration is determined using a BCA Protein Assay Reagent Kit. Cell lysates containing 30 μg proteins are electrophoresed on 10% SDS-PAGE and then transferred onto a PVDF membrane. The membranes are rinsed with TBST, followed by incubation with α-ERK (mouse, 1/1000, SCBT) or ERK (rabbit, 1/1000, SCBT) for 2 or 1 hour, respectively, at room temperature. After being washed with TBST, the membranes are incubated with the anti-mouse or anti-rabbit, respectively, HRP antibody (1:5000; Rockland) for 1 hour. Immunoreactive bands are visualized by ECL Western blotting detection (PIERCE). As shown in the Figure 25 (Westernblot), Test compound blocked pERK1/2 norepinephrine mediated effects in rat pancreatic islets.

Example B33

Human clinical studies

The compound is studied in a clinical trial of hypertensive patients who have not reached their blood pressure goals on current therapy. The target patient population are patients with refractory hypertension that have not reached their blood pressure goals despite use of at least 3 different blood pressure agents. The study compares the active compound against a matched placebo compound with the primary objective of comparing mean blood pressure change from baseline to the end of the study between the active compound and placebo.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method of:
   (a) treating a cognitive disorder, psychotic disorder, neurotransmitter-mediated disorder or a neuronal disorder;
   (b) lowering blood pressure;
   (c) (i) increasing renal blood flow, and/or (ii) decreasing or inhibiting sodium reabsorption;
   (d) treating a disease or condition that is hypertension, hypertensive emergency or a cardiac or renal disease or condition;
   (e) regulating blood glucose levels;
   (f) (i) increasing insulin secretion, and/or (ii) promoting insulin release into the blood stream;
   (g) treating a disease or condition that is type 2 diabetes, glucose intolerance or metabolic syndrome; or
   (h) delaying the onset of a disease or condition that is type 2 diabetes, glucose intolerance or metabolic syndrome;
   in an individual in need thereof comprising administering to the individual an effective amount of a compound of the formula (IA), (J-1), (J-2), (J-3), (J-4), (J-5), (K-1), (K-2), (K-3), (K-4) or (K-5):
wherein the formula (IA) is:

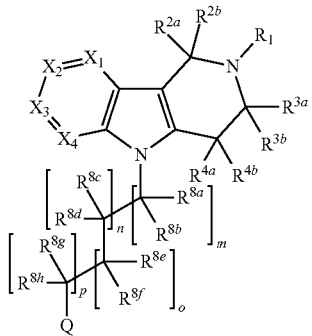

(IA)

or a salt or solvate thereof; wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^{4a}$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^{2a}$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $X^1$, $X^2$, $X^3$ and $X^4$ is independently N, CH or $CR^6$;
each m, n, o and p is independently 0 or 1;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula $-CR^9=CR^{10a}R^{10b}$, wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

the formula (J-1), (J-2), (J-3), (J-4), or (J-5) is:

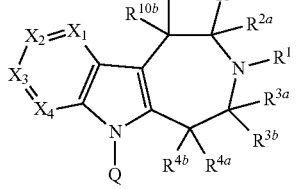

(J-1)

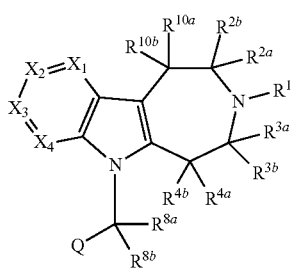

(J-2)

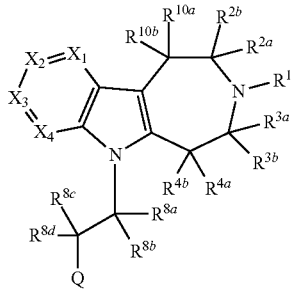

(J-3)

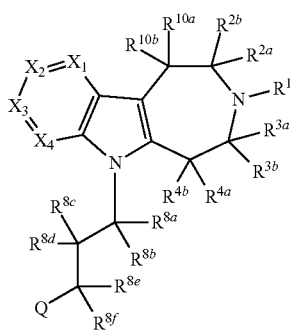

(J-4)

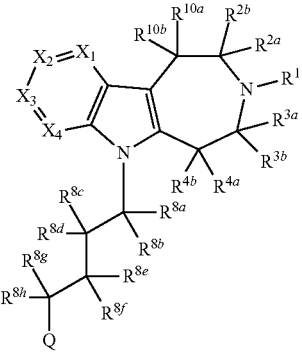

(J-5)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $X^1$, $X^2$, $X^3$ and $X^4$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —$OCH_2CH_2O$—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —$CR^9$=$CR^{10a}R^{10b}$ or of the structure:

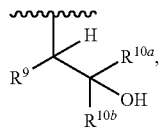

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety;

the formula (K-1), (K-2), (K-3), (K-4), or (K-5) is:

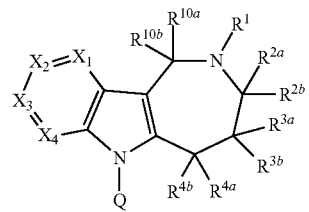

(K-1)

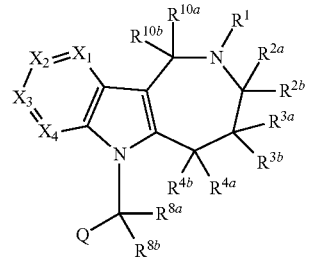

(K-2)

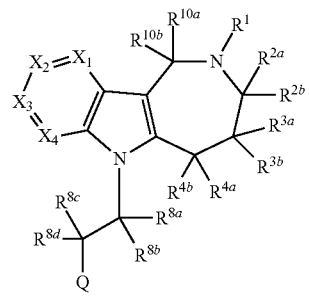

(K-3)

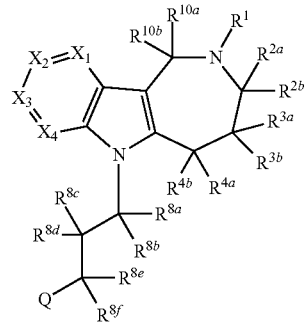

(K-4)

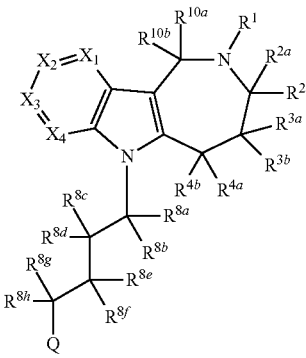

(K-5)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$, $R^{2b}$ $R^{3a}$, $R^{3b}$, $R^{4a}$, $R^{4b}$, $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$, $R^3$, $R^4$ or $R^{10}$ to form a carbonyl moiety or a cycloalkyl moiety;

each $X^1$, $X^2$, $X^3$ and $X^4$ is independently N, CH or $CR^6$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$, $R^{8f}$, $R^{8g}$ and $R^{8h}$ is independently H, hydroxyl, alkoxy, acyloxy, thiol, —S-alkyl, —S-aryl, —S-aralkyl, —S(O)-alkyl, —S(O)-aryl, —S(O)-aralkyl, —S(O)$_2$-alkyl, —S(O)$_2$-aryl, —S(O)$_2$-aralkyl, substituted or unsubstituted amino, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl, $C_1$-$C_8$ alkyl substituted with a carbonylalkoxy, carboxyl or acylamino moiety, or is taken together with a geminal $R^{8(a-h)}$ to form a substituted or unsubstituted methylene moiety or a moiety of the formula —OCH$_2$CH$_2$O—, or is taken together with a geminal $R^{8(a-h)}$ and the carbon to which they are attached to form a carbonyl moiety or a cycloalkyl moiety, or is taken together with a vicinal $R^{8(a-h)}$ and the carbon atoms to which they are attached to form a substituted or unsubstituted $C_3$-$C_8$ cycloalkyl, substituted or unsubstituted $C_3$-$C_8$ cycloalkenyl, or substituted or unsubstituted heterocyclyl moiety, or is taken together with a vicinal $R^{8(a-h)}$ to form a bond provided when an $R^{8(a-h)}$ is taken together with a vicinal $R^{8(a-h)}$ to form a bond, the geminal $R^{8(a-h)}$ is other than hydroxyl and thiol; and Q is a group of the formula —CR$^9$═CR$^{10a}$R$^{10b}$ or of the structure:

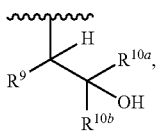

wherein $R^9$ is H or a substituted or unsubstituted $C_1$-$C_8$ alkyl and $R^{10a}$ and $R^{10b}$ are taken together with the carbon to which they are attached to form a substituted or unsubstituted cycloalkyl, cycloalkenyl or heterocyclyl moiety.

2. The method of claim 1, wherein $R^1$ is H or methyl.

3. The method of claim 1, wherein each $R^{2a}$, $R^{2b}$, $R^{3a}$, $R^{3b}$, $R^{4a}$ and $R^{4b}$ is independently H or methyl.

4. The method of claim 1, wherein $X^1$ is CH and $X^3$ is CH.

5. The method of claim 1, wherein $R^6$ is H, chloro or methyl.

6. The method of claim 1, wherein $R^{8c}$, when present, is H, OH or methyl; $R^{8d}$, when present, is H or unsubstituted $C_1$-$C_8$ alkyl; and $R^{8e}$, when present, is H or methyl.

7. A method of:
(a) treating a cognitive disorder, psychotic disorder, neurotransmitter-mediated disorder or a neuronal disorder;
(b) lowering blood pressure;
(c) (i) increasing renal blood flow, and/or (ii) decreasing or inhibiting sodium reabsorption;
(d) treating a disease or condition that is hypertension, hypertensive emergency or a cardiac or renal disease or condition;
(e) regulating blood glucose levels;
(f) (i) increasing insulin secretion, and/or (ii) promoting insulin release into the blood stream;
(g) treating a disease or condition that is type 2 diabetes, glucose intolerance or metabolic syndrome; or
(h) delaying the onset of a disease or condition that is type 2 diabetes, glucose intolerance or metabolic syndrome;
in an individual in need thereof comprising administering to the individual an effective amount of a compound of the formula (IB):

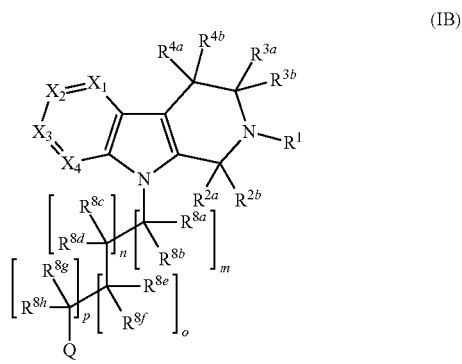

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—CH$_2$CH$_2$CH$_2$—) moiety or a butylene (—CH$_2$CH$_2$CH$_2$CH$_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or $R^1$ and $R^{4a}$ are taken together to form an ethylene (—CH$_2$CH$_2$—) moiety or a propylene (—CH$_2$CH$_2$CH$_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—CH$_2$CH$_2$CH$_2$—) moiety or a butylene (—CH$_2$CH$_2$CH$_2$CH$_2$—) moiety, or $R^{2a}$ and $R^{3a}$ are taken together to form an ethylene (—CH$_2$CH$_2$—) moiety or a propylene (—CH$_2$CH$_2$CH$_2$—) moiety, or $R^{2a}$ and $R^{4a}$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^{2a}$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;

each R$^{4a}$ and R$^{4b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^{4a}$ and R$^{4b}$ are taken together with the carbon to which they are attached to form a carbonyl moiety or a cycloalkyl moiety, or R$^{4a}$ and R$^1$ are taken together to form an ethylene (—CH$_2$CH$_2$—) moiety or a propylene (—CH$_2$CH$_2$CH$_2$—) moiety, or R$^{4a}$ and R$^{2a}$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;

each X$^1$, X$^2$, X$^3$ and X$^4$ is independently N, CH or CR$^6$;

each m, n, o and p is independently 0 or 1;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$, R$^{8f}$, R$^{8g}$ and R$^{8h}$ is independently H, hydroxyl, alkoxy, acyloxy, thiol, —S-alkyl, —S-aryl, —S-aralkyl, —S(O)-alkyl, —S(O)-aryl, —S(O)aralkyl, —S(O)$_2$-alkyl, —S(O)$_2$-aryl, —S(O)$_2$-aralkyl, substituted or unsubstituted amino, halo, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxyl, carbonylalkoxy, substituted or unsubstituted aryl, substituted or unsubstituted heteroaryl, C$_1$-C$_8$ alkyl substituted with a carbonylalkoxy, carboxyl or acylamino moiety, or is taken together with a geminal R$^{8(a-h)}$ to form a substituted or unsubstituted methylene moiety or a moiety of the formula —OCH$_2$CH$_2$O—, or is taken together with a geminal R$^{8(a-h)}$ and the carbon to which they are attached to form a carbonyl moiety or a cycloalkyl moiety, or is taken together with a vicinal R$^{8(a-h)}$ and the carbon atoms to which they are attached to form a substituted or unsubstituted C$_3$-C$_8$ cycloalkyl, substituted or unsubstituted C$_3$-C$_8$ cycloalkenyl, or substituted or unsubstituted heterocyclyl moiety, or is taken together with a vicinal R$^{8(a-h)}$ to form a bond provided when an R$^{8(a-h)}$ is taken together with a vicinal R$^{8(a-h)}$ to form a bond, the geminal R$^{8(a-h)}$ is other than hydroxyl and thiol; and Q is a group of the formula —CR$^9$=CR$^{10a}$R$^{10b}$, wherein R$^9$ is H or a substituted or unsubstituted C$_1$-C$_8$ alkyl and R$^{10a}$ and R$^{10b}$ are taken together with the carbon to which they are attached to form a substituted or unsubstituted cycloalkyl, cycloalkenyl or heterocyclyl moiety.

8. A method of:
(a) treating a cognitive disorder, psychotic disorder, neurotransmitter-mediated disorder or a neuronal disorder;
(b) lowering blood pressure;
(c) (i) increasing renal blood flow, and/or (ii) decreasing or inhibiting sodium reabsorption;
(d) treating a disease or condition that is hypertension, hypertensive emergency or a cardiac or renal disease or condition;
(e) regulating blood glucose levels;
(f) (i) increasing insulin secretion, and/or (ii) promoting insulin release into the blood stream;
(g) treating a disease or condition that is type 2 diabetes, glucose intolerance or metabolic syndrome; or
(h) delaying the onset of a disease or condition that is type 2 diabetes, glucose intolerance or metabolic syndrome;
in an individual in need thereof comprising administering to the individual an effective amount of a compound selected from the group consisting of compounds i-1 to i-112 or ii-1 to ii-113, or a pharmaceutically acceptable salt thereof.

9. The method of claim 1, wherein the method is of treating a cognitive disorder, psychotic disorder, neurotransmitter-mediated disorder or a neuronal disorder.

10. The method of claim 8, wherein the method is of treating a cognitive disorder, psychotic disorder, neurotransmitter-mediated disorder or a neuronal disorder.

11. The method of claim 7, wherein the method is of treating a cognitive disorder, psychotic disorder, neurotransmitter-mediated disorder or a neuronal disorder.

12. The method of claim 1, wherein the method is of lowering blood pressure.

13. The method of claim 1, wherein the method is of (i) increasing renal blood flow, and/or (ii) decreasing or inhibiting sodium reabsorption.

14. The method of claim 1, wherein the method is of treating a disease or condition that is hypertension, hypertensive emergency or a cardiac or renal disease or condition.

15. The method of claim 1, wherein the method is of regulating blood glucose levels.

16. The method of claim 1, wherein the method is of (i) increasing insulin secretion, and/or (ii) promoting insulin release into the blood stream.

17. The method of claim 1, wherein the method is of treating a disease or condition that is type 2 diabetes, glucose intolerance or metabolic syndrome.

18. The method of claim 1, wherein the method is of delaying the onset of a disease or condition that is type 2 diabetes, glucose intolerance or metabolic syndrome.

* * * * *